United States Patent
Bungard et al.

(10) Patent No.: US 9,636,337 B2
(45) Date of Patent: May 2, 2017

(54) QUINOLINE CARBOXAMIDE AND QUINOLINE CARBONITRILE DERIVATIVES AS MGLUR2-NEGATIVE ALLOSTERIC MODULATORS, COMPOSITIONS, AND THEIR USE

(71) Applicant: Merck Sharp & Dohme Corp, Rahway, NJ (US)

(72) Inventors: Christopher James Bungard, Lansdale, PA (US); Antonella Converso, Elkins Park, PA (US); Pablo De Leon, Philadelphia, PA (US); Barbara Hanney, Pennsburg, PA (US); Timothy John Hartingh, Blue Bell, PA (US); Jesse Josef Manikowski, Worcester, PA (US); Peter J. Manley, Harleysville, PA (US); Robert Meissner, Newton, MA (US); Zhaoyang Meng, Lansdale, PA (US); James J. Perkins, Churchville, PA (US); Michael T. Rudd, Collegeville, PA (US); Youheng Shu, Blue Bell, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/047,224

(22) Filed: Feb. 18, 2016

(65) Prior Publication Data
US 2016/0158217 A1 Jun. 9, 2016

Related U.S. Application Data

(62) Division of application No. 14/356,080, filed as application No. PCT/US2012/062027 on Oct. 26, 2012, now Pat. No. 9,278,960.
(Continued)

(51) Int. Cl.
*A61K 31/47* (2006.01)
*A61K 31/506* (2006.01)
(Continued)

(52) U.S. Cl.
CPC .......... *A61K 31/47* (2013.01); *A61K 31/4709* (2013.01); *A61K 31/496* (2013.01);
(Continued)

(58) Field of Classification Search
CPC ............................. C07D 413/14; C07D 401/06
See application file for complete search history.

(56) References Cited

U.S. PATENT DOCUMENTS 5,576,338 A   11/1996  Friesen et al.
7,960,409 B2 *  6/2011  Grimm ................ C07D 401/06
                                                    514/314
(Continued)

FOREIGN PATENT DOCUMENTS

EP   0551831 A1   1/1993
WO   WO9719928 A1   6/1997
(Continued)

OTHER PUBLICATIONS

EP Search Report, corresponding to PCT/US2012/062027, Apr. 8, 2015, 6 pages.
Hamana, M. et al., Reactions of 2-Phenyl-, 4-Phenyl-,and 2,4-Diphenyl-quinoline N-oxides with Acylating Agents, Faculty of Pharmaceutical Sciences, Kyushu University, Dec. 31, 1966, vol. 86(1), p. 59-66.
International Search Report and Written Opinion for PCT/US12/62027 dated Jan. 11, 2013.
Zhang et al., Investigation on Quantitative Structure Activity Relationships and Pharmacore 1-24 Modeling of a Series of mGluR2 Antagonists, Int J Mol Sci 12, pp. 5999-6023, 2011, p. 6001, para 2; p. 6002; para 1—p. 6014, para 1; p. 6015, Table 6.

*Primary Examiner* — Matthew Coughlin
(74) *Attorney, Agent, or Firm* — Keith D. MacMillan; John C. Todaro

(57) ABSTRACT

The present invention provides quinoline carboxamide and quinoline carbonitrile compounds of formula (I)

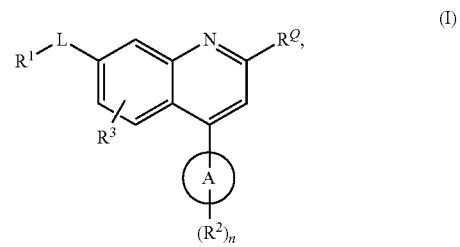

wherein ring A, $R^Q$, -L-, $R^1$, n, $R^2$, and $R^3$ are as defined herein. The compounds of the invention are useful as non-competitive mGluR2 antagonists, or mGluR2 negative allosteric modulators (NAMs), and in methods of treating a patient (preferably a human) for diseases or disorders in which the mGluR2-NAM receptor is involved, including potentially Alzheimer's disease, cognitive impairment, schizophrenia and other mood disorders, pain disorders and sleep disorders, by administering to the patient a therapeutically effective amount of a compound of the invention, or a pharmaceutically acceptable salt thereof. The invention is also directed to pharmaceutical compositions comprising a compound of the invention, or a pharmaceutically acceptable salt thereof, (optionally in combination with one or more additional active ingredients), and a pharmaceutically acceptable carrier, and the use of the compounds and pharmaceutical compositions of the invention in the treatment of such diseases.

30 Claims, No Drawings

Related U.S. Application Data

(60) Provisional application No. 61/672,334, filed on Jul. 17, 2012, provisional application No. 61/555,227, filed on Nov. 3, 2011.

(51) Int. Cl.
| | |
|---|---|
| *A61K 31/4985* | (2006.01) |
| *A61K 31/496* | (2006.01) |
| *A61K 31/4709* | (2006.01) |
| *A61K 31/541* | (2006.01) |
| *A61K 31/5377* | (2006.01) |
| *C07D 401/14* | (2006.01) |
| *C07D 413/14* | (2006.01) |
| *C07D 215/48* | (2006.01) |
| *C07D 401/04* | (2006.01) |
| *C07D 401/06* | (2006.01) |
| *C07D 409/04* | (2006.01) |
| *C07D 413/06* | (2006.01) |
| *C07D 417/06* | (2006.01) |
| *C07D 417/14* | (2006.01) |
| *C07D 471/04* | (2006.01) |
| *C07D 491/10* | (2006.01) |

(52) U.S. Cl.
CPC ........ *A61K 31/4985* (2013.01); *A61K 31/506* (2013.01); *A61K 31/5377* (2013.01); *A61K 31/541* (2013.01); *C07D 215/48* (2013.01); *C07D 401/04* (2013.01); *C07D 401/06* (2013.01); *C07D 401/14* (2013.01); *C07D 409/04* (2013.01); *C07D 413/06* (2013.01); *C07D 413/14* (2013.01); *C07D 417/06* (2013.01); *C07D 417/14* (2013.01); *C07D 471/04* (2013.01); *C07D 491/10* (2013.01)

(56) References Cited

U.S. PATENT DOCUMENTS

| | | |
|---|---|---|
| 9,278,960 B2 | 3/2016 | Bungard et al. |
| 2007/0287716 A1 | 12/2007 | Hu et al. |
| 2008/0188521 A1* | 8/2008 | Grimm ............... C07D 401/06 514/314 |
| 2016/0159744 A1 | 6/2016 | Bungard et al. |

FOREIGN PATENT DOCUMENTS

| | | |
|---|---|---|
| WO | WO2005/010484 | 2/2005 |
| WO | WO2005030129 A2 | 4/2005 |
| WO | WO2006049968 A1 | 5/2006 |
| WO | WO2007/038865 | 4/2007 |
| WO | WO2008095293 A1 | 8/2008 |
| WO | WO2011153553 A2 | 12/2011 |
| WO | W02012083866 A1 | 6/2012 |

* cited by examiner

QUINOLINE CARBOXAMIDE AND QUINOLINE CARBONITRILE DERIVATIVES AS MGLUR2-NEGATIVE ALLOSTERIC MODULATORS, COMPOSITIONS, AND THEIR USE

FIELD OF THE INVENTION

The invention is directed to certain quinoline carboxamide and quinoline carbonitrile derivatives, their salts, pharmaceutical compositions comprising them and their use in therapy of the human body. The quinoline carboxamide derivatives of the invention metabotropic glutamate receptor 2 (mGluR2) modulators, and hence are useful in the treatment of Alzheimer's Disease and other diseases mediated by the mGluR2 receptor.

BACKGROUND OF THE INVENTION

Alzheimer's Disease is a common neurodegenerative disease affecting the elderly, resulting in progressive memory impairment, loss of language and visuospatial skills, and behavior deficits. Modulation of metabotropic glutamate receptor 2, which is prevalent in the cortex and hippocampus and regulates the release of the brain's major excitatory neurotransmitter glutamate at key neural synapses has been demonstrated to have a major role in cognitive processing. Further, modulation of mGluR2 improves cognitive performance in preclinical species (Higgins, G. A. et al. (2004) Pharmacological manipulation of mGlu2 receptors influences cognitive performance in the rodent. Neuropharmacology 46, 907-917).

The metabotropic glutamate receptors are known to contain one or more allosteric sites, which may alter the affinity with which glutamate and other mGluR ligands bind to the primary binding or orthosteric sites. As the orthosteric binding site is highly conserved between all of the known metabotropic glutamate receptors, functional selectivity may best be achieved through allosteric interaction with the receptor.

Certain substituted quinoline carboxamides and quinoline carbonitriles are known in the art. See, for example, US Patent Application No. 2008/0188521, WO2007/038865, WO 1996/13500, each disclosing compounds as leukotriene inhibitors, and Canadian Patent Application No. 2169231, disclosing compounds as leukotriene and SRS-A inhibitors. There remains a need in the art for novel compounds that are effective as non-competitive mGluR2 modulators, and/or mGluR2 negative allosteric modulators (NAMs).

SUMMARY OF THE INVENTION

The present invention provides certain novel substituted quinoline carboxamide and quinoline carbonitrile derivatives, which are collectively or individually referred to herein as "compound(s) of the invention," as described herein. The compounds of the invention are useful as non-competitive mGluR2 antagonists, or mGluR2 negative allosteric modulators (NAMs), and in methods of treating a patient (preferably a human) for diseases or disorders in which the mGluR2-NAM receptor is involved, such as Alzheimer's disease, cognitive impairment, schizophrenia and other mood disorders, pain disorders and sleep disorders, by administering to the patient a therapeutically effective amount of a compound of the invention, or a pharmaceutically acceptable salt thereof. The invention is also directed to pharmaceutical compositions which include an effective amount of a compound of the invention, or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the compounds of the invention have the structural Formula (I):

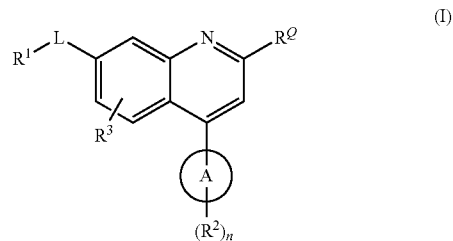

or a stereoisomer thereof, or a pharmaceutically acceptable salt of said compound or said stereoisomer, wherein:

ring A is a moiety selected from the group consisting of phenyl, —($C_5$-$C_6$) cycloalkyl, —($C_5$-$C_6$) cycloalkyenl, -pyridinyl, pyrimidinyl, -pyrazolyl, -thienyl, -thiazolyl, -thiadiazolyl, and -oxazolyl;

$R^Q$ is selected from the group consisting of —CN and —C(O)NH$_2$;

-L- is a bond or a divalent moiety selected from the group consisting of:

—(C($R^{1L}$)$_2$)$_p$—,

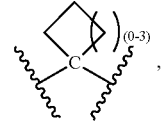

—C(O)—, —S(O)—, and —S(O)$_2$—;

p is 1, 2, or 3;

each $R^{1L}$ is independently selected from the group consisting of H, —CH$_3$, —CF$_3$, —OH, —C(O)—, halogen, -cyclopropyl, —O—CH$_3$, and —O—CF$_3$;

$R^1$ is selected from the group consisting of:

(1) heterocycloalkyl and heterocycloalkenyl, wherein said heterocycloalkyl and said heterocycloalkenyl are monocyclic or multicyclic ring systems comprising from 3 to 10 ring atoms in which 1, 2, or 3 of the atoms of each said ring system is a ring heteroatom independently selected from the group consisting of N, S, S(O), S(O)$_2$, and O, and wherein each said heterocycloalkyl group and each said heterocycloalkenyl group is unsubstituted or substituted with 1 to 5 groups independently selected from the group consisting of oxo, CN, —OH, halogen, —(C$_1$-C$_6$) alkyl, hydroxy-substituted —(C$_1$-C$_6$) alkyl, —(C$_1$-C$_6$) alkynyl, —(C$_1$-C$_6$) haloalkyl, hydroxy-substituted —(C$_1$-C$_6$) haloalkyl, —O—(C$_1$-C$_6$) alkyl, —(C$_3$-C$_8$) cycloalkyl, -alkyl-cycloalkyl, —CH(OH)cycloalkyl, phenyl, -alkyl-phenyl, monocyclic heteroaryl, -alkyl-monocyclic heteroaryl, —(C$_3$-C$_8$) spirocycloalkyl, —(C$_3$-C$_8$) spiroheterocycloalkyl, —C(O)H, —C(O)OH, —C(O)(C$_1$-C$_6$) alkyl, —C(O)O($C_1$-$C_6$) alkyl, —N($R^{1A}$)C(O)—($C_1$-$C_6$) alkyl, —N($R^{1A}$)$_2$, —C(O)N($R^{1A}$)$_2$, —S(O)$_2$H, —S(O)-phenyl, —S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl, wherein each $R^{1A}$ group is independently selected from the group consisting of H and —($C_1$-$C_6$ alkyl);

(2) heteroaryl, wherein said heteroaryl is a monocyclic or multicyclic ring system comprising from 5 to 10 ring atoms in which from 1 to 4 of the atoms of said ring system is a ring nitrogen atom, and wherein said heteroaryl is unsubstituted or substituted with 1 to 5 groups independently selected from the group consisting of oxo, CN, —OH, halogen, —($C_1$-$C_6$) alkyl, hydroxy-substituted —($C_1$-$C_6$) alkyl, —($C_1$-$C_6$) alkynyl, —($C_1$-$C_6$) haloalkyl, hydroxy-substituted —($C_1$-$C_6$) haloalkyl, —O—($C_1$-$C_6$) alkyl, —($C_3$-$C_8$) cycloalkyl, -alkyl-cycloalkyl, —CH(OH)cycloalkyl, phenyl, -alkyl-phenyl, monocyclic heteroaryl, -alkyl-monocyclic heteroaryl, —($C_3$-$C_8$) spirocycloalkyl, —C(O)H, —C(O)OH, —C(O)($C_1$-$C_6$) alkyl, —C(O)O($C_1$-$C_6$) alkyl, —N($R^{1B}$)C(O)—($C_1$-$C_6$) alkyl, —N($R^{1B}$)$_2$, —C(O)N($R^{1B}$)$_2$, —S(O)$_2$H, —S(O)-phenyl, —S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl, wherein each $R^{1B}$ group is independently selected from the group consisting of H and —($C_1$-$C_6$ alkyl), with the proviso that $R^1$ is not unsubstituted or substituted triazolyl, and with the further proviso that when $R^1$ is substituted oxadiazolyl, substituted thiazolyl, or substituted thiadiazolyl, then -L- is selected from the group consisting of —(C($R^{1L}$)$_2$)$_p$—, and

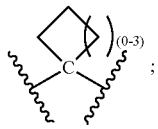

(3) phenyl, wherein said phenyl is unsubstituted or substituted with from 1 to 5 groups independently selected from the group consisting of oxo, CN, —OH, halogen, —($C_1$-$C_6$) alkyl, —($C_1$-$C_6$) alkynyl, —($C_1$-$C_6$) haloalkyl, —O—($C_1$-$C_6$) alkyl, —($C_3$-$C_8$) cycloalkyl, -alkyl-cycloalkyl, —CH(OH) cycloalkyl, monocyclic heteroaryl, -alkyl-monocyclic heteroaryl, —($C_3$-$C_8$) spirocycloalkyl, —C(O)H, —C(O)OH, —C(O)($C_1$-$C_6$) alkyl, —C(O)O($C_1$-$C_6$) alkyl, —N($R^{1C}$)C(O)—($C_1$-$C_6$) alkyl, —N($R^{1C}$)$_2$, —C(O)N($R^{1C}$)$_2$, —S(O)$_2$H, —S(O)-phenyl, —S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl, wherein each $R^{1C}$ group is independently selected from the group consisting of H and —($C_1$-$C_6$ alkyl);

(4) H and —($C_1$-$C_6$) alkyl;

(5) —CH$_2$N($R^{1D}$)$R^{1E}$, wherein:

$R^{1D}$ is selected from the group consisting of H, —($C_1$-$C_6$) alkyl, and —C(O)O$R^{1H}$; and $R^{1E}$ is selected from the group consisting of —O—($C_1$-$C_6$) alkyl, heteroalkyl, -alkyl-C(O)N($R^{1H}$), and —C(O)O$R^{1H}$, wherein each $R^{1H}$ is independently selected from the group consisting of H and —($C_1$-$C_6$) alkyl; and (6) —CH$_2$N($R^{1F}$)O$R^{1G}$, wherein:

$R^{1F}$ is selected from the group consisting of H, —($C_1$-$C_6$) alkyl, and —C(O)O$R^{1H}$, wherein each $R^{1H}$ is independently selected from the group consisting of H and —($C_1$-$C_6$) alkyl; and $R^{1G}$ is selected from the group consisting of H and —($C_1$-$C_6$) alkyl;

n is 0, 1, 2, or 3;

each $R^2$ (when present) is independently selected from the group consisting of halogen, —CN, —OH, —($C_1$-$C_6$) alkyl, —O—($C_1$-$C_6$) alkyl, —($C_1$-$C_6$) haloalkyl, —O—($C_1$-$C_6$) haloalkyl, cyclopropyl, cyclobutyl, cyclopentyl, cyclohexyl, —NH$_2$, —NH($C_1$-$C_6$)alkyl, —N($C_1$-$C_6$alkyl)$_2$, —C(O)O ($C_1$-$C_6$) alkyl, and phenyl; and $R^3$ is selected from the group consisting of hydrogen and fluorine.

In one embodiment, the compounds of the invention have the structural Formula (I.1):

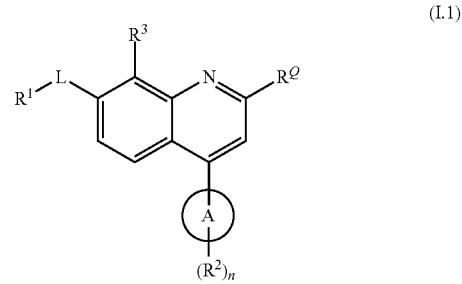

(I.1)

or a stereoisomer thereof, or a pharmaceutically acceptable salt of said compound or said stereoisomer, wherein:

ring A is a moiety selected from the group consisting of phenyl, —($C_5$-$C_6$) cycloalkyl, —($C_5$-$C_6$) cycloalkyenl, -pyridinyl, pyrimidinyl, -pyrazolyl, and -thienyl;

$R^Q$ is selected from the group consisting of —CN and —C(O)NH$_2$;

-L- is a bond or a divalent moiety selected from the group consisting of:

—(C($R^{1L}$)$_2$)$_p$—,

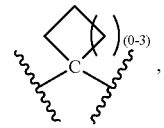

—S(O)—, and —S(O)$_2$—;

p is 1, 2, or 3;

each $R^{1L}$ is independently selected from the group consisting of H, —CH$_3$, —CF$_3$, —OH, —C(O)—, halogen, -cyclopropyl, —O—CH$_3$, and —O—CF$_3$;

$R^1$ is selected from the group consisting of:

(1) heterocycloalkyl, heterocycloalkenyl, wherein said heterocycloalkyl and said heterocycloalkenyl are monocyclic or multicyclic ring systems comprising from 3 to 10 ring atoms in which 1, 2, or 3 of the atoms of each said ring system is a ring heteroatom independently selected from the group consisting of N, S, S(O), S(O)$_2$, and O, and wherein each said heterocycloalkyl group and each said heterocycloalkenyl group is unsubstituted or substituted with 1 to 4 groups independently selected from the group consisting of oxo, CN, —OH, halogen, —($C_1$-$C_6$) alkyl, wherein said alkyl is unsubstituted or substituted with hydroxyl, —($C_1$-$C_6$)alkynyl, —($C_1$-$C_6$) haloalkyl, hydroxy-substituted —($C_1$-$C_6$) haloalkyl, —O—($C_1$-$C_6$) alkyl, —($C_3$-$C_8$) cycloalkyl, -alkyl-cycloalkyl, —CH(OH)cycloalkyl, phenyl, -alkyl-phenyl, monocyclic heteroaryl, -alkyl-monocyclic heteroaryl, —($C_3$-$C_8$) spirocycloalkyl, —C(O)H, —C(O)OH, —C(O)($C_1$-$C_6$) alkyl, —C(O)O($C_1$-$C_6$) alkyl, —N($R^{1A}$)C(O)—($C_1$-$C_6$) alkyl, —N($R^{1A}$)$_2$, —C(O)N($R^{1A}$)$_2$, —S(O)$_2$H, —S(O)$_2$H, —S(O)-phenyl, —S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl, wherein each $R^{1A}$ group is independently selected from the group consisting of H and —($C_1$-$C_6$ alkyl);

(2) heteroaryl, wherein said heteroaryl is a monocyclic or multicyclic ring system comprising from 5 to 10 ring atoms in which from 1 to 4 of the atoms of said ring system is a ring nitrogen atom, and wherein said heteroaryl is unsubstituted or substituted with 1 to 4 groups independently selected from the group consisting of oxo, CN, —OH, halogen, —($C_1$-$C_6$) alkyl, wherein said alkyl is unsubstituted or substituted with hydroxyl, —($C_1$-$C_6$) alkynyl, —($C_1$-$C_6$) haloalkyl, hydroxy-substituted —($C_1$-$C_6$) haloalkyl, —O—($C_1$-$C_6$) alkyl, —($C_3$-$C_8$) cycloalkyl, -alkyl-cycloalkyl, —CH(OH)cycloalkyl, phenyl, -alkyl-phenyl, monocyclic heteroaryl, -alkyl-monocyclic heteroaryl, —($C_3$-$C_8$) spirocycloalkyl, —C(O)H, —C(O)OH, —C(O)($C_1$-$C_6$) alkyl, —C(O)O($C_1$-$C_6$) alkyl, —N($R^{1B}$)C(O)—($C_1$-$C_6$) alkyl, —N($R^{1B}$)$_2$, —C(O)N($R^{1B}$)$_2$, —S(O)$_2$H, —S(O)-phenyl, —S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl, wherein each $R^{1B}$ group is independently selected from the group consisting of H and —($C_1$-$C_6$ alkyl), with the proviso that $R^1$ is not unsubstituted or substituted triazolyl, and with the further proviso that when $R^1$ is substituted oxadiazolyl, substituted thiazolyl, or substituted thiadiazolyl, then -L- is selected from the group consisting of —(C($R^{1L}$)$_2$)$_p$—, and

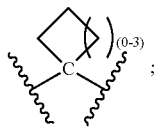

(4) phenyl, wherein said phenyl is unsubstituted or substituted with from 1 to 4 groups independently selected from the group consisting of oxo, CN, —OH, halogen, —($C_1$-$C_6$) alkyl, —($C_1$-$C_6$) alkynyl, —($C_1$-$C_6$) haloalkyl, —O—($C_1$-$C_6$) alkyl, —($C_3$-$C_8$) cycloalkyl, -alkyl-cycloalkyl, —CH(OH)cycloalkyl, monocyclic heteroaryl, -alkyl-monocyclic heteroaryl, —($C_3$-$C_8$) spirocycloalkyl, —C(O)H, —C(O)OH, —C(O)($C_1$-$C_6$) alkyl, —C(O)O($C_1$-$C_6$) alkyl, —N($R^{1C}$)C(O)—($C_1$-$C_6$) alkyl, —N($R^{1C}$)$_2$, —C(O)N($R^{1C}$)$_2$, —S(O)$_2$H, —S(O)-phenyl, —S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl, wherein each $R^{1C}$ group is independently selected from the group consisting of H and —($C_1$-$C_6$ alkyl);

(4) H, —($C_1$-$C_6$) alkyl; and (5) —CH$_2$N($R^{1D}$)$R^{1E}$, wherein:

$R^{1D}$ is selected from the group consisting of H, —($C_1$-$C_6$) alkyl, and —C(O)O$R^{1H}$; and $R^{1E}$ is selected from the group consisting of —O—($C_1$-$C_6$) alkyl, heteroalkyl, -alkyl-C(O)N($R^{1H}$), and —C(O)O$R^{1H}$, wherein each $R^{1H}$ is independently selected from the group consisting of H and —($C_1$-$C_6$) alkyl;

n is 0, 1, 2, or 3;

each $R^2$ (when present) is independently selected from the group consisting of halogen, —CN, —OH, —($C_1$-$C_6$) alkyl, —O—($C_1$-$C_6$) alkyl, —($C_1$-$C_6$) haloalkyl, —O—($C_1$-$C_6$) haloalkyl, —C(O)O($C_1$-$C_6$) alkyl, and phenyl; and $R^3$ is selected from the group consisting of hydrogen and fluorine.

In one embodiment, in Formula (I), n is 0.

In one embodiment, in Formula (I), n is 1.

In one embodiment, in Formula (I), n is 2.

In one embodiment, in Formula (I), n is 3.

In one embodiment, in Formula (I), n is 0, 1, 2, or 3; and each $R^2$ is independently selected from the group consisting of F, Cl, Br, methyl, ethyl, propyl, i-propyl, n-propyl, i-butyl, n-butyl, tert-butyl, —OCH$_3$, —OCH$_2$CH$_3$, —CFH$_2$, —CF$_2$H, —CF$_3$, —CH$_2$CFH$_2$, —CH$_2$CF$_2$H, —CH$_2$CF$_3$, —NH$_2$, —NH($C_1$-$C_6$alkyl), —N($C_1$-$C_6$alkyl)$_2$, and phenyl.

In one embodiment, the compounds of the invention have the structural Formula (II):

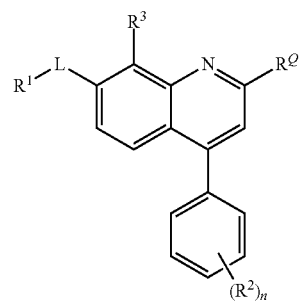

(II)

or a pharmaceutically acceptable salt thereof, wherein $R^1$, $R^Q$, -L-, n, $R^2$, and $R^3$ are as defined in Formula (I).

An alternative embodiment of Formula (II) comprises a compound of the Formula (II.1):

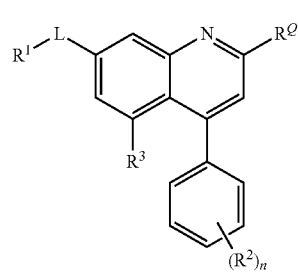

(II.1)

or a pharmaceutically acceptable salt thereof, wherein $R^1$, $R^Q$, -L-, n, $R^2$, and $R^3$ are as defined in Formula (I).

Another alternative embodiment of Formula (II) comprises a compound of the Formula (II.2):

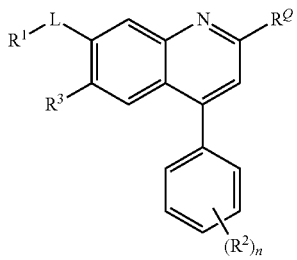
(II.2)

or a pharmaceutically acceptable salt thereof, wherein $R^1$, $R^Q$, -L-, n, $R^2$, and $R^3$ are as defined in Formula (I).

In one embodiment, in each of Formulas (II), (II.1), and (II.2), n is 0.

In one embodiment, in each of Formulas (II), (II.1), and (II.2) n is 1, and each $R^2$ is as defined in Formula (I).

In one embodiment, in each of Formulas (II), (II.1), and (II.2), n is 2, and each $R^2$ independently is as defined in Formula (I).

In one embodiment, in each of Formulas (II), (II.1), and (II.2), n is 3, and each $R^2$ is independently as defined in Formula (I).

In one embodiment, in each of Formulas (II), (II.1), and (II.2), n is 0, 1, 2, or 3; and each $R^2$ is independently selected from the group consisting of halogen, CN, OH, —$(C_1$-$C_6)$ alkyl, —$(C_1$-$C_6)$ haloalkyl, —O—$(C_1$-$C_6)$ alkyl, —O—$(C_1$-$C_6)$ haloalkyl, —$NH_2$, —$NH(C_1$-$C_6$alkyl), —$N(C_1$-$C_6$ alkyl$)_2$, and phenyl.

In one embodiment, the compounds of the invention have the structural Formula (III):

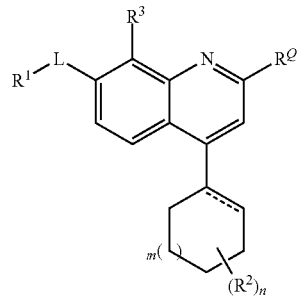
(III)

or a pharmaceutically acceptable salt thereof, wherein m is 0, 1 or 2, the dotted line represents an optional double bond, and $R^1$, $R^Q$, -L-, n, $R^2$, and $R^3$ are as defined in Formula (I).

An alternative embodiment of Formula (III) comprises a compound of the Formula (III.1):

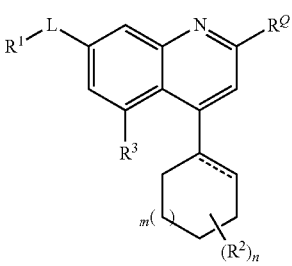
(III.1)

or a pharmaceutically acceptable salt thereof, wherein m is 0, 1 or 2, the dotted line represents an optional double bond, and $R^1$, $R^Q$, -L-, n, $R^2$, and $R^3$ are as defined in Formula (I).

Another alternative embodiment of Formula (III) comprises a compound of the Formula (III.2):

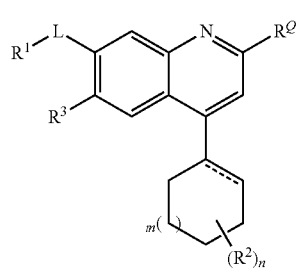
(III.2)

or a pharmaceutically acceptable salt thereof, wherein m is 0, 1 or 2, the dotted line represents an optional double bond, and $R^1$, $R^Q$, -L-, n, $R^2$, and $R^3$ are as defined in Formula (I).

In one embodiment, in each of Formulas (III), (III.1) and (III.2), the moiety

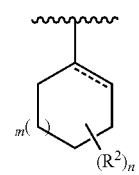

is selected from the group consisting of:

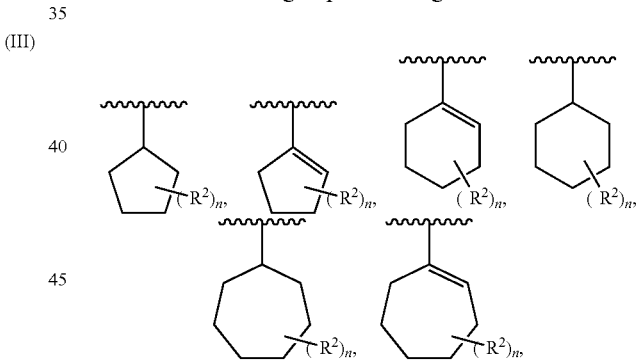

wherein n and each $R^2$ is defined as in Formula (I).

In one embodiment, in each of Formulas (III), (III.1) and (III.2), each $R^2$ is independently selected from the group consisting of halogen, CN, OH, —$(C_1$-$C_6)$ alkyl, —$(C_1$-$C_6)$ haloalkyl, —O—$(C_1$-$C_6)$ alkyl, —O—$(C_1$-$C_6)$ haloalkyl, —$NH_2$, —$NH(C_1$-$C_6$alkyl), —$N(C_1$-$C_6$alkyl$)_2$, and phenyl.

In one embodiment, in each of Formulas (III), (III.1) and (III.2), m is 0 and n is 0.

In one embodiment, in each of Formulas (III), (III.1) and (III.2), m is 0, n is 1, and $R^2$ is selected from the group consisting of halogen, CN, OH, —$(C_1$-$C_6)$ alkyl, —$(C_1$-$C_6)$ haloalkyl, —O—$(C_1$-$C_6)$ alkyl, —O—$(C_1$-$C_6)$ haloalkyl, —$NH_2$, —$NH(C_1$-$C_6$alkyl), —$N(C_1$-$C_6$alkyl$)_2$, and phenyl.

In one embodiment, in each of Formulas (III), (III.1) and (III.2), m is 0, n is 2, and $R^2$ is independently selected from the group consisting of halogen, CN, OH, —$(C_1$-$C_6)$ alkyl, —$(C_1$-$C_6)$ haloalkyl, —O—$(C_1$-$C_6)$ alkyl, —O—$(C_1$-$C_6)$ haloalkyl, —$NH_2$, —$NH(C_1$-$C_6$alkyl), —$N(C_1$-$C_6$alkyl$)_2$, and phenyl.

In one embodiment, in each of Formulas (III), (III.1) and (III.2), m is 0, n is 3, and $R^2$ is independently selected from the group consisting of halogen, CN, OH, —($C_1$-$C_6$) alkyl, —($C_1$-$C_6$) haloalkyl, —O—($C_1$-$C_6$) alkyl, —O—($C_1$-$C_6$) haloalkyl, —$NH_2$, —NH($C_1$-$C_6$alkyl), —N($C_1$-$C_6$alkyl)$_2$, and phenyl.

In one embodiment, the compounds of the invention have the structural Formula (IV):

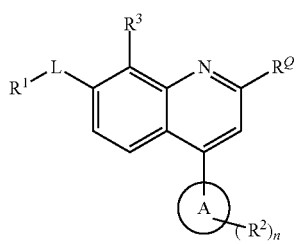

(IV)

or a pharmaceutically acceptable salt thereof, wherein:
ring A is a moiety selected from the group consisting of: -pyridinyl, pyrimidinyl, -pyrazolyl, -thienyl, -thiazolyl, -thiadiazolyl, and -oxazolyl; and $R^1$, $R^Q$, -L-, n, $R^2$ and $R^3$ are as defined in Formula (I).

An alternative embodiment of Formula (IV) comprises a compound of the Formula (IV.1):

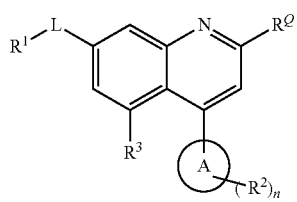

(IV.1)

or a pharmaceutically acceptable salt thereof, wherein:
ring A is a moiety selected from the group consisting of: -pyridinyl, pyrimidinyl, -pyrazolyl, -thienyl, -thiazolyl, -thiadiazolyl, and -oxazolyl; and $R^1$, $R^Q$, -L-, n, $R^2$ and $R^3$ are as defined in Formula (I).

Another alternative embodiment of Formula (IV) comprises a compound of the Formula (IV.2):

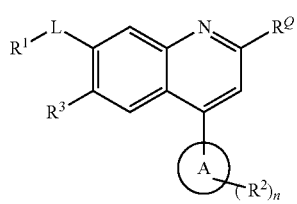

(IV.2)

or a pharmaceutically acceptable salt thereof, wherein:
ring A is a moiety selected from the group consisting of: -pyridinyl, pyrimidinyl, -pyrazolyl, -thienyl, -thiazolyl, -thiadiazolyl, and -oxazolyl; and $R^1$, $R^Q$, -L-, n, $R^2$ and $R^3$ are as defined in Formula (I).

In one embodiment, in each of Formulas (IV), (IV.1), and (IV.2), Ring A is pyrazolyl, which is unsubstituted or substituted with 1 to 2 $R^2$ groups.

In one embodiment, in each of Formulas (IV), (IV.1), and (IV.2), Ring A is thienyl, which is unsubstituted or substituted with 1 to 3 $R^2$ groups.

In one embodiment, in each of Formulas (IV), (IV.1), and (IV.2), Ring A is pyridinyl, which is unsubstituted or substituted with 1 to 3 $R^2$ groups.

In one embodiment, in each of Formulas (IV), (IV.1), and (IV.2), Ring A is pyrimidinyl, which is unsubstituted or substituted with 1 to 3 $R^2$ groups.

In one embodiment, in each of Formulas (IV), (IV.1), and (IV.2), Ring A is -thiazolyl, which is unsubstituted or substituted with 1 to 2 $R^2$ groups.

In one embodiment, in each of Formulas (IV), (IV.1), and (IV.2), Ring A is -thiadiazolyl, which is unsubstituted or substituted with 1 $R^2$ group.

In one embodiment, in each of Formulas (IV), (IV.1), and (IV.2), Ring A is -oxazolyl, which is unsubstituted or substituted with 1 to 2 $R^2$ groups.

In one embodiment, in each of Formulas (IV), (IV.1), and (IV.2), n is 0.

In one embodiment, in each of Formulas (IV), (IV.1), and (IV.2), n is 0, 1, 2, or 3; and each $R^2$ is independently selected from the group consisting of halogen, CN, —OH, —($C_1$-$C_6$) alkyl, —($C_1$-$C_6$) haloalkyl, —O—($C_1$-$C_6$) alkyl, —O—($C_1$-$C_6$) haloalkyl, and phenyl.

In one embodiment, in each of Formulas (IV), (IV.1), and (IV.2), n is 0, 1, 2, or 3; and each $R^2$ is independently selected from the group consisting of —($C_1$-$C_6$)alkyl, —($C_1$-$C_6$)haloalkyl, phenyl.

In one embodiment, in each of Formulas (IV), (IV.1), and (IV.2), n is 1; and each $R^2$ is independently selected from the group consisting of halogen, CN, —OH, —($C_1$-$C_6$) alkyl, —($C_1$-$C_6$) haloalkyl, —O—($C_1$-$C_6$) alkyl, —O—($C_1$-$C_6$) haloalkyl, —$NH_2$, —NH($C_1$-$C_6$alkyl), —N($C_1$-$C_6$alkyl)$_2$, and phenyl.

In one embodiment, in each of Formulas (IV), (IV.1), and (IV.2), n is 1; and $R^2$ is selected from the group consisting of halogen. In one such embodiment, $R^2$ is fluoro.

In one embodiment, in each of Formulas (IV), (IV.1), and (IV.2), n is 2; and each $R^2$ is independently selected from the group consisting of halogen, —($C_1$-$C_6$)alkyl, —($C_1$-$C_6$) haloalkyl, and phenyl.

In one embodiment, in each of Formulas (IV), (IV.1), and (IV.2), the Ring A is pyrazolyl and the moiety

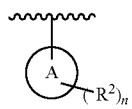

is selected from the group consisting of:

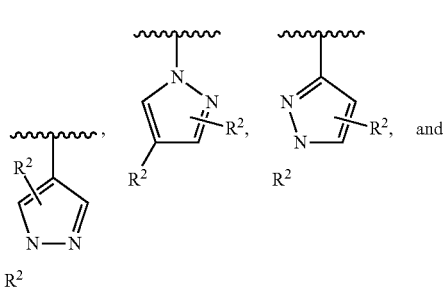

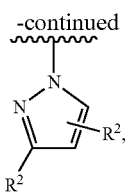

wherein each $R^2$ is independently as defined in Formula (I). In another such embodiment, $R^2$ is selected from the group consisting of —($C_1$-$C_6$)alkyl, —($C_1$-$C_6$)haloalkyl, and phenyl. In another such embodiment, n is 1 or 2 and each $R^2$ is independently selected from the group consisting of halogen, —($C_1$-$C_6$)alkyl, and phenyl.

In one embodiment, in each of Formulas (IV), (IV.1), and (IV.2), the Ring A is pyrazolyl and the moiety

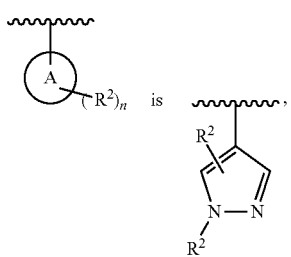

wherein each $R^2$ is independently as defined in Formula (I). In another such embodiment, $R^2$ is selected from the group consisting of —($C_1$-$C_6$)alkyl, —($C_1$-$C_6$)haloalkyl, phenyl. In another such embodiment, each $R^2$ is independently selected from the group consisting of —($C_1$-$C_6$)alkyl and phenyl.

In one embodiment, in each of Formulas (IV), (IV.1), and (IV.2), the Ring A is pyrazolyl and the moiety

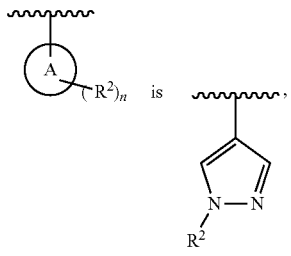

wherein $R^2$ is as defined in Formula (I). In another such embodiment, $R^2$ is selected from the group consisting of —($C_1$-$C_6$)alkyl, —($C_1$-$C_6$)haloalkyl, phenyl. In another such embodiment, $R^2$ is selected from the group consisting of —($C_1$-$C_6$)alkyl and phenyl.

In one embodiment, in each of Formulas (IV), (IV.1), and (IV.2), the Ring A is thienyl and the moiety

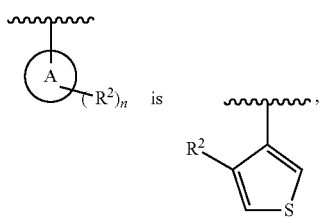

wherein $R^2$ is as defined in Formula (I). In another such embodiment, $R^2$ is selected from the group consisting of halo, —($C_1$-$C_6$)alkyl, —($C_1$-$C_6$)haloalkyl, —O—($C_1$-$C_6$)alkyl, —$NH_2$, —NH($C_1$-$C_6$alkyl), —N($C_1$-$C_6$alkyl)$_2$, -cyclopropyl, -cyclobutyl, and -cyclopentyl.

In one embodiment, in each of Formulas (IV), (IV.1), and (IV.2), the Ring A is pyridinyl and the moiety

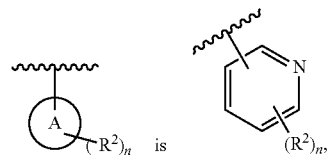

wherein $R^2$ and n are each as defined in Formula (I). In another such embodiment, $R^2$ is selected from the group consisting of halo, —($C_1$-$C_6$)alkyl, —($C_1$-$C_6$)haloalkyl, —O—($C_1$-$C_6$)alkyl, —$NH_2$, —NH($C_1$-$C_6$alkyl), —N($C_1$-$C_6$alkyl)$_2$, -cyclopropyl, - cyclobutyl, and -cyclopentyl.

In one embodiment, in each of Formulas (IV), (IV.1), and (IV.2), the Ring A is pyrimidinyl and the moiety

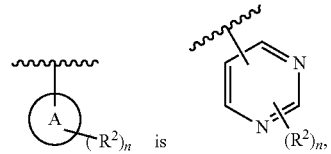

wherein $R^2$ and n are each as defined in Formula (I). In another such embodiment, $R^2$ is selected from the group consisting of halo, —($C_1$-$C_6$)alkyl, —($C_1$-$C_6$)haloalkyl, —O—($C_1$-$C_6$)alkyl, —$NH_2$, —NH($C_1$-$C_6$alkyl), —N($C_1$-$C_6$alkyl)$_2$, -cyclopropyl, - cyclobutyl, and -cyclopentyl.

In one embodiment, in each of Formulas (IV), (IV.1), and (IV.2), the Ring A is thiazolyl and the moiety

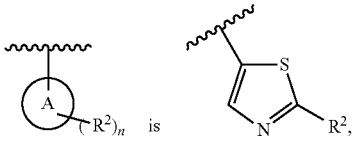

wherein $R^2$ is each as defined in Formula (I). In another such embodiment, $R^2$ is selected from the group consisting of halo, —($C_1$-$C_6$)alkyl, —($C_1$-$C_6$)haloalkyl, —O—($C_1$-$C_6$)alkyl, —$NH_2$, —NH($C_1$-$C_6$alkyl), —N($C_1$-$C_6$alkyl)$_2$, -cyclopropyl, -cyclobutyl, and -cyclopentyl.

In one embodiment, in each of Formulas (IV), (IV.1), and (IV.2), the Ring A is thiazolyl and the moiety

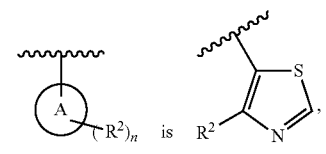

wherein $R^2$ is each as defined in Formula (I). In another such embodiment, $R^2$ is selected from the group consisting of halo, —($C_1$-$C_6$)alkyl, —($C_1$-$C_6$)haloalkyl, —O—($C_1$-$C_6$)alkyl, —$NH_2$, —NH($C_1$-$C_6$alkyl), —N($C_1$-$C_6$alkyl)$_2$, -cyclopropyl, -cyclobutyl, and -cyclopentyl.

In one embodiment, in each of Formulas (IV), (IV.1), and (IV.2), the Ring A is thiadiazolyl and the moiety

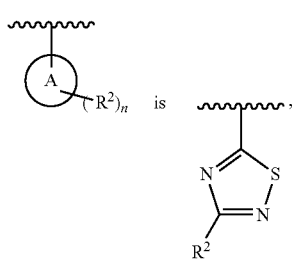

wherein $R^2$ is each as defined in Formula (I). In another such embodiment, $R^2$ is selected from the group consisting of halo, —$(C_1$-$C_6)$alkyl, —$(C_1$-$C_6)$haloalkyl, —O—$(C_1$-$C_6)$alkyl, —$NH_2$, —$NH(C_1$-$C_6$alkyl), —$N(C_1$-$C_6$alkyl)$_2$, -cyclopropyl, - cyclobutyl, and -cyclopentyl.

In one embodiment, in each of Formulas (IV), (IV.1), and (IV.2), the Ring A is thiadiazolyl and the moiety

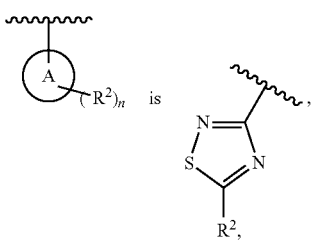

wherein $R^2$ is each as defined in Formula (I). In another such embodiment, $R^2$ is selected from the group consisting of halo, —$(C_1$-$C_6)$alkyl, —$(C_1$-$C_6)$haloalkyl, —O—$(C_1$-$C_6)$alkyl, —$NH_2$, —$NH(C_1$-$C_6$alkyl), —$N(C_1$-$C_6$alkyl)$_2$, -cyclopropyl, - cyclobutyl, and -cyclopentyl.

In one embodiment, in each of Formulas (IV), (IV.1), and (IV.2), the Ring A is oxazolyl and the moiety

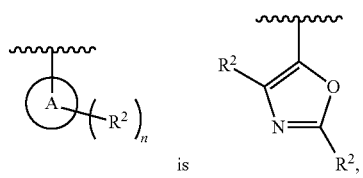

wherein $R^2$ is each as defined in Formula (I). In another such embodiment, $R^2$ is selected from the group consisting of halo, —$(C_1$-$C_6)$alkyl, —$(C_1$-$C_6)$haloalkyl, —O—$(C_1$-$C_6)$alkyl, —$NH_2$, —$NH(C_1$-$C_6$alkyl), —$N(C_1$-$C_6$alkyl)$_2$, -cyclopropyl, -cyclobutyl, and -cyclopentyl.

In one embodiment, in each of Formulas (IV), (IV.1), and (IV.2), the Ring A is oxazolyl and the moiety

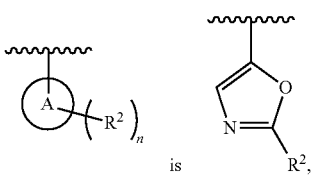

wherein $R^2$ is each as defined in Formula (I). In another such embodiment, $R^2$ is selected from the group consisting of halo, —$(C_1$-$C_6)$alkyl, —$(C_1$-$C_6)$haloalkyl, —O—$(C_1$-$C_6)$alkyl, —$NH_2$, —$NH(C_1$-$C_6$alkyl), —$N(C_1$-$C_6$alkyl)$_2$, -cyclopropyl, -cyclobutyl, and -cyclopentyl.

In one embodiment, in each of Formulas (IV), (IV.1), and (IV.2), the Ring A is oxazolyl and the moiety

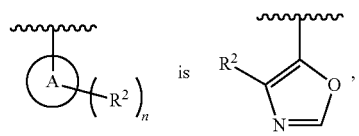

wherein $R^2$ is each as defined in Formula (I). In another such embodiment, $R^2$ is selected from the group consisting of halo, —$(C_1$-$C_6)$alkyl, —$(C_1$-$C_6)$haloalkyl, —O—$(C_1$-$C_6)$alkyl, —$NH_2$, —$NH(C_1$-$C_6$alkyl), —$N(C_1$-$C_6$alkyl)$_2$, -cyclopropyl, -cyclobutyl, and -cyclopentyl.

In another embodiment, the compounds of the invention have the structural Formula (V), shown below.

In one embodiment, in each of Formulas (I), (I.1), (II), (II.1), (II.2), (III), (III.1), (III.2), (IV), (IV.1), (IV.2), (V), (V.1), and (V.2):

$R^Q$ is CN.

In one embodiment, in each of Formulas (I), (I.1), (II), (II.1), (II.2), (III), (III.1), (III.2), (IV), (IV.1), (IV.2), (V), (V.1), and (V.2):

$R^Q$ is —$C(O)NH_2$.

In one embodiment, in each of Formulas (I), (I.1), (II), (II.1), (II.2), (III), (III.1), (III.2), (IV), (IV.1), (IV.2), (V), (V.1), and (V.2):

$R^3$ is hydrogen.

In one embodiment, in each of Formulas (I), (I.1), (II), (II.1), (II.2), (III), (III.1), (III.2), (IV), (IV.1), (IV.2), (V), (V.1), and (V.2):

$R^3$ is fluorine.

In one embodiment, in each of Formulas (I), (I.1), (II), (II.1), (II.2), (III), (III.1), (III.2), (IV), (IV.1), (IV.2), (V), (V.1), and (V.2):

-L- represents a covalent bond.

In one embodiment, in each of Formulas (I), (I.1), (II), (II.1), (II.2), (III), (III.1), (III.2), (IV), (IV.1), (IV.2), (V), (V.1), and (V.2):

-L- is —C(O)—.

In one embodiment, in each of Formulas (I), (I.1), (II), (II.1), (II.2), (III), (III.1), (III.2), (IV), (IV.1), (IV.2), (V), (V.1), and (V.2):

-L- is —$C(R^{1L})_p$—, wherein p is 0, 1, or 2, and each $R^{1L}$ is as defined in Formula (I).

In one embodiment, in each of Formulas (I), (I.1), (II), (II.1), (II.2), (III), (III.1), (III.2), (IV), (IV.1), (IV.2), (V), (V.1), and (V.2):

-L- is selected from the group consisting of:
—$CH_2$—, —$CH_2CH_2$—, —$CH_2CH_2CH_2$—, —$CH(CF_3)$—, —$CH(CH_3)$—, —$CH(CH_3)CH_2$—, —$CH_2CH(CH_3)$—, —$C(CH_3)_2$—, —$CH(OH)$—, —$CH_2CH(OH)$—, —$CH(OH)CH_2$—, —$CH(F)$—, —$CF_2$—, —$C(CH_3)(OH)$—, —$CH(OCH_3)$—,

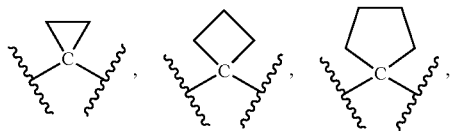

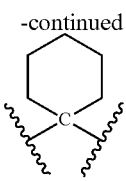

—C(O)—, —S(O)—, and —S(O)$_2$—.

In one embodiment, in each of Formulas (I), (I.1), (II), (II.1), (II.2), (III), (III.1), (III.2), (IV), (IV.1), (IV.2), (V), (V.1), and (V.2):

-L- is selected from the group consisting of:
—CH$_2$—, —CH$_2$CH$_2$—, —CH$_2$CH$_2$CH$_2$—, —CH(CF$_3$)—, —CH(CH$_3$)—, —CH(CH$_3$)CH$_2$—, —CH$_2$CH(CH$_3$)—, —C(CH$_3$)$_2$—, —CH(OH)—, —CH$_2$CH(OH)—, —CH(OH)CH$_2$—, —CH(F)—, —CF$_2$—, —C(CH$_3$)(OH)—, —CH(OCH$_3$)—,

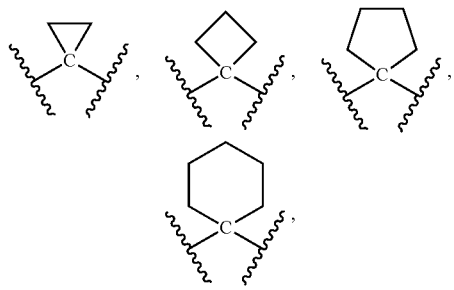

and —C(O)—.

In one embodiment, in each of Formulas (I), (I.1), (II), (II.1), (II.2), (III), (III.1), (III.2), (IV), (IV.1), (IV.2), (V), (V.1), and (V.2), R$^1$ is selected from the group consisting of heterocycloalkyl and heterocycloalkenyl, wherein each of said heterocycloalkyl and said heterocycloalkenyl contains 1, 2, or 3 ring heteroatoms independently selected from the group consisting of N, S, S(O), S(O)2, and O, and wherein each said heterocycloalkyl group and each said heterocycloalkenyl group is unsubstituted or substituted with 1 to 5 groups independently selected from the group consisting of oxo, CN, —OH, halogen, —(C$_1$-C$_6$) alkyl, hydroxy-substituted —(C$_1$-C$_6$) alkyl, —(C$_1$-C$_6$) alkynyl, —(C$_1$-C$_6$) haloalkyl, hydroxy-substituted —(C$_1$-C$_6$) haloalkyl, —O—(C$_1$-C$_6$) alkyl, —(C$_3$-C$_8$) cycloalkyl, -alkyl-cycloalkyl, —CH(OH)cycloalkyl, phenyl, -alkyl-phenyl, monocyclic heteroaryl, -alkyl-monocyclic heteroaryl, —(C$_3$-C$_8$) spirocycloalkyl, —C(O)H, —C(O)OH, —C(O)(C$_1$-C$_6$) alkyl, —C(O)O(C$_1$-C$_6$) alkyl, —N(R$^{1A}$)C(O)—(C$_1$-C$_6$) alkyl, —N(R$^{1A}$)$_2$, —C(O)N(R$^{1A}$)$_2$, —S(O)$_2$H, —S(O)-phenyl, —S(O)—(C$_1$-C$_6$) alkyl-phenyl, —S(O)$_2$-phenyl, —S(O)$_2$—(C$_1$-C$_6$) alkyl-phenyl, —S(O)$_2$OH, and —S(O)$_2$—(C$_1$-C$_6$) alkyl, and wherein each R$^{1A}$ group is independently selected from the group consisting of H and —(C$_1$-C$_6$ alkyl).

In one embodiment, in each of Formulas (I), (I.1), (II), (II.1), (II.2), (III), (III.1), (III.2), (IV), (IV.1), (IV.2), (V), (V.1), and (V.2), R$^1$ is selected from the group consisting of heterocycloalkyl and heterocycloalkenyl, wherein each of said heterocycloalkyl and said heterocycloalkenyl contains 1, 2, or 3 ring heteroatoms independently selected from the group consisting of N, S, S(O), S(O)2, and O, and wherein each said heterocycloalkyl group and each said heterocycloalkenyl group is unsubstituted or substituted with 1 to 5 groups independently selected from the group consisting of oxo, —CN, —OH, —(C$_1$-C$_6$) alkyl, —O—(C$_1$-C$_6$) alkyl, —N(H)C(O)—(C$_1$-C$_6$) alkyl, —C(O)NH$_2$, —C(O)N(H)(C$_1$-C$_6$ alkyl), —C(O)N(C$_1$-C$_6$ alkyl)$_2$, phenyl, —(C$_3$-C$_8$) spirocycloalkyl, —(C$_3$-C$_8$) cycloalkyl, —(C$_1$-C$_6$) haloalkyl, and phenyl. In alternatives of this embodiment, each said heterocycloalkyl group and each said heterocycloalkenyl group is unsubstituted or substituted with 1 to 4 groups, or, alternatively, 1 to 3 groups, or, alternatively 1 to 2 groups, wherein each said group is independently selected from the group consisting of oxo, —CN, —OH, —(C$_1$-C$_6$) alkyl, —O—(C$_1$-C$_6$) alkyl, —N(H)C(O)—(C$_1$-C$_6$) alkyl, —C(O)NH$_2$, —C(O)N(H)(C$_1$-C$_6$ alkyl), —C(O)N(C$_1$-C$_6$ alkyl)$_2$, phenyl, —(C$_3$-C$_8$) spirocycloalkyl, —(C$_3$-C$_8$) cycloalkyl, —(C$_1$-C$_6$) haloalkyl, and phenyl.

In one embodiment, in each of Formulas (I), (I.1), (II), (II.1), (II.2), (III), (III.1), (III.2), (IV), (IV.1), (IV.2), (V), (V.1), and (V.2), R$^1$ is selected from the group consisting of heterocycloalkyl and heterocycloalkenyl, wherein each of said heterocycloalkyl and said heterocycloalkenyl contains 1, 2, or 3 ring heteroatoms independently selected from the group consisting of N, S, S(O), S(O)2, and O, and wherein each of said heterocycloalkyl and said heterocycloalkenyl is unsubstituted or substituted with 1 to 5 groups, alternatively 1 to 4 groups, alternatively 1 to 3 groups, or, alternatively, 1 to 2 groups, independently selected from the group consisting of oxo, alkyl, —(C$_3$-C$_8$) spirocycloalkyl, —(C$_3$-C$_8$) cycloalkyl, and —(C$_1$-C$_6$) haloalkyl.

In each of the above embodiments, non-limiting examples of the heterocycloalkyl portion of said optionally substituted heterocycloalkyl includes piperidinyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides (including N-oxides) thereof.

In each of the above embodiments, non-limiting examples of the heterocycloalkenyl portion of said optionally substituted heterocycloalkenyl includes 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, and dihydrothiopyranyl.

In one embodiment, in each of in each of Formulas (I), (I.1), (II), (II.1), (II.2), (III), (III.1), (III.2), (IV), (IV.1), (IV.2), (V), (V.1), and (V.2), le is heteroaryl, wherein said heteroaryl is mono or bicyclic and comprises from 1 to 3 ring nitrogen atoms, and wherein said heteroaryl is unsubstituted or substituted with 1 to 5 groups, alternatively 1 to 4 groups, alternatively 1 to 3 groups, or, alternatively, 1 to 2 groups, independently selected from the group consisting of oxo, CN, —OH, halogen, —(C$_1$-C$_6$) alkyl, hydroxy-substituted —(C$_1$-C$_6$) alkyl, —(C$_1$-C$_6$) alkynyl, —(C$_1$-C$_6$) haloalkyl, hydroxy-substituted —(C$_1$-C$_6$) haloalkyl, —O—(C$_1$-C$_6$) alkyl, —(C$_3$-C$_8$) cycloalkyl, -alkyl-cycloalkyl, —CH(OH)cycloalkyl, phenyl, -alkyl-phenyl, monocyclic heteroaryl, -alkyl-monocyclic heteroaryl, —(C$_3$-C$_8$) spirocycloalkyl, —C(O)H, —C(O)OH, —C(O)(C$_1$-C$_6$) alkyl, —C(O)O(C$_1$-C$_6$) alkyl, —N(R$^{1B}$)C(O)—(C$_1$-C$_6$) alkyl, —N(R$^{1B}$)$_2$, —C(O)N(R$^{1B}$)$_2$, —S(O)$_2$ H, —S(O)-phenyl, S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl, and wherein each $R^{1B}$ group is independently selected from the group consisting of H and —($C_1$-$C_6$ alkyl), with the proviso that $R^1$ is not unsubstituted or substituted triazolyl, and with the further proviso that when $R^1$ is substituted oxadiazolyl, substituted thiazolyl, or substituted thiadiazolyl, then -L- is selected from the group consisting of —(C($R^{1L}$)$_2$)$_p$—, and

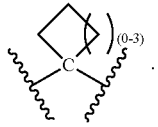

In one embodiment, in each of in each of Formulas (I), (I.1), (II), (II.1), (II.2), (III), (III.1), (III.2), (IV), (IV.1), (IV.2), (V), (V.1), and (V.2), $R^1$ is heteroaryl, wherein said heteroaryl is mono or bicyclic and comprises from 1 to 3 ring nitrogen atoms, and wherein said heteroaryl is unsubstituted or substituted with 1 to 4 groups independently selected from the group consisting of oxo, CN, —OH, halogen, —($C_1$-$C_6$) alkyl, hydroxy-substituted —($C_1$-$C_6$) alkyl, —($C_1$-$C_6$) alkynyl, —($C_1$-$C_6$) haloalkyl, hydroxy-substituted —($C_1$-$C_6$) haloalkyl, —O—($C_1$-$C_6$) alkyl, —($C_3$-$C_8$) cycloalkyl, -alkyl-cycloalkyl, —CH(OH)cycloalkyl, phenyl, -alkyl-phenyl, monocyclic heteroaryl, -alkyl-monocyclic heteroaryl, —($C_3$-$C_8$) spirocycloalkyl, —C(O)H, —C(O)OH, —C(O)($C_1$-$C_6$) alkyl, —C(O)O($C_1$-$C_6$) alkyl, —N($R^{1B}$)C(O)—($C_1$-$C_6$) alkyl, —N($R^{1B}$)$_2$, —C(O)N($R^{1B}$)$_2$, —S(O)$_2$H, —S(O)-phenyl, S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl, and wherein each $R^{1B}$ group is independently selected from the group consisting of H and —($C_1$-$C_6$ alkyl), with the proviso that $R^1$ is not unsubstituted or substituted triazolyl, substituted oxadiazolyl, substituted thiazolyl, or substituted thiadiazolyl.

In one embodiment, in each of in each of Formulas (I), (I.1), (II), (II.1), (II.2), (III), (III.1), (III.2), (IV), (IV.1), (IV.2), (V), (V.1), and (V.2), $R^1$ is heteroaryl, wherein said heteroaryl is mono or bicyclic and comprises from 1 to 3 ring nitrogen atoms, and wherein said heteroaryl is unsubstituted or substituted with 1 to 5 groups independently selected from the group consisting of oxo, —CN, —OH, —($C_1$-$C_6$) alkyl, —O—($C_1$-$C_6$) alkyl, —N(H)C(O)—($C_1$-$C_6$) alkyl, —C(O)NH$_2$, —C(O)N(H)($C_1$-$C_6$ alkyl), —C(O)N($C_1$-$C_6$ alkyl)$_2$, phenyl, —($C_3$-$C_8$) spirocycloalkyl, —($C_3$-$C_8$) cycloalkyl, —($C_1$-$C_6$) haloalkyl, and phenyl, with the proviso that $R^1$ is not unsubstituted or substituted triazolyl, substituted oxadiazolyl, substituted thiazolyl, or substituted thiadiazolyl. In alternatives of this embodiment, each said heteroaryl group is unsubstituted or substituted with 1 to 4 groups, or, alternatively, 1 to 3 groups, or, alternatively 1 to 2 groups, wherein each said group is independently selected from the group consisting of oxo, —CN, —OH, —($C_1$-$C_6$) alkyl, —O—($C_1$-$C_6$) alkyl, —N(H)C(O)—($C_1$-$C_6$) alkyl, —C(O)NH$_2$, —C(O)N(H)($C_1$-$C_6$ alkyl), —C(O)N($C_1$-$C_6$ alkyl)$_2$, phenyl, —($C_3$-$C_8$) spirocycloalkyl, —($C_3$-$C_8$) cycloalkyl, —($C_1$-$C_6$) haloalkyl, and phenyl, with the proviso that $R^1$ is not unsubstituted or substituted triazolyl, substituted oxadiazolyl, substituted thiazolyl, or substituted thiadiazolyl.

In one embodiment, in each of in each of Formulas (I), (I.1), (II), (II.1), (II.2), (III), (III.1), (III.2), (IV), (IV.1), (IV.2), (V), (V.1), and (V.2), $R^1$ is selected from the group consisting of heteroaryl, wherein said heteroaryl is mono or bicyclic and comprise from 1 to 3 ring nitrogen atoms, and wherein said heteroaryl is unsubstituted or substituted with 1 to 5 groups independently selected from the group consisting of oxo, halogen, —($C_1$-$C_6$) alkyl, hydroxy-substituted —($C_1$-$C_6$) alkyl, —O—($C_1$-$C_6$) alkyl, —N($R^6$)$_2$, —C(O)N($R^6$)$_2$, CN, —($C_1$-$C_6$) haloalkyl, hydroxy-substituted —($C_1$-$C_6$) haloalkyl, —S(O)$_2$H, —S(O)$_2$—($C_1$-$C_6$) alkyl, and —($C_1$-$C_6$) alkynyl, with the proviso that when $R^1$ is not unsubstituted or substituted triazolyl, substituted oxadiazolyl, substituted thiazolyl, or substituted thiadiazolyl. In alternatives of this embodiment, said heteroaryl is unsubstituted or substituted with 1 to 4 groups, alternatively 1 to 3 groups, alternatively 1 to 2 groups, wherein each said group is independently selected from the group consisting of oxo, halogen, —($C_1$-$C_6$) alkyl, hydroxy-substituted —($C_1$-$C_6$) alkyl, —O—($C_1$-$C_6$) alkyl, —N($R^6$)$_2$, —C(O)N($R^6$)$_2$, CN, —($C_1$-$C_6$) haloalkyl, hydroxy-substituted —($C_1$-$C_6$) haloalkyl, —S(O)$_2$H, —S(O)$_2$—($C_1$-$C_6$) alkyl, and —($C_1$-$C_6$) alkynyl, with the proviso that when $R^1$ is not unsubstituted or substituted triazolyl, substituted oxadiazolyl, substituted thiazolyl, or substituted thiadiazolyl.

In one embodiment, in each of Formulas (I), (I.1), (II), (II.1), (II.2), (III), (III.1), (III.2), (IV), (IV.1), and (IV.2), the heteroaryl portion of said optionally substituted heteroaryl of $R^1$ is selected from the group consisting of pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl (including 1,2,4-thiadiazolyl), pyrazolyl, furazanyl, pyrrolyl, pyrazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl, and oxides (including N-oxides) thereof, and benzo-fused versions thereof, wherein each said oxadiazolyl, thiazolyl, and thiadiazolyl, when present, is unsubstituted.

In one embodiment, in each of in each of Formulas (V), (V.1), and (V.2), the heteroaryl portion of said optionally substituted heteroaryl of $R^1$ is selected from the group consisting of pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl (including 1,2,4-thiadiazolyl), pyrazolyl, furazanyl, pyrrolyl, pyrazolyl, triazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl, and oxides (including N-oxides) thereof, and benzo-fused versions thereof.

In one embodiment, in each of Formulas (I), (I.1), (II), (II.1), (II.2), (III), (III.1), (III.2), (IV), (IV.1), (IV.2), (V), (V.1), and (V.2), $R^1$ is phenyl, wherein said phenyl is unsubstituted or substituted with from 1 to 5 groups independently selected from the group consisting of oxo, CN, —OH, halogen, —($C_1$-$C_6$) alkyl, —($C_1$-$C_6$) alkynyl, —($C_1$-$C_6$) haloalkyl, —O—($C_1$-$C_6$) alkyl, —($C_3$-$C_8$) cycloalkyl, -alkyl-cycloalkyl, —CH(OH)cycloalkyl, monocyclic heteroaryl, -alkyl-monocyclic heteroaryl, —($C_3$-$C_8$) spirocycloalkyl, —C(O)H, —C(O)OH, —C(O)($C_1$-$C_6$) alkyl, —C(O)O($C_1$-$C_6$) alkyl, —N($R^{1C}$)C(O)—($C_1$-$C_6$) alkyl, —N($R^{1C}$)$_2$, —C(O)N($R^{1C}$)$_2$, —S(O)$_2$H, —S(O)-phenyl, —S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl, and wherein each $R^{1C}$ group is independently selected from the group consisting of H and —($C_1$-$C_6$ alkyl).

In one embodiment, in each of Formulas (I), (I.1), (II), (II.1), (II.2), (III), (III.1), (III.2), (IV), (IV.1), (IV.2), (V), (V.1), and (V.2), $R^1$ is phenyl, wherein said phenyl is unsubstituted or substituted with from 1 to 5 groups independently selected from the group consisting of halogen, —($C_1$-$C_6$) alkyl, phenyl, —O—($C_1$-$C_6$) alkyl, CN, —S(O)-phenyl, —S(O)$_2$-phenyl, —S(O)—($C_1$-$C_6$) alkyl-phenyl, and —S(O)$_2$—($C_1$-$C_6$) alkyl-phenyl. In alternatives of this embodiment, said phenyl is unsubstituted or substituted with 1 to 4 groups, alternatively 1 to 3 groups, alternatively 1 to 2 groups, wherein said group is independently selected from the group consisting of halogen, —($C_1$-$C_6$) alkyl, phenyl, —O—($C_1$-$C_6$) alkyl, CN, —S(O)-phenyl, —S(O)$_2$-phenyl, —S(O)—($C_1$-$C_6$) alkyl-phenyl, and —S(O)$_2$—($C_1$-$C_6$) alkyl-phenyl.

In one embodiment, in each of Formulas (I), (I.1), (II), (II.1), (II.2), (III), (III.1), (III.2), (IV), (IV.1), (IV.2), (V), (V.1), and (V.2), $R^1$ is phenyl, wherein said phenyl is unsubstituted or substituted with from 1 to 5 groups independently selected from the group consisting of halogen, —O—($C_1$-$C_6$) alkyl, CN, —S(O)-phenyl, —S(O)$_2$-phenyl, —S(O)—($C_1$-$C_6$) alkyl-phenyl, and —S(O)$_2$—($C_1$-$C_6$) alkyl-phenyl. In alternatives of this embodiment, said phenyl is unsubstituted or substituted with 1 to 4 groups, alternatively 1 to 3 groups, alternatively 1 to 2 groups, wherein said group is independently selected from the group consisting of halogen, —O—($C_1$-$C_6$) alkyl, CN, —S(O)-phenyl, —S(O)$_2$-phenyl, —S(O)—($C_1$-$C_6$) alkyl-phenyl, and —S(O)$_2$—($C_1$-$C_6$) alkyl-phenyl.

In one embodiment, in each of Formulas (I), (I.1), (II), (II.1), (II.2), (III), (III.1), (III.2), (IV), (IV.1), (IV.2), (V), (V.1), and (V.2), $R^1$-L- is selected from the group consisting of optionally substituted phenyl, optionally substituted benzyl, and optionally substituted —CH$_2$CH$_2$-phenyl, wherein said optional substituents are one to three substituents independently selected from the group consisting of halogen, —O—($C_1$-$C_6$) alkyl, CN, —S(O)-phenyl, —S(O)$_2$-phenyl, —S(O)—($C_1$-$C_6$) alkyl-phenyl, and —S(O)$_2$—($C_1$-$C_6$) alkyl-phenyl.

In one embodiment, in each of Formulas (I), (I.1), (II), (II.1), (II.2), (III), (III.1), (III.2), (IV), (IV.1), (IV.2), (V), (V.1), and (V.2), $R^1$ is selected from the group consisting of H and —($C_1$-$C_6$) alkyl.

In one embodiment, in each of Formulas (I), (I.1), (II), (II.1), (II.2), (III), (III.1), (III.2), (IV), (IV.1), (IV.2), (V), (V.1), and (V.2), $R^1$ is —CH$_2$N($R^{1D}$)$R^{1E}$, wherein:

$R^{1D}$ is selected from the group consisting of H, —($C_1$-$C_6$) alkyl, and —C(O)O$R^{1H}$; and $R^{1E}$ is selected from the group consisting of —O—($C_1$-$C_6$) alkyl, heteroalkyl, —($C_1$-$C_6$) alkyl-C(O)N($R^{1H}$), and —C(O)O$R^{1H}$, wherein each $R^{1H}$ is independently selected from the group consisting of H and —($C_1$-$C_6$) alkyl.

In one embodiment, in each of Formulas (I), (I.1), (II), (II.1), (II.2), (III), (III.1), (III.2), (IV), (IV.1), (IV.2), (V), (V.1), and (V.2), $R^1$ is —CH$_2$N($R^{1F}$)O$R^{1G}$, wherein:

$R^{1F}$ is selected from the group consisting of H, —($C_1$-$C_6$) alkyl, and —C(O)O$R^{1H}$, wherein each $R^{1H}$ is independently selected from the group consisting of H and —($C_1$-$C_6$) alkyl; and $R^{1G}$ is selected from the group consisting of H and —($C_1$-$C_6$) alkyl;

n is 0, 1, 2, or 3.

In one embodiment, the compounds of the invention comprise, collectively and individually, each of the example compounds shown in the tables below, and pharmaceutically acceptable salts thereof. Suitable pharmaceutically acceptable salts of each of these compounds include those discussed hereinbelow.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. In the event where the chemical name and structure for a compound of the invention disagree, the structure controls. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy," etc.

It shall be understood that, in the various embodiments of the invention described herein, any variable not explicitly defined in the context of the embodiment is as defined in Formula (I). All valences not explicitly filled are assumed to be filled by hydrogen.

In the various embodiments described herein, each variable is selected independently of the others unless otherwise indicated.

"Patient" includes both human and non-human animals. Non-human animals include research animals and companion animals such as mice, rats, primates, monkeys, great apes, chimpanzees, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The term "pharmaceutically acceptable" means the carrier, diluent or excipient must be compatible with the other ingredients of the formulation and not deleterious to the recipient thereof.

The terms "administration of" or "administering a" compound means providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" mean an amount of compound or a composition of the invention effective for inhibiting the herein-noted diseases and thus producing the desired therapeutic, ameliorative, inhibitory or preventative effect.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

"Halogen" (or "halo") means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, i-propyl, n-butyl, i-butyl, t-butyl, pentyl, hexyl, heptyl, octanyl, etc., each of which may be straight or branched.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

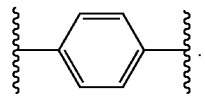

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butyryl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl, cyclooctyl, and the like. Non-limiting examples of suitable multicyclic cycloalkyls include 1-decalinyl, norbornyl, adamantyl and the like. Further non-limiting examples of cycloalkyl include the following:

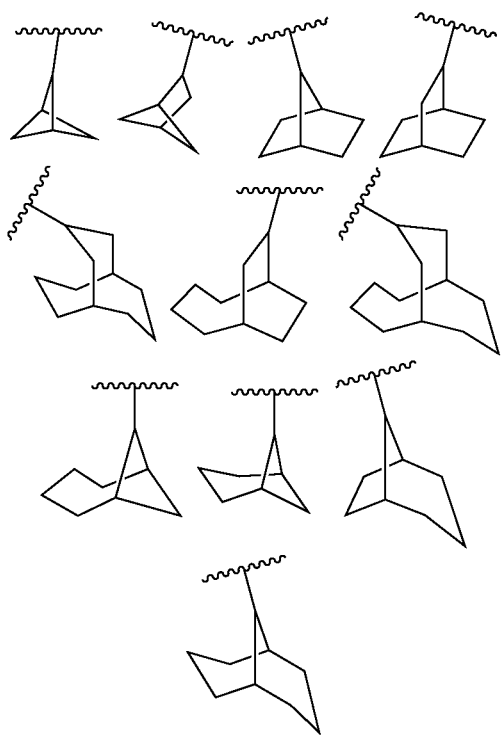

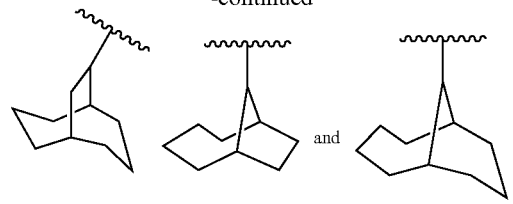

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cycloheptenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

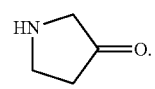

As used herein, the term "monocyclic heterocycloalkyl" refers monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

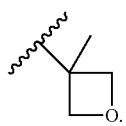

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidinone (or pyrrolone):

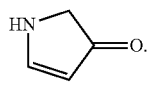

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

It should be noted that in hetero-atom containing ring systems of this invention, there are no hydroxyl groups on carbon atoms adjacent to a N, O or S, as well as there are no N or S groups on carbon adjacent to another heteroatom.

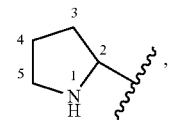

there is no —OH attached directly to carbons marked 2 and 5.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl-group in which alkyl is as previously defined. Preferred cyanoalkyls contain lower alkyl. Non-limiting examples of suitable cyanoalkyl groups include cyanomethyl and 2-cyanoethyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Spriocycloalkyl" means a cycloalkyl group attached to a parent moiety at a single carbon atom. Non-limiting examples of spirocycloalkyl wherein the parent moiety is a cycloalkyl include Spiro [2.5] octane, Spiro [2.4] heptane, etc. The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

When a variable appears more than once in a group, e.g., $R^{14}$ in $N(R^{14})_2$, or a variable appears more than once in a structure presented herein, the variables can be the same or different.

The line ----, as a bond generally indicates a mixture of, or either of, the possible isomers, e.g., containing (R)- and (S)-stereochemistry. For example:

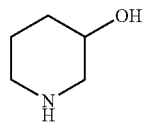 means containing both 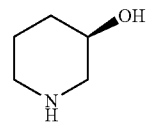 and

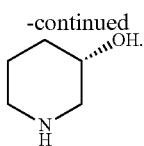

The wavy line ~~~, as used herein, indicates a point of attachment to the rest of the compound. Lines drawn into the ring systems, such as, for example:

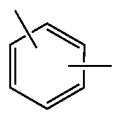

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

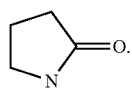

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

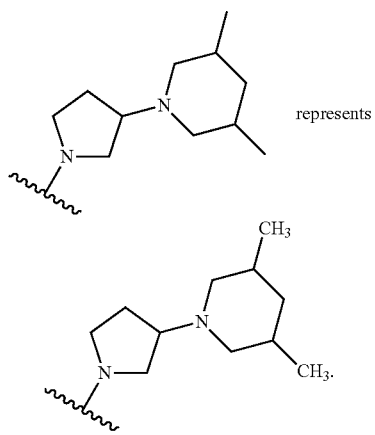

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It shall be understood that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Another embodiment provides prodrugs and/or solvates of the compounds of the invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt thereof, contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_6$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Another embodiment provides pharmaceutically acceptable salts of the compounds of the invention. Thus, reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Another embodiment provides pharmaceutically acceptable esters of the compounds of the invention. Such esters include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Another embodiment provides tautomers of the compounds of the invention, and salts, solvates, esters and prodrugs thereof. Also, for example, all keto-enol and imine-enamine forms of the compounds are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Additional examples of isotopes that can be incorporated into compounds of the invention include (when present) isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

In an additional embodiment, the compounds of the invention are isotopically labeled for use as research or diagnostic agents. For example, compounds of the invention can be labeled for use in compound and/or substrate tissue distribution assays. Tritiated (i.e., $^3$H) and carbon-14 (i.e., $^{14}$C) isotopes are preferred for their ease of preparation and detectability. In another embodiment, the compounds of the invention can be labeled with heavier isotopes such as deuterium (i.e., $^2$H). Deuterium enrichment of the compounds of the invention may afford certain therapeutic advantages resulting from greater metabolic stability (e.g., increased in vivo half-life or reduced dosage requirements), or may provide a compound useful as a standard for characterization of biological samples, and hence may be preferred in some circumstances. Isotopically labelled compounds of the invention can generally be prepared without undue experimentation by following procedures analogous to those disclosed in the Schemes and/or in the Examples hereinbelow, by substituting an appropriate isotopically labelled reagent for a non-isotopically labelled reagent.

Polymorphic forms of the compounds of the invention, and of the salts, solvates, esters and prodrugs of the compounds of the invention, are intended to be included in the present invention.

Compositions and Administration

Another embodiment provides pharmaceutical compositions which comprise a therapeutically effective amount of a compound of the invention, or a stereoisomer thereof, or a pharmaceutically acceptable salt of said compound or said stereoisomer, and a pharmaceutically acceptable carrier.

A preferred dosage is about 0.001 to 100 mg/kg of body weight/day of the compound of the invention. An especially preferred dosage is about 0.01 to 10 mg/kg of body weight/day of a compound of the invention, or a pharmaceutically acceptable salt of said compound.

The term "pharmaceutical composition" is also intended to encompass both the bulk composition and individual dosage units comprised of more than one (e.g., two) pharmaceutically active agents such as, for example, a compound of the present invention and an additional therapeutic agent selected from the lists of the additional agents described herein below, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* 18th Edition, (1990), Mack Publishing Co., Easton, Pa.

Liquid form preparations include solutions, suspensions and emulsions. Examples of materials useful for forming such liquid form preparations include water or water-propylene glycol solutions for parenteral injection, or sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention can also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 100 mg per kg body weight of a mammal, preferably from about 0.01 mg to about 10 mg per kg. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The compositions of the invention can further comprise one or more additional therapeutic agents, as discussed in further detail below. Accordingly, in one embodiment, the present invention provides compositions comprising: (i) a compound of the invention, or a stereoisomer thereof, or a pharmaceutically acceptable salt of said compound or said stereoisomer; (ii) one or more additional therapeutic agents, that are not compounds of the invention; and (iii) a pharmaceutically acceptable carrier, wherein the amounts in the composition are together effective to treat one of the disease or conditions discussed herein.

Uses of the Compounds of the Invention

Another embodiment provides a method of treating a patient (e.g., a human patient or a research animal) for diseases or disorders in which the mGluR2 receptor is involved. These methods comprise administering an effective amount of a compound of the invention, or composition comprising a compound of the invention (or a stereoisomer thereof, or a pharmaceutically acceptable salt of said compound or said stereoisomer), to a patient in need thereof, to treat a disease or disorder in which the mGluR2 receptor is involved.

Another embodiment provides for the use of a compound of the invention for treating a disease or disorder in which the mGluR2 receptor is involved, by administering an effective amount of a compound of the invention, or a pharmaceutically acceptable salt thereof, to a patient in need thereof.

In one embodiment, the compounds of the invention useful in said methods or said uses comprise a compound according to any one of Formulas (I), (I.1), (II), (II.1), (II.2), (III), (III.1), (III.2), (IV), (IV.1), (IV.2), (V), (V.1), and/or (V.2), as described above, or according to any of the various embodiments described above. In another embodiment, the compounds of the invention useful in said methods and said uses comprise the compounds of the examples, e.g., as set forth in the Tables below.

Another embodiment comprises a method of using, in each of the methods and/or uses described herein, a compound according to Formula (I.2):

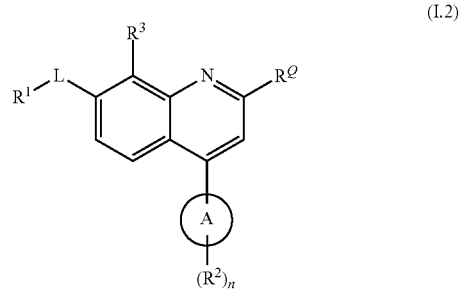

(I.2)

or a stereoisomer thereof, or a pharmaceutically acceptable salt of said compound or said stereoisomer, wherein:
$R^1$ is heteroaryl,
wherein said heteroaryl is a monocyclic or multicyclic ring system comprising from 5 to 10 ring atoms in which from 1 to 4 of the atoms of said ring system is a ring nitrogen atom,
and wherein said heteroaryl is unsubstituted or substituted with 1 to 5 groups independently selected from the group consisting of oxo, CN, —OH, halogen, —($C_1$-$C_6$) alkyl, hydroxy-substituted —($C_1$-$C_6$) alkyl, —($C_1$-$C_6$) alkynyl, —($C_1$-$C_6$) haloalkyl, hydroxy-substituted —($C_1$-$C_6$) haloalkyl, —O—($C_1$-$C_6$) alkyl, —($C_3$-$C_8$) cycloalkyl, -alkyl-cycloalkyl, —CH(OH)cycloalkyl, phenyl, -alkyl-phenyl, monocyclic heteroaryl, -alkyl-monocyclic heteroaryl, —($C_3$-$C_8$) spirocycloalkyl, —C(O)H, —C(O)OH, —C(O)($C_1$-$C_6$) alkyl, —C(O)O($C_1$-$C_6$) alkyl, —N($R^{1B}$)C(O)—($C_1$-$C_6$) alkyl, —N($R^{1B}$)$_2$, —C(O)N($R^{1B}$)$_2$, —S(O)$_2$H, —S(O)-phenyl, —S(O)—($C_1$-$C_6$) alkyl-phenyl, —S(O)$_2$-phenyl, —S(O)$_2$—($C_1$-$C_6$) alkyl-phenyl, —S(O)$_2$OH, and —S(O)$_2$—($C_1$-$C_6$) alkyl,
wherein each $R^{1B}$ group is independently selected from the group consisting of H and —($C_1$-$C_6$ alkyl);
and -L-, $R^3$, $R^Q$, Ring A, $R^2$, and n are each as described in Formula (I.1) above.

Another embodiment comprises a method of using, in each of the methods and/or uses described herein, a compound according to Formula (V):

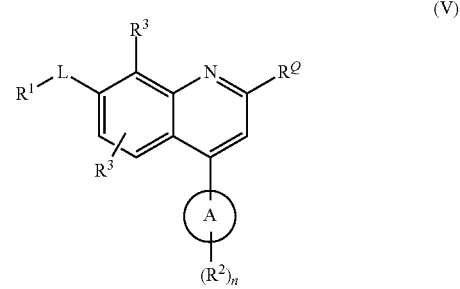

(V)

or a stereoisomer thereof, or a pharmaceutically acceptable salt of said compound or said stereoisomer, wherein:

ring A is a moiety selected from the group consisting of: phenyl, —($C_5$-$C_6$) cycloalkyl, —($C_5$-$C_6$) cycloalkyenl, -pyridinyl, pyrimidinyl, -pyrazolyl, -thienyl, -thiazolyl, -thiadiazolyl, and -oxazolyl;

$R^Q$ is selected from the group consisting of —CN and —C(O)NH$_2$;

-L- is a bond or a divalent moiety selected from the group consisting of:

—(C($R^{1L}$)$_2$)$_p$—,

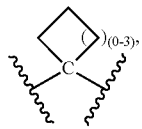

—C(O)—, —S(O)—, and —S(O)$_2$—;

p is 1, 2, or 3;

each $R^{1L}$ is independently selected from the group consisting of H, —CH$_3$, —CF$_3$, —OH, —C(O)—, halogen, -cyclopropyl, —O—CH$_3$, and —O—CF$_3$;

$R^1$ is selected from the group consisting of:

(1) heterocycloalkyl, heterocycloalkenyl, wherein said heterocycloalkyl and said heterocycloalkenyl are monocyclic or multicyclic ring systems comprising from 3 to 10 ring atoms in which 1, 2, or 3 of the atoms of each said ring system is a ring heteroatom independently selected from the group consisting of N, S, S(O), S(O)$_2$, and O, and wherein each said heterocycloalkyl group and each said heterocycloalkenyl group is unsubstituted or substituted with 1 to 5 groups independently selected from the group consisting of oxo, CN, —OH, halogen, —(C$_1$-C$_6$) alkyl, hydroxy-substituted —(C$_1$-C$_6$) alkyl, —(C$_1$-C$_6$) alkynyl, —(C$_1$-C$_6$) haloalkyl, hydroxy-substituted —(C$_1$-C$_6$) haloalkyl, —O—(C$_1$-C$_6$) alkyl, —(C$_3$-C$_8$) cycloalkyl, -alkyl-cycloalkyl, —CH(OH)cycloalkyl, phenyl, -alkyl-phenyl, monocyclic heteroaryl, -alkyl-monocyclic heteroaryl, —(C$_3$-C$_8$) spirocycloalkyl, —(C$_3$-C$_8$) spiroheterocycloalkyl, —C(O)H, —C(O)OH, —C(O)(C$_1$-C$_6$) alkyl, —C(O)O(C$_1$-C$_6$) alkyl, —N(R$^{1A}$)C(O)—(C$_1$-C$_6$) alkyl, —N(R$^{1A}$)$_2$, —C(O)N(R$^{1A}$)$_2$, —S(O)$_2$H, —S(O)-phenyl, —S(O)—(C$_1$-C$_6$) alkyl-phenyl, —S(O)$_2$-phenyl, —S(O)$_2$—(C$_1$-C$_6$) alkyl-phenyl, —S(O)$_2$OH, and —S(O)$_2$—(C$_1$-C$_6$) alkyl, wherein each R$^{1A}$ group is independently selected from the group consisting of H and —(C$_1$-C$_6$ alkyl);

(2) heteroaryl, wherein said heteroaryl is a monocyclic or multicyclic ring system comprising from 5 to 10 ring atoms in which from 1 to 4 of the atoms of said ring system is a ring nitrogen atom, and wherein said heteroaryl is unsubstituted or substituted with 1 to 5 groups independently selected from the group consisting of oxo, CN, —OH, halogen, —(C$_1$-C$_6$) alkyl, hydroxy-substituted —(C$_1$-C$_6$) alkyl, —(C$_1$-C$_6$) alkynyl, —(C$_1$-C$_6$) haloalkyl, hydroxy-substituted —(C$_1$-C$_6$) haloalkyl, —O—(C$_1$-C$_6$) alkyl, —(C$_3$-C$_8$) cycloalkyl, -alkyl-cycloalkyl, —CH(OH)cycloalkyl, phenyl, -alkyl-phenyl, monocyclic heteroaryl, -alkyl-monocyclic heteroaryl, —(C$_3$-C$_8$) spirocycloalkyl, —C(O)H, —C(O)OH, —C(O)(C$_1$-C$_6$) alkyl, —C(O)O(C$_1$-C$_6$) alkyl, —N(R$^{1B}$)C(O)—(C$_1$-C$_6$) alkyl, —N(R$^{1B}$)$_2$, —C(O)N(R$^{1B}$)$_2$, —S(O)$_2$H, —S(O)-phenyl, —S(O)—(C$_1$-C$_6$) alkyl-phenyl, —S(O)$_2$-phenyl, —S(O)$_2$—(C$_1$-C$_6$) alkyl-phenyl, —S(O)$_2$OH, and —S(O)$_2$—(C$_1$-C$_6$) alkyl, wherein each R$^{1B}$ group is independently selected from the group consisting of H and —(C$_1$-C$_6$ alkyl);

(5) phenyl, wherein said phenyl is unsubstituted or substituted with from 1 to 5 groups independently selected from the group consisting of oxo, CN, —OH, halogen, —(C$_1$-C$_6$) alkyl, —(C$_1$-C$_6$) alkynyl, —(C$_1$-C$_6$) haloalkyl, —O—(C$_1$-C$_6$) alkyl, —(C$_3$-C$_8$) cycloalkyl, -alkyl-cycloalkyl, —CH(OH) cycloalkyl, monocyclic heteroaryl, -alkyl-monocyclic heteroaryl, —(C$_3$-C$_8$) spirocycloalkyl, —C(O)H, —C(O)OH, —C(O)(C$_1$-C$_6$) alkyl, —C(O)O(C$_1$-C$_6$) alkyl, —N(R$^{1C}$)C(O)—(C$_1$-C$_6$) alkyl, —N(R$^{1C}$)$_2$, —C(O)N(R$^{1C}$)$_2$, —S(O)$_2$H, —S(O)-phenyl, —S(O)—(C$_1$-C$_6$) alkyl-phenyl, —S(O)$_2$-phenyl, —S(O)$_2$—(C$_1$-C$_6$) alkyl-phenyl, —S(O)$_2$OH, and —S(O)$_2$—(C$_1$-C$_6$) alkyl, wherein each R$^{1C}$ group is independently selected from the group consisting of H and —(C$_1$-C$_6$ alkyl);

(4) H, —(C$_1$-C$_6$) alkyl;

(5) —CH$_2$N(R$^{1D}$)R$^{1E}$, wherein:

R$^{1D}$ is selected from the group consisting of H, —(C$_1$-C$_6$) alkyl, and —C(O)OR$^{1H}$; and R$^{1E}$ is selected from the group consisting of —O—(C$_1$-C$_6$) alkyl, heteroalkyl, -alkyl-C(O)N(R$^{1H}$), and —C(O)OR$^{1H}$, wherein each R$^{1H}$ is independently selected from the group consisting of H and —(C$_1$-C$_6$) alkyl; and (6) —CH$_2$N(R$^{1F}$)OR$^{1G}$, wherein:

R$^{1F}$ is selected from the group consisting of H, —(C$_1$-C$_6$) alkyl, and —C(O)OR$^{1H}$, wherein each R$^{1H}$ is independently selected from the group consisting of H and —(C$_1$-C$_6$) alkyl; and R$^{1G}$ is selected from the group consisting of H and —(C$_1$-C$_6$) alkyl;

n is 0, 1, 2, or 3;

each R$^2$ (when present) is independently selected from the group consisting of halogen, —CN, —OH, —(C$_1$-C$_6$) alkyl, —O—(C$_1$-C$_6$) alkyl, —(C$_1$-C$_6$) haloalkyl, —O—(C$_1$-C$_6$) haloalkyl, cyclopropyl, cyclobutyl, cyclopentyl, cyclohexyl, —NH$_2$, —NH(C$_1$-C$_6$)alkyl, —N(C$_1$-C$_6$alkyl)$_2$, —C(O)O(C$_1$-C$_6$) alkyl, and phenyl; and R$^3$ is selected from the group consisting of hydrogen and fluorine.

An alternative embodiment of the compounds of Formula (V) useful in said methods or said uses comprises a compound according to Formula (V.1):

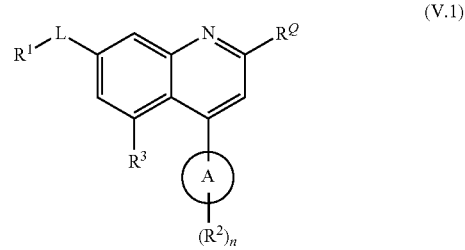

(V.1)

or a stereoisomer thereof, or a pharmaceutically acceptable salt of said compound or said stereoisomer, wherein each of R$^1$, -L-, Ring A, R$^2$, n, R$^3$, and R$^Q$ are as defined in Formula (V).

Another alternative embodiment of the compounds of Formula (V) useful in said methods or said uses comprises a compound according to Formula (V.2):

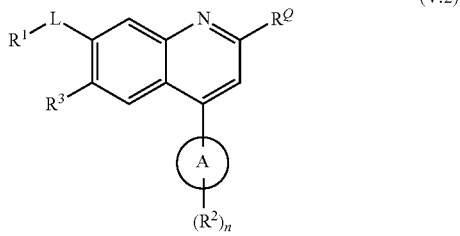

(V.2)

or a stereoisomer thereof, or a pharmaceutically acceptable salt of said compound or said stereoisomer, wherein each of $R^1$, -L-, Ring A, $R^2$, n, $R^3$, and $R^Q$ are as defined in Formula (V).

In alternative embodiments of Formulas (V), (V.1) and (V.2), when $R^1$ is heterocycloalkyl, heterocycloalkenyl, heteroaryl, or phenyl, each said $R^1$ group is unsubstituted or substituted with 1 to 4 groups, or, alternatively, 1 to 3 groups, or, alternatively 1 to 2 groups, wherein each said group is as defined in Formula (V).

Diseases or disorders in which the mGluR2 receptor may be involved include, but are not limited to, Alzheimer's Disease, cognitive impairment, schizophrenia, mood disorders, including depression and anxiety, gastrointestinal disorders, pain disorders and sleep disorders.

Additional examples of pain disorders include acute pain, inflammatory pain and neuropathic pain. Neuropathic pain includes, but is not limited to, postherpetic neuralgia, nerve injury, the "dynias", e.g., vulvodynia, phantom limb pain, root avulsions, painful diabetic neuropathy, painful traumatic mononeuropathy, painful polyneuropathy. Additional examples of pain disorders include central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Additional examples of cognitive disorders include mild cognitive impairment. Other conditions that may be treated by the compounds and compositions of the invention include Parkinson's Disease, pulmonary hypertension, chronic obstructive pulmonary disease (COPD), asthma, urinary incontinence, glaucoma, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention may be useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another embodiment, the present invention provides a method for treating schizophrenia or psychosis comprising administering to a patient in need thereof an effective amount of a compound (or composition providing a compound) of the invention, or a stereoisomer thereof.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally a human being, male or female, in whom mGluR2 receptor inhibition is desired, but may also encompass other mammals such as those listed above, including dogs, cats, mice, rats, cattle, horses, sheep, rabbits, monkeys, chimpanzees or other apes or primates, for which treatment the above noted disorders, or the study of mGluR2, is desired.

Another embodiment provides a medicament or pharmaceutical composition for the inhibition of mGluR2 receptor, and/or for the treatment of any of the diseases or disorders listed above to a patient (preferably a human) in need of such treatment, which comprise a compound (or composition comprising a compound) of the invention, or a stereoisomer thereof, or a pharmaceutically acceptable salt of said compound or said stereoisomer, and a pharmaceutically acceptable carrier.

Another embodiment provides a method for the manufacture of a medicament or a pharmaceutical composition for the inhibition of an mGluR2-NAM receptor, and/or for treating one or more diseases or conditions listed above, comprising combining a compound (or composition comprising a compound) of the invention, or a stereoisomer thereof, or a pharmaceutically acceptable salt of said compound or said stereoisomer, with a pharmaceutically acceptable carrier.

Combination Therapy

The compounds and compositions of the invention may be used in combination with one or more other drugs in the treatment of diseases or conditions for which the compounds of the invention have utility, where the combination of the drugs is desired, e.g., where the combination is safer or more effective than either drug alone. Additionally, the compounds of the invention may be used in combination with one or more other drugs that treat, prevent, control, ameliorate, or reduce the risk of side effects or toxicity of the compounds of the invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen. In one embodiment, the compounds of the invention useful in said combinations comprise a compound according to any one of Formulas (I), (I.1), (I.2), (II), (II.1), (II.2), (III), (III.1), (III.2), (IV), (IV.1), (IV.2), (V), (V.1), and/or (V.2) as described herein, or according to any of the various embodiments described herein. In another embodiment, the compounds of the invention useful in said combinations comprise the compounds of the examples, e.g., as set forth as example compounds of the invention in the Tables herein.

In another embodiment, a compound or composition of the invention may be employed in combination with acetylcholinesterase inhibitors such as donepezil and rivastigmine, NMDA antagonist such as memantine, muscarinic receptor modulators, AMPA receptor modulators, mGluR3 receptor modulators, nicotinic alpha-7 and alpha4-beta 2 receptor modulators, 5-HT6 and 5-HT4 receptor modulators, modulators of phosphodiesterases (PDEs), alpha 2c receptor antagonists, histone deacetylases, and antioxidant therapies.

In another embodiment, a compound or composition of the invention may be employed in combination with therapies that may alter or modify the course of disease progression, including beta-amyloid modulating therapies such as BACE1 inhibitors, gamma-secretase modulators, tau and/or phosphor-tau modulators, and biologic therapies which modulate placques associated with neurological disorders including antibodies, RNAi, miRNA, and cell-therapies.

In another embodiment, a compound or composition of the invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide or pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

Additional examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B 1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

In another embodiment, the compounds and compositions of the invention may be administered in combination with compounds useful for the treatment of schizophrenia or enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, or the compound of the present invention may be administered in conjunction with the use of physical methods such as with light therapy or electrical stimulation.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of the invention is administered during a time when the additional therapeutic agent(s) exert their prophylactic or therapeutic effect, or vice versa.

In another embodiment, the compound of the invention and the additional therapeutic agent(s) are administered in doses commonly employed when such agents are used as monotherapy for treating the disorder.

In another embodiment, the compound of the invention and the additional therapeutic agent(s) are administered in doses lower than the doses commonly employed when such agents are used as monotherapy for treating the disorder.

In one embodiment, the compound of the invention and the additional therapeutic agent(s) are present in the same composition, which is suitable for oral administration.

In some embodiments, the compound of the invention and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the viral infection or related disease or disorder.

Another embodiment provides a kit comprising a therapeutically effective amount of the compound (or a composition comprising a compound) of the invention, or a stereoisomer thereof, or a pharmaceutically acceptable salt of said compound or said stereoisomer, optionally together with at least one additional therapeutic agent listed above, and a pharmaceutically acceptable carrier, vehicle or diluent.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of the invention is administered during a time when the additional therapeutic agent(s) exert their prophylactic or therapeutic effect, or vice versa.

In another embodiment, the compound of the invention and the additional therapeutic agent(s) are administered in doses commonly employed when such agents are used as monotherapy for treating the disorder.

In another embodiment, the compound of the invention and the additional therapeutic agent(s) are administered in doses lower than the doses commonly employed when such agents are used as monotherapy for treating the disorder.

In one embodiment, the compound of the invention and the additional therapeutic agent(s) are present in the same composition, which is suitable for oral administration.

PREPARATIVE EXAMPLES

In general, the compounds in the invention may be produced by a variety of processes known to those skilled in the art and by know, processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatibility.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme or for the preparation described below.

Where NMR data are presented, $^1$H spectra were obtained on either a Varian VXR-400 (400 MHz, $^1$H), Varian Gemini-300 (300 MHz), Varian Mercury VX-400 (400 MHz), Bruker-Biospin AV-500 (500 MHz) or Bruker Avance DRX-500 (500 MHz), and chemical shifts are reported as ppm with number of protons and multiplicities indicated parenthetically. Where LC/MS data are presented, analyses was performed using a 1200 series Agilent 6140 Quadrupole LCMS with a 1.8 µM Zorbax SB-$C_{18}$ column (10-95% of MeCN—H2O with 0.1% TFA over 2.7 min, 1 mL/min) or with an Applied Biosystems API-150 mass spectrometer and Gemini $C_{18}$ column (50×4.6 mm, 10-95% $CH_3CN$-1120 with 0.05% TFA over 5 min, 1 mL/min).

Preparative chiral HPLC separations were generally carried out using supercritical fluid chromatography by eluting a chiral column such as OJ-H, (4.6×250 mm, Chiral Technologies, Inc., West Chester, Pa.) with a mobile phase of isopropanol and supercritical CO2.

The starting materials and reagents used in preparing compounds described below are either available from commercial suppliers such as Aldrich Chemical Co. (Wisconsin, USA) and Acros Organics Co. (New Jersey, USA) or were prepared by literature methods known to those skilled in the art.

In the Schemes below, R¹ corresponds to the moiety

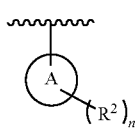

shown in the various embodiments of the compounds of the invention, including in Formula (I). Compounds of the invention may be prepared as outlined in Schemes A-G. Preparation of key intermediate A-9 is described in Scheme A below. 7-Methylquinoline A-1 can be converted to 7-methylquinoline-2-carbonitrile A-2 by oxidation followed by nucleophilic attack of cyanide on the activated N-oxide. Further oxidation of A-2 followed by treatment with POCl₃ yields 4-chloro-7-methylquinoline-2-carbonitrile A-3. Metal catalyzed coupling introduces group $R_1$ to give A-5, which can then be brominated at the benzylic position giving A-6. Bromide A-6 can be displaced by nucleophile A-7 in the presence of base in a polar solvent to yield A-8. The nitrile in A-8 can subsequently be hydrolyzed to primary amide A-9 using basic peroxide or under acidic conditions. Compounds A-3 to A-9 of Scheme A can be further modified by manipulation of the substitutent groups by general methods known in the art, including (but not limited to) cross coupling, oxidation, reduction, dealkylation, alkylation, acylation, and the like, and this modification may occur prior to or after deprotection.

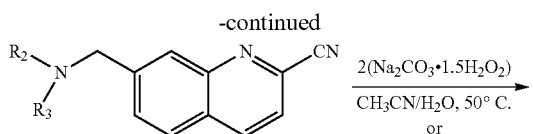

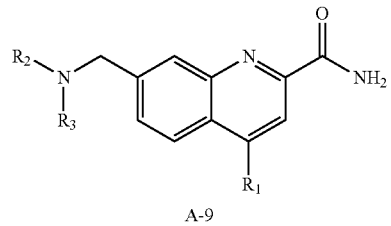

An alternative route to compounds like A-9 is shown in Scheme B. Starting from A-3, bromination followed by nucleophilic displacement yields B-2, which undergoes metal catalyzed cross coupling to give cyanoquinoline A-8. Hydrolysis of the nitrile in A-8 to primary amide A-9 can be achieved using conditions similar to those in Scheme A. Additionally, the order of the nucleophilic displacement and hydrolysis steps to give A-9 can be reversed as needed. Compound B-2 of Scheme B can be further modified by manipulation of the substitutent groups by general methods known in the art, including (but not limited to) cross coupling, oxidation, reduction, dealkylation, alkylation, acylation, and this modification may occur prior to or after deprotection.

Scheme A

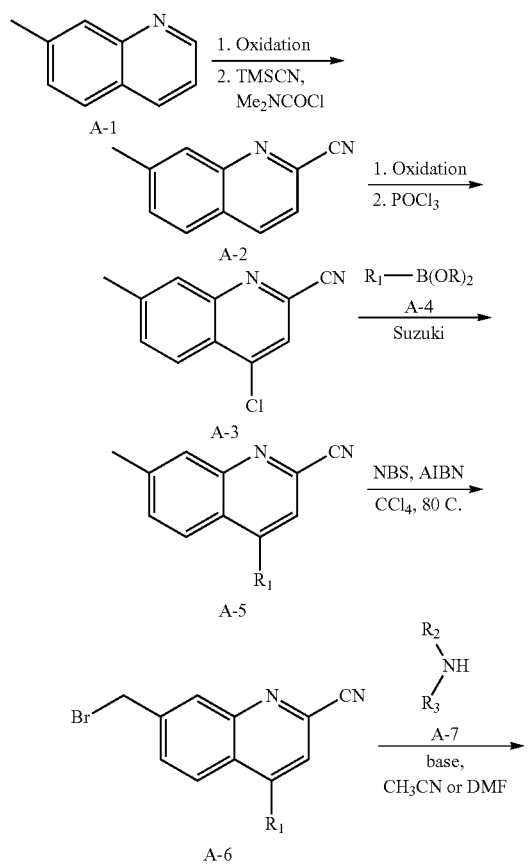

Scheme B

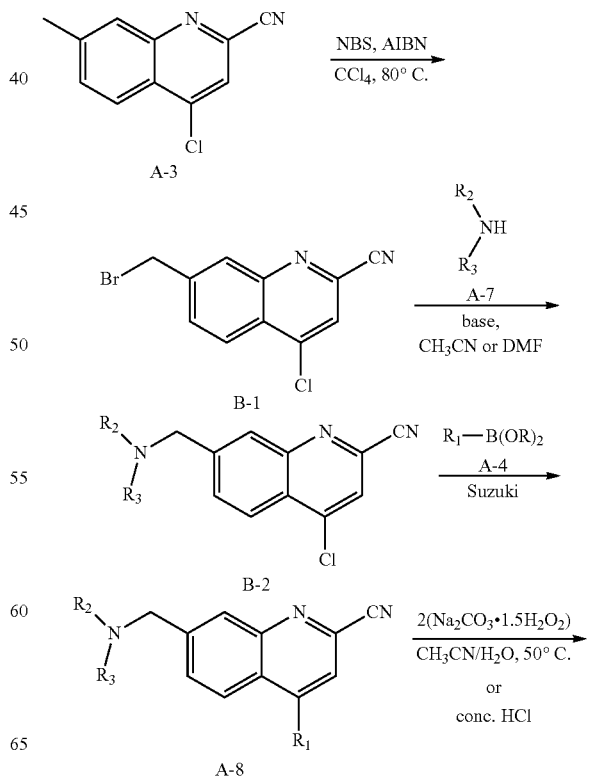

-continued

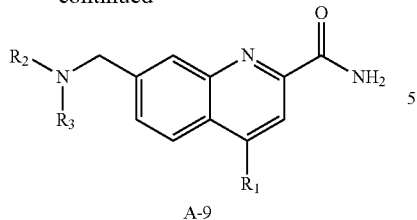
A-9

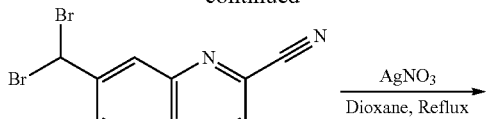
D-1

The metal catalyzed cross coupling step can also be carried out in the presence of the primary carboxamide in C-1 as in Scheme C for the synthesis of compounds of general formula A-9.

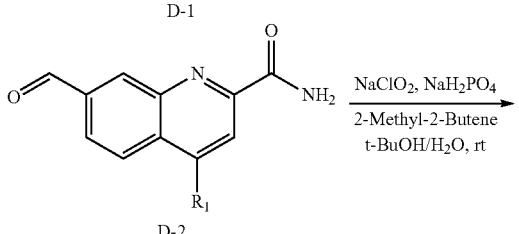
D-2

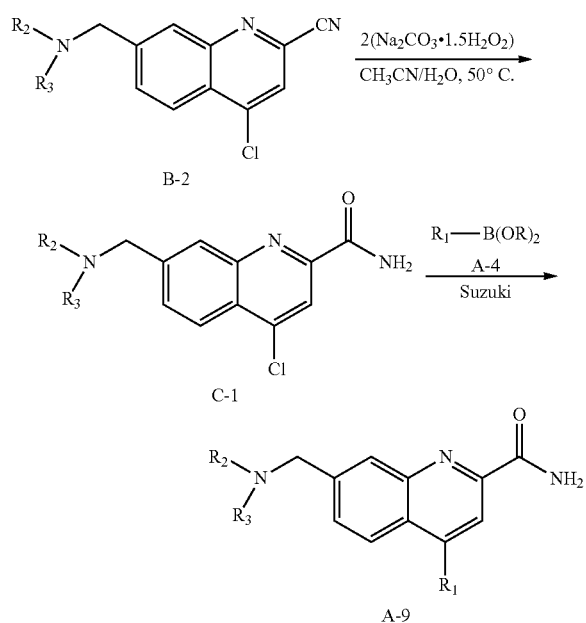

Scheme C

B-2

C-1

A-9

Compounds of general formula D-4 can be synthesized according to synthetic Scheme D below. Cyanoquinoline A-5 can be bis-brominated with NBS to yield gem-dibromide D-1 which can be converted to the corresponding aldehyde D-2 with silver nitrate. Oxidation to carboxylic acid D-3 followed by amide coupling with amine A-7 yields amide D-4. Compounds D-2 to D-4 of Scheme D can be further modified by manipulation of the substitutent groups by general methods known in the art, including (but not limited to) cross coupling, oxidation, reduction, dealkylation, alkylation, acylation, and the like, and this modification may occur prior to or after deprotection.

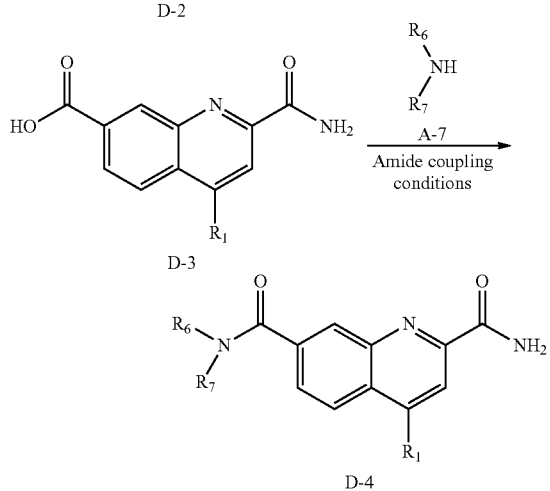

D-3

D-4

Compounds of general formula E-1 can be synthesized according to synthetic Scheme E below. Addition of organometallic reagents to aldehyde D-2 yields alcohol E-1. Compound E-1 of Scheme E can be further modified by manipulation of the substituent groups by general methods known in the art, including (but not limited to) cross coupling, oxidation, reduction, dealkylation, alkylation, acylation, and the like, and this modification may occur prior to or after deprotection.

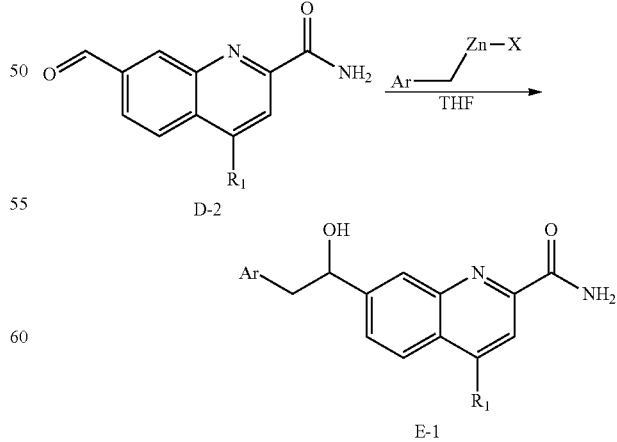

Scheme E

D-2

E-1

Keto-carboxamides F-4 can be prepared according to synthetic Scheme F. Displacement of bromide A-6 with aldehyde-containing nucleophile F-5 yields cyanoquinoline

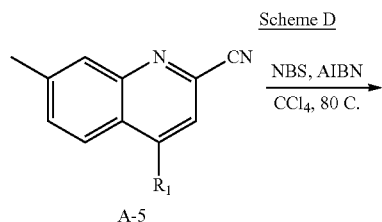
Scheme D

A-5

F-1. Hydrolysis of the nitrile to the corresponding carboxamide F-2 and subsequent reaction of the aldehyde with organometallic reagents yields alcohol F-3 which can be oxidized to F-4 with an oxidant such as Dess-Martin periodinane. Compounds F-1 to F-4 of Scheme F can be further modified by manipulation of the substituent groups by general methods known in the art, including (but not limited to) cross coupling, oxidation, reduction, dealkylation, alkylation, acylation, and the like, and this modification may occur prior to or after deprotection.

by succinimide in the presence of base in a polar solvent to yield G-7. Hydrolysis of the ester and subsequent coupling with ammonium hydroxide yields primary amide G-9. Compounds G-4 to G-9 of Scheme G can be further modified by manipulation of the substituent groups by general methods known in the art, including (but not limited to) cross coupling, oxidation, reduction, dealkylation, alkylation, acylation, and the like, and this modification may occur prior to or after deprotection.

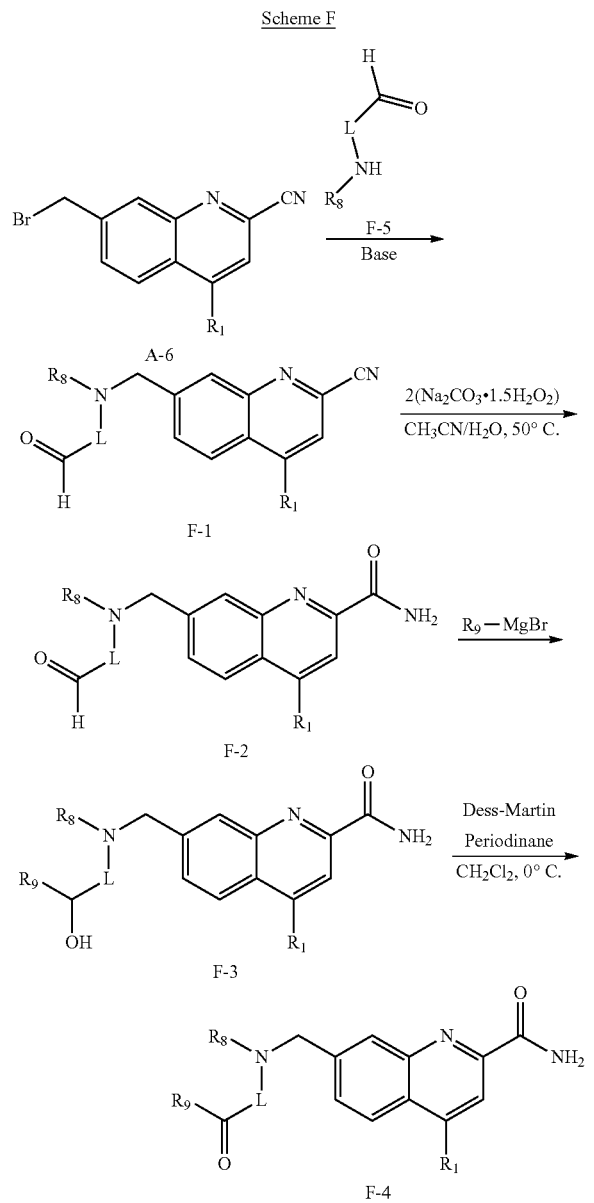

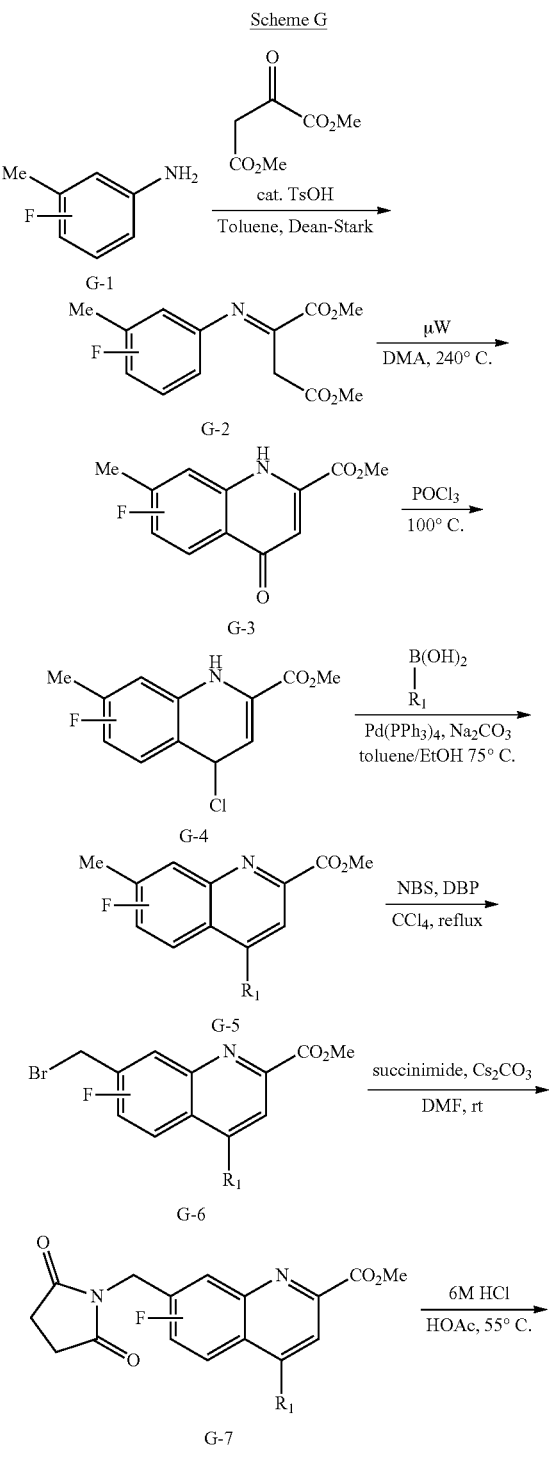

Preparation of key compounds such as G-9 is described in Scheme G below. Fluoro-substituted aniline G-1 can be converted to the corresponding butanedioates G-2 by condensation with dimethyl 2-oxobutanedioate in the presence of TsOH. Microwave irradiation of G-2 followed by treatment with POCl₃ yields fluoro-4-chloro-7-methylquinoline-2-carboxylate G-4. Metal catalyzed coupling introduces group $R_1$ to give G-5, which can then be brominated at the benzylic position giving G-6. Bromide G-6 can be displaced -continued

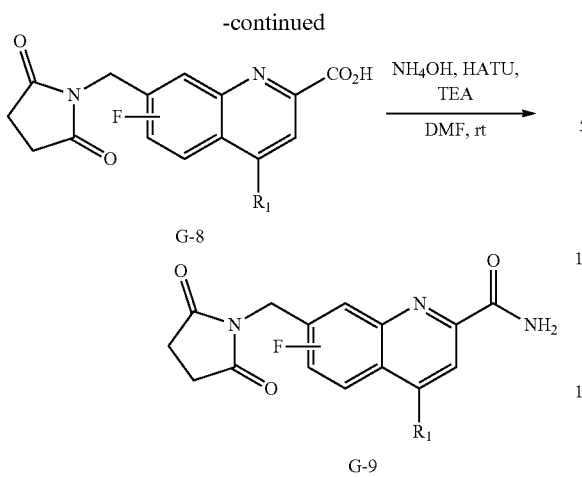

Metal catalyzed cross couplings can be carried out with bromide A-6 and arylbornic acids as in Scheme H for the synthesis of compounds of general formula H-2. Compound H-1 and H-2 of Scheme H can be further modified by manipulation of the substitutent groups by general methods known in the art, including (but not limited to) cross coupling, oxidation, reduction, dealkylation, alkylation, acylation, and the like, and this modification may occur prior to or after deprotection.

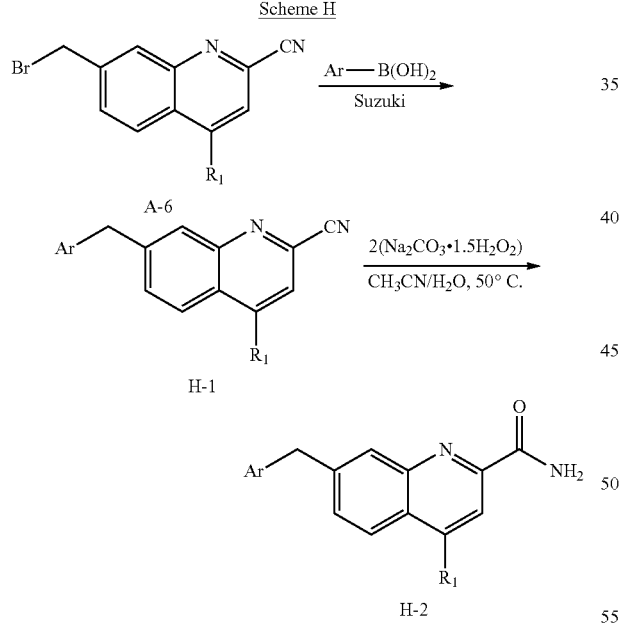

Compounds of general formula I-6 can be synthesized according to Scheme I. Metal catalyzed cross coupling of dichloride I-1 affords I-3 after hydrolysis of the nitrile to the methyl ester. Chloride I-3 can be cross coupled with vinyl trifluoroborate salts to yield styrenly compounds I-4. Hydroboration of the vinyl substituent and subsequent cross coupling with aryl or heteroaryl halides yields compound I-5. Aminolysis of the ester affords I-6. Compounds I-2 to I-6 of Scheme I can be further modified by manipulation of the substitutent groups by general methods known in the art, including (but not limited to) cross coupling, oxidation, reduction, dealkylation, alkylation, acylation, and the like, and this modification may occur prior to or after deprotection.

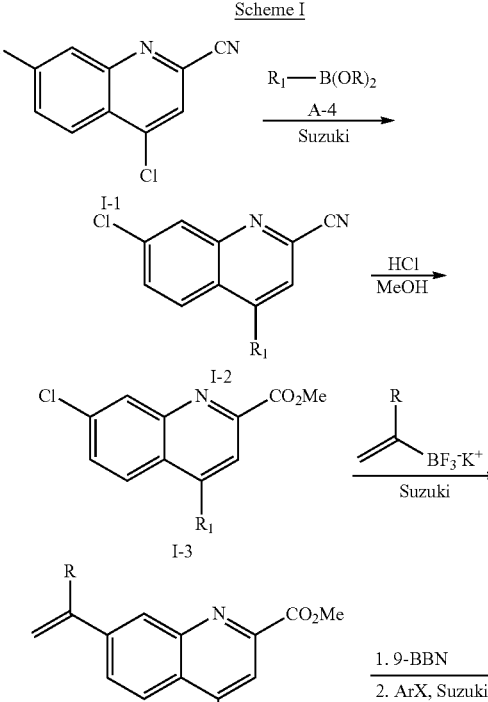

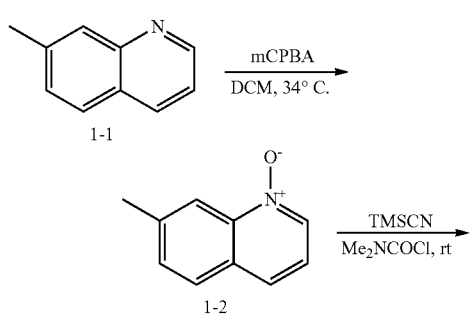

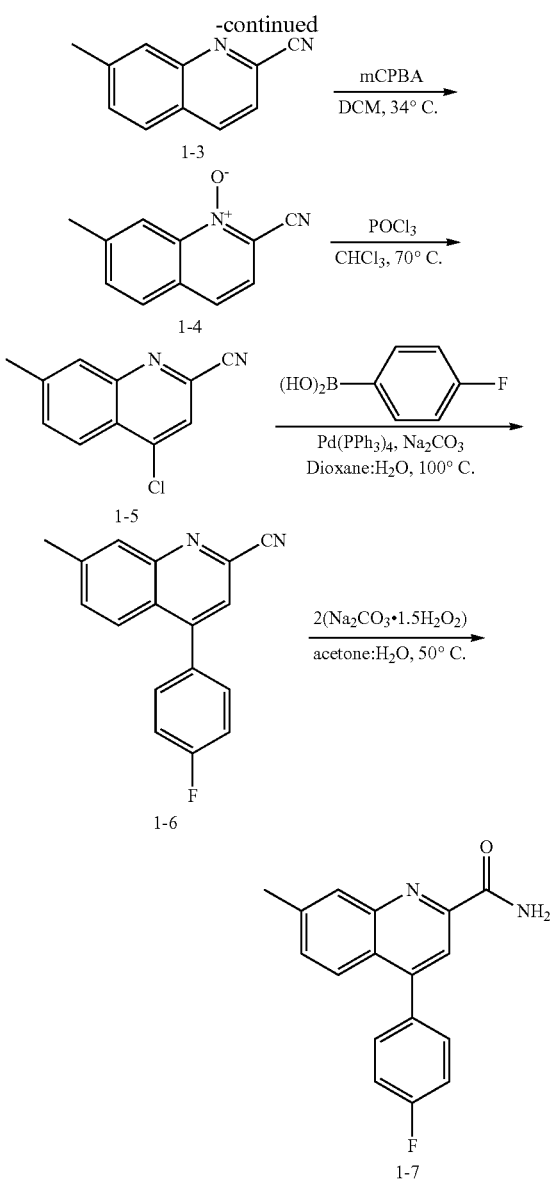

7-Methylquinoline-2-carbonitrile (1-3)

To a solution of 7-methylquinoline N-oxide (1-2, 246 g, 1.54 mol, 1.0 equiv) in methylene chloride (5 L, 0.31 M) was added TMS-CN (414 ml, 3.1 mol., 2 equiv.) followed by dimethylcarbamoyl chloride (284 ml, 3.1 mol. 2 equiv), and the resulting mixture was stirred at room temperature overnight. The solution was quenched with saturated sodium bicarbonate, diluted with water, and extracted with dichloromethane. The combined organic layers were dried over $MgSO_4$, filtered and the solvent removed to give 260 g of crude material which was recrystallized from methanol to give 186 g of 7-methylquinoline-2-carbonitrile (1-3) in two crops. LRMS m/z $(M+H)^+$ 169.1 found, 169.2 required.

7-Methylquinoline-2-carbonitrile N-oxide (1-4)

7-Methylquinoline-2-carbonitrile (181 g, 1.1 mol, 1.0 equiv.) was dissolved in dichloromethane (3.3 L, 0.3 M). m-Chloroperbenzoic acid (500 g, 2.9 mol, 2.6 equiv) was added and the reaction mixture was heated to 40° C. After 3 hr mCPBA (7 g, 40 mmol, 0.04 equiv.) was added and the mixture was allowed to stir overnight at room temperature. The mixture was extracted with 3 L of 1N NaOH aq., washed twice with 20 ml of dichloromethane and the combined organic phases were washed with DI water then dried over $MgSO_4$. The organics were filtered and the solvent was removed to give 192 g of 7-methylquinoline-2-carbonitrile N-oxide (1-4). LRMS m/z $(M+H)^+$ 185.2 found, 185.2 required.

4-Chloro-7-methylquinoline-2-carbonitrile (1-5)

7-Methylquinoline-2-carbonitrile N-oxide (1-4, 5.3 g, 28.8 mmol, 1.0 equiv.) was dissolved in $CHCl_3$ (80 ml, 0.36 M), and $POCl_3$ was added (16.09 ml, 173 mmol, 6.0 equiv.). The mixture was heated to 70° C. overnight, quenched onto crushed ice and extracted three times with dichloromethane. The combined organic layers were washed with water followed by saturated aqueous sodium bicarbonate, dried over $MgSO_4$, filtered and the solvent was removed to yield crude yellow solid. Recrystallization from heptane/EtOAc gave 95 g of 4-chloro-7-methylquinoline-2-carbonitrile (1-5). LRMS m/z $(M+H)^+$ 203.2 found, 203.6 required.

4-(4-Fluorophenyl)-7-methylquinoline-2-carbonitrile (1-6)

4-Chloro-7-methylquinoline-2-carbonitrile (1-5, 2.47 g, 12.2 mmol, 1.0 equiv.), 4-fluorophenylboronic acid (2.05 g, 14.63 mmol, 1.2 equiv.), $Pd(PPh_3)_4$ (0.7 g, 0.61 mmol, 0.05 equiv), and 1M aqueous $Na_2CO_3$ (12.2 ml, 2.39 mmol) was added into 1,4-dioxane (40 mL). The mixture was degassed and stirred at 100° C. for 16 hours, until disappearance of the starting material. The mixture was cooled, saturated aqueous sodium hydrogen carbonate (2 mL) was added and the mixture was extracted with ethyl acetate (2×50 mL). The combined organic fractions were washed with brine, dried ($MgSO_4$), filtered and the solvent was evaporated under reduced pressure. The residue was treated with 50 ml of MeOH, stirred vigorously at rt for 1 h, the mixture was filtered and washed with MeOH. The solid was collected and dried under vacuum. The filtrate was concentrated and retreated with MeOH to get a second crop of white solid that was combined to the first to give 2.75 g of 4-(4-fluorophenyl)-7-methylquinoline-2-carbonitrile (1-6). LRMS m/z $(M+H)^+$ 263.3 found, 263.3 required.

4-(4-Fluorophenyl)-7-methylquinoline-2-carboxamide (1-7)

4-(4-Fluorophenyl)-7-methylquinoline-2-carbonitrile (1-6, 25 mg, 0.095 mmol, 1.0 equiv.) was dissolved in

Example 1.1

Synthesis of 4-(4-fluorophenyl)-7-methylquinoline-2-carboxamide (1-7)

7-Methylquinoline N-oxide (1-2)

7-Methylquinoline (1-1, 240 g, 1.7 mol, 1.0 equiv) was dissolved in methylene chloride (5 L, 0.34 M). 3-Chloroperoxybenzoic acid (488 g, 2.2 mol, 1.3 equiv) was added portionwise with cooling so that the reaction temperature did not rise above 34° C. After stirring for 1 h, the reaction mixture was quenched with 2L of 1N aqueous NaOH and the product was extracted with methylene chloride. The combined organic layers were washed with saturated aqueous sodium bicarbonate, dried over $MgSO_4$ and filtered. Heptane was added and the organic layer was evaporated to dryness, giving 246 g of 7-methylquinoline N-oxide (1-2) as a pink solid that was carried on without further purification. LRMS m/z $(M+H)^+$ 160.1 found, 160.2 required.

acetone (2.3 mL)/water (1.5 mL) and sodium percarbonate (79.0 mg, 0.477 mmol, 5.0 equiv) was added. The resulting mixture was stirred at 50° C. for 1 hour. The mixture was cooled and concentrated. The crude residue was purified by reverse phase HPLC (H$_2$O/CH$_3$CN gradient w/ 0.1% TFA modifier). Fractions containing product were pooled and treated with Na$_2$CO$_3$. The resulting mixture was extracted with CHCl$_3$. The combined organic layers were dried (MgSO$_4$), filtered, and concentrated to afford 4-(4-fluorophenyl)-7-methylquinoline-2-carboxamide (1-7). LRMS m/z (M+H)$^+$ 280.9 found, 281.3 required.

Scheme 1.2

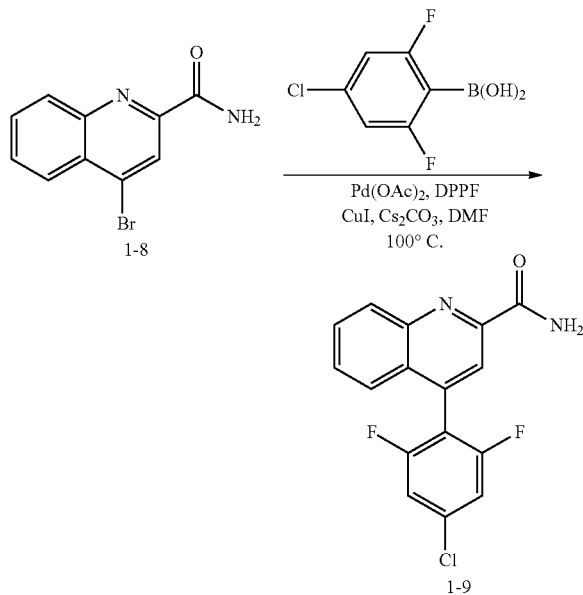

Example 1.2

Synthesis of 4-(2,6-dichloro-4-fluorophenyl)quinoline-2-carboxamide (1-9)

4-(2,6-Dichloro-4-fluorophenyl)quinoline-2-carboxamide (1-9)

4-Bromoquinoline-2-carboxamide (1-8, 50.0 mg, 0.199 mmol, 1.0 equiv.), (2,6-dichloro-4-fluorophenyl)boronic acid (77.0 mg, 0.398 mmol, 2.0 equiv.), cesium carbonate (130.0 mg, 0.398 mmol, 2.0 equiv), Pd(OAc)$_2$ (2.2 mg, 0.01 mmol, 0.05 equiv.), DPPF (11.0 mg, 0.020 mmol, 0.1 equiv.) and copper(I) chloride (19.7 mg, 0.199 mmol, 1.0 equiv.) were added into DMF (1.0 mL). The mixture was stirred at 100° C. overnight. After cooling, aqueous sodium hydrogen carbonate (saturate, 2.0 mL) was added and the mixture was extracted with dichloromethane (2×5 mL). The combined organic layers were washed with brine, dried over MgSO$_4$, filtered and concentrated. The residue was purified by reverse phase HPLC (H$_2$O/CH$_3$CN gradient w/ 0.1% TFA modifier) to afford 4-(2,6-dichloro-4-fluorophenyl)quinoline-2-carboxamide (1-9, 6.20 mg, 9.8%) as a colorless solid. $^1$H NMR (400 MHz, CDCl$_3$): δ 8.281 (s, 1H); 8.200-8.226 (m, 1H); 8.175 (br s, 1H); 7.801-7.843 (m, 1H); 7.601-7.637 (m, 2H); 7.137-7.183 (m, 2H); 6.140 (br s, 1H). LRMS m/z (M+H)$^+$ 319.0 found, 319.0 required.

The following compounds have been prepared according to procedures similar to those in Scheme 1.1 and 1.2 selecting the appropriate quinoline derivative and boronic acid derivative and provide examples of compounds in the invention.

TABLE 1

| Example | Structure | IUPAC Name | Exact Mass [M + H]$^+$ |
|---|---|---|---|
| 1-10 | 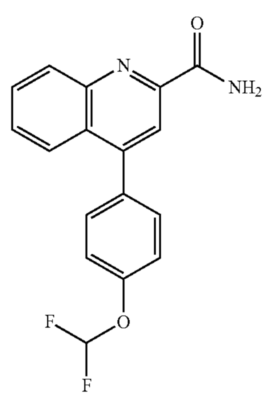 [SMILES: NC(=O)c1cc(-c2ccc(OC(F)F)cc2)c2ccccc2n1] | 4-[4-(difluoromethoxy)phenyl]quinoline-2-carboxamide | Calc'd 315.1, Found 315.1 |
| 1-11 | 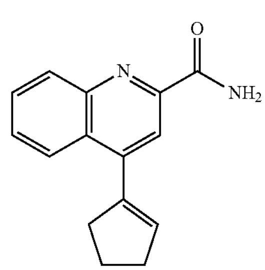 [SMILES: NC(=O)c1cc(C2=CCCC2)c2ccccc2n1] | 4-cyclopent-1-en-1-ylquinoline-2-carboxamide (TFA salt) | Calc'd 466.07, Found 466.07 |

TABLE 1-continued

| Example | Structure | IUPAC Name | Exact Mass [M + H]+ |
|---|---|---|---|
| 1-12 | 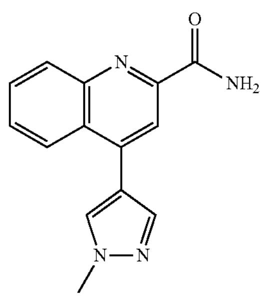 [SMILES: Cn1cc(-c2cc(C(N)=O)nc3ccccc23)cn1] | 4-(1-methyl-1H-pyrazol-4-yl)quinoline-2-carboxamide | Calc'd 253.1, Found 253.1 |
| 1-13 | 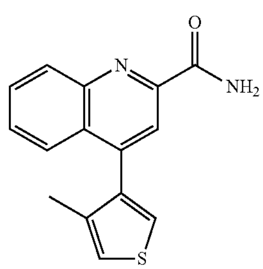 [SMILES: Cc1cscc1-c1cc(C(N)=O)nc2ccccc12] | 4-(4-methylthiophen-3-yl)quinoline-2-carboxamide | Calc'd 269.1, Found 267.07 |
| 1-14 | 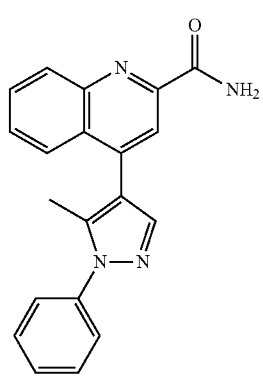 [SMILES: Cc1c(-c2cc(C(N)=O)nc3ccccc23)cnn1-c1ccccc1] | 4-(5-methyl-1-phenyl-1H-pyrazol-4-yl)quinoline-2-carboxamide | Calc'd 329.1, Found 329.1 |
| 1-15 | 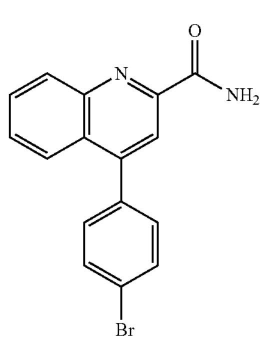 [SMILES: NC(=O)c1cc(-c2ccc(Br)cc2)c2ccccc2n1] | 4-(4-bromophenyl)quinoline-2-carboxamide | Calc'd 327.0, Found 327.0 |

TABLE 1-continued

| Example | Structure | IUPAC Name | Exact Mass [M + H]+ |
|---|---|---|---|
| 1-16 | 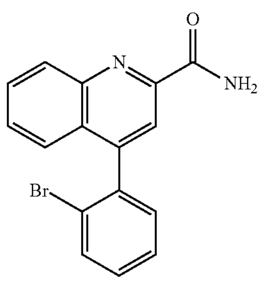 [SMILES: NC(=O)c1cc(-c2ccccc2Br)c2ccccc2n1] | 4-(2-bromophenyl)quinoline-2-carboxamide | Calc'd 327.0, Found 327.0 |
| 1-17 | 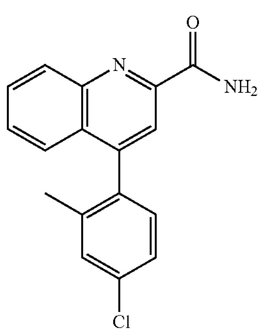 [SMILES: Cc1cc(Cl)ccc1-c1cc(C(N)=O)nc2ccccc12] | 4-(4-chloro-2-methylphenyl)quinoline-2-carboxamide | Calc'd 297.1, Found 297.08 |
| 1-18 | 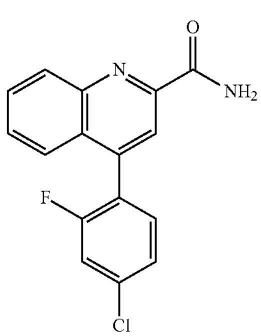 [SMILES: NC(=O)c1cc(-c2ccc(Cl)cc2F)c2ccccc2n1] | 4-(4-chloro-2-fluorophenyl)quinoline-2-carboxamide | Calc'd 301.1, Found 301.05 |
| 1-19 | 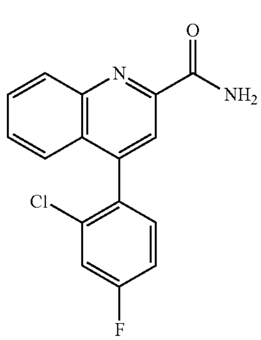 [SMILES: NC(=O)c1cc(-c2ccc(F)cc2Cl)c2ccccc2n1] | 4-(2-chloro-4-fluorophenyl)quinoline-2-carboxamide | Calc'd 301.1, Found 301.05 |

TABLE 1-continued

| Example | Structure | IUPAC Name | Exact Mass [M + H]+ |
|---------|-----------|------------|---------------------|
| 1-20 | 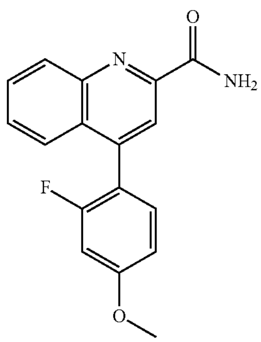 [SMILES: COc1ccc(-c2cc(C(N)=O)nc3ccccc23)c(F)c1] | 4-(2-fluoro-4-methoxyphenyl)quinoline-2-carboxamide | Calc'd 297.1, Found 297.1 |
| 1-21 | 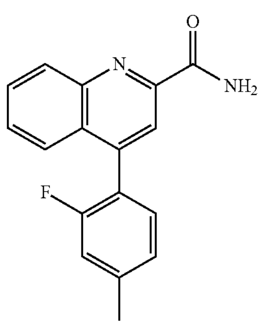 [SMILES: Cc1ccc(-c2cc(C(N)=O)nc3ccccc23)c(F)c1] | 4-(2-fluoro-4-methylphenyl)quinoline-2-carboxamide | Calc'd 281.1, Found 281.1 |
| 1-22 | 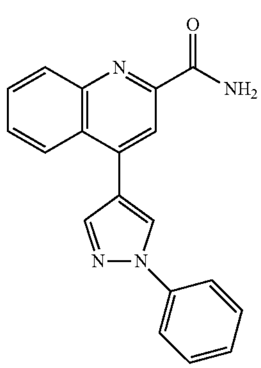 [SMILES: NC(=O)c1cc(-c2cnn(-c3ccccc3)c2)c2ccccc2n1] | 4-(1-phenyl-1H-pyrazol-4-yl)quinoline-2-carboxamide | Calc'd 315.1, Found 315.1 |
| 1-23 | 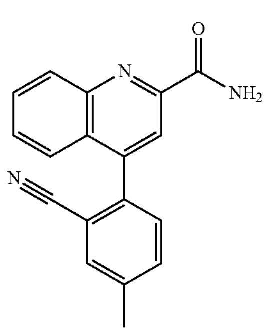 [SMILES: Cc1ccc(-c2cc(C(N)=O)nc3ccccc23)c(C#N)c1] | 4-(2-cyano-4-methyphenyl)quinoline-2-carboxamide | Calc'd 288.1, Found 288.1 |

TABLE 1-continued

| Example | Structure | IUPAC Name | Exact Mass [M + H]+ |
|---|---|---|---|
| 1-24 | 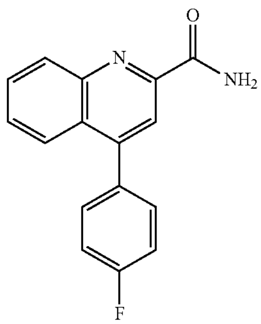 [SMILES: NC(=O)c1cc(-c2ccc(F)cc2)c2ccccc2n1] | 4-(4-fluorophenyl)quinoline-2-carboxamide | Calc'd 267.1, Found 267.1 |
| 1-25 | 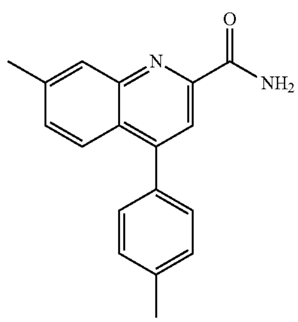 [SMILES: Cc1ccc(-c2cc(C(N)=O)nc3cc(C)ccc23)cc1] | 7-methyl-4-(4-methylphenyl)quinoline-2-carboxamide | Calc'd 277.1, Found 277.0 |
| 1-26 | 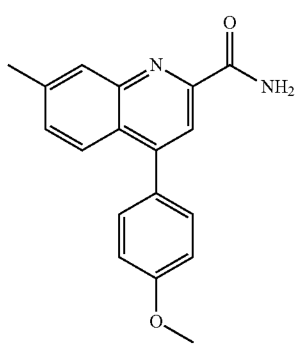 [SMILES: COc1ccc(-c2cc(C(N)=O)nc3cc(C)ccc23)cc1] | 4-(4-methoxyphenyl)-7-methylquinoline-2-carboxamide | Calc'd 293.1, Found 293.0 |
| 1-27 | 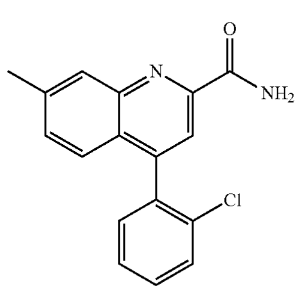 [SMILES: Cc1ccc2c(-c3ccccc3Cl)cc(C(N)=O)nc2c1] | 4-(2-chlorophenyl)-7-methylquinoline-2-carboxamide | Calc'd 297.1, Found 297.0 |

TABLE 1-continued
| Example | Structure | IUPAC Name | Exact Mass [M + H]+ |
|---|---|---|---|
| 1-28 | 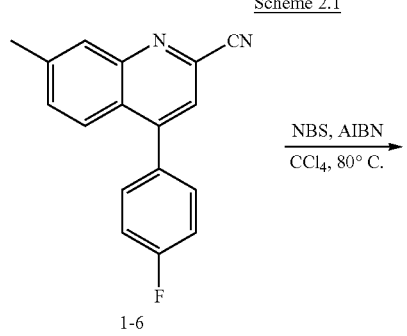 | 4-(2-fluorophenyl)-7-methylquinoline-2-carboxamide | Calc'd 281.1, Found 281.0 |
| 1-29 | 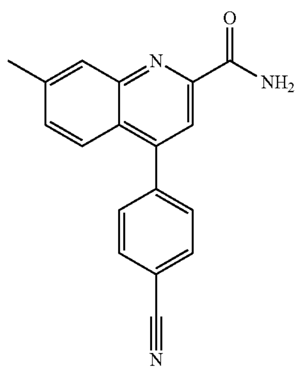 [SMILES: Cc1ccc2c(-c3ccc(C#N)cc3)cc(C(N)=O)nc2c1] | 4-(4-cyanophenyl)-7-methylquinoline-2-carboxamide | Calc'd 288.1, Found 287.9 |
Scheme 2.1
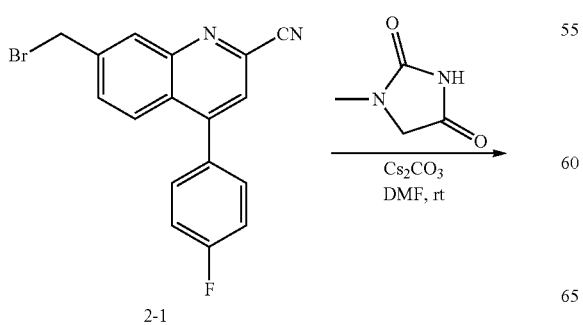
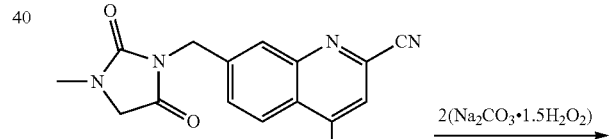

Example 2.1

Synthesis of 4-(4-fluorophenyl)-7-((3-methyl-2,5-dioxoimidazolidin-1-yl)methyl)quinoline-2-carboxamide (2-3)

7-(Bromomethyl)-4-(4-fluorophenyl)quinoline-2-carbonitrile (2-1)

4-(4-Fluorophenyl)-7-methylquinoline-2-carbonitrile (1-6, 450 mg, 1.7 mmol, 1.0 equiv) was dissolved in carbon tetrachloride (8.5 mL). NBS (310 mg, 1.7 mmol, 1.0 equiv) and AIBN (8 mg, 0.05 mmol, 0.03 equiv) were added and the mixture was refluxed overnight. The mixture was then cooled to room temperature and the white precipitate was filtered off to give 7-(bromomethyl)-4-(4-fluorophenyl)quinoline-2-carbonitrile (2-1). LRMS m/z (M+H)⁺ 342.7 found, 342.0 required.

4-(4-Fluorophenyl)-7-[(3-methyl-2,5-dioxoimidazolidin-1-yl)methyl]quinoline-2-carbonitrile (2-2)

7-(Bromomethyl)-4-(4-fluorophenyl)quinoline-2-carbonitrile (2-1, 50.0 mg, 0.147 mmol, 1.0 equiv.), 1-methylimidazolidine-2,4-dione (18.4 mg, 0.161 mmol, 1.1 equiv.) and cesium carbonate (95.0 mg, 0.293 mmol, 2.0 equiv.) were combined into 1.0 ml of DMF. The resulting mixture was stirred at ambient temperature for 16 hours. The solid was filtered and the filtrate was purified by reverse phase HPLC (H₂O/CH₃CN gradient w/ 0.1% TFA modifier) to afford 4-(4-fluorophenyl)-7-[(3-methyl-2,5-dioxoimidazolidin-1-yl)methyl]quinoline-2-carbonitrile (2-2, 48.0 mg, 87.0%) as a colorless solid. $^1$H NMR (400 MHz, CDCl₃): δ 8.205 (d, J=1.09 Hz, 1H); 7.941 (d, J=8.79 Hz, 1H); 7.681 (dd, J₁=8.79 Hz, J₂=1.83 Hz, 1H); 7.647 (s, 1H); 7.454-7.503 (m, 2H); 7.251-7.309 (m, 2H); 4.935 (s, 2H); 4.049 (s, 2H); 3.057 (s, 3H). LRMS m/z (M+H)⁺375.1 found, 375.1 required.

4-(4-Fluorophenyl)-7-[(3-methyl-2,5-dioxoimidazolidin-1-yl)methyl]quinoline-2-carboxamide (2-3)

4-(4-Fluorophenyl)-7-[(3-methyl-2,5-dioxoimidazolidin-1-yl)methyl]quinoline-2-carbonitrile (2-2, 44.9 mg, 0.120 mmol, 1.0 equiv.) was dissolved in acetone (1.5 mL)/water (0.75 mL) and sodium percarbonate (188.0 mg, 0.600 mmol, 5.0 equiv) was added. The resulting mixture was stirred at 50° C. for two hours. The mixture was cooled and poured over aqueous NH₄Cl (1.0 mL), extracted with ethyl acetate (3×5.0 mL), dried over MgSO₄, filtered and concentrated. The crude residue was purified by reverse phase HPLC (H₂O/CH₃CN gradient w/ 0.1% TFA modifier) to afford 4-(4-fluorophenyl)-7-[(3-methyl-2,5-dioxoimidazolidin-1-yl)methyl]quinoline-2-carboxamide (2-3, 35.3 mg, 75.0%) as a colorless solid. $^1$H NMR (400 MHz, CDCl₃): δ 8.498 (br s, 1H); 8.221 (d, J=1.29 Hz, 1H); 8.180 (s, 1H); 7.947 (d, J=8.60 Hz, 1H); 7.672 (dd, J₁=8.79 Hz, J₂=1.83 Hz, 1H); 7.532 (br s, 1H); 7.462-7.512 (m, 2H); 7.219-7.276 (m, 2H); 4.918 (s, 2H); 3.985 (s, 2H); 3.040 (s, 3H). LRMS m/z (M+H)⁺ 393.1 found, 393.1 required.

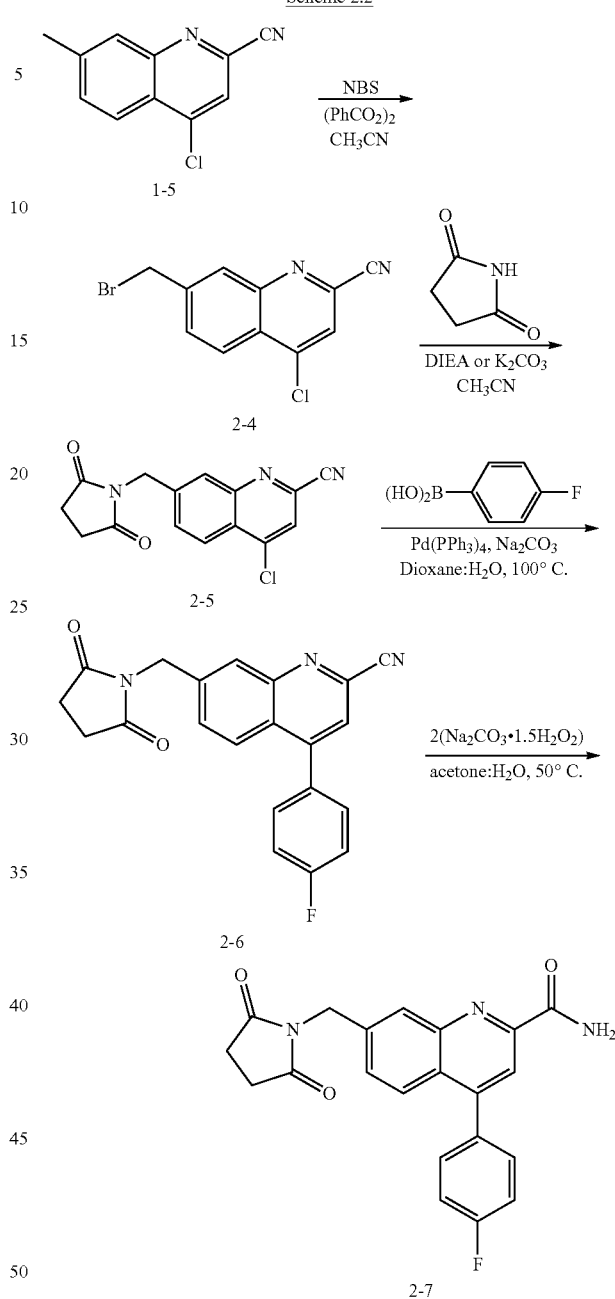

Scheme 2.2

Example 2.2

Synthesis of 7-((2,5-dioxopyrrolidin-1-yl)methyl)-4-(4-fluorophenyl)quinoline-2-carboxamide (2-7)

7-(Bromomethyl)-4-chloroquinoline-2-carbonitrile (2-4)

4-Chloro-7-methyl-2-quinolinecarbonitrile (1-5, 57 g, 0.37 mol, 1.0 equiv.), NBS (75 g, 0.42 mol, 1.14 equiv.) and benzoyl peroxide (0.8 g, 3.3 mmol, 0.01 equiv.) were stirred in CH₃CN (30 ml, 12.3 M) at room temperature. After 16 h, the solvent was removed and the residue was partitioned between AcOEt and water, the organic layer was washed with water, dried over MgSO$_4$ and filtered. After removal of the solvent, the residue was recrystallized from methanol to give 60 g of desired 7-(bromomethyl)-4-chloroquinoline-2-carbonitrile (2-4). LRMS m/z (M+H)$^+$ 283.1 found, 282.9 required.

4-Chloro-7-[(2,5-dioxopyrrolidin-1-yl)methyl]quinoline-2-carbonitrile (2-5)

To a room temperature solution of succinimide (4.22 g, 42.6 mmol, 1.2 equiv.) in anhydrous acetonitrile (89 mL, 0.4 M) was added Hunig's base (12.4 ml, 71.0 mmol, 2.0 equiv.) and 7-(bromomethyl)-4-chloroquinoline-2-carbonitrile (2-4, 10.0 g, 35.5 mmol). The resulting mixture was warmed in the microwave to 100° C. for 1 h. The reaction was then cooled to 0° C. and a precipitate formed. The solids were then collected by vacuum filtration and washed with cold acetonitrile to afford 4-chloro-7-[(2,5-dioxopyrrolidin-1-yl)methyl]quinoline-2-carbonitrile (2-5) which was taken to the next step without further purification. LRMS m/z (M+H)$^+$ 300.2 found, 300.0 required.

7-[(2,5-Dioxopyrrolidin-1-yl)methyl]-4-(4-fluorophenyl)quinoline-2-carbonitrile (2-6)

To a room temperature solution of 4-fluorophenylboronic acid (5.96 g, 42.6 mmol, 1.2 equiv.) in dioxane:water (10:1, 177 mL, 0.2 M) was added sodium bicarbonate (5.96 g, 71.0 mmol, 2.0 equiv.), 4-chloro-7-[(2,5-dioxopyrrolidin-1-yl)methyl]quinoline-2-carbonitrile (2-5, 10.6 g, 35.5 mmol), and Pd(PPh$_3$)$_4$ (4.1 g, 3.55 mmol, 0.1 equiv.). The resulting mixture was warmed to 100° C. for 4 hr. The reaction was then cooled to 0° C. and a precipitate formed. The solids were then collected by vacuum filtration and washed with water and cold acetonitrile to afford 7-[(2,5-dioxopyrrolidin-1-yl)methyl]-4-(4-fluorophenyl)quinoline-2-carbonitrile (2-6) which was taken to the next step without further purification. $^1$H NMR (400 MHz, CDCl$_3$): δ 8.115 (d, J=1.10 Hz, 1H); 7.897 (d, J=8.79 Hz, 1H); 7.655 (dd, J$_1$=8.79 Hz, J$_2$=1.83 Hz, 1H); 7.603 (s, 1H); 7.439-7.475 (m, 2H); 7.243-7.286 (m, 2H); 4.909 (s, 2H); 2.796 (s, 4H). LRMS m/z (M+H)$^+$ 360.3 found, 360.1 required.

7-[(2,5-Dioxopyrrolidin-1-yl)methyl]-4-(4-fluorophenyl)quinoline-2-carboxamide (2-7)

7-[(2,5-Dioxopyrrolidin-1-yl)methyl]-4-(4-fluorophenyl)quinoline-2-carbonitrile (2-6, 12.8 g, 35.5 mmol, 1.0 equiv.) was dissolved in acetone (473 mL)/water (237 mL) and sodium percarbonate (55.7 g, 178 mmol, 5.0 equiv) was added. The resulting mixture was stirred at 50° C. for 1.5 hours. The mixture was cooled and poured over aqueous NH$_4$Cl (saturated, 250 mL), extracted with ethyl acetate (3×200 mL), dried over Na$_2$SO$_4$, filtered and concentrated to afford 7-[(2,5-dioxopyrrolidin-1-yl)methyl]-4-(4-fluorophenyl)quinoline-2-carboxamide (2-7, 5.5 g, 41% over 3 steps) as a colorless solid. $^1$H NMR (400 MHz, CDCl$_3$): δ 8.216 (s, 1H); 8.156 (s, 1H); 8.091 (br s, 1H); 7.908 (d, J=8.69 Hz, 1H); 7.614 (dd, J$_1$=8.79 Hz, J$_2$=1.71 Hz, 1H); 7.470-7.498 (m, 2H); 7.211-7.262 (m, 2H); 5.668 (br s, 1H); 4.902 (s, 2H); 2.776 (s, 4H). LRMS m/z (M+H)$^+$ 378.3 found, 378.1 required.

The following compounds have been prepared according to procedures similar to those found in Scheme 2.1 and 2.2 selecting the appropriate quinoline derivative, nucleophile, and boronic acid derivative and provide examples of compounds in the invention.

TABLE 2

| Example | Structure | IUPAC Name | Exact Mass [M + H]$^+$ |
|---|---|---|---|
| 2-8 | 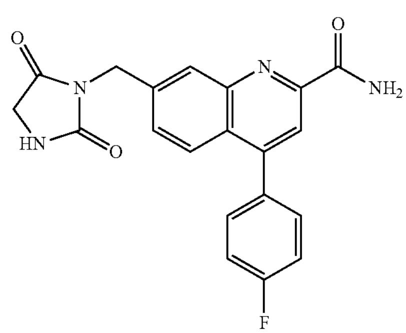 [SMILES: NC(=O)c1cc(-c2ccc(F)cc2)c2ccc(CN3C(=O)CNC3=O)cc2n1] | 7-[(2,5-dioxoimidazolidin-1-yl)methyl]-4-(4-fluorophenyl)quinoline-2-carboxamide | Calc'd 379.1, Found 379.1 |
| 2-9 | 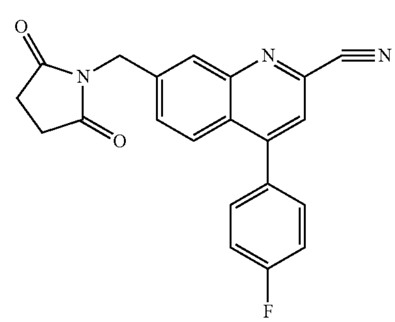 [SMILES: N#Cc1cc(-c2ccc(F)cc2)c2ccc(CN3C(=O)CCC3=O)cc2n1] | 7-[(2,5-dioxopyrrolidin-1-yl)methyl]-4-(4-fluorophenyl)quinoline-2-carbonitrile | Calc'd 360.1, Found 360.3 |

TABLE 2-continued

| Example | Structure | IUPAC Name | Exact Mass [M + H]+ |
|---|---|---|---|
| 2-10 | 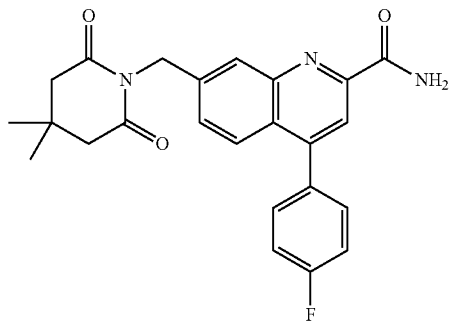 [SMILES: CC1(C)CC(=O)N(Cc2ccc3c(-c4ccc(F)cc4)cc(C(N)=O)nc3c2)C(=O)C1] | 7-[(4,4-dimethyl-2,6-dioxopiperidin-1-yl)methyl]-4-(4-fluorophenyl)quinoline-2-carboxamide | Calc'd 420.2, Found 420.2 |
| 2-11 | 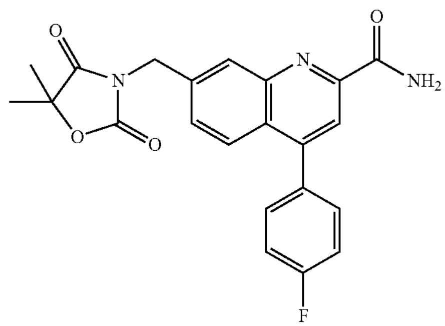 [SMILES: CC1(C)OC(=O)N(Cc2ccc3c(-c4ccc(F)cc4)cc(C(N)=O)nc3c2)C1=O] | 7-[(5,5-dimethyl-2,4-dioxo-1,3-oxazolidin-3-yl)methyl]-4-(4-fluorophenyl)quinoline-2-carboxamide | Calc'd 408.1, Found 408.1 |
| 2-12 | 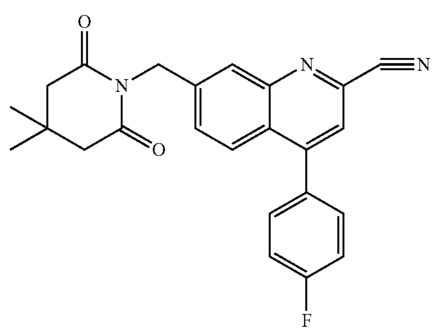 [SMILES: CC1(C)CC(=O)N(Cc2ccc3c(-c4ccc(F)cc4)cc(C#N)nc3c2)C(=O)C1] | 7-[(4,4-dimethyl-2,6-dioxopiperidin-1-yl)methyl]-4-(4-fluorophenyl)quinoline-2-carbonitrile | Calc'd 402.2, Found 402.2 |
| 2-13 | 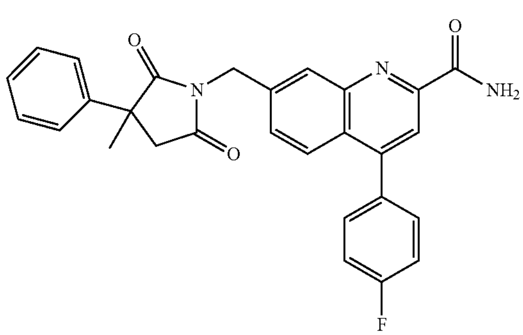 [SMILES: CC1(c2ccccc2)CC(=O)N(Cc2ccc3c(-c4ccc(F)cc4)cc(C(N)=O)nc3c2)C1=O] | 4-(4-fluorophenyl)-7-[(3-methyl-2,5-dioxo-3-phenylpyrrolidin-1-yl)methyl]quinoline-2-carboxamide | Calc'd 468.2, Found 468.2 |

TABLE 2-continued

| Example | Structure | IUPAC Name | Exact Mass [M + H]+ |
|---|---|---|---|
| 2-14 | 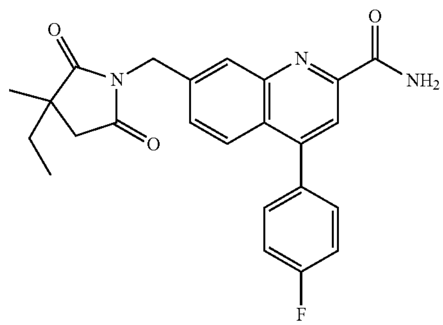 [SMILES: CCC1(C)CC(=O)N(Cc2ccc3c(-c4ccc(F)cc4)cc(C(N)=O)nc3c2)C1=O] | 7-[(3-ethyl-3-methyl-2,5-dioxopyrrolidin-1-yl)methyl]-4-(4-fluorophenyl)quinoline-2-carboxamide | Calc'd 420.2, Found 420.2 |
| 2-15 | 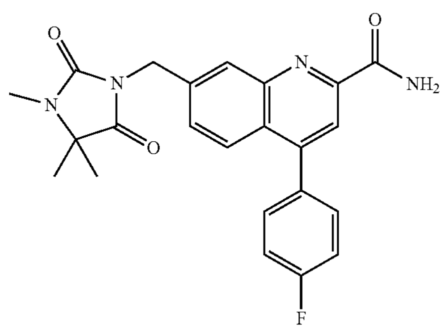 [SMILES: CN1C(=O)N(Cc2ccc3c(-c4ccc(F)cc4)cc(C(N)=O)nc3c2)C(=O)C1(C)C] | 4-(4-fluorophenyl)-7-[(3,4,4-trimethyl-2,5-dioxoimidazolidin-1-yl)methyl]quinoline-2-carboxamide | Calc'd 421.2, Found 421.2 |
| 2-16 | 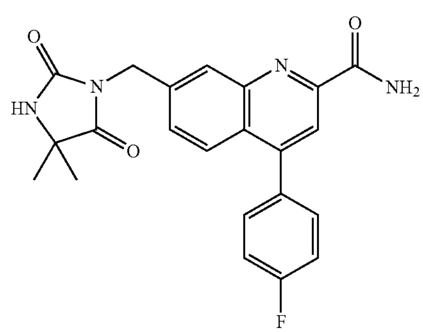 [SMILES: CC1(C)NC(=O)N(Cc2ccc3c(-c4ccc(F)cc4)cc(C(N)=O)nc3c2)C1=O] | 7-[(4,4-dimethyl-2,5-dioxoimidazolidin-1-yl)methyl]-4-(4-fluorophenyl)quinoline-2-carboxamide | Calc'd 407.2, Found 407.2 |
| 2-17 | 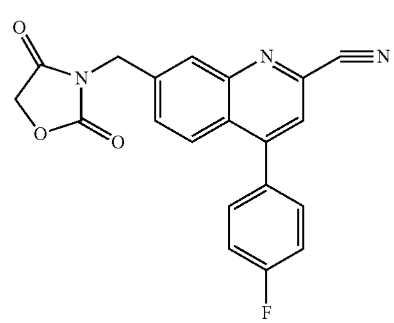 | 7-[(2,4-dioxo-1,3-oxazolidin-3-yl)methyl]-4-(4-fluorophenyl)quinoline-2-carbonitrile | Calc'd 362.1, Found 362.1 |

TABLE 2-continued

| Example | Structure | IUPAC Name | Exact Mass [M + H]+ |
|---|---|---|---|
| 2-18 | 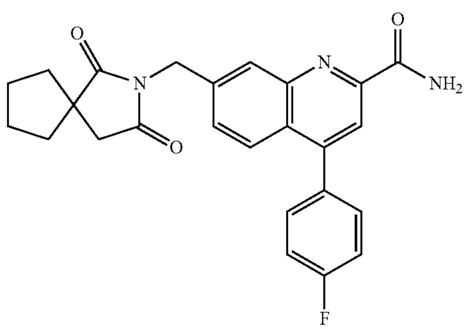 [SMILES: NC(=O)c1cc(-c2ccc(F)cc2)c2ccc(CN3C(=O)CC4(CCCC4)C3=O)cc2n1] | 7-[(1,3-dioxo-2-azaspiro[4.4]non-2-yl)methyl]-4-(4-fluorophenyl)quinoline-2-carboxamide | Calc'd 432.2, Found 432.2 |
| 2-19 | 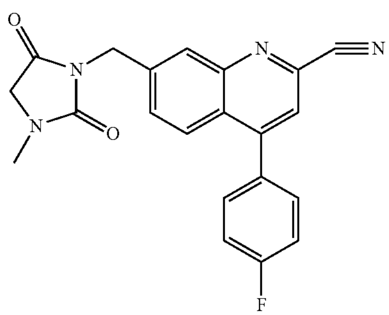 [SMILES: CN1CC(=O)N(Cc2ccc3c(-c4ccc(F)cc4)cc(C#N)nc3c2)C1=O] | 4-(4-fluorophenyl)-7-[(3-methyl-2,5-dioxoimidazolidin-1-yl)methyl]quinoline-2-carbonitrile | Calc'd 375.1, Found 375.1 |
| 2-20 | 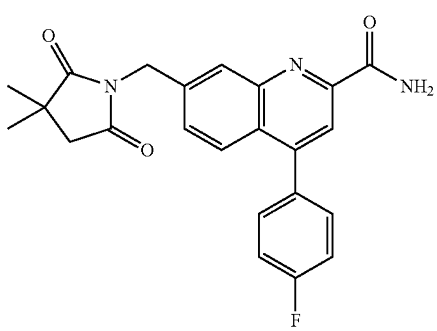 [SMILES: CC1(C)CC(=O)N(Cc2ccc3c(-c4ccc(F)cc4)cc(C(N)=O)nc3c2)C1=O] | 7-[(3,3-dimethyl-2,5-dioxopyrrolidin-1-yl)methyl]-4-(4-fluorophenyl)quinoline-2-carboxamide | Calc'd 406.2, Found 406.2 |
| 2-21 | 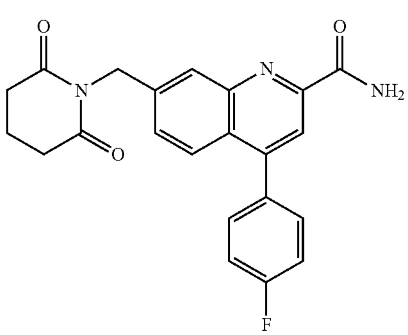 [SMILES: NC(=O)c1cc(-c2ccc(F)cc2)c2ccc(CN3C(=O)CCCC3=O)cc2n1] | 7-[(2,6-dioxopiperidin-1-yl)methyl]-4-(4-fluorophenyl)quinoline-2-carboxamide | Calc'd 392.1, Found 392.1 |

TABLE 2-continued

| Example | Structure | IUPAC Name | Exact Mass [M + H]+ |
|---|---|---|---|
| 2-22 | 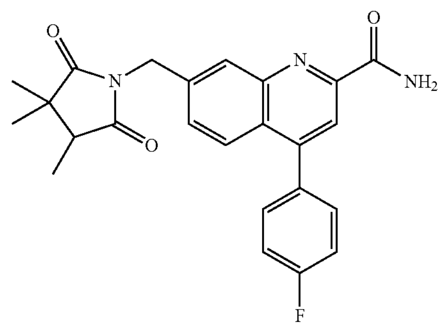 [SMILES: CC1C(=O)N(Cc2ccc3c(-c4ccc(F)cc4)cc(C(N)=O)nc3c2)C(=O)C1(C)C] | 4-(4-fluorophenyl)-7-[(3,3,4-trimethyl-2,5-dioxopyrrolidin-1-yl)methyl]quinoline-2-carboxamide | Calc'd 420.2, Found 420.2 |
| 2-23 | 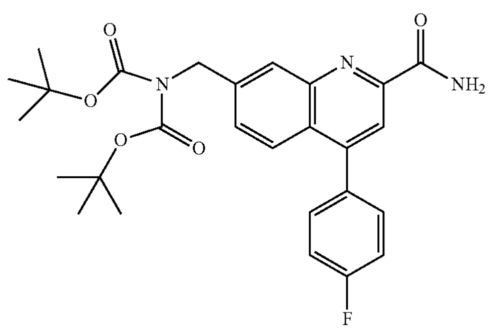 [SMILES: CC(C)(C)OC(=O)N(Cc1ccc2c(-c3ccc(F)cc3)cc(C(N)=O)nc2c1)C(=O)OC(C)(C)C] | di-tert-butyl {[2-carbamoyl-4-(4-fluorophenyl)quinolin-7-yl]methyl}imidodicarbonate | Calc'd 496.2, Found 496.2 |
| 2-24 | 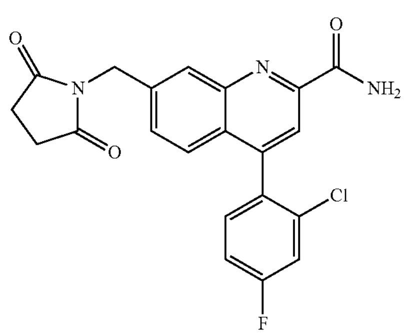 [SMILES: NC(=O)c1cc(-c2ccc(F)cc2Cl)c2ccc(CN3C(=O)CCC3=O)cc2n1] | 4-(2-chloro-4-fluorophenyl)-7-[(2,5-dioxopyrrolidin-1-yl)methyl]quinoline-2-carboxamide | Calc'd 412.1, Found 412.1 |
| 2-25 | 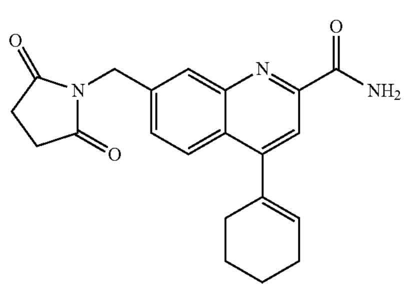 [SMILES: NC(=O)c1cc(C2=CCCCC2)c2ccc(CN3C(=O)CCC3=O)cc2n1] | 4-cylcohex-1-en-1-yl-7-[(2,5-dioxopyrrolidin-1-yl)methyl]quinoline-2-carboxamide | Calc'd 364.2, Found 364.2 |

TABLE 2-continued

| Example | Structure | IUPAC Name | Exact Mass [M + H]+ |
|---|---|---|---|
| 2-26 | 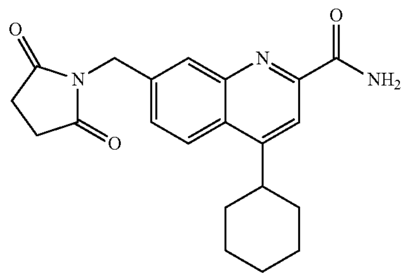 [SMILES: NC(=O)c1cc(C2CCCCC2)c2ccc(CN3C(=O)CCC3=O)cc2n1] | 4-cyclohexyl-7-[(2,5-dioxopyrrolidin-1-yl)methyl]quinoline-2-carboxamide | Calc'd 366.2, Found 366.3 |
| 2-27 | 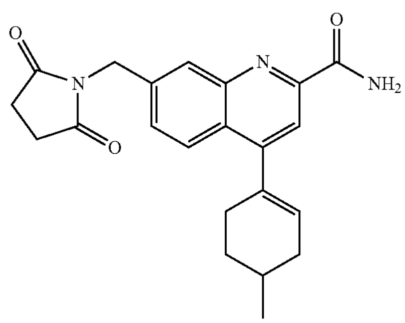 [SMILES: CC1CC=C(c2cc(C(N)=O)nc3cc(CN4C(=O)CCC4=O)ccc23)CC1] | 7-[(2,5-dioxopyrrolidin-1-yl)methyl]-4-(4-methylcyclohex-1-en-1-yl)quinoline-2-carboxamide | Calc'd 378.2, Found 378.2 |
| 2-28 | 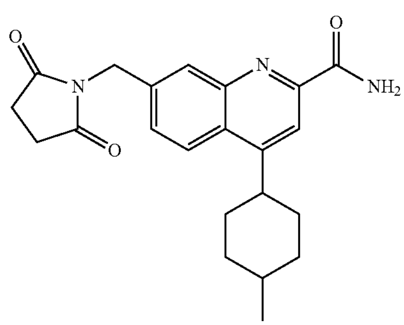 [SMILES: CC1CCC(c2cc(C(N)=O)nc3cc(CN4C(=O)CCC4=O)ccc23)CC1] | 7-[(2,5-dioxopyrrolidin-1-yl)methyl]-4-(4-methylcyclohexyl)quinoline-2-carboxamide | Calc'd 380.2, Found 380.2 |
| 2-29 | 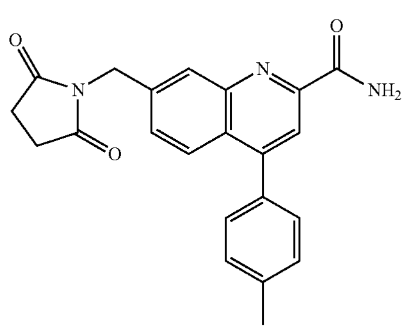 [SMILES: Cc1ccc(-c2cc(C(N)=O)nc3cc(CN4C(=O)CCC4=O)ccc23)cc1] | 7-[(2,5-dioxopyrrolidin-1-yl)methyl]-4-(4-methylphenyl)quinoline-2-carboxamide | Calc'd 374.2, Found 374.2 |

TABLE 2-continued

| Example | Structure | IUPAC Name | Exact Mass [M + H]+ |
|---|---|---|---|
| 2-30 | 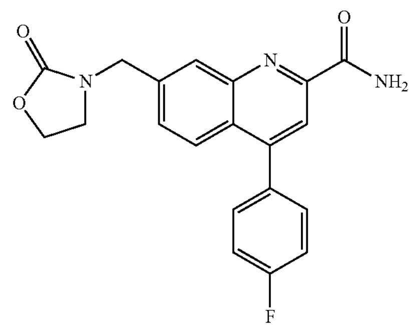 [SMILES: NC(=O)c1cc(-c2ccc(F)cc2)c2ccc(CN3CCOC3=O)cc2n1] | 4-(4-fluorophenyl)-7-[(2-oxo-1,3-oxazolidin-3-yl)methyl]quinoline-2-carboxamide | Calc'd 366.1, Found 366.1 |
| 2-31 | 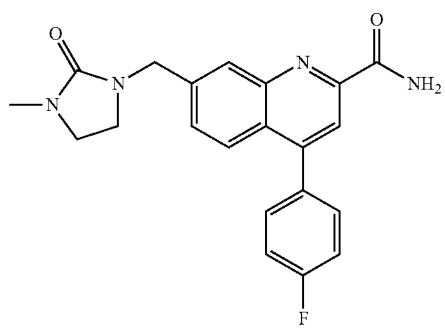 [SMILES: CN1CCN(Cc2ccc3c(-c4ccc(F)cc4)cc(C(N)=O)nc3c2)C1=O] | 4-(4-fluorophenyl)-7-[(3-methyl-2-oxoimidazolidin-1-yl)methyl]quinoline-2-carboxamide | Calc'd 379.2, Found 379.2 |
| 2-32 | 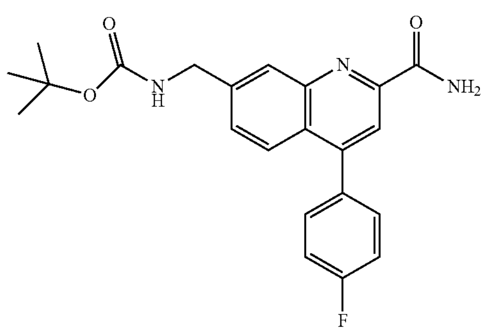 [SMILES: CC(C)(C)OC(=O)NCc1ccc2c(-c3ccc(F)cc3)cc(C(N)=O)nc2c1] | tert-butyl {[2-carbamoyl-4-(4-fluorophenyl)quinolin-7-yl]methyl}carbamate | Calc'd 396.2, Found 396.2 |
| 2-33 | 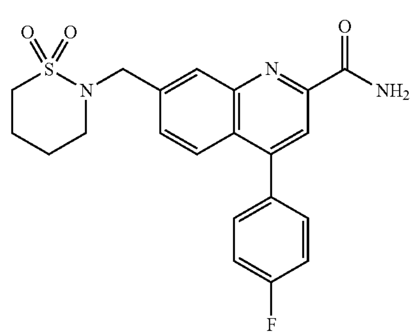 [SMILES: NC(=O)c1cc(-c2ccc(F)cc2)c2ccc(CN3CCCCS3(=O)=O)cc2n1] | 7-[(1,1-dioxido-1,2-thiazinan-2-yl)methyl]-4-(4-fluorophenyl)quinoline-2-carboxamide | Calc'd 414.1, Found 414.1 |

TABLE 2-continued

| Example | Structure | IUPAC Name | Exact Mass [M + H]+ |
|---|---|---|---|
| 2-34 | 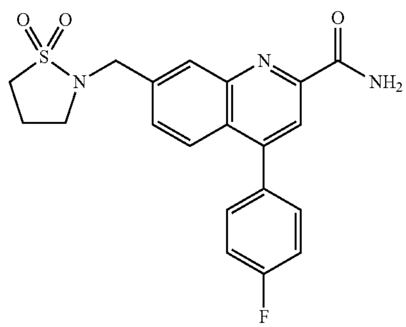 [SMILES: NC(=O)c1cc(-c2ccc(F)cc2)c2ccc(CN3CCCS3(=O)=O)cc2n1] | 7-[(1,1-dioxidoisothiazolidin-2-yl)methyl]-4-(4-fluorophenyl)quinoline-2-carboxamide | Calc'd 400.1, Found 400.1 |
| 2-35 | 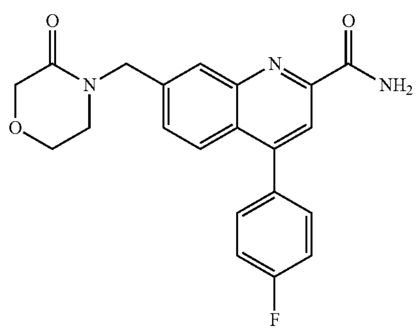 [SMILES: NC(=O)c1cc(-c2ccc(F)cc2)c2ccc(CN3CCOCC3=O)cc2n1] | 4-(4-fluorophenyl)-7-[(3-oxomorpholin-4-yl)methyl]quinoline-2-carboxamide | Calc'd 380.1, Found 380.1 |
| 2-36 | 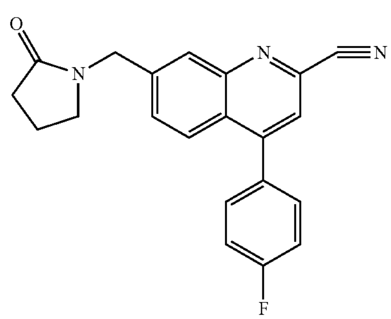 [SMILES: N#Cc1cc(-c2ccc(F)cc2)c2ccc(CN3CCCC3=O)cc2n1] | 4-(4-fluorophenyl)-7-[(2-oxopyrrolidin-1-yl)methyl]quinoline-2-carbonitrile | Calc'd 346.1, Found 346.3 |
| 2-37 | 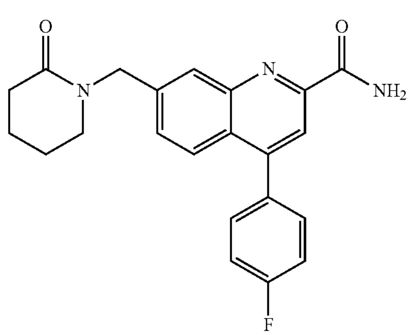 [SMILES: NC(=O)c1cc(-c2ccc(F)cc2)c2ccc(CN3CCCCC3=O)cc2n1] | 4-(4-fluorophenyl)-7-[(2-oxopiperidin-1-yl)methyl]quinoline-2-carboxamide | Calc'd 378.2, Found 378.2 |

TABLE 2-continued

| Example | Structure | IUPAC Name | Exact Mass [M + H]+ |
|---|---|---|---|
| 2-38 | 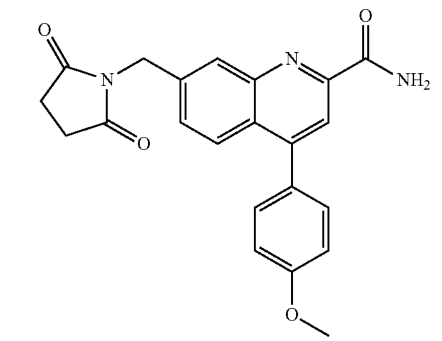 [SMILES: COc1ccc(-c2cc(C(N)=O)nc3cc(CN4C(=O)CCC4=O)ccc23)cc1] | 7-[(2,5-dioxopyrrolidin-1-yl)methyl]-4-(4-methoxyphenyl)quinoline-2-carboxamide | Calc'd 390.1, Found 390.0 |
| 2-39 | 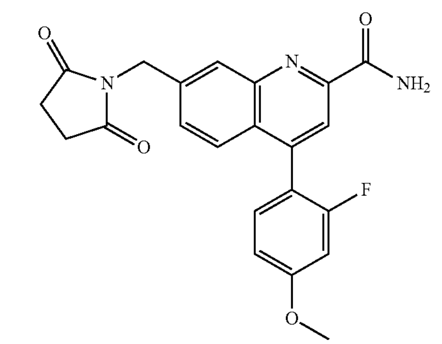 [SMILES: COc1ccc(-c2cc(C(N)=O)nc3cc(CN4C(=O)CCC4=O)ccc23)c(F)c1] | 7-[(2,5-dioxopyrrolidin-1-yl)methyl]-4-(2-fluoro-4-methoxyphenyl)quinoline-2-carboxamide | Calc'd 408.1, Found 408.0 |

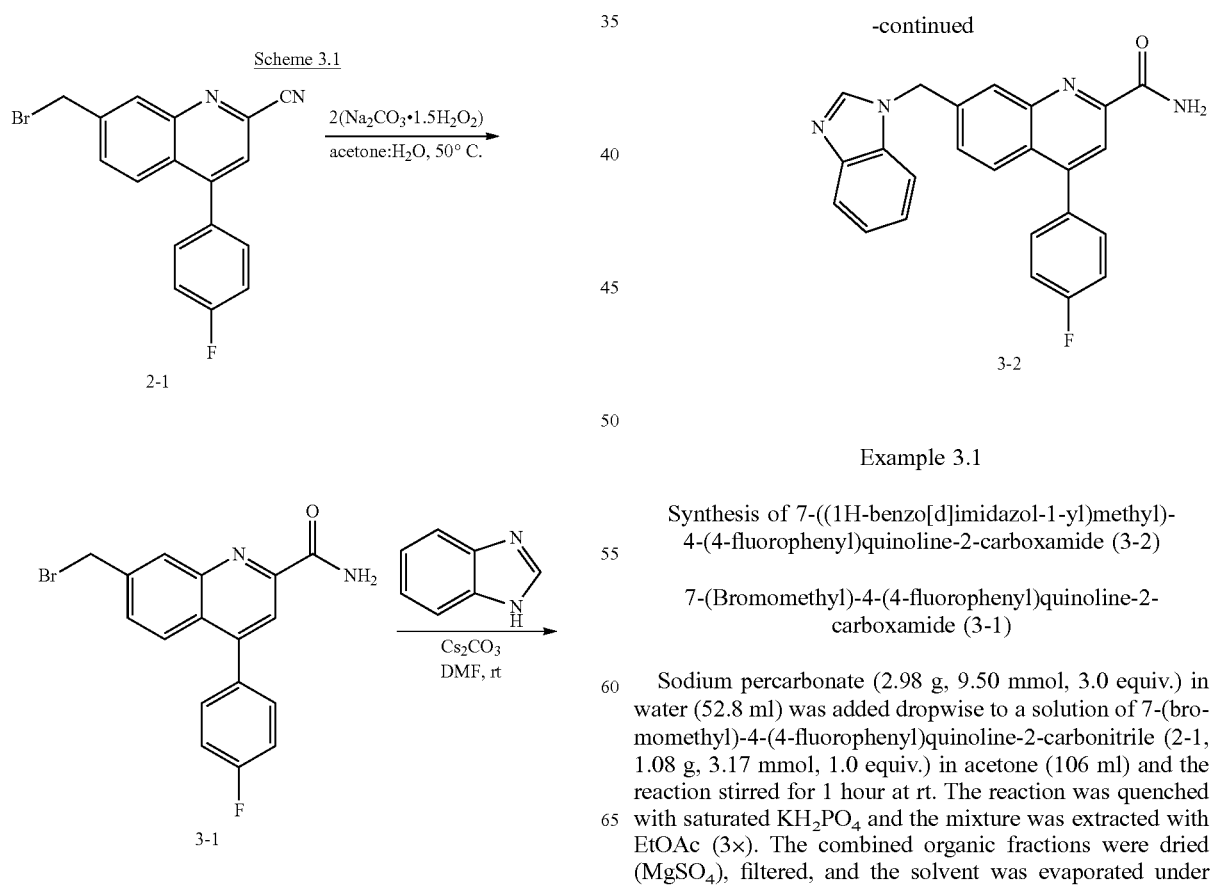

Scheme 3.1

Example 3.1

Synthesis of 7-((1H-benzo[d]imidazol-1-yl)methyl)-4-(4-fluorophenyl)quinoline-2-carboxamide (3-2)

7-(Bromomethyl)-4-(4-fluorophenyl)quinoline-2-carboxamide (3-1)

Sodium percarbonate (2.98 g, 9.50 mmol, 3.0 equiv.) in water (52.8 ml) was added dropwise to a solution of 7-(bromomethyl)-4-(4-fluorophenyl)quinoline-2-carbonitrile (2-1, 1.08 g, 3.17 mmol, 1.0 equiv.) in acetone (106 ml) and the reaction stirred for 1 hour at rt. The reaction was quenched with saturated $KH_2PO_4$ and the mixture was extracted with EtOAc (3×). The combined organic fractions were dried ($MgSO_4$), filtered, and the solvent was evaporated under reduced pressure. The crude product was purified by silica gel chromatography (120 g SiO₂, 0-100% EtOAc/hexanes) to afford 7-(bromomethyl)-4-(4-fluorophenyl)quinoline-2-carboxamide (3-1, 650 mg, 57%) as a white solid. LRMS m/z (M+H)⁺ 359.05 found, 359.19 required.

7-((1H-Benzo[d]imidazol-1-yl)methyl)-4-(4-fluorophenyl)quinoline-2-carboxamide (3-2)

Cs₂CO₃ (91 mg, 0.278 mmol, 2.0 equiv.) was added to a solution of 7-(bromomethyl)-4-(4-fluorophenyl)quinoline-2-carboxamide (3-1, 50 mg, 0.139 mmol, 1.0 equiv.) and benzimidazole (18.09 mg, 0.153 mmol, 1.1 equiv.) in DMF (696 µl) and the reaction stirred at rt for 2 hours. The crude residue was purified by reverse phase HPLC (H₂O/CH₃CN gradient w/ 0.1% TFA modifier). A Waters Porapak® Rxn CX (6 cc) was conditioned with MeOH (5 mL). Fractions containing the desired product were loaded onto the cartridge and the cartridge was washed with MeOH (10 mL). The desired product was eluted with 2M NH₃ in MeOH (5 mL) and the solvent removed in vacuo to afford 7-((1H-Benzo[d]imidazol-1-yl)methyl)-4-(4-fluorophenyl)quinoline-2-carboxamide (3-2, 23.6 mg, 43%) as a white solid. ¹H NMR (400 MHz, CD₃OD): δ 8.40 (s, 1H); 8.09 (s, 1H); 8.00-7.91 (m, 2H); 7.73-7.70 (m, 1H); 7.61-7.55 (m, 3H); 7.47 (dd, J=7.2, 2.0 Hz, 1H); 7.33-7.23 (m, 4H); 5.80 (s, 2H). LRMS m/z (M+H)⁺ 397.17 found, 397.42 required.

Scheme 3.2

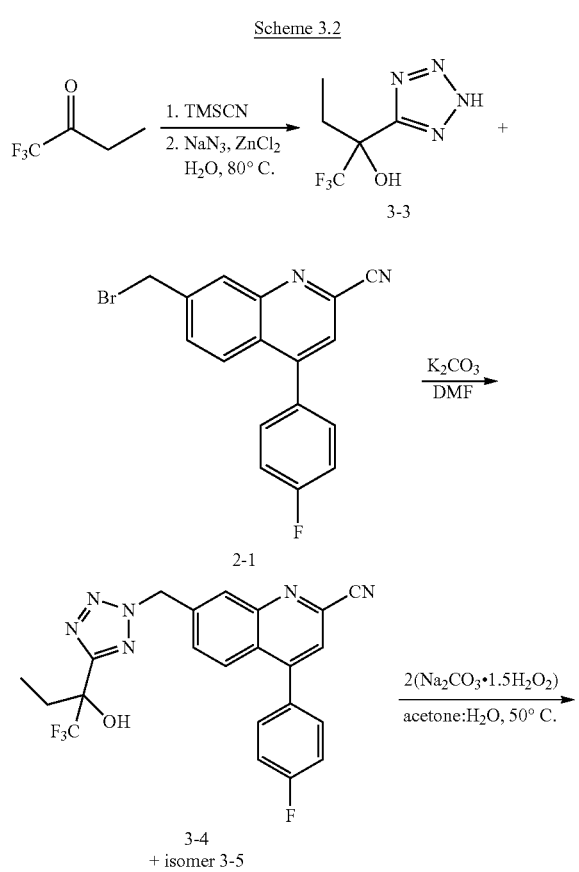

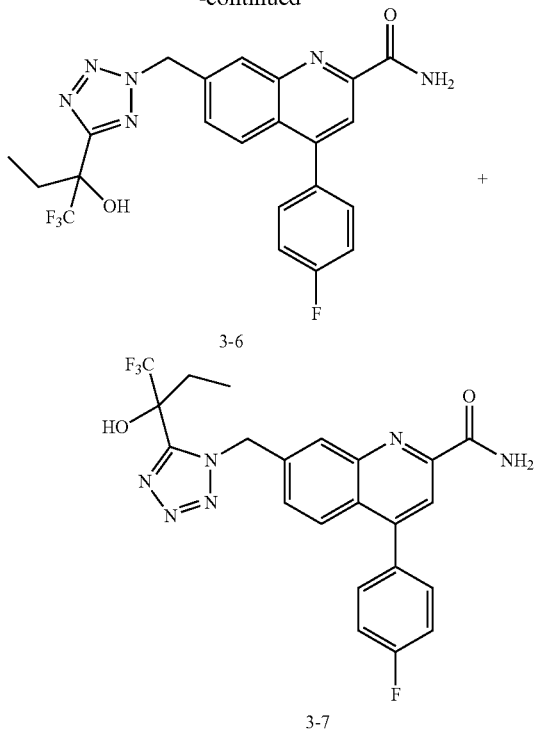

Example 3.2

Synthesis of 4-(4-fluorophenyl)-7-((5-(1,1,1-trifluoro-2-hydroxybutan-2-yl)-2H-tetrazol-2-yl)methyl)quinoline-2-carboxamide (3-6)

1,1,1-Trifluoro-2-(2H-tetrazol-5-yl)butan-2-ol (3-3)

To 1,1,1-trifluorobutan-2-one (5.0 g, 39.7 mmol, 1.0 equiv) was slowly added trimethylsilylcyanide (4.7 g, 47.6 mmol, 1.2 equiv) and the resulting mixture stirred overnight at ambient temperature. To the resulting mixture was added water (80 mL) followed by zinc chloride (5.4 g, 39.7 mmol, 1.0 equiv) and sodium azide (3.1 g, 47.1 mmol, 1.2 equiv) and the mixture was heated at 80° C. for three hours. The mixture was cooled to room temperature and the precipitate was filtered and dried in vacuo to afford 1,1,1-trifluoro-2-(2H-tetrazol-5-yl)butan-2-ol (3-3) as a white solid. LRMS m/z (M+H)⁺ 197.0 found, 197.1 required.

4-(4-fluorophenyl)-7-{[5-(1,1,1-trifluoro-2-hydroxybutan-2-yl)-2H-tetrazol-2-yl]methyl}quinoline-2-carbonitrile (3-4)

7-(Bromomethyl)-4-(4-fluorophenyl)quinoline-2-carbonitrile (2-1, 120 mg, 0.35 mmol, 1.0 equiv), 1,1,1-trifluoro-2-(2H-tetrazol-5-yl)butan-2-ol (3-3, 83 mg, 0.42 mmol, 1.2 equiv) and potassium carbonate (146 mg, 1.1 mmol, 3.0 equiv) were combined in DMF (1.8 mL) and stirred at ambient temperature for 16 hours. The solids were filtered and the filtrate was purified by reverse phase HPLC (H₂O/CH₃CN gradient w/0.1% TFA modifier) to afford 4-(4-fluorophenyl)-7-{[5-(1,1,1-trifluoro-2-hydroxybutan-2-yl)-2H-tetrazol-2-yl]methyl}quinoline-2-carbonitrile (3-4) and 4-(4-fluorophenyl)-7-{[5-(1,1,1-trifluoro-2-hydroxybutan-2-yl)-1H-tetrazol-1-yl]methyl}quinoline-2-carbonitrile (3-5). $^1$H NMR (3-4) (500 MHz, CDCl$_3$): δ 8.26 (d, J=1.7 Hz, 1H); 7.99 (d, J=8.8 Hz, 1H); 7.68 (s, 1H); 7.59 (dd, J=8.8, 1.9 Hz, 1H); 7.50-7.45 (m, 2H); 7.31-7.25 (m, 2H); 6.07 (s, 2H); 2.33 (dt, J=14.3, 7.4 Hz, 1H); 2.24-2.16 (m, 1H); 0.84 (t, J=7.5 Hz, 3H). LRMS m/z (M+H)$^+$ 456.8 found, 457.1 required. $^1$H NMR (3-5) (500 MHz, CDCl$_3$): δ 8.15 (s, 1H); 7.94 (d, J=8.8 Hz, 1H); 7.65-7.61 (m, 2H); 7.48-7.44 (m, 2H); 7.30-7.24 (m, 2H); 6.13 (d, J=15.0 Hz, 1H); 6.01 (d, J=15.0 Hz, 1H); 3.14-3.06 (brs, 1H); 2.75 (dt, J=14.8, 7.5 Hz, 1H); 2.16 (dq, J=14.7, 7.3 Hz, 1H); 0.89 (t, J=7.4 Hz, 3H). LRMS m/z (M+H)$^+$ 456.8 found, 457.1 required.

4-(4-fluorophenyl)-7-{[5-(1,1,1-trifluoro-2-hydroxybutan-2-yl)-2H-tetrazol-2-yl]methyl}quinoline-2-carboxamide (3-6)

4-(4-Fluorophenyl)-7-{[5-(1,1,1-trifluoro-2-hydroxybutan-2-yl)-2H-tetrazol-2-yl]methyl}quinoline-2-carbonitrile (3-4, 14 mg, 0.031 mmol, 1.0 equiv) was dissolved in acetone (0.5 mL)/water (0.25 mL) and sodium percarbonate (48 mg, 0.15 mmol, 5.0 equiv) was added. The resulting mixture was heated to 50° C. for two hours. The mixture was cooled and poured over aqueous NH$_4$Cl (1 mL), extracted with ethyl acetate (3×5 mL), dried over MgSO$_4$, filtered and concentrated. The crude residue was purified by flash column chromatography (SiO$_2$, 12 g ISCO column, 0-100% EtOAc/hexanes) to give 4-(4-fluorophenyl)-7-{[5-(1,1,1-trifluoro-2-hydroxybutan-2-yl)-2H-tetrazol-2-yl]methyl}quinoline-2-carboxamide (3-6) as a white solid. $^1$H NMR (3-6) (500 MHz, CDCl$_3$): δ 8.28 (s, 1H); 8.17 (s, 1H); 8.06 (s, 1H); 7.99 (d, J=8.7 Hz, 1H); 7.55-7.44 (m, 3H); 6.05 (s, 2H); 5.84 (s, 1H); 3.92 (s, 1H); 2.33 (dt, J=14.4, 7.4 Hz, 1H); 2.20 (dt, J=14.3, 7.2 Hz, 1H); 0.84 (t, J=7.4 Hz, 3H). LRMS m/z (M+H) 474.9 found, 475.1 required. $^1$H NMR (3-7) (500 MHz, CD$_3$OD): δ 8.12 (s, 1H); 8.08 (s, 1H); 7.96 (d, J=8.8 Hz, 1H); 7.64-7.55 (m, 3H); 7.34-7.29 (m, 2H); 6.25 (d, J=15.1 Hz, 1H); 6.15 (d, J=15.1 Hz, 1H); 2.57 (dd, J=14.4, 7.3 Hz, 1H); 2.13 (dq, J=14.4, 7.2 Hz, 1H); 0.78 (t, J=7.4 Hz, 3H). LRMS m/z (M+H)$^+$ 474.7 found, 475.1 required.

Scheme 3.3

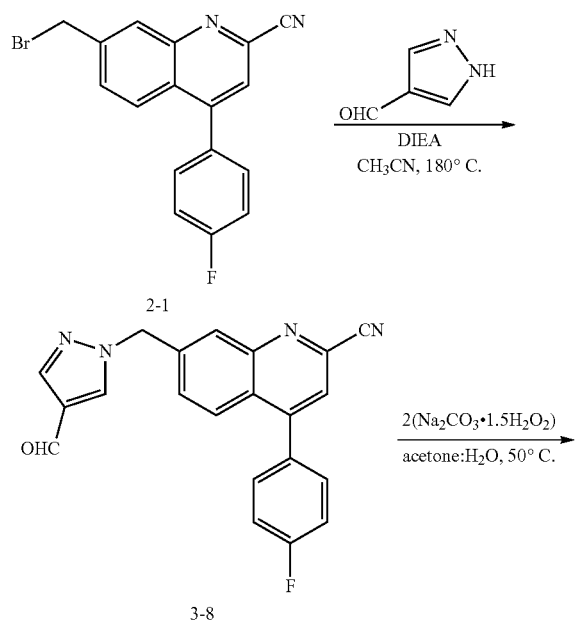

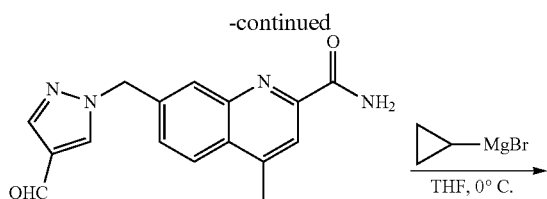

3-9

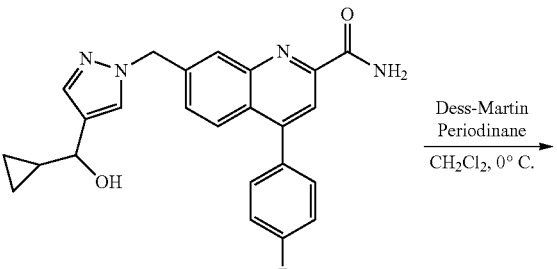

3-10

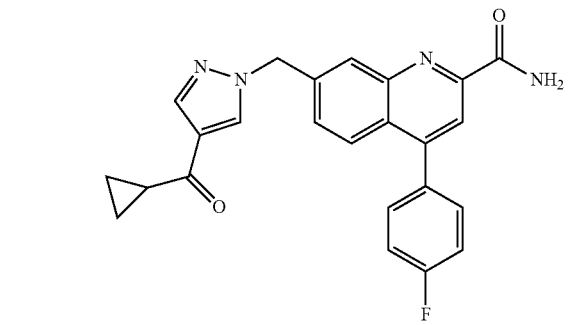

3-11

Example 3.3

Synthesis of 7-{[4-(cyclopropylcarbonyl)-1H-pyrazol-1-yl]methyl}-4-(4-fluorophenyl)quinoline-2-carboxamide (3-11)

4-(4-Fluorophenyl)-7-[(4-formyl-1H-pyrazol-1-yl)methyl]quinoline-2-carbonitrile (3-8)

7-(Bromomethyl)-4-(4-fluorophenyl)quinoline-2-carbonitrile (2-1, 100.0 mg, 0.293 mmol, 1.0 equiv.), DIEA (0.051 ml, 0.293 mmol, 1.0 equiv.), and 1-H-pyrazole-4-carbaldehyde (33.8 mg, 0.352 mmol, 1.2 equiv.) were added to acetonitrile (1.0 mL) in a microwave reaction vessel and the resulting mixture was irradiated with microwave at 180° C. for 30 minutes. The reaction mixture was cooled and concentrated and the residue was purified by reverse phase HPLC (H$_2$O/CH$_3$CN gradient w/ 0.1% TFA modifier) to afford 4-(4-fluorophenyl)-7-[(4-formyl-1H-pyrazol-1-yl)methyl]quinoline-2-carbonitrile (3-8, 55.0 mg, 52.7%) as a colorless solid. LRMS m/z (M+H)$^+$ 357.1 found, 357.1 required.

4-(4-Fluorophenyl)-7-[(4-formyl-1H-pyrazol-1-yl)methyl]quinoline-2-carboxamide (3-9)

4-(4-Fluorophenyl)-7-[(4-formyl-1H-pyrazol-1-yl)methyl]quinoline-2-carbonitrile (3-8), 51 mg, 0.143 mmol, 1.0 equiv.) was dissolved in acetone (1.0 mL)/water (0.5 mL) and sodium percarbonate (225.0 mg, 0.716 mmol, 5.0 equiv) was added. The resulting mixture was stirred at 50° C. for two hours. The mixture was cooled and poured over aqueous NH₄Cl (saturate, 1.0 mL), extracted with Ethyl Acetate (3×5.0 mL), dried over MgSO₄, filtered and concentrated. The residue was purified by reverse phase HPLC (H₂O/CH₃CN gradient w/ 0.1% TFA modifier) to afford 4-(4-Fluorophenyl)-7-[(4-formyl-1H-pyrazol-1-yl)methyl]quinoline-2-carbonitrile (3-9, 40.0 mg, 74.7%) as a colorless solid. ¹H NMR (400 MHz, CDCl₃): δ 9.879 (s, 1H); 8.262 (s, 1H); 8.056 (br s, 2H); 8.021 (br s, 2H); 7.972 (d, J=8.80 Hz, 1H); 7.462-7.512 (m, 3H); 7.216-7.259 (m, 2H); 5.705 (br s, 1H); 5.589 (s, 2H). LRMS m/z (M+H)⁺ 375.1 found, 375.1 required.

7-({4-[Cyclopropyl(hydroxy)methyl]-1H-pyrazol-1-yl}methyl)-4-(4-fluorophenyl)quinoline-2-carboxamide (3-10)

To a 0° C. solution of 4-(4-fluorophenyl)-7-[(4-formyl-1H-pyrazol-1-yl)methyl]quinoline-2-carboxamide (3-9, 36.0 mg, 0.0960 mmol, 1.0 equiv.) in anhydrous THF, under nitrogen was added dropwise 0.5 M cyclopropylmagnesium bromide in THF (0.769 mL, 0.385 mmol, 4.0 equiv.). The resulting mixture was stirred at 0° C. for 1 hour, quenched with sat. aqueous NH₄Cl, extracted with ethyl acetate (3×5.0 mL), dried over MgSO₄, filtered and concentrated. The residue was purified by reverse phase HPLC (H₂O/CH₃CN gradient w/ 0.1% TFA modifier) to afford 7-({4-[cyclopropyl(hydroxy)methyl]-1H-pyrazol-1-yl}methyl)-4-(4-fluorophenyl)quinoline-2-carboxamide (3-10, 25.0 mg, 62.4%) as a colorless solid. ¹H NMR (400 MHz, CDCl₃): δ 8.228 (s, 1H); 8.084 (br s, 1H); 7.995 (s, 1H); 7.929 (d, J=8.81 Hz, 1H); 7.625 (s, 1H); 7.515 (s, 1H); 7.442-7.506 (m, 3H); 7.206-7.249 (m, 2H); 5.777 (br s, 1H); 5.526 (s, 2H); 4.044 (d, J=8.48 Hz, 1H); 1.185-1.258 (m, 1H); 0.599-0.638 (m, 2H); 0.331-0.454 (m, 2H). LRMS m/z (M+H)⁺ 417.2 found, 417.2 required.

7-{[4-(Cyclopropylcarbonyl)-1H-pyrazol-1-yl]methyl}-4-(4-fluorophenyl)quinoline-2-carboxamide (3-11)

To a room temperature solution of 7-({4-[cyclopropyl(hydroxy)methyl]-1H-pyrazol-1-yl}methyl)-4-(4-fluorophenyl)quinoline-2-carboxamide (3-10, 22 mg, 0.053 mmol, 1.0 equiv.) in methylene chloride (1.0 mL) was added Dess-Martin Periodinane (67.2 mg, 0.158 mmol, 3.0 equiv.) and the mixture was stirred at room temperature overnight. Aqueous Na₂S₂O₃ (saturate, 2.0 mL) and aqueous sodium hydrogen carbonate (saturate, 5.0 mL) were added and the mixture was extracted with ethyl acetate (3×5 mL). The combined organic layers were washed with brine, dried over MgSO₄, filtered and concentrated. The residue was purified by reverse phase HPLC (H₂O/CH₃CN gradient w/ 0.1% TFA modifier) to afford 7-{[4-(cyclopropylcarbonyl)-1H-pyrazol-1-yl]methyl}-4-(4-fluorophenyl)quino line-2-carboxamide (3-11, 3.30 mg, 15.1%) as a colorless solid. ¹H NMR (400 MHz, CDCl₃): δ 8.239 (s, 1H); 8.179 (br s, 1H); 8.088 (s, 1H); 8.039 (s, 1H); 8.017 (s, 1H); 7.965 (d, J=8.81 Hz, 1H); 7.466-7.510 (m, 3H); 7.219-7.263 (m, 2H); 6.369 (br s, 1H); 5.585 (s, 2H); 2.283-2.345 (m, 1H); 1.187-1.225 (m, 2H); 0.958-1.004 (m, 2H). LRMS m/z (M+H)⁺ 415.2 found, 415.2 required.

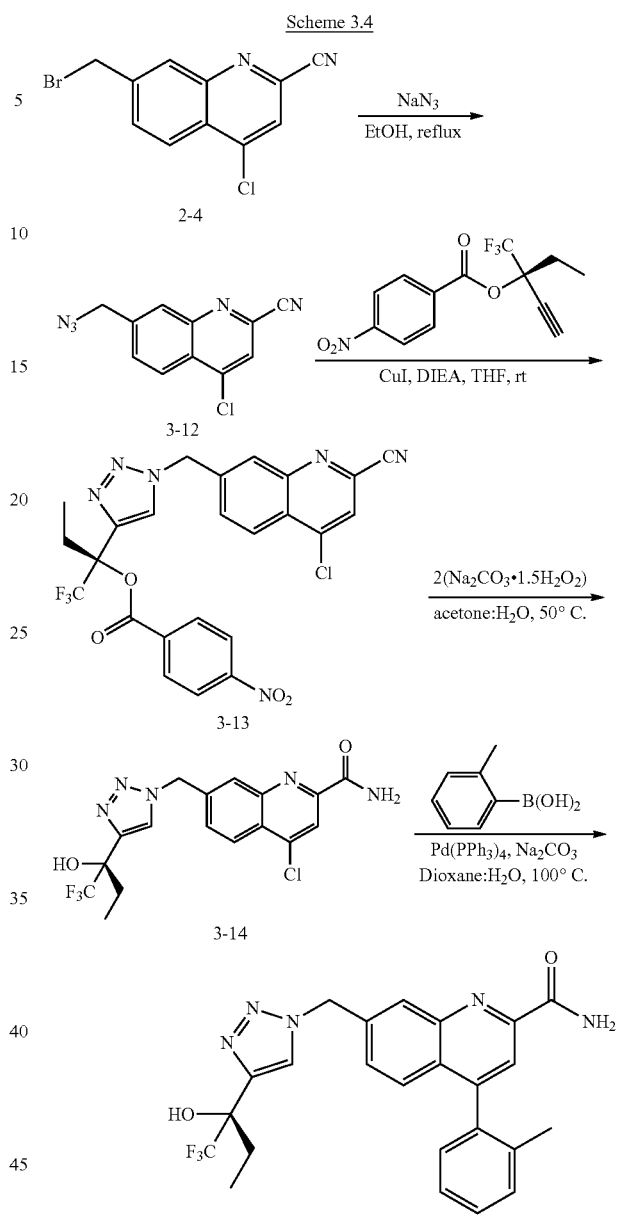

Example 3.4

4-(o-Tolyl)-7-((4-(1,1,1-trifluoro-2-hydroxybutan-2-yl)-1H-1,2,3-triazol-1-yl)methyl)quinoline-2-carboxamide (3-15)

7-(Azidomethyl)-4-chloroquinoline-2-carbonitrile (3-12)

Sodium azide (1.690 g, 26.0 mmol, 1.3 equiv.) was added to a stirred solution of 7-(bromomethyl)-4-chloroquinoline-2-carbonitrile (2-4, 5.63 g, 20.00 mmol) in 100 ml of EtOH, and the resulting slurry mixture was refluxed for 1 h. The mixture was cooled to rt, water (100 ml) was added, and the slurry was stirred at rt for 30 min. The resulting solid was collected by filtration and air dried to afford 7-(azidomethyl)-4-chloroquinoline-2-carbonitrile (3-12, 4.75 g, 97%) as a white solid. LRMS m/z (M+H)$^+$ 244.1 found, 244.65 required.

(S)-2-(1-((4-Chloro-2-cyanoquinolin-7-yl)methyl)-1H-1,2,3-triazol-4-yl)-1,1,1-trifluorobutan-2-yl 4-nitrobenzoate (3-13)

To a solution of 7-(azidomethyl)-4-chloroquinoline-2-carbonitrile (3-12, 1 g, 4.10 mmol, 1 equiv.) and (S)-3-(trifluoromethyl)pent-1-yl-3-yl 4-nitrobenzoate (1.360 g, 4.51 mmol, 1.1 equiv.) in THF (20.5 mL) was added DIEA (3.58 ml, 20.52 mmol, 5 equiv.) and copper (I) iodide (1.172 g, 6.16 mmol, 1.5 equiv.), then stirred at rt for 2 h. The reaction was stopped by addition of saturated NH$_4$Cl. The resulting mixture was extracted with EtOAc. The combined organic layers were dried over Na$_2$SO$_4$, filtered and concentrated. The residue was treated with MeOH. The resulting solid was collected by filtration, washed with MeOH, and air dried to afford (S)-2-(1-((4-chloro-2-cyanoquinolin-7-yl)methyl)-1H-1,2,3-triazol-4-yl)-1,1,1-trifluorobutan-2-yl 4-nitrobenzoate (3-13, 1.58 g, 71%) as a colorless solid. LRMS m/z (M+H)$^+$ 545.4 found, 545.9 required.

4-Chloro-7-((4[(2S)-(1,1,1-trifluoro-2-hydroxybutan-2-yl)]-1H-1,2,3-triazol-1-yl)methyl)quinoline-2-carboxamide (3-14)

To (S)-2-(1-((4-chloro-2-cyanoquinolin-7-yl)methyl)-1H-1,2,3-triazol-4-yl)-1,1,1-trifluorobutan-2-yl 4-nitrobenzoate (3-13, 1.58 g, 2.90 mmol, 1 equiv.) in acetone/H$_2$O (38.7 ml/19.33 mL) was added sodium percarbonate (4.55 g, 14.50 mmol, 5 equiv.) and the mixture was heated to 50° C. overnight. The reaction was incomplete. Sodium percarbonate (4.55 g, 14.50 mmol, 5 equiv.) was added and stirred for an additional 5 hr. The mixture was cooled, water was added, and the mixture was extracted with EtOAc. The combined organic fractions were washed with brine, dried (MgSO$_4$), filtered, and the solvent was evaporated under reduced pressure to afford 4-chloro-7-((4-[(2S)-(1,1,1-trifluoro-2-hydroxybutan-2-yl)]-1H-1,2,3-triazol-1-yl)methyl)quinoline-2-carboxamide (3-14, 1.09 g, 91%) as light yellow solid. LRMS m/z (M+H)$^+$ 414.3 found, 414.8 required.

7-({4-[(1S)-1-hydroxy-1-(trifluoromethyl)propyl]-1H-1,2,3-triazol-1-yl}methyl)-4-(2-methylphenyl)quinoline-2-carboxamide (3-15)

4-chloro-7-({4-[(2S)-1,1,1-trifluoro-2-hydroxybutan-2-yl]-1H-1,2,3-triazol-1-yl}methyl)quinoline-2-carboxamide (3-14, 8 mg, 0.02 mmol, 1.0 equiv.), (2-methylphenyl)boronic acid (5 mg, 0.04 mmol, 2 equiv.), Pd(PPh$_3$)$_4$ (0.7 mg, 0.0006 mmol, 0.03 equiv.) and 2M aqueous Na$_2$CO$_3$ (0.02 mL, 0.05 mmol, 2.5 equiv.) were suspended in Dioxane (0.4 mL) and the reaction mixture was heated overnight at 100° C. The crude mixture was filtered, concentrated and purified by reverse phase HPLC (H$_2$O/CH$_3$CN gradient w/ 0.1% TFA modifier) to afford 7-({4-[(1S)-1-hydroxy-1-(trifluoromethyl)propyl]-1H-1,2,3-triazol-1-yl}methyl)-4-(2-methylphenyl)quinoline-2-carboxamide (3-15). LRMS m/z (M+H)$^+$ 470.1 found, 470.2 required.

Scheme 3.5

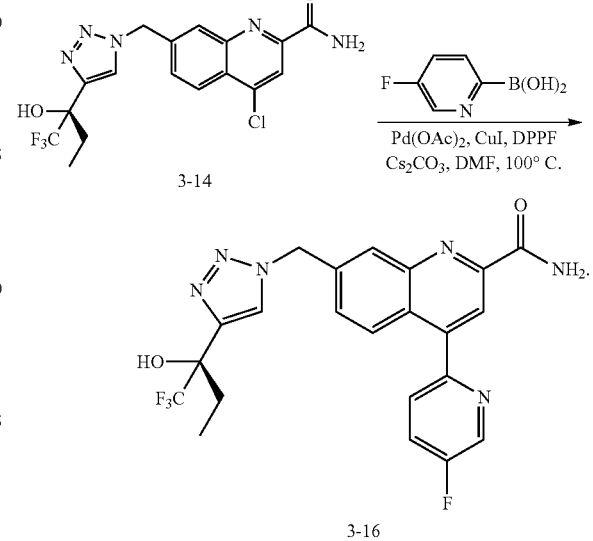

Example 3.5

Synthesis of 4-(5-fluoropyridin-2-yl)-7-({4-[(2S)-1,1,1-trifluoro-2-hydroxybutan-2-yl]-1H-1,2,3-triazol-1-yl}methyl)quinoline-2-carboxamide (3-16)

4-(5-Fluoropyridin-2-yl)-7-({4-[(2S)-1,1,1-trifluoro-2-hydroxybutan-2-yl]-1H-1,2,3-triazol-1-yl}methyl)quinoline-2-carboxamide (3-16)

4-chloro-7-({4-[(2S)-1,1,1-trifluoro-2-hydroxybutan-2-yl]-1H-1,2,3-triazol-1-yl}methyl)quinoline-2-carboxamide (3-14, 16.0 mg, 0.039 mmol, 1.0 equiv), (5-fluoropyridin-2-yl)boronic acid (22 mg, 0.097 mmol, 2.5 equiv), cesium carbonate (25 mg, 0.077 mmol, 2.0 equiv), DPPF (2.1 mg, 0.004 mmol, 0.1 equiv), copper(I) chloride (3.8 mg, 0.039 mmol, 1.0 equiv) and palladium(II) acetate (0.43 mg, 0.002 mmol, 0.05 equiv) were combined and purged with argon. DMF (0.4 mL) was added and the mixture was heated at 100° C. for 14 hours. The mixture was filtered purified by reverse phase HPLC (H$_2$O/CH$_3$CN gradient w/ 0.1% TFA modifier) to afford 4-(5-fluoropyridin-2-yl)-7-({4-[(2S)-1,1,1-trifluoro-2-hydroxybutan-2-yl]-1H-1,2,3-triazol-1-yl}methyl)quinoline-2-carboxamide (3-16) as a white solid. LRMS m/z (M+H)$^+$ 475.1 found, 475.2 required The following compounds have been prepared according to procedures similar to those found in Scheme 2.1, 3.1, 3.2, 3.3, 3.4, and 3.5 selecting the appropriate quinoline derivative, nucleophile, and boronic acid derivative and provide examples of compounds in the invention.

TABLE 3

| Example | Structure | IUPAC Name | Exact Mass [M + H]+ |
|---|---|---|---|
| 3-17 | 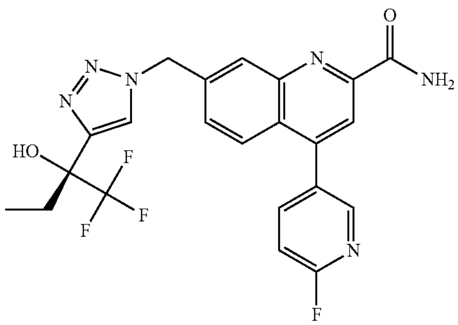 [SMILES: CC[C@@](O)(c1cn(Cc2ccc3c(-c4ccc(F)nc4)cc(C(N)=O)nc3c2)nn1)C(F)(F)F] | 4-(6-fluoropyridin-3-yl)-7-({4-[(1R)-1-hydroxy-1-(trifluoromethyl)propyl]-1H-1,2,3-triazol-1-yl}methyl)quinoline-2-carboxamide | Calc'd 475.2, Found 475.2 |
| 3-18 | 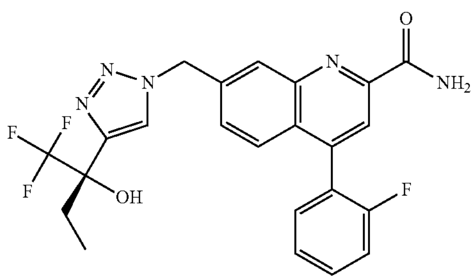 [SMILES: CC[C@](O)(c1cn(Cc2ccc3c(-c4ccccc4F)cc(C(N)=O)nc3c2)nn1)C(F)(F)F] | 4-(2-fluorophenyl)-7-({4-[(1S)-1-hydroxy-1-(trifluoromethyl)propyl]-1H-1,2,3-triazol-1-yl}methyl)quinoline-2-carboxamide | Calc'd 474.2, Found 474.1 |
| 3-19 | 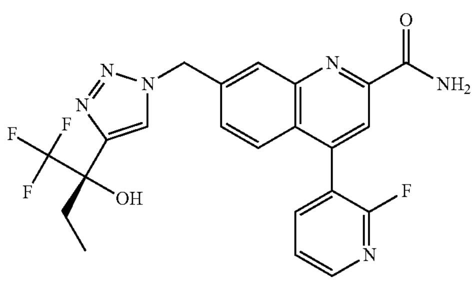 [SMILES: CC[C@](O)(c1cn(Cc2ccc3c(-c4cccnc4F)cc(C(N)=O)nc3c2)nn1)C(F)(F)F] | 4-(2-fluoropyridin-3-yl)-7-({4-[(1S)-1-hydroxy-1-(trifluoromethyl)propyl]-1H-1,2,3-triazol-1-yl}methyl)quinoline-2-carboxamide | Calc'd 475.2, Found 475.1 |
| 3-20 | 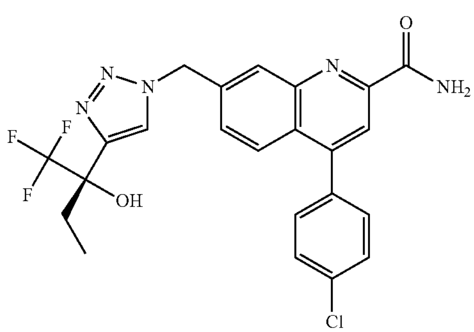 [SMILES: CC[C@](O)(c1cn(Cc2ccc3c(-c4ccc(Cl)cc4)cc(C(N)=O)nc3c2)nn1)C(F)(F)F] | 4-(4-chlorophenyl)-7-({4-[(1S)-1-hydroxy-1-(trifluoromethyl)propyl]-1H-1,2,3-triazol-1-yl}methyl)quinoline-2-carboxamide | Calc'd 490.1, Found 490.0 |
| 3-21 | 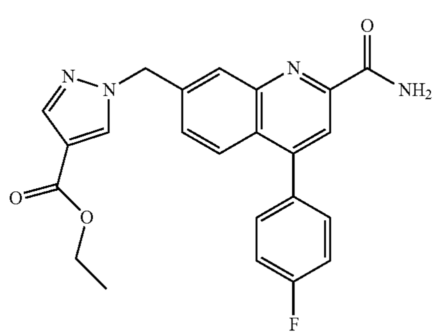 [SMILES: CCOC(=O)c1cnn(Cc2ccc3c(-c4ccc(F)cc4)cc(C(N)=O)nc3c2)c1] | ethyl 1-{[2-carbamoyl-4-(4-fluorophenyl)quinolin-7-yl]methyl}-1H-pyrazol-4-carboxylate | Calc'd 419.2, Found 419.2 |

TABLE 3-continued

| Example | Structure | IUPAC Name | Exact Mass [M + H]+ |
|---|---|---|---|
| 3-22 | 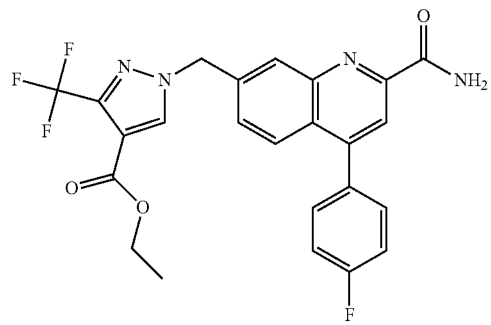 [SMILES: CCOC(=O)c1cn(Cc2ccc3c(-c4ccc(F)cc4)cc(C(N)=O)nc3c2)nc1C(F)(F)F] | ethyl 1-{[2-carbamoyl-4-(4-fluorophenyl)quinolin-7-yl]methyl}-3-(trifluoromethyl)-1H-pyrazole-4-carboxylate | Calc'd 487.1, Found 487.1 |
| 3-23 | 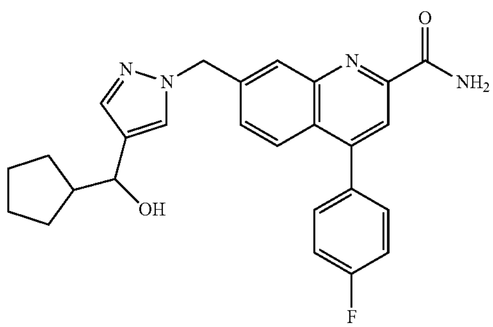 [SMILES: NC(=O)c1cc(-c2ccc(F)cc2)c2ccc(Cn3cc(C(O)C4CCCC4)cn3)cc2n1] | 7-({4-[cyclopentyl(hydroxy)methyl]-1H-pyrazol-1-yl}methyl)-4-(4-fluorophenyl)quinoline-2-carboxamide | Calc'd 445.2, Found 445.2 |
| 3-24 | 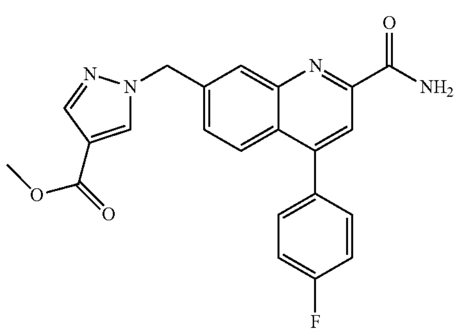 [SMILES: COC(=O)c1cnn(Cc2ccc3c(-c4ccc(F)cc4)cc(C(N)=O)nc3c2)c1] | methyl 1-{[2-carbamoyl-4-(4-fluorophenyl)quinolin-7-yl]methyl}-1H-pyrazole-4-carboxylate | Calc'd 405.1, Found 405.1 |
| 3-25 | 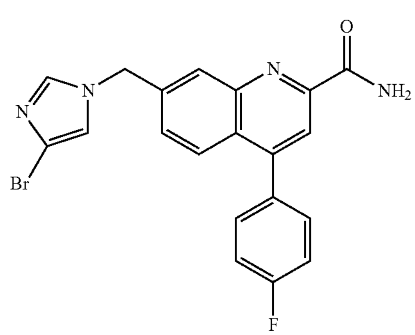 [SMILES: NC(=O)c1cc(-c2ccc(F)cc2)c2ccc(Cn3cnc(Br)c3)cc2n1] | 7-[(4-bromo-1H-imidazol-1-yl)methyl]-4-(4-fluorophenyl)quinoline-2-carboxamide | Calc'd 425.0, found 425.0 |

TABLE 3-continued

| Example | Structure | IUPAC Name | Exact Mass [M + H]+ |
|---|---|---|---|
| 3-26 | 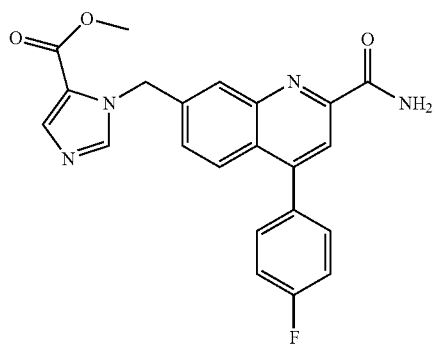 [SMILES: COC(=O)c1cncn1Cc1ccc2c(-c3ccc(F)cc3)cc(C(N)=O)nc2c1] | methyl 1-{[2-carbamoyl-4-(4-fluorophenyl)quinolin-7-yl]methyl}-1H-imidazole-5-carboxylate | Calc'd 405.1, Found 405.1 |
| 3-27 | 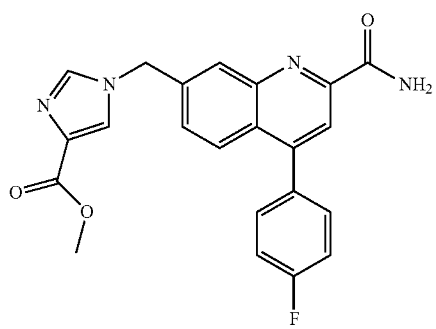 [SMILES: COC(=O)c1cn(Cc2ccc3c(-c4ccc(F)cc4)cc(C(N)=O)nc3c2)cn1] | methyl 1-{[2-carbamoyl-4-(4-fluorophenyl)quinolin-7-yl]methyl}-1H-imidazole-4-carboxylate | Calc'd 405.1, Found 405.1 |
| 3-28 | 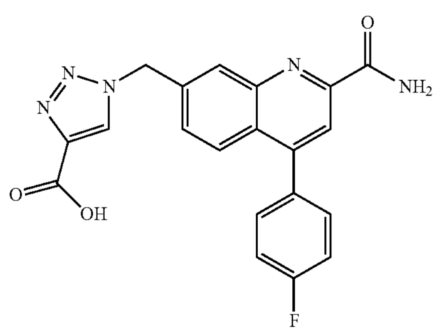 [SMILES: NC(=O)c1cc(-c2ccc(F)cc2)c2ccc(Cn3cc(C(=O)O)nn3)cc2n1] | 1-{[2-carbamoyl-4-(4-fluorophenyl)quinolin-7-yl]methyl}-1H-1,2,3-triazole-4-carboxylic acid | Calc'd 392.1, Found 392.1 |
| 3-29 | 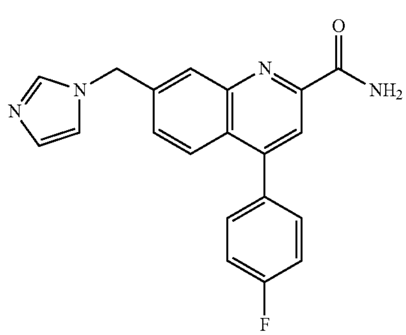 [SMILES: NC(=O)c1cc(-c2ccc(F)cc2)c2ccc(Cn3ccnc3)cc2n1] | 4-(4-fluorophenyl)-7-(1H-imidazol-1-ylmethyl)quinoline-2-carboxamide | Calc'd 347.1, Found 347.1 |

TABLE 3-continued

| Example | Structure | IUPAC Name | Exact Mass [M + H]+ |
|---|---|---|---|
| 3-30 | 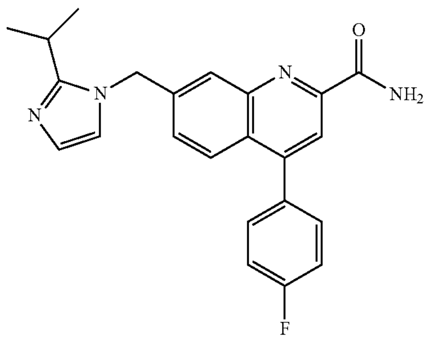 [SMILES: CC(C)c1nccn1Cc1ccc2c(-c3ccc(F)cc3)cc(C(N)=O)nc2c1] | 4-(4-fluorophenyl)-7-{[2-(1-methylethyl)-1H-imidazol-1-yl]methyl}quinoline-2-carboxamide | Calc'd 389.2, Found 389.2 |
| 3-31 | 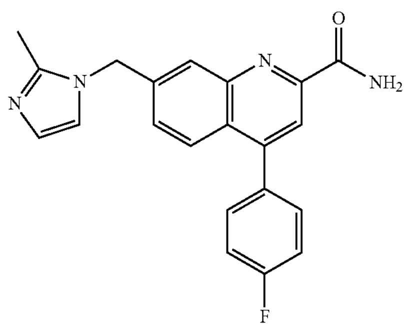 [SMILES: Cc1nccn1Cc1ccc2c(-c3ccc(F)cc3)cc(C(N)=O)nc2c1] | 4-(4-fluorophenyl)-7-[(2-methyl-1H-imidazol-1-yl)methyl]quinoline-2-carboxamide | Calc'd 361.1, Found 361.1 |
| 3-32 | 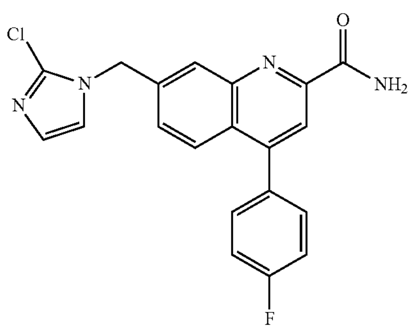 [SMILES: NC(=O)c1cc(-c2ccc(F)cc2)c2ccc(Cn3ccnc3Cl)cc2n1] | 7-[(2-chloro-1H-imidazol-1-yl)methyl]-4-(4-fluorophenyl)quinoline-2-carboxamide | Calc'd 381.1, Found 381.1 |
| 3-33 | 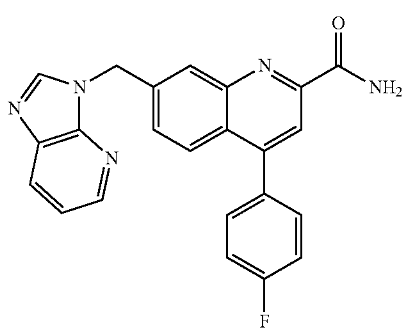 [SMILES: NC(=O)c1cc(-c2ccc(F)cc2)c2ccc(Cn3cnc4cccnc43)cc2n1] | 4-(4-fluorophenyl)-7-(3H-imidazo[4,5-b]pyridin-3-ylmethyl)quinoline-2-carboxamide | Calc'd 398.1, Found 398.1 |

TABLE 3-continued

| Example | Structure | IUPAC Name | Exact Mass [M + H]+ |
|---|---|---|---|
| 3-34 | 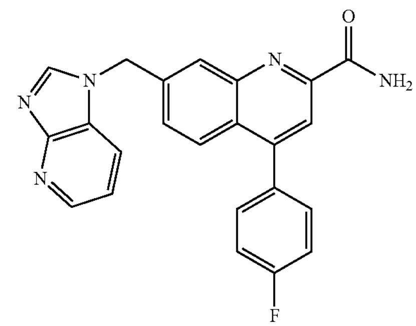 [SMILES: NC(=O)c1cc(-c2ccc(F)cc2)c2ccc(Cn3cnc4ncccc43)cc2n1] | 4-(4-fluorophenyl)-7-(1H-imidazo[4,5-b]pyridin-1-ylmethyl)quinoline-2-carboxamide | Calc'd 398.1, Found 398.1 |
| 3-35 | 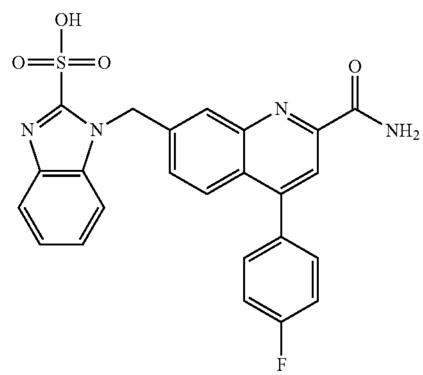 [SMILES: NC(=O)c1cc(-c2ccc(F)cc2)c2ccc(Cn3c(S(=O)(=O)O)nc4ccccc43)cc2n1] | 1-{[2-carbamoyl-4-(4-fluorophenyl)quinolin-7-yl]methyl}-1H-benzimidazole-2-sulfonic acid | Calc'd 477.1, Found 477.1 |
| 3-36 | 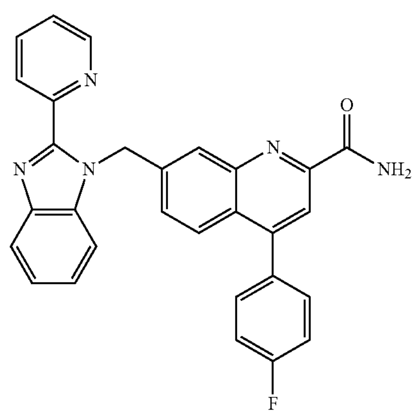 [SMILES: NC(=O)c1cc(-c2ccc(F)cc2)c2ccc(Cn3c(-c4ccccn4)nc4ccccc43)cc2n1] | 4-(4-fluorophenyl)-7-[(2-pyridin-2-yl-1H-benzimidazol-1-yl)methyl]quinolin-2-carboxamide | Calc'd 474.2, Found 474.2 |
| 3-37 | 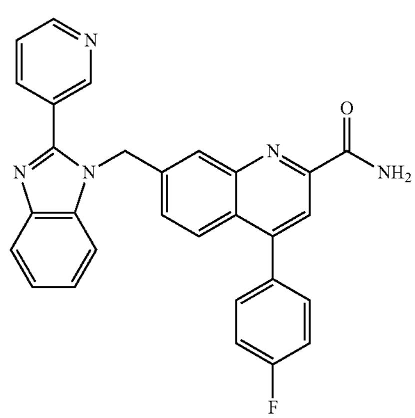 [SMILES: NC(=O)c1cc(-c2ccc(F)cc2)c2ccc(Cn3c(-c4cccnc4)nc4ccccc43)cc2n1] | 4-(4-fluorophenyl)-7-[(2-pyridin-3-yl-1H-benzimidazol-1-yl)methyl]quinoline-2-carboxamide | Calc'd 474.2, Found 474.2 |

TABLE 3-continued

| Example | Structure | IUPAC Name | Exact Mass [M + H]+ |
|---|---|---|---|
| 3-38 | 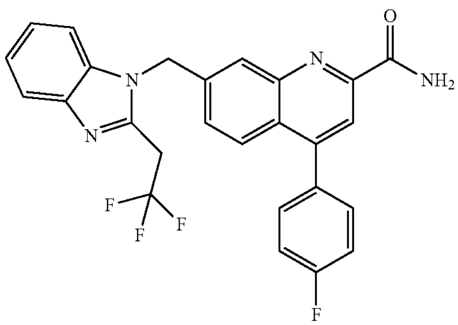 [SMILES: NC(=O)c1cc(-c2ccc(F)cc2)c2ccc(Cn3c(CC(F)(F)F)nc4ccccc43)cc2n1] | 4-(4-fluorophenyl)-7-{[2-(2,2,2-trifluoroethyl)-1H-benzimidazol-1-yl]methyl}quinoline-2-carboxamide | Calc'd 480.1, Found 480.1 |
| 3-39 | 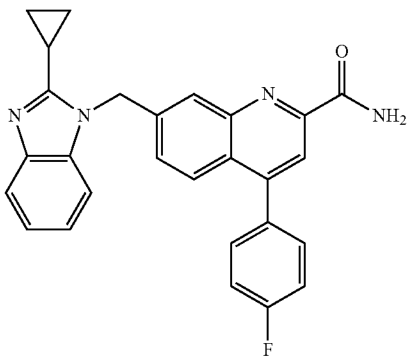 [SMILES: NC(=O)c1cc(-c2ccc(F)cc2)c2ccc(Cn3c(C4CC4)nc4ccccc43)cc2n1] | 7-[(2-cyclopropyl-1H-benzimidazol-1-yl)methyl]-4-(4-fluorophenyl)quinoline-2-carboxamide | Calc'd 437.2, Found 437.2 |
| 3-40 | 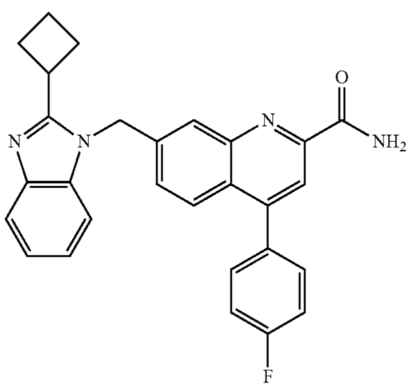 [SMILES: NC(=O)c1cc(-c2ccc(F)cc2)c2ccc(Cn3c(C4CCC4)nc4ccccc43)cc2n1] | 7-[(2-cyclobutyl-1H-benzimidazol-1-yl)methyl]-4-(4-fluorophenyl)quinoline-2-carboxamide | Calc'd 451.2, Found 451.2 |
| 3-41 | 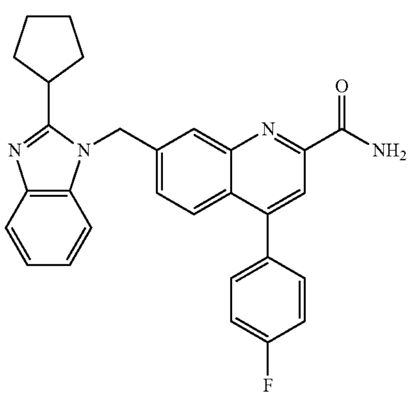 [SMILES: NC(=O)c1cc(-c2ccc(F)cc2)c2ccc(Cn3c(C4CCCC4)nc4ccccc43)cc2n1] | 7-[(2-cyclopentyl-1H-benzimidazol-1-yl)methyl]-4-(4-fluorophenyl)quinoline-2-carboxamide | Calc'd 465.2, Found 465.2 |

TABLE 3-continued

| Example | Structure | IUPAC Name | Exact Mass [M + H]+ |
|---|---|---|---|
| 3-42 | 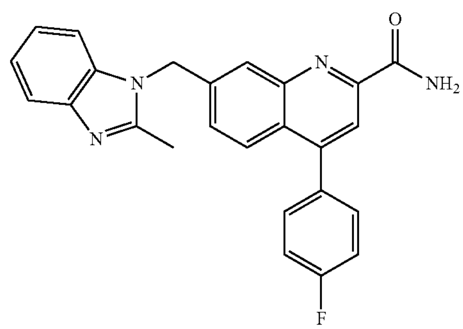 [SMILES: Cc1nc2ccccc2n1Cc1ccc2c(-c3ccc(F)cc3)cc(C(N)=O)nc2c1] | 4-(4-fluorophenyl)-7-[(2-methyl-1H-benzimidazol-1-yl)methyl]quinoline-2-carboxamide | Calc'd 411.2, Found 411.2 |
| 3-43 | 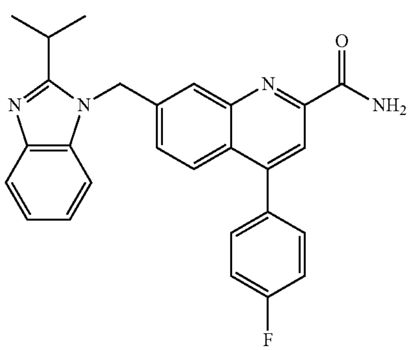 [SMILES: CC(C)c1nc2ccccc2n1Cc1ccc2c(-c3ccc(F)cc3)cc(C(N)=O)nc2c1] | 4-(4-fluorophenyl)-7-{[2-(1-methylethyl)-1H-benzimidazol-1-yl]methyl}quinoline-2-carboxamide | Calc'd 439.2, Found 439.2 |
| 3-44 | 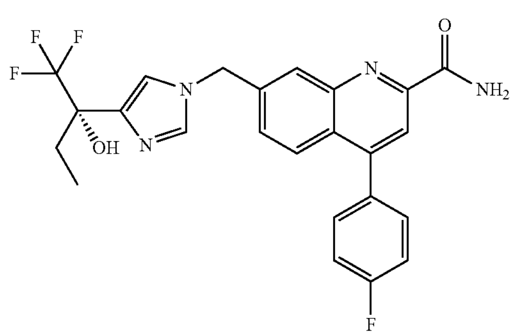 | 4-(4-fluorophenyl)-7-({4-[(1S)-1-hydroxy-1-(trifluoromethyl)propyl]-1H-imidazol-1-yl}methyl)quinoline-2-carboxamide | Calc'd 473.2, Found 473.2 |
| 3-45 | 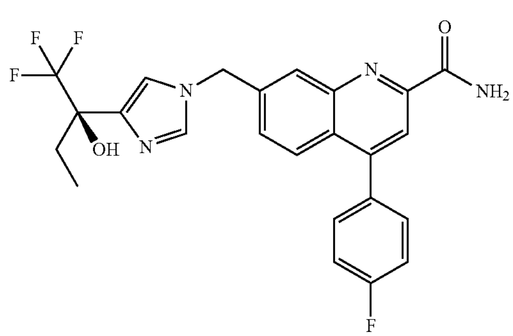 [SMILES: CC[C@@](O)(c1cn(Cc2ccc3c(-c4ccc(F)cc4)cc(C(N)=O)nc3c2)cn1)C(F)(F)F] | 4-(4-fluorophenyl)-7-({4-[(1R)-1-hydroxy-1-(trifluoromethyl)propyl]-1H-imidazol-1-yl}methyl)quinoline-2-carboxamide | Calc'd 473.2, Found 473.2 |

TABLE 3-continued

| Example | Structure | IUPAC Name | Exact Mass [M + H]+ |
|---|---|---|---|
| 3-46 | 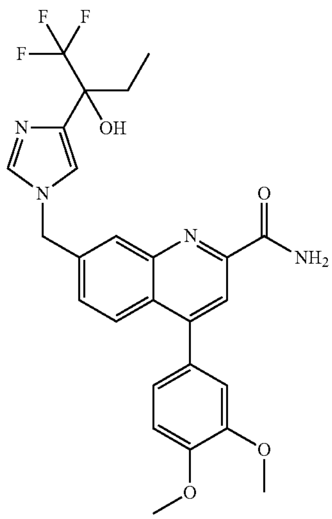 [SMILES: CCC(O)(c1cn(Cc2ccc3c(-c4ccc(OC)c(OC)c4)cc(C(N)=O)nc3c2)cn1)C(F)(F)F] | 4-(3,4-dimethoxyphenyl)-7-({4-[1-hydroxy-1-(trifluoromethyl)propyl]-1H-imidazol-1-yl}methyl)quinoline-2-carboxamide | Calc'd 515.2, Found 515.3 |
| 3-47 | 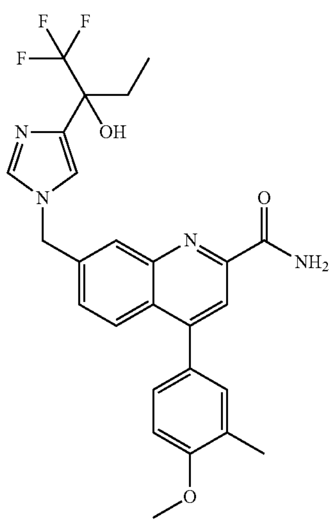 [SMILES: CCC(O)(c1cn(Cc2ccc3c(-c4ccc(OC)c(C)c4)cc(C(N)=O)nc3c2)cn1)C(F)(F)F] | 7-({4-[1-hydroxy-1-(trifluoromethyl)propyl]-1H-imidazol-1-yl}methyl)-4-(4-methoxy-3-methylphenyl)quinoline-2-carboxamide | Calc'd 499.2, Found 499.3 |
| 3-48 | 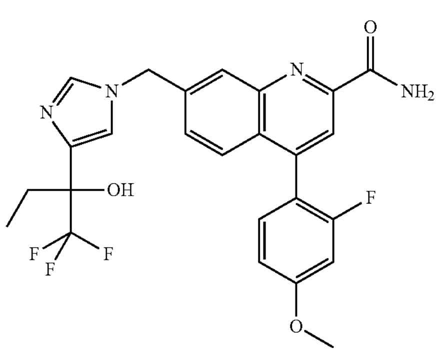 [SMILES: CCC(O)(c1cn(Cc2ccc3c(-c4ccc(OC)cc4F)cc(C(N)=O)nc3c2)cn1)C(F)(F)F] | 4-(2-fluoro-4-methoxyphenyl)-7-({4-[1-hydroxy-1-(trifluoromethyl)propyl]-1H-imidazol-1-yl}methyl)quinoline-2-carboxamide | Calc'd 503.2, Found 503.2 |

TABLE 3-continued

| Example | Structure | IUPAC Name | Exact Mass [M + H]+ |
|---|---|---|---|
| 3-49 | 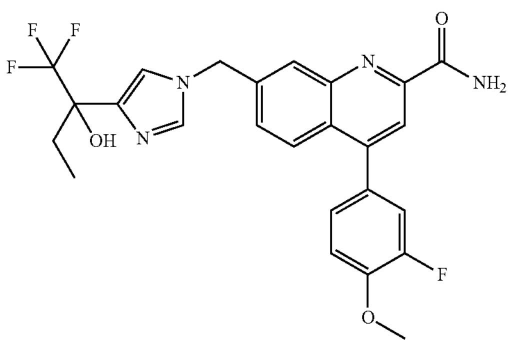 [SMILES: CCC(O)(c1cn(Cc2ccc3c(-c4ccc(OC)c(F)c4)cc(C(N)=O)nc3c2)cn1)C(F)(F)F] | 4-(3-fluoro-4-methoxyphenyl)-7-({4-[1-hydroxy-1-(trifluoromethyl)propyl]-1H-imidazol-1-yl}methyl)quinoline-2-carboxamide | Calc'd 503.2, Found 503.2 |
| 3-50 | 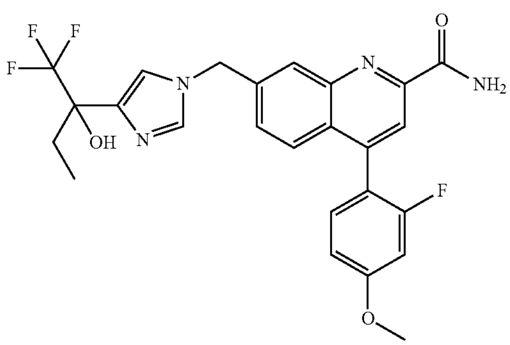 | 4-(2-fluoro-4-methoxyphenyl)-7-({4-[1-hydroxy-1-(trifluoromethyl)propyl]-1H-imidazol-1-yl}methyl)quinoline-2-carboxamide | Calc'd 503.2, Found 503.2 |
| 3-51 | 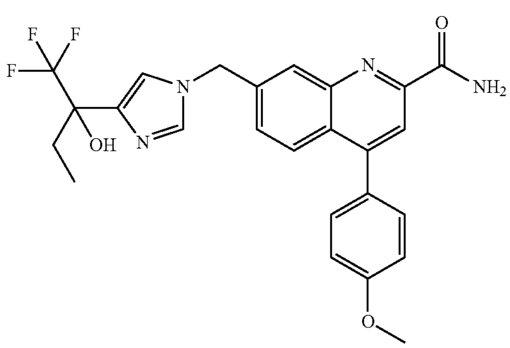 [SMILES: CCC(O)(c1cn(Cc2ccc3c(-c4ccc(OC)cc4)cc(C(N)=O)nc3c2)cn1)C(F)(F)F] | 7-({4-[1-hydroxy-1-(trifluoromethyl)propyl]-1H-imidazol-1-yl}methyl)-4-(4-methoxyphenyl)quinoline-2-carboxamide | Calc'd 485.2, Found 485.4 |

Scheme 4.1

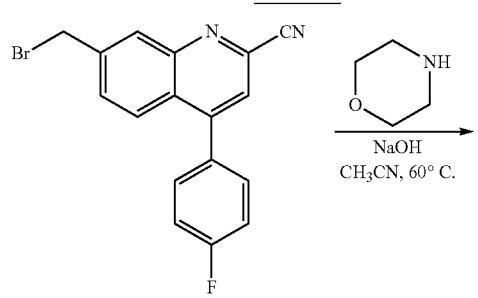

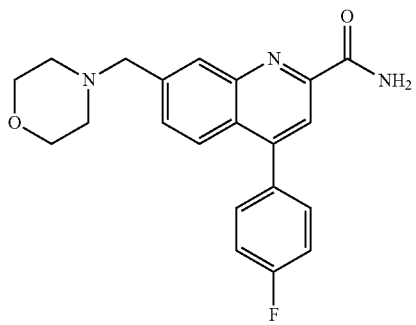

Example 4.1

Synthesis of 4-(4-fluorophenyl)-7-(morpholin-4-ylmethyl)quinoline-2-carboxamide (4-1)

4-(4-Fluorophenyl)-7-(morpholin-4-ylmethyl)quinoline-2-carboxamide (4-1)

To a room temperature solution of 7-(bromomethyl)-4-(4-fluorophenyl)quinoline-2-carbonitrile (2-1, 311.0 mg, 0.895 mmol, 1.0 equiv.) in acetonitrile (10.0 mL) was added morpholine (85.77 mg, 0.985 mmol, 1.1 equiv.) and 5.0 M aqueous NaOH (2.69 mL, 13.43 mmol, 15 equiv.), and the resulting mixture was stirred at 50° C. for 4 days. After cooling to room temperature, water (100.0 mL) was added and the mixture was stirred for 30 minutes. A yellow solid was collected via suction filtration, washed with water, dried in vacuo. The solid was purified by reverse phase HPLC ($H_2O$/$CH_3CN$ gradient w/ 0.1% TFA modifier) to afford 4-(4-fluorophenyl)-7-(morpholin-4-ylmethyl)quinoline-2-carboxamide (4-1, 291.0 mg, 80.0%) as a colorless solid. $^1H$ NMR (500 MHz, $CDCl_3$): δ 8.216 (s, 1H); 8.098 (br s, 2H); 7.911 (d, J=8.54 Hz, 1H); 7.642 (d, J=8.55 Hz, 1H); 7.503-7.529 (m, 2H); 7.219-7.263 (m, 2H); 5.798 (br s, 1H); 3.734 (br s, 6H); 2.528 (br s, 2H). LRMS m/z (M+H)$^+$ 366.2 found, 366.2 required.

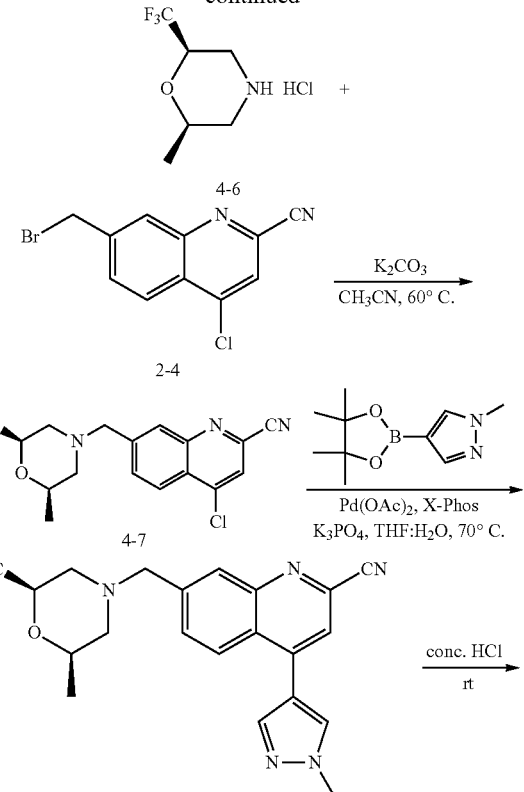

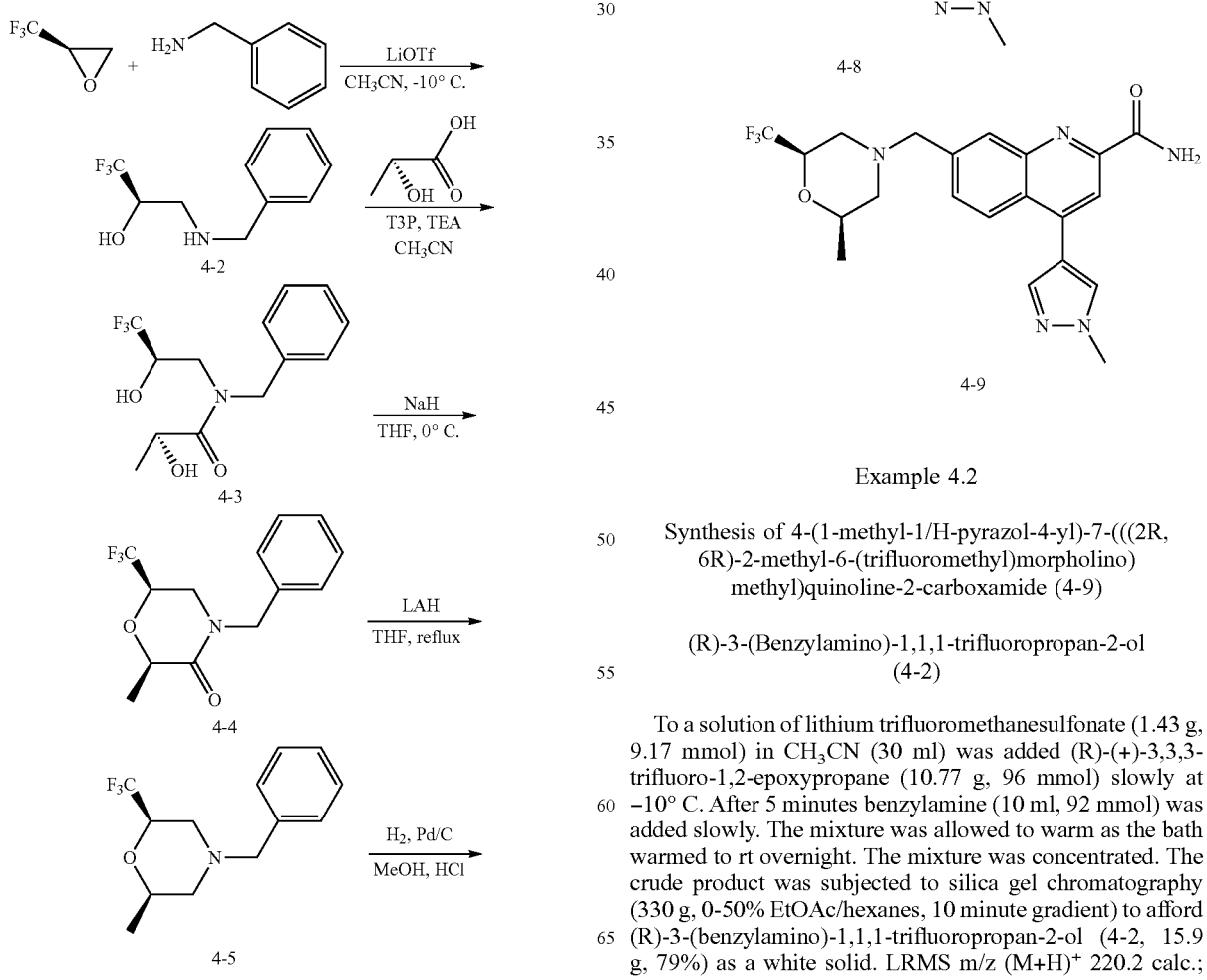

Example 4.2

Synthesis of 4-(1-methyl-1/H-pyrazol-4-yl)-7-(((2R,6R)-2-methyl-6-(trifluoromethyl)morpholino)methyl)quinoline-2-carboxamide (4-9)

(R)-3-(Benzylamino)-1,1,1-trifluoropropan-2-ol (4-2)

To a solution of lithium trifluoromethanesulfonate (1.43 g, 9.17 mmol) in $CH_3CN$ (30 ml) was added (R)-(+)-3,3,3-trifluoro-1,2-epoxypropane (10.77 g, 96 mmol) slowly at −10° C. After 5 minutes benzylamine (10 ml, 92 mmol) was added slowly. The mixture was allowed to warm as the bath warmed to rt overnight. The mixture was concentrated. The crude product was subjected to silica gel chromatography (330 g, 0-50% EtOAc/hexanes, 10 minute gradient) to afford (R)-3-(benzylamino)-1,1,1-trifluoropropan-2-ol (4-2, 15.9 g, 79%) as a white solid. LRMS m/z (M+H)$^+$ 220.2 calc.; 220.1 found.

(S)—N—Benzyl-2-hydroxy-((R)-3,3,3-trifluoro-2-hydroxypropyl)propanamide (4-3)

To a solution of (R)-3-(benzylamino)-1,1,1-trifluoropropan-2-ol (4-2, 5 g, 22.81 mmol) in $CH_3CN$ (200 ml) was added DIEA (12 ml, 68.7 mmol), (S)-2-chloropropionic acid (2.4 ml, 27.4 mmol), then 2,4,6-tripropyl-1,3,5,2,4,6-trioxatriphosphorinane-2,4,6-trioxide (16.3 ml, 27.4 mmol) slowly at rt. After 2.5 hr the mixture was concentrated. The material was taken up in EtOAc and washed with saturated $NaHCO_3$, $H_2O$, and brine. The organic layer was filtered through a pad of silica gel washing with ethyl acetate then concentrated to afford (S)—N-benzyl-2-hydroxy-N—((R)-3,3,3-trifluoro-2-hydroxypropyl)propanamide (4-3) as a clear oil which was sufficiently pure for use in the next step.

(2R,6R)-4-Benzyl-2-methyl-6-(trifluoromethyl)morpholin-3-one (4-4)

A solution of (S)—N-benzyl-2-hydroxy-N—((R)-3,3,3-trifluoro-2-hydroxypropyl)propanamide (4-3) in THF (200 ml) was cooled to 0° C. To this was added NaH (60% dispersion in mineral oil, 1.05 g, 26.3 mmol) portionwise as a solid. After 1 hr the cooling bath was removed and the mixture allowed to warm to rt. After an additional hour the mixture was quenched with brine. The mixture was diluted with $H_2O$ and extracted with EtOAc (3×). The combined organic layers were dried ($MgSO_4$), filtered, and concentrated to afford (2R,6R)-4-benzyl-2-methyl-6-(trifluoromethyl)morpholin-3-one (4-4) as a clear oil which was sufficiently pure for use in the next step.

(2R,6R)-4-Benzyl-2-methyl-6-(trifluoromethyl)morpholine (4-5)

To a solution of (2R,6R)-4-benzyl-2-methyl-6-(trifluoromethyl)morpholin-3-one (4-4) was added 1M LAH (48 ml, 48.0 mmol) in THF slowly at rt. After the addition was complete the mixture was heated to reflux. After 1 hr the mixture was cooled to rt then 0° C. The mixture was slowly quenched with 2M NaOH until gas evolution had ceased and a fine white precipitate formed. Anhydrous $MgSO_4$ was added and the mixture stirred for 15 minutes The slurry was filtered through a pad of celite washing with EtOAc then concentrated. The crude product was subjected to silica gel chromatography (120 g, 0-10% EtOAc/hexanes, 15 minute gradient) to give a afford (2R,6R)-4-benzyl-2-methyl-6-(trifluoromethyl)morpholine (4-5, 4.1 g, 66% over 3 steps) as clear oil. $^1$H NMR (400 MHz, $CDCl_3$): δ 7.35-7.26 (m, 5H); 4.02 (dqd, J=10.7, 6.4, 2.5 Hz, 1H); 3.76-3.69 (m, 1H); 3.60-3.48 (m, 2H); 2.89 (d, J=11.1 Hz, 1H); 2.73-2.68 (m, 1H); 2.16-2.04 (m, 1H); 1.91-1.79 (m, 1H); 1.19 (d, J=6.3 Hz, 3H).

(2R,6R)-2-Methyl-6-(trifluoromethyl)morpholine hydrochloride (4-6)

To a solution of (2R,6R)-4-benzyl-2-methyl-6-(trifluoromethyl)morpholine (4-5, 4.1 g, 15.81 mmol) in MeOH (80 ml) was added concentrated HCl (6.6 ml, 79 mmol). This mixture was transferred to a Parr bottle containing 10% Pd/C (1.7 g, 1.597 mmol). The mixture was hydrogenated (45 psi) overnight. The mixture was filtered through a pad of Celite washing with MeOH then concentrated. The residue was taken up in MeOH and concentrated (3×) to afford (2R,6R)-2-methyl-6-(trifluoromethyl)morpholine hydrochloride (4-6, 3.34 g, 103%) as an off-white solid. $^1$H NMR (400 MHz, $CDCl_3$): δ 4.59 (bs, 2H); 4.27 (bs, 2H); 3.01 (bs, 1H); 2.79 (bs, 1H); 1.33 (s, 3H).

4-Chloro-7-(((2R,6R)-2-methyl-6-(trifluoromethyl)morpholino)methyl)quinoline-2-carbonitrile (4-7)

(2R,6R)-2-Methyl-6-(trifluoromethyl)morpholine hydrochloride (4-6, 500 mg, 2.432 mmol) and $K_2CO_3$ (739 mg, 5.35 mmol) were combined in $CH_3CN$ (10 ml) at rt. To this was added 7-(bromomethyl)-4-chloroquinoline-2-carbonitrile (2-4, 753 mg, 2.68 mmol) all at once as a solid then the mixture was heated to 60° C. overnight. The mixture was cooled to rt, diluted with $H_2O$, and extracted with EtOAc (3×). The combined organic layers were filtered through a pad of Celite washing with EtOAc then concentrated. The crude product was subjected to silica gel chromatography (50 g, 0-10% EtOAc/hexanes, 15 minute gradient) to afford 4-chloro-7-(((2R,6R)-2-methyl-6-(trifluoromethyl)morpholino)methyl)quinoline-2-carbonitrile (4-7, 859, 96%) as a white foam. $^1$H NMR (400 MHz, $CDCl_3$): δ 8.26 (d, J=8.7 Hz, 1H); 8.11 (s, 1H); 7.83 (dd, J=8.6, 1.6 Hz, 1H); 7.78 (s, 1H); 4.09-4.01 (m, 1H); 3.79 (m, 3H); 2.90 (d, J=10.9 Hz, 1H); 2.73 (d, J=11.4 Hz, 1H); 2.28-2.17 (m, 1H); 2.03-1.92 (m, 1H); 1.20 (d, J=6.2 Hz, 3H).

4-(1-Methyl-1H-pyrazol-4-yl)-7-(((2R,6R)-2-methyl-6-(trifluoromethyl)morpholino)methyl)quinoline-2-carbonitrile (4-8)

4-Chloro-7-((2R,6R)-2-methyl-6-(trifluoromethyl)morpholino)methyl)quinoline-2-carbonitrile (4-7, 859 mg, 2323 mmol), 1-methyl-4-(4,4,5,5-tetramethyl-1,3,2-dioxaborolan-2-yl)-1H-pyrazole (725 mg, 3.48 mmol), $Pd(OAc)_2$ (26 mg, 0.116 mmol), and X-Phos (111 mg, 0.232 mmol) were combined in THF (10 ml). To this was added 1M $K_3PO_4$ (7 ml, 7.00 mmol). The mixture was degassed (3× pump/$N_2$) then heated to 70° C. overnight. The mixture was cooled to rt, diluted with $H_2O$, and extracted with EtOAc (3×). The combined organic layers were filtered through a pad of Celite washing with EtOAc then concentrated. The crude product was subjected to silica gel chromatography (100 g, 50% EtOAc/hexanes) to afford 4-(1-methyl-1H-pyrazol-4-yl)-7-(((2R,6R)-2-methyl-6-(trifluoromethyl)morpholino)methyl)quinoline-2-carbonitrile (4-8, 650 mg, 67%) as a white solid. $^1$H NMR (399 MHz, $CDCl_3$): δ 8.22 (d, J=8.7 Hz, 1H); 8.10 (s, 1H); 7.86 (s, 1H); 7.78 (s, 1H); 7.71 (dd, J=8.7, 1.7 Hz, 1H); 7.63 (s, 1H); 4.07 (m, 3H); 3.78 (m, 3H); 2.92 (d, J=11.0 Hz, 1H); 2.75 (d, J=11.4 Hz, 1H); 2.22 (t, J=10.8 Hz, 1H); 1.97 (t, J=10.8 Hz, 1H); 1.20 (d, J=6.3 Hz, 3H).

4-(1-Methyl-1H-pyrazol-4-yl)-7-(((2R,6R)-2-methyl-6-(trifluoromethyl)morpholino)methyl)quinoline-2-carboxamide (4-9)

4-(1-Methyl-1H-pyrazol-4-yl)-7-(((2R,6R)-2-methyl-6-(trifluoromethyl)morpholino)methyl)quinoline-2-carbonitrile (4-8, 650 mg, 1.565 mmol) was taken up in concentrated HCl (10 ml) and stirred at rt. After 3 hrs the mixture was quenched by slow addition of it to a solution of $K_2CO_3$ (17 g) in 100 ml $H_2O$. The reaction flask was rinsed into the quench with $H_2O$ bringing the total volume to 150 mL $H_2O$. The resulting mixture was stirred at rt for 1 hr. The off-white solid was collected by filtration, washed with $H_2O$, and air dried. The crude product was subjected to silica gel chromatography (40 g, 100% EtOAc) to afford 4-(1-methyl-1H-pyrazol-4-yl)-7-(((2R,6R)-2-methyl-6-(trifluoromethyl)

morpholino)methyl)quinoline-2-carboxamide (4-9, 592 mg, 87%) as a white foam. $^1$H NMR (399 MHz, CDCl$_3$): δ 8.27-8.22 (m, 2H); 8.10 (bs, 1H); 8.04 (s, 1H); 7.90 (s, 1H); 7.80 (s, 1H); 7.65 (dd, J=8.7, 1.7 Hz, 1H); 5.67 (bs, 1H); 4.06 (m, 3H); 3.82-3.74 (m, 3H); 2.95 (d, J=11.0 Hz, 1H); 2.77 (d, J=11.5 Hz, 1H); 2.21 (t, J=10.8 Hz, 1H); 2.05 (s, 1H); 1.96 (t, J=10.8 Hz, 1H); 1.20 (d, J=6.3 Hz, 3H); LRMS m/z (M+H)$^+$ 434.4 calc.; 434.3 found.

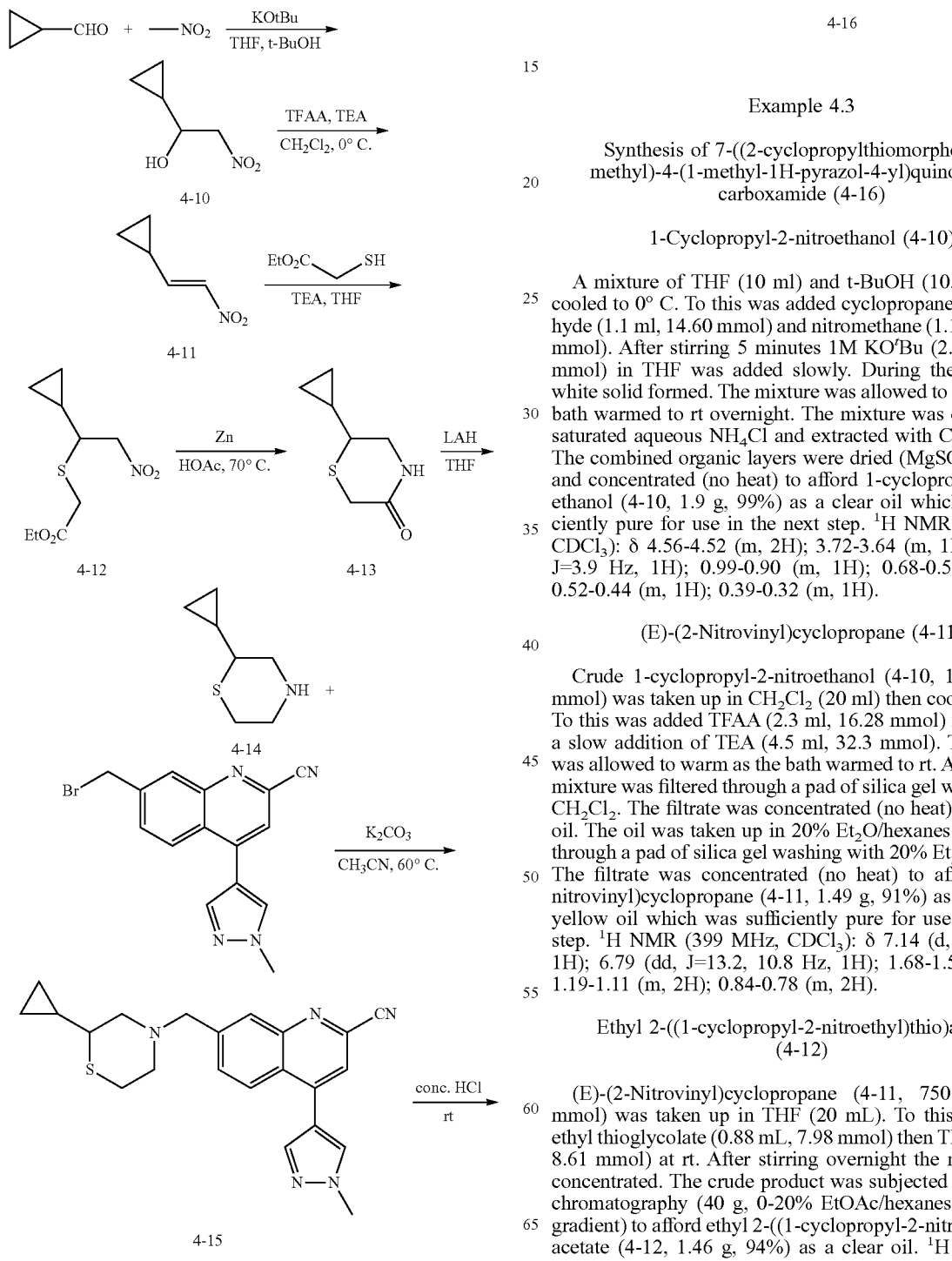

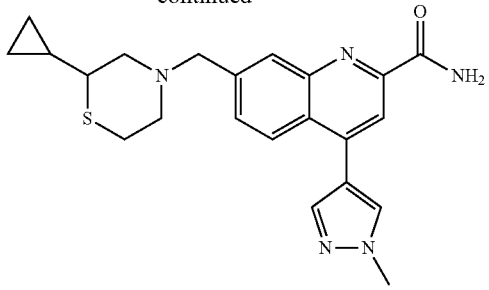

4-16

Example 4.3

Synthesis of 7-((2-cyclopropylthiomorpholino)methyl)-4-(1-methyl-1H-pyrazol-4-yl)quinoline-2-carboxamide (4-16)

1-Cyclopropyl-2-nitroethanol (4-10)

A mixture of THF (10 ml) and t-BuOH (10.00 ml) was cooled to 0° C. To this was added cyclopropanecarboxaldehyde (1.1 ml, 14.60 mmol) and nitromethane (1.18 ml, 21.88 mmol). After stirring 5 minutes 1M KO$^t$Bu (2.92 ml, 2.92 mmol) in THF was added slowly. During the addition a white solid formed. The mixture was allowed to warm as the bath warmed to rt overnight. The mixture was diluted with saturated aqueous NH$_4$Cl and extracted with CH$_2$Cl$_2$ (3×). The combined organic layers were dried (MgSO$_4$), filtered, and concentrated (no heat) to afford 1-cyclopropyl-2-nitroethanol (4-10, 1.9 g, 99%) as a clear oil which was sufficiently pure for use in the next step. $^1$H NMR (399 MHz, CDCl$_3$): δ 4.56-4.52 (m, 2H); 3.72-3.64 (m, 1H); 2.42 (d, J=3.9 Hz, 1H); 0.99-0.90 (m, 1H); 0.68-0.59 (m, 2H); 0.52-0.44 (m, 1H); 0.39-0.32 (m, 1H).

(E)-(2-Nitrovinyl)cyclopropane (4-11)

Crude 1-cyclopropyl-2-nitroethanol (4-10, 1.9 g, 14.49 mmol) was taken up in CH$_2$Cl$_2$ (20 ml) then cooled to 0° C. To this was added TFAA (2.3 ml, 16.28 mmol) followed by a slow addition of TEA (4.5 ml, 32.3 mmol). The mixture was allowed to warm as the bath warmed to rt. After 3 hr the mixture was filtered through a pad of silica gel washing with CH$_2$Cl$_2$. The filtrate was concentrated (no heat) to a yellow oil. The oil was taken up in 20% Et$_2$O/hexanes and filtered through a pad of silica gel washing with 20% Et$_2$O/hexanes. The filtrate was concentrated (no heat) to afford (E)-(2-nitrovinyl)cyclopropane (4-11, 1.49 g, 91%) as a very pale yellow oil which was sufficiently pure for use in the next step. $^1$H NMR (399 MHz, CDCl$_3$): δ 7.14 (d, J=13.2 Hz, 1H); 6.79 (dd, J=13.2, 10.8 Hz, 1H); 1.68-1.58 (m, 1H); 1.19-1.11 (m, 2H); 0.84-0.78 (m, 2H).

Ethyl 2-((1-cyclopropyl-2-nitroethyl)thio)acetate (4-12)

(E)-(2-Nitrovinyl)cyclopropane (4-11, 750 mg, 6.63 mmol) was taken up in THF (20 mL). To this was added ethyl thioglycolate (0.88 mL, 7.98 mmol) then TEA (1.2 mL, 8.61 mmol) at rt. After stirring overnight the mixture was concentrated. The crude product was subjected to silica gel chromatography (40 g, 0-20% EtOAc/hexanes, 10 minute gradient) to afford ethyl 2-((1-cyclopropyl-2-nitroethyl)thio)acetate (4-12, 1.46 g, 94%) as a clear oil. $^1$H NMR (399 MHz, CDCl$_3$): δ 4.73-4.58 (m, 2H); 4.21 (q, J=7.1 Hz, 2H);

3.34 (d, J=6.2 Hz, 2H); 2.93 (dt, J=9.9, 7.2 Hz, 1H); 1.30 (t, J=7.1 Hz, 3H); 1.00-0.90 (m, 1H); 0.69 (dd, J=8.0, 1.6 Hz, 2H); 0.47-0.36 (m, 2H).

6-Cyclopropylthiomorpholin-3-one (4-13)

Ethyl 2-((1-cyclopropyl-2-nitroethyl)thio)acetate (4-12, 1.46 g, 6.26 mmol) was taken up in AcOH (30 ml). To this was added zinc powder (4093 mg, 62.6 mmol) then the mixture was heated to 70° C. After stirring overnight the mixture was cooled to rt, diluted with AcOH, filtered through a pad of Celite washing with AcOH, and concentrated. The crude product was subjected to silica gel chromatography (40 g, 0-100% EtOAc/hexanes, 10 minute gradient) to afford 6-cyclopropylthiomorpholin-3-one (4-13, 355 mg, 36%) as an amber oil which solidified slowly under vacuum. $^1$H NMR (399 MHz, CDCl$_3$): δ 6.65 (s, 1H); 3.65 (dt, J=13.2, 4.4 Hz, 1H); 3.54-3.46 (m, 1H); 3.32 (s, 2H); 2.47-2.39 (m, 1H); 0.98-0.89 (m, 1H); 0.67-0.58 (m, 2H); 0.41-0.25 (m, 2H).

2-Cyclopropylthiomorpholine (4-14)

A solution of 6-cyclopropylthiomorpholin-3-one (4-13, 355 mg, 2.258 mmol) in THF (10 ml) was cooled to 0° C. To this was added 2M LAH (2.3 ml, 4.60 mmol) slowly. After the addition was complete the cooling bath was removed and the mixture allowed to warm to it. After stirring overnight the mixture was cooled to 0° C. and slowly quenched with 2M NaOH until gas evolution had ceased and a fine white precipitate formed. Anhydrous Na$_2$SO$_4$ was added and the mixture stirred for 15 minutes. The slurry was filtered through a pad of Celite washing with THF and the filtrate concentrated to afford 2-cyclopropylthiomorpholine (4-14, 242 mg, 75%) as a pale yellow oil which was used in subsequent steps as is.

7-((2-Cyclopropylthiomorpholino)methyl)-4-(1-methyl-1H-pyrazol-4-yl)quinoline-2-carbonitrile (4-15)

To a solution of crude 2-cyclopropylthiomorpholine (4-14, 100 mg, 0.698 mmol) in CH$_3$CN (3 ml) was added K$_2$CO$_3$ (289 mg, 2.094 mmol) then 7-(bromomethyl)-4-(1-methyl-1H-pyrazol-4-yl)quinoline-2-carbonitrile (251 mg, 0.768 mmol) all at once as solid. The resulting mixture was heated to 60° C. overnight. The mixture was cooled to rt, diluted with EtOAc, filtered through a pad of Celite washing with EtOAc, and concentrated. The crude product was subjected to silica gel chromatography (25 g, 0-100% EtOAc/hexanes, 10 minute gradient) to afford 7-((2-Cyclopropylthiomorpholino)methyl)-4-(1-methyl-1H-pyrazol-4-yl)quinoline-2-carbonitrile (4-15, 123 mg, 45%) as a light orange foam. $^1$H NMR (399 MHz, CDCl$_3$): δ 8.19 (d, J=8.7 Hz, 1H); 8.09 (s, 1H); 7.85 (s, 1H); 7.77 (s, 1H); 7.71 (d, J=8.8 Hz, 1H); 7.61 (s, 1H); 4.07 (s, 3H); 3.85-3.70 (m, 2H); 3.16 (dd, J=11.6, 2.7 Hz, 1H); 3.01 (d, J=11.6 Hz, 1H); 2.83 (ddd, J=13.4, 10.6, 2.7 Hz, 1H); 2.61-2.53 (m, 1H); 2.45-2.34 (m, 2H); 2.20-2.13 (m, 1H); 0.88-0.80 (m, 1H); 0.61-0.44 (m, 2H); 0.36-0.27 (m, 1H); 0.23-0.16 (m, 1H).

7-((2-Cyclopropylthiomorpholino)methyl)-4-(1-methyl)-1H-pyrazol-4-yl)quinoline-2-carboxamide (4-16)

7-((2-Cyclopropylthiomorpholino)methyl)-4-(1-methyl-1H-pyrazol-4-yl)quinoline-2-carbonitrile (4-15, 40 mg, 0.103 mmol) was taken up in concentrated HCl (0.6 ml) and stirred at rt. After 4 hr the mixture was quenched by slow addition of it to saturated NaHCO$_3$. The resulting mixture was extracted with CH$_2$Cl$_2$ (3×). The combined organic layers were filtered through a pad of Celite washing with CH$_2$Cl$_2$ then concentrated. The crude product was subjected to silica gel chromatography (25 g, 100% EtOAc) to afford 7-((2-cyclopropylthiomorpholino)methyl)-4-(1-methyl-1H-pyrazol-4-yl)quinoline-2-carboxamide (4-16, 28 mg, 67%) as an off-white foam. $^1$H NMR (399 MHz, CDCl$_3$): δ 8.22 (m, 2H); 8.10 (s, 1H); 8.04 (s, 1H); 7.89 (s, 1H); 7.80 (s, 1H); 7.65 (d, J=8.7 Hz, 1H); 5.62 (s, 1H); 4.05 (s, 3H); 3.87-3.68 (m, 2H); 3.19 (d, J=11.6 Hz, 1H); 3.04 (d, J=11.6 Hz, 1H); 2.91-2.79 (m, 1H); 2.61-2.53 (m, 1H); 2.46-2.35 (m, 2H); 2.23-2.15 (m, 1H); 0.88-0.79 (m, 1H); 0.60-0.46 (m, 2H); 0.36-0.27 (m, 1H); 0.26-0.18 (m, 1H). LRMS m/z (M+H)$^+$ 408.5 calc.; 408.3 found.

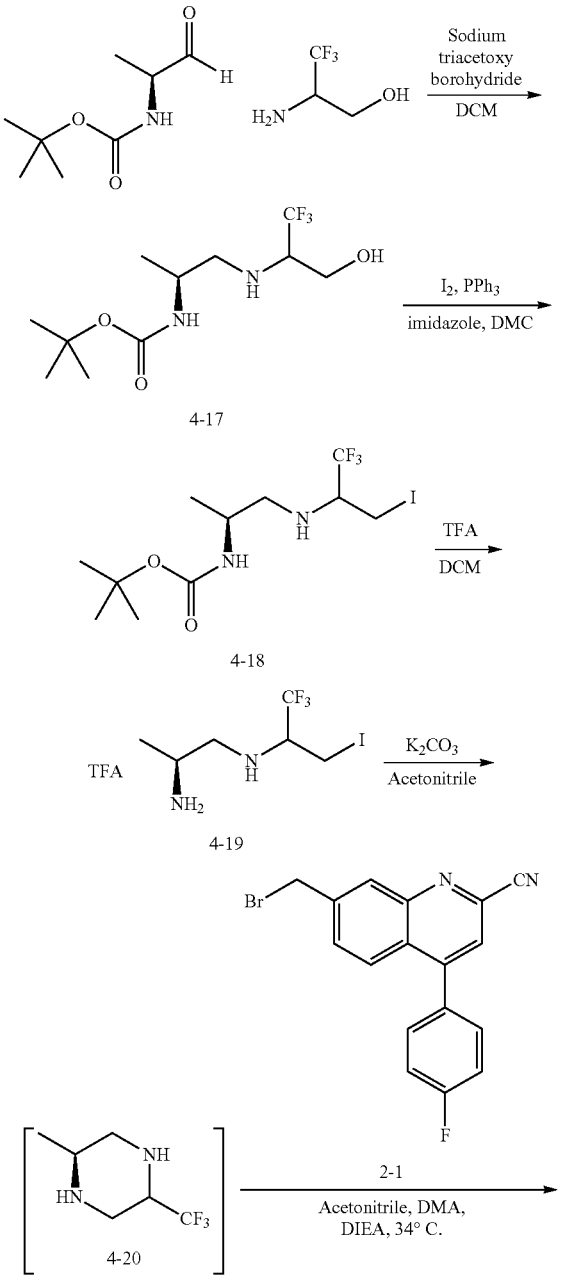

Scheme 4.4

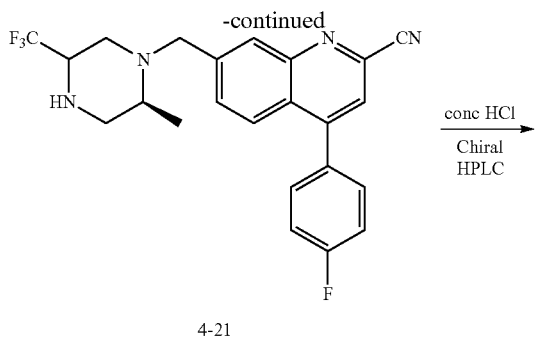

4-21

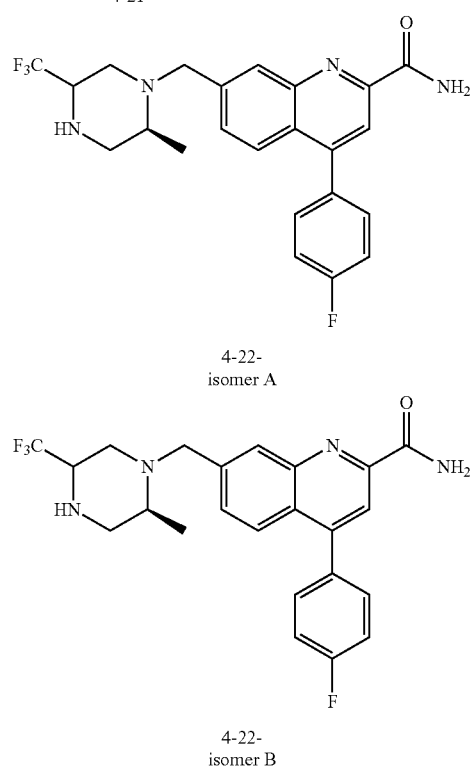

4-22-
isomer A 4-22-
isomer B

Example 4.4

Synthesis of 4-(4-fluorophenyl)-7-(((2S)-2-methyl-5 (R or S)-(trifluoromethyl)piperazin-1-yl)methyl) quinoline-2-carboxamide (4-22)

Tert-butyl ((2S)-1-((1,1,1-trifluoro-3-hydroxypropan-2-yl)amino)propan-2-yl)carbamate (4-17)

To a stirred solution of (S)-tert-butyl (1-oxopropan-2-yl) carbamate (3.15 g, 18.18 mmol), and DCM (91 ml) was added 2-amino-3,3,3-trifluoropropan-1-ol (2.230 g, 17.28 mmol). Stirred at ambient temperature for 10 minutes and then added sodium triacetoxyborohydride (5.78 g, 27.3 mmol). The mixture was stirred overnight. The reaction was diluted with DCM and then washed with 1 N NaOH, brine dried over MgSO$_4$, filtered and the solvent removed to provide 4.0 grams of tert-butyl ((2S)-1-((1,1,1-trifluoro-3-hydroxypropan-2-yl)amino)propan-2-yl)carbamate as a colorless oil that was used without further purification. LRMS m/z (M+H)$^+$ 287.3 found, 287.3 required.

Tert-butyl ((2S)-1-((1,1,1-trifluoro-3-iodopropan-2-yl)amino)propan-2-yl)carbamate (4-18)

To a stirred mixture of triphenylphosphine (resin bound, 1.88 mmol/gram, 7.70 g, 14.67 mmol) in DCM (48.9 ml) was added iodine (3.72 g, 14.67 mmol). Stirred for 15 minutes. Added imidazole (1.332 g, 19.56 mmol) and stirred for 15 minutes, then added tert-butyl ((2S)-1-((1,1,1-trifluoro-3-hydroxypropan-2-yl)amino)propan-2-yl)carbamate (2.8 g, 9.78 mmol), dissolved in DCM (48 ml), and then the mixture was heated to reflux for 3 hours. Cooled to room temperature and filtered through celite. The resulting solution was washed with saturated sodium thiosulfate, dried over MgSO$_4$, filtered and concentrated. The crude residue was purified by column chromatography on silica gel eluting with hexanes to EtOAc to provide tert-butyl ((2S)-1-((1,1,1-trifluoro-3-iodopropan-2-yl)amino)propan-2-yl)carbamate as a colorless oil. LRMS m/z (M+H)$^+$ 397.1 found, 397.2 required.

(2 S)—N1-(1,1,1-trifluoro-3-iodopropan-2-yl)propane-1,2-diamine 2,2,2-trifluoroacetate (4-19)

To a stirred solution of tert-butyl ((2S)-1-((1,1,1-trifluoro-3-iodopropan-2-yl)amino)propan-2-yl)carbamate (1.6 g, 4.04 mmol) and DCM (8.08 ml) was added TFA (6.22 ml, 81 mmol). Stirred for 1 hour at ambient temperature and then the solution was concentrated. The residue was azeotroped with toluene (3×10 ml) to provide (2S)—N1-(1,1,1-trifluoro-3-iodopropan-2-yl)propane-1,2-diamine 2,2,2-trifluoroacetate as a yellow oil that was used without further purification. LRMS m/z (M+H)$^+$ 297.1 found, 297.0 required.

4-(4-Fluorophenyl)-7-((2S)-2-methyl-5-(trifluoromethyl)piperazin-1-yl)methyl)quinoline-2-carbonitrile (4-21)

(2S)—N1-(1,1,1-trifluoro-3-iodopropan-2-yl)propane-1,2-diamine 2,2,2-trifluoroacetate (1.66 g, 4.05 mmol) and acetonitrile (20.24 ml) were combined and then added potassium carbonate (1.678 g, 12.14 mmol). The mixture was stirred for 4 hours at ambient temperature and then was filtered through a celite pad and concentrated to ⅓ of original volume.

To the solution of (2S)-2-methyl-5-(trifluoromethyl)piperazine (4-20) was added DMA (1.76 ml), DIEA (0.614 ml, 3.52 mmol) followed by 7-(bromomethyl)-4-(4-fluorophenyl)quinoline-2-carbonitrile (300 mg, 0.879 mmol). The reaction was heated to 50° C. for 4 hours. The reaction was diluted with EtOAc and then washed with H$_2$O, brine, dried (MgSO$_4$) and concentrated. The residue was purified by column chromatography on silica gel eluting with hexanes to EtOAc to provide 4-(4-fluorophenyl)-7-(((2S)-2-methyl-5-(trifluoromethyl)piperazin-1-yl)methyl)quinoline-2-carbonitrile as a colorless solid. LRMS m/z (M+H)$^+$ 429.2 found, 429.4 required.

4-(4-Fluorophenyl)-7-(((2S)-2-methyl-5(R or S)-(trifluoromethyl)piperazin-1-yl)methyl)quinoline-2-carboxamide (4-22)

4-(4-fluorophenyl)-7-(((2S)-2-methyl-5-(trifluoromethyl)piperazin-1-yl)methyl)quinoline-2-carbonitrile (275 mg, 0.642 mmol) was dissolved in conc HCl (2636 μl, 32.1 mmol) and then stirred at ambient temperature for 4 hours. The yellow solution was slowly poured into aq potassium carbonate (12.8 ml, 5M, 64 mmol) at 0° C. The resulting mixture was extracted with chloroform. The organic portion was dried over MgSO$_4$ and concentrated. The residue was purified by preparative HPLC Chiralpak AD, 5 cm×500 cm, 50 ml/min eluting with 20% IPA/hexanes +0.1% Et$_2$NH, to provide isomers A and B of 4-(4-fluorophenyl)-7-(((2S)-2-methyl-5(R or S)-(trifluoromethyl)piperazin-1-yl)methyl) quinoline-2-carboxamide as colorless foams. Isomer A, LRMS m/z (M+H)$^+$ 447.3 found, 447.4 required $^1$H NMR (500 MHz, CDCl$_3$): 8.22 (1H, s), 8.10 (2H, d, J=12.11 Hz), 7.91 (1H, d, J=8.69 Hz), 7.65 (1H, dd, J=8.72, 1.66 Hz), 7.52 (2H, dd, J=8.44, 5.36 Hz), 5.64 (1H, s), 3.89 (1H, d, J=13.93 Hz), 3.77 (1H, d, J=13.94 Hz), 3.39-3.34 (1H, m), 3.08-3.04 (1H, m), 2.94-2.87 (2H, m), 2.73 (1H, dd, J=11.54, 8.93 Hz), 2.60 (1H, dd, J=11.55, 3.62 Hz), 1.17 (3H, d, J=6.41 Hz).

Isomer B, LRMS m/z (M+H)$^+$ 447.3 found, 447.4 required $^1$H NMR (500 MHz, CDCl$_3$): 8.21 (1H, s), 8.10 (2H, d, J=14.50 Hz), 7.91 (1H, d, J=8.70 Hz), 7.65 (1H, d, J=8.75 Hz), 7.52 (2H, dd, J=8.22, 5.34 Hz), 5.74 (1H, s), 3.89 (1H, d, J=13.95 Hz), 3.77 (1H, d, J=13.95 Hz), 3.37 (1H, t, J=7.88 Hz), 3.09-2.98 (2H, m), 2.91 (2H, d, J=11.86 Hz), 2.73 (1H, t, J=10.19 Hz), 2.60 (1H, dd, J=11.55, 3.52 Hz), 1.17 (3H, d, J=6.36 Hz).

Chiral HPLC Analytical data: 1 ml/min 20% IPa/hexanes, 4.6×250 mm AD column

Isomer A: 7.63 minutes
Isomer B: 8.63 minutes

The following compounds have been prepared according to procedures similar to those found in Scheme 4.1, 4.2, 4.3, and 4.4 selecting the appropriate quinoline derivative, nucleophile, and boronic acid derivative and provide examples of compounds in the invention.

TABLE 4

| Example | Structure | IUPAC Name | Exact Mass [M + H]$^+$ |
|---|---|---|---|
| 4-23 | 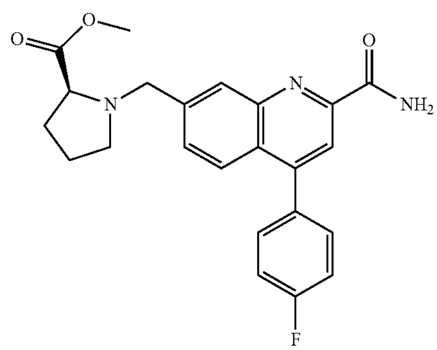 [SMILES: COC(=O)[C@@H]1CCCN1Cc1ccc2c(-c3ccc(F)cc3)cc(C(N)=O)nc2c1] | methyl 1-{[2-carbamoyl-4-(4-fluorophenyl)quinolin-7-yl]methyl}-L-prolinate | Calc'd 408.2, Found 408.2 |
| 4-24 | 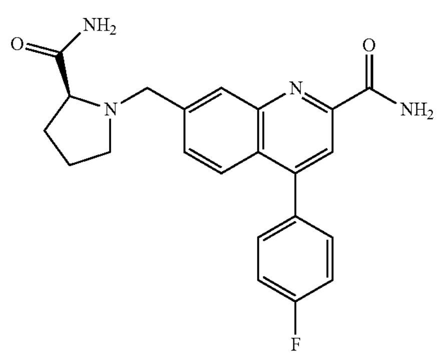 [SMILES: NC(=O)c1cc(-c2ccc(F)cc2)c2ccc(CN3CCC[C@H]3C(N)=O)cc2n1] | 7-{[(2S)-2-carbamoylpyrrolidin-1-yl]methyl}-4-(4-fluorophenyl)quinoline-2-carboxamide | Calc 393.2, Found 393.2 |
| 4-25 | 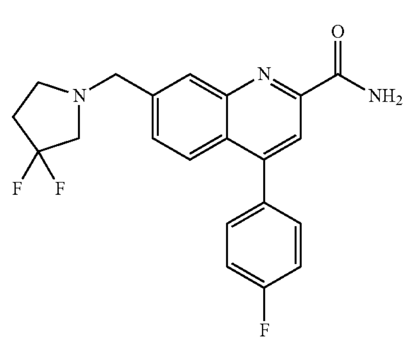 [SMILES: NC(=O)c1cc(-c2ccc(F)cc2)c2ccc(CN3CCC(F)(F)C3)cc2n1] | 7-[(3,3-difluoropyrrolidin-1-yl)methyl]-4-(4-fluorophenyl)quinoline-2-carboxamide | Calc 386.1, Found 386.1 |

TABLE 4-continued

| Example | Structure | IUPAC Name | Exact Mass [M + H]+ |
|---|---|---|---|
| 4-26 | 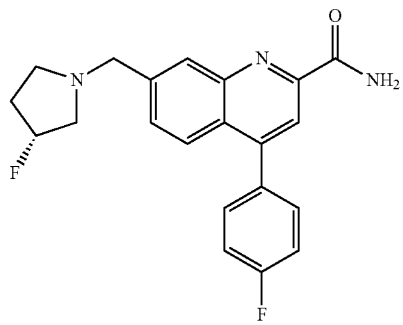 [SMILES: NC(=O)c1cc(-c2ccc(F)cc2)c2ccc(CN3CC[C@@H](F)C3)cc2n1] | 4-(4-fluorophenyl)-7-{[(3R)-3-fluoropyrrolidin-1-yl]methyl}quinoline-2-carboxamide | Calc'd 368.2, Found 368.2 |
| 4-27 | 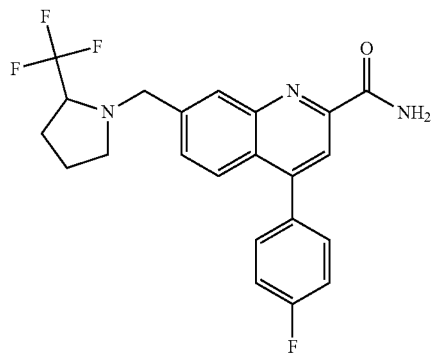 [SMILES: NC(=O)c1cc(-c2ccc(F)cc2)c2ccc(CN3CCCC3C(F)(F)F)cc2n1] | 4-(4-fluorophenyl)-7-{[2-(trifluoromethyl)pyrrolidin-1-yl]methyl}quinoline-2-carboxamide | Calc'd 418.2, Found 418.2 |
| 4-28 | 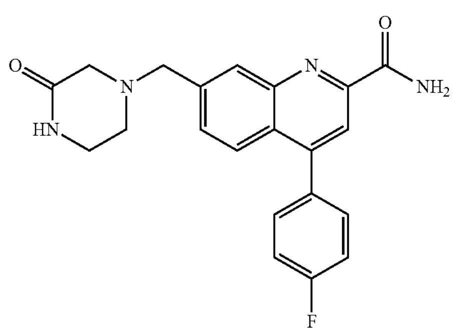 [SMILES: NC(=O)c1cc(-c2ccc(F)cc2)c2ccc(CN3CCNC(=O)C3)cc2n1] | 4-(4-fluorophenyl)-7-[(3-oxopiperazin-1-yl)methyl]quinoline-2-carboxamide | Calc'd 379.2, Found 379.2 |
| 4-29 | 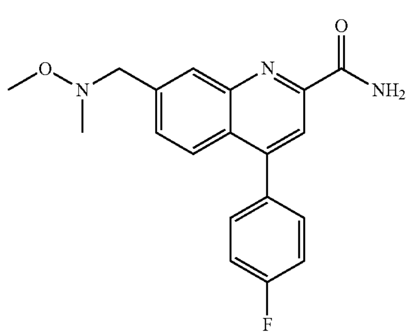 [SMILES: CON(C)Cc1ccc2c(-c3ccc(F)cc3)cc(C(N)=O)nc2c1] | 4-(4-fluorophenyl)-7-{[methoxy(methyl)amino]methyl}quinoline-2-carboxamide | Calc'd 340.1, Found 340.1 |

TABLE 4-continued

| Example | Structure | IUPAC Name | Exact Mass [M + H]+ |
|---|---|---|---|
| 4-30 | 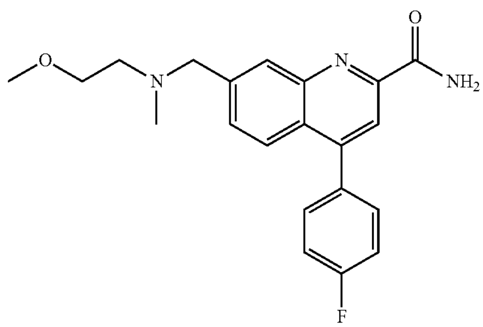 [SMILES: COCCN(C)Cc1ccc2c(-c3ccc(F)cc3)cc(C(N)=O)nc2c1] | 4-(4-fluorophenyl)-7-{[(2-methoxyethyl)(methyl)amino]methyl}quinoline-2-carboxamide | Calc'd 368.2, Found 368.2 |
| 4-31 | 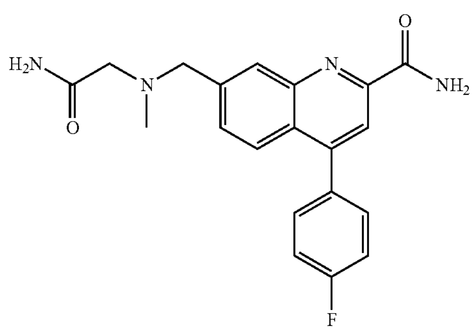 [SMILES: CN(CC(N)=O)Cc1ccc2c(-c3ccc(F)cc3)cc(C(N)=O)nc2c1] | 7-{[(2-amino-2-oxoethyl)(methyl)amino]methyl}-4-(4-fluorophenyl)quinoline-2-carboxamide | Calc'd 367.2, Found 367.2 |
| 4-32 | 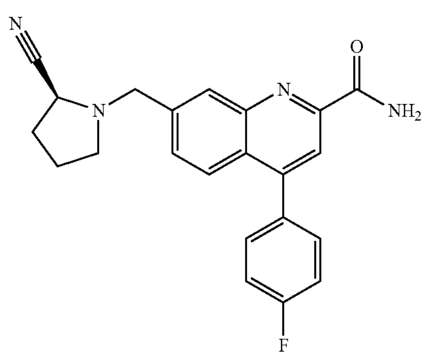 [SMILES: N#C[C@@H]1CCCN1Cc1ccc2c(-c3ccc(F)cc3)cc(C(N)=O)nc2c1] | 7-{[(2S)-2-cyanopyrrolidin-1-yl]methyl}-4-(4-fluorophenyl)quinoline-2-carboxamide | Calc'd 375.2, Found 375.2 |
| 4-33 | 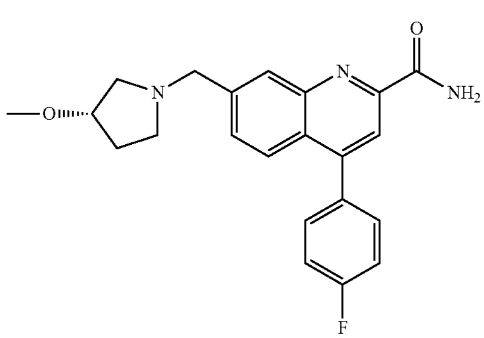 [SMILES: CO[C@H]1CCN(Cc2ccc3c(-c4ccc(F)cc4)cc(C(N)=O)nc3c2)C1] | 4-(4-fluorophenyl)-7-{[(3S)-3-methoxypyrrolidin-1-yl]methyl}quinoline-2-carboxamide | Calc'd 380.2, Found 380.2 |

TABLE 4-continued

| Example | Structure | IUPAC Name | Exact Mass [M + H]+ |
|---|---|---|---|
| 4-34 | 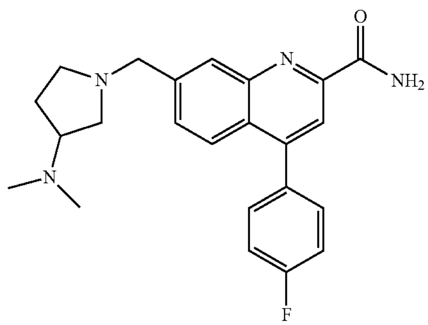 [SMILES: CN(C)C1CCN(Cc2ccc3c(-c4ccc(F)cc4)cc(C(N)=O)nc3c2)C1] | 7-{[3-(dimethylamino)pyrrolidin-1-yl]methyl}-4-(4-fluorophenyl)quinoline-2-carboxamide | Calc'd 393.2, Found 393.2 |
| 4-35 | 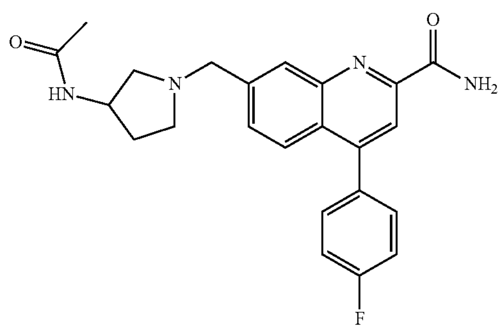 [SMILES: CC(=O)NC1CCN(Cc2ccc3c(-c4ccc(F)cc4)cc(C(N)=O)nc3c2)C1] | 7-{[3-(acetylamino)pyrrolidin-1-yl]methyl}-4-(4-fluorophenyl)quinoline-2-carboxamide | Calc'd 407.2, Found 407.2 |
| 4-36 | 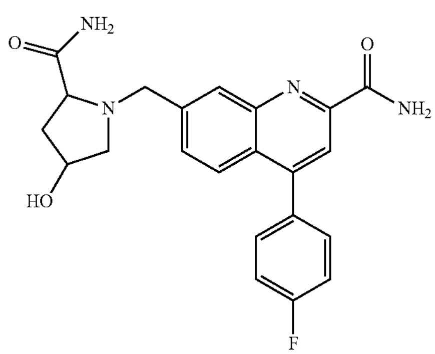 [SMILES: NC(=O)c1cc(-c2ccc(F)cc2)c2ccc(CN3CC(O)CC3C(N)=O)cc2n1] | 7-[(2-carbamoyl-4-hydroxypyrrolidin-1-yl)methyl]-4-(4-fluorophenyl)quinoline-2-carboxamide | Calc'd 409.2, Found 409.2 |
| 4-37 | 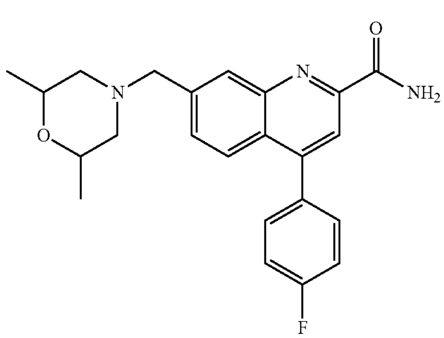 [SMILES: CC1CN(Cc2ccc3c(-c4ccc(F)cc4)cc(C(N)=O)nc3c2)CC(C)O1] | 7-[(2,6-dimethylmorpholin-4-yl)methyl]-4-(4-fluorophenyl)quinoline-2-carboxamide | Calc'd 394.2, Found 394.2 |

TABLE 4-continued

| Example | Structure | IUPAC Name | Exact Mass [M + H]+ |
|---|---|---|---|
| 4-38 | 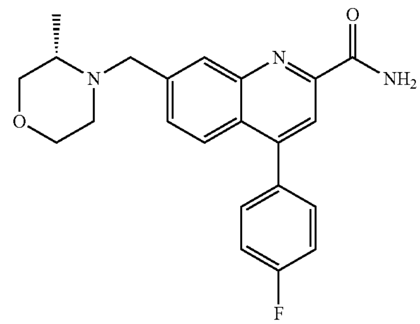 [SMILES: C[C@H]1COCCN1Cc1ccc2c(-c3ccc(F)cc3)cc(C(N)=O)nc2c1] | 4-(4-fluorophenyl)-7-{[(3S)-3-methylmorpholin-4-yl]methyl}quinoline-2-carboxamide | Calc'd 380.2, Found 380.2 |
| 4-39 | 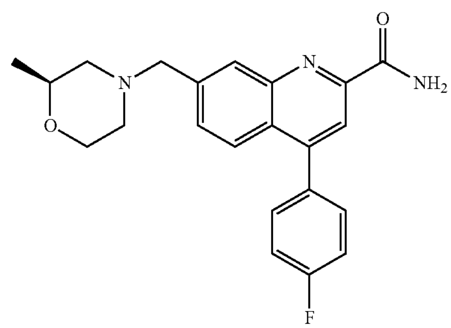 [SMILES: C[C@H]1CN(Cc2ccc3c(-c4ccc(F)cc4)cc(C(N)=O)nc3c2)CCO1] | 4-(4-fluroophenyl)-7-{[(2S)-2-methylmorpholin-4-yl]methyl}quinoline-2-carboxamide | Calc'd 380.2, Found 380.2 |
| 4-40 | 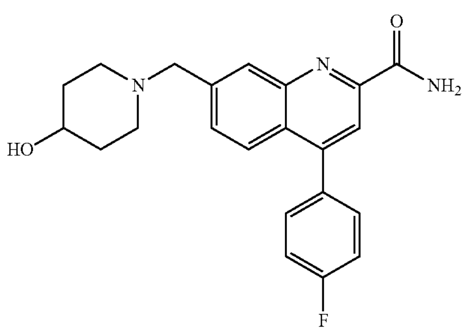 [SMILES: NC(=O)c1cc(-c2ccc(F)cc2)c2ccc(CN3CCC(O)CC3)cc2n1] | 4-(4-fluorophenyl)-7-[(4-hydroxypiperidin-1-yl)methyl]quinoline-2-carboxamide | Calc'd 380.2, Found 380.2 |
| 4-41 | 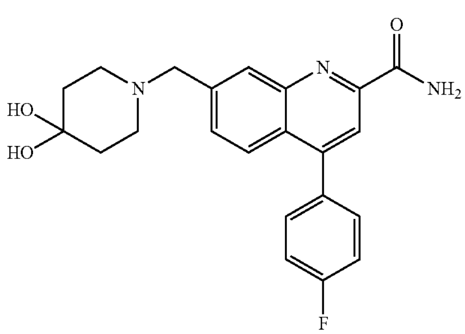 [SMILES: NC(=O)c1cc(-c2ccc(F)cc2)c2ccc(CN3CCC(O)(O)CC3)cc2n1] | 7-[(4,4-dihydroxypiperidin-1-yl)methyl]-4-(4-fluorophenyl)quinoline-2-carboxamide | Calc'd 396.2, Found 396.2 |

TABLE 4-continued

| Example | Structure | IUPAC Name | Exact Mass [M + H]+ |
|---|---|---|---|
| 4-42 | 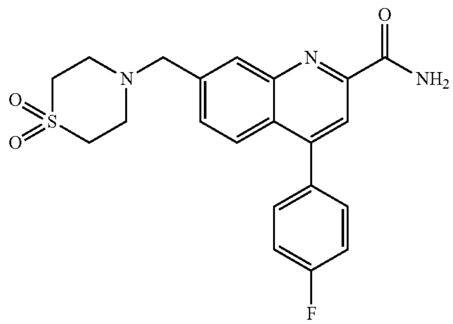 [SMILES: NC(=O)c1cc(-c2ccc(F)cc2)c2ccc(CN3CCS(=O)(=O)CC3)cc2n1] | 7-[(1,1-dioxidothiomorpholin-4-yl)methyl]-4-(4-fluorophenyl)quinoline-3-carboxamide | Calc'd 414.1, Found 414.1 |
| 4-43 | 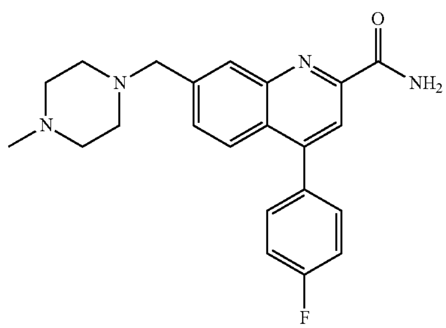 [SMILES: CN1CCN(Cc2ccc3c(-c4ccc(F)cc4)cc(C(N)=O)nc3c2)CC1] | 4-(4-fluorophenyl)-7-[(4-methylpiperazin-1-yl)methyl]quinoline-2-carboxamide | Calc'd 379.2, Found 379.2 |
| 4-44 | 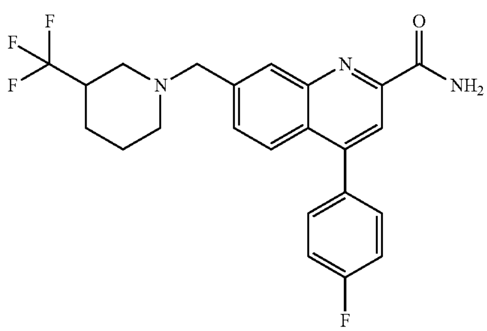 [SMILES: NC(=O)c1cc(-c2ccc(F)cc2)c2ccc(CN3CCCC(C(F)(F)F)C3)cc2n1] | 4-(4-fluorophenyl)-7-{[3-(trifluoromethyl)piperidin-1-yl]methyl}quinoline-2-carboxamide | Calc'd 432.2, Found 432.2 |
| 4-45 | 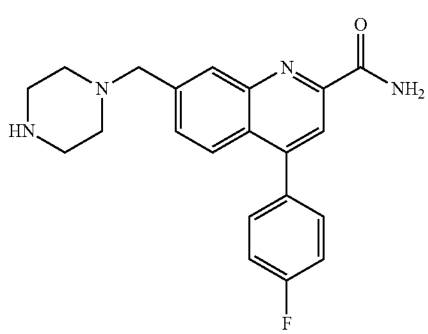 [SMILES: NC(=O)c1cc(-c2ccc(F)cc2)c2ccc(CN3CCNCC3)cc2n1] | 4-(4-fluorophenyl)-7-(piperazin-1-ylmethyl)quinoline-2-carboxamide | Calc'd 365.2, Found 365.2 |

TABLE 4-continued

| Example | Structure | IUPAC Name | Exact Mass [M + H]+ |
|---|---|---|---|
| 4-46 | 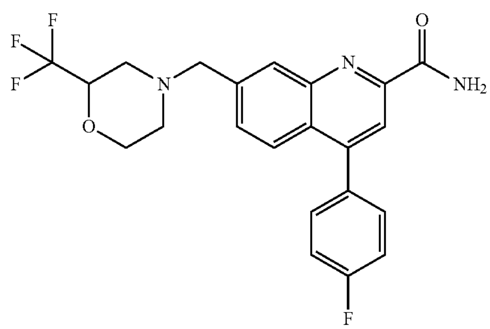 [SMILES: NC(=O)c1cc(-c2ccc(F)cc2)c2ccc(CN3CCOC(C(F)(F)F)C3)cc2n1] | 4-(4-fluorophenyl)-7-{[2-(trifluoromethyl)morpholin-4-yl]methyl}quinoline-2-carboxamide | Calc'd 434.1, Found 434.1 |
| 4-47 | 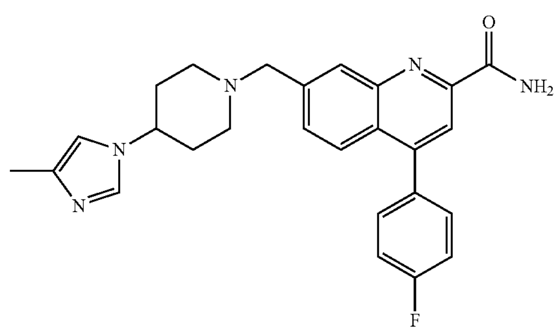 [SMILES: Cc1cn(C2CCN(Cc3ccc4c(-c5ccc(F)cc5)cc(C(N)=O)nc4c3)CC2)cn1] | 4-(4-fluorophenyl)-7-{[4-(4-methyl-1H-imidazol-1-yl)piperidin-1-yl]methyl}quinoline-2-carboxamide | Calc'd 444.2, Found 444.3 |
| 4-48 | 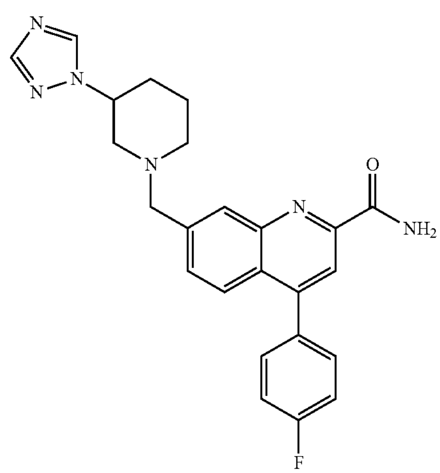 [SMILES: NC(=O)c1cc(-c2ccc(F)cc2)c2ccc(CN3CCCC(n4cncn4)C3)cc2n1] | 4-(4-fluorophenyl)-7-{[3-(1H-1,2,4-triazol-1-yl)piperidin-1-yl]methyl}quinoline-2-carboxamide | Calc'd 431.2, Found 431.2 |
| 4-49 | 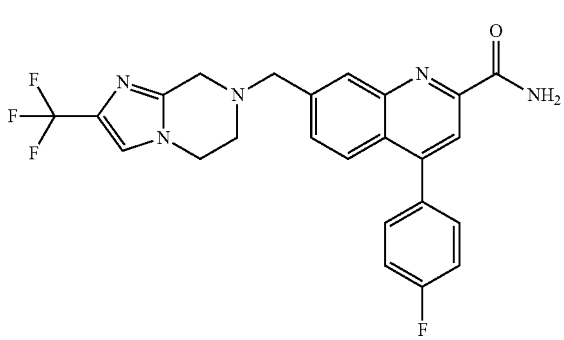 [SMILES: NC(=O)c1cc(-c2ccc(F)cc2)c2ccc(CN3CCn4cc(C(F)(F)F)nc4C3)cc2n1] | 4-(4-fluorophenyl)-7-{[2-(trifluoromethyl)-5,6-dihydroimidazo[1,2-a]pyrazin-7(8H)-yl]methyl}quinoline-2-carboxamide | Calc'd 470.2, Found 470.2 |

TABLE 4-continued

| Example | Structure | IUPAC Name | Exact Mass [M + H]+ |
|---|---|---|---|
| 4-50 | 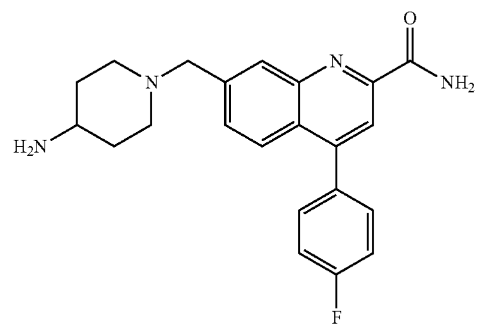 [SMILES: NC(=O)c1cc(-c2ccc(F)cc2)c2ccc(CN3CCC(N)CC3)cc2n1] | 7-[(4-aminopiperidin-1-yl)methyl]-4-(4-fluorophenyl)quinoline-2-carboxamide | Calc'd 379.2, Found 379.2 |
| 4-51 | 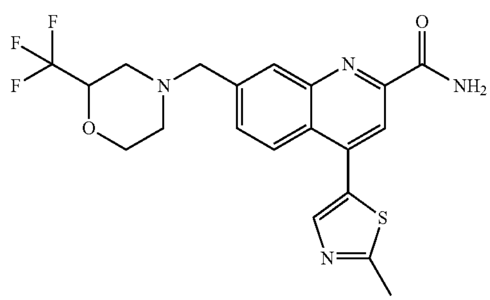 | 4-(2-methyl-1,3-thiazol-5-yl)-7-{[2-(trifluoromethyl)morpholin-4-yl]methyl}quinoline-2-carboxamide | Calc'd 437.1, Found 437.2 |
| 4-52 | 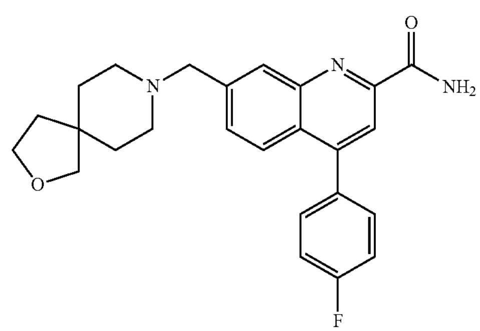 [SMILES: NC(=O)c1cc(-c2ccc(F)cc2)c2ccc(CN3CCC4(CCOC4)CC3)cc2n1] | 4-(4-fluorophenyl)-7-(2-oxa-8-azaspiro[4.5]dec-8-ylmethyl)quinoline-2-carboxamide | Calc'd 420.2, Found 420.2 |
| 4-53 | 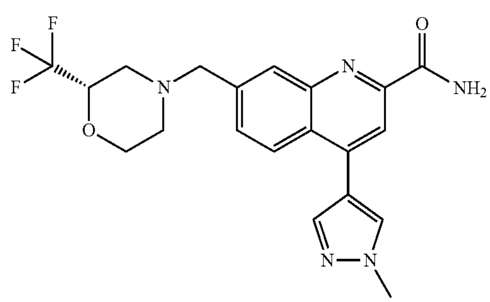 [SMILES: Cn1cc(-c2cc(C(N)=O)nc3cc(CN4CCO[C@H](C(F)(F)F)C4)ccc23)cn1] | 4-(1-methyl-1H-pyrazol-4-yl)-7-{[(2S)-2-(trifluoromethyl)morpholin-4-yl]methyl}quinoline-2-carboxamide | Calc'd 420.2, Found 420.1 |

TABLE 4-continued

| Example | Structure | IUPAC Name | Exact Mass [M + H]+ |
|---|---|---|---|
| 4-54 | 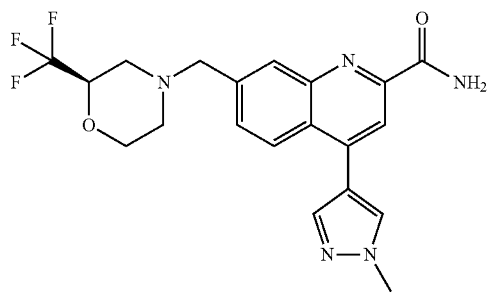 [SMILES: Cn1cc(-c2cc(C(N)=O)nc3cc(CN4CCO[C@@H](C(F)(F)F)C4)ccc23)cn1] | 4-(1-methyl-1H-pyrazol-4-yl)-7-{[(2R)-2-(trifluoromethyl)morpholin-4-yl]methyl}quinoline-2-carboxamide | Calc'd 420.2, Found 420.5 |
| 4-55 | 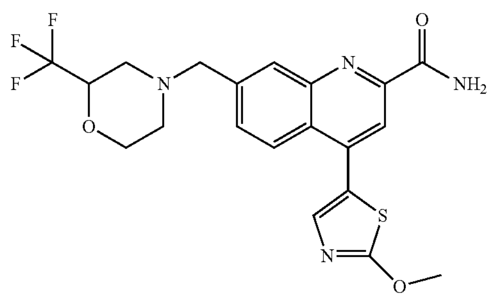 [SMILES: COc1ncc(-c2cc(C(N)=O)nc3cc(CN4CCOC(C(F)(F)F)C4)ccc23)s1] | 4-(2-methoxy-1,3-thiazol-5-yl)-7-{[2-(trifluoromethyl)morpholin-4-yl]methyl}quinoline-2-carboxamide | Calc'd 453.1, Found 453.2 |
| 4-56 | 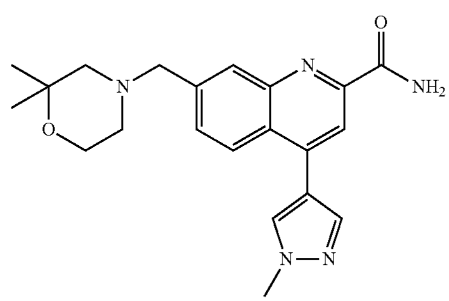 [SMILES: Cn1cc(-c2cc(C(N)=O)nc3cc(CN4CCOC(C)(C)C4)ccc23)cn1] | 7-[(2,2-dimethylmorpholin-4-yl)methyl]-4-(1-methyl-1H-pyrazol-4-yl)quinoline-2-carboxamide | Calc'd 380.2, Found 380.3 |
| 4-57 | 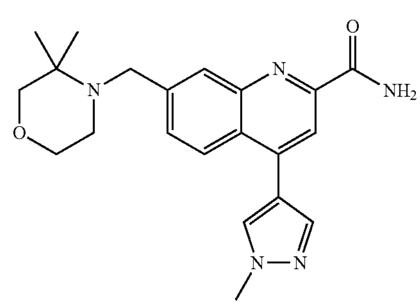 [SMILES: Cn1cc(-c2cc(C(N)=O)nc3cc(CN4CCOCC4(C)C)ccc23)cn1] | 7-[(3,3-dimethylmorpholin-4-yl)methyl]-4-(1-methyl-1H-pyrazol-4-yl)quinoline-2-carboxamide | Calc'd 380.2, Found 380.3 |
| 4-58 | 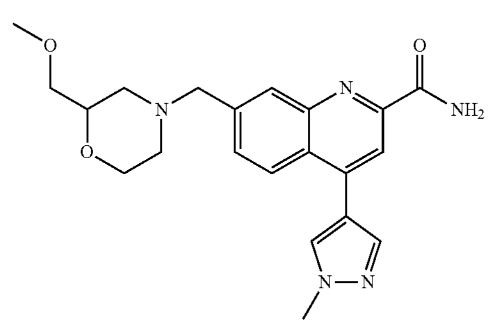 [SMILES: COCC1CN(Cc2ccc3c(-c4cnn(C)c4)cc(C(N)=O)nc3c2)CCO1] | 7-{[2-(methoxymethyl)morpholin-4-yl]methyl}-4-(1-methyl-1H-pyrazol-4-yl)quinoline-2-carboxamide | Calc'd 396.2, Found 396.3 |

TABLE 4-continued

| Example | Structure | IUPAC Name | Exact Mass [M + H]+ |
|---|---|---|---|
| 4-59 | 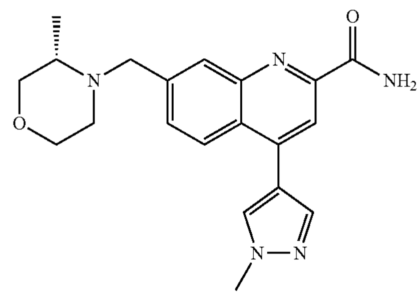 [SMILES: C[C@H]1COCCN1Cc1ccc2c(-c3cnn(C)c3)cc(C(N)=O)nc2c1] | 7-{[(3S)-3-methylmorpholin-4-yl]methyl}-4-(1-methyl-1H-pyrazol-4-yl)quinoline-2-carboxamide | Calc'd 366.2, Found 366.2 |
| 4-60 | 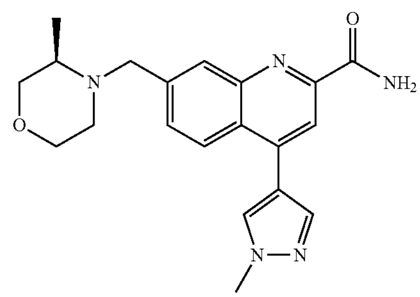 [SMILES: C[C@@H]1COCCN1Cc1ccc2c(-c3cnn(C)c3)cc(C(N)=O)nc2c1] | 7-{[(3R)-3-methylmorpholin-4-yl]methyl}-4-(1-methyl-1H-pyrazol-4-yl)quinoline-2-carboxamide | Calc'd 366.2, Found 366.2 |
| 4-61 | 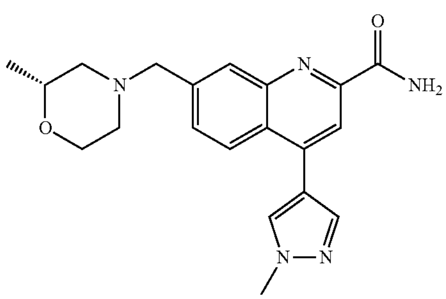 [SMILES: C[C@@H]1CN(Cc2ccc3c(-c4cnn(C)c4)cc(C(N)=O)nc3c2)CCO1] | 7-{[(2R)-2-methylmorpholin-4-yl]methyl}-4-(1-methyl-1H-pyrazol-4-yl)quinoline-2-carboxamide | Calc'd 366.2, Found 366.2 |
| 4-62 | 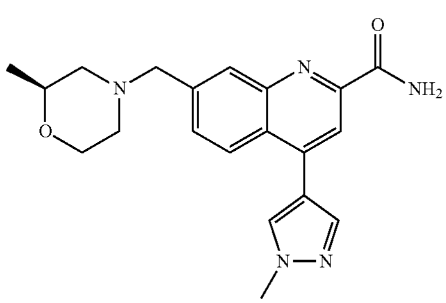 [SMILES: C[C@H]1CN(Cc2ccc3c(-c4cnn(C)c4)cc(C(N)=O)nc3c2)CCO1] | 7-{[(2S)-2-methymorpholin-4-yl]methyl}-4-(1-methyl-1H-pyrazol-4-yl)quinoline-2-carboxamide | Calc'd 366.2, Found 366.2 |
| 4-63 | 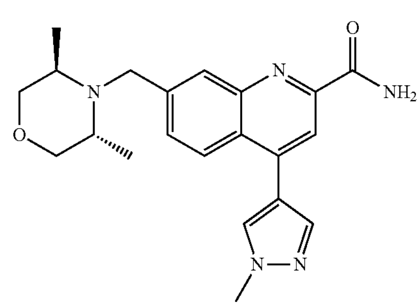 [SMILES: C[C@@H]1COC[C@@H](C)N1Cc1ccc2c(-c3cnn(C)c3)cc(C(N)=O)nc2c1] | 7-{[(3R,5R)-3,5-dimethymorpholin-4-yl]methyl}-4-(1-methyl-1H-pyrazol-4-yl)quinoline-2-carboxamide | Calc'd 380.2, Found 380.2 |

TABLE 4-continued

| Example | Structure | IUPAC Name | Exact Mass [M + H]+ |
|---------|-----------|------------|---------------------|
| 4-64 | 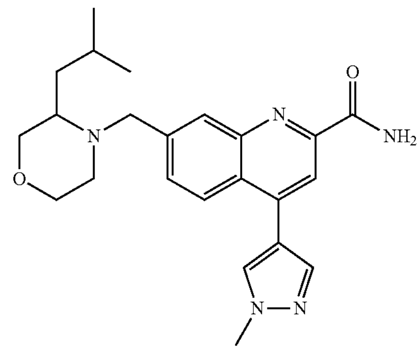 [SMILES: CC(C)CC1COCCN1Cc1ccc2c(-c3cnn(C)c3)cc(C(N)=O)nc2c1] | 7-{[3-(2-methylpropyl)morpholin-4-yl]methyl}-4-(1-methyl-1H-pyrazol-4-yl)quinoline-2-carboxamide | Calc'd 408.2, Found 408.2 |
| 4-65 | 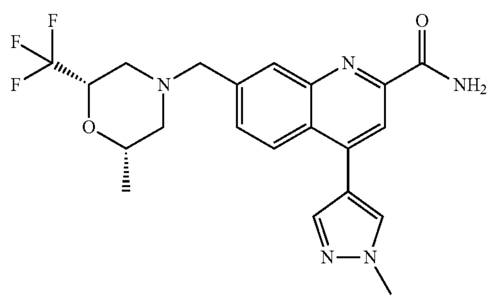 [SMILES: C[C@H]1CN(Cc2ccc3c(-c4cnn(C)c4)cc(C(N)=O)nc3c2)C[C@@H](C(F)(F)F)O1] | 4-(1-methyl-1H-pyrazol-4-yl)-7-{[(2S,6S)-2-methyl-6-(trifluoromethyl)morpholin-4-yl]methyl}quinoline-2-carboxamide | Calc'd 434.2, Found 434.3 |
| 4-66 | 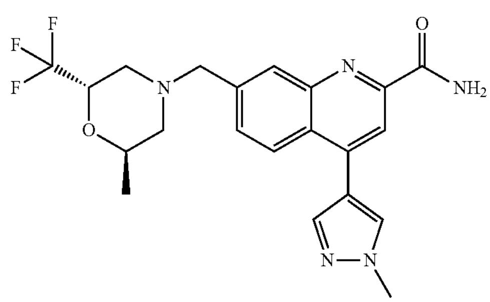 [SMILES: C[C@@H]1CN(Cc2ccc3c(-c4cnn(C)c4)cc(C(N)=O)nc3c2)C[C@@H](C(F)(F)F)O1] | 4-(1-methyl-1H-pyrazol-4-yl)-7-{[(2R,6S)-2-methyl-6-(trifluoromethyl)morpholin-4-yl]methyl}quinoline-2-carboxamide | Calc'd 434.2, Found 434.3 |
| 4-67 | 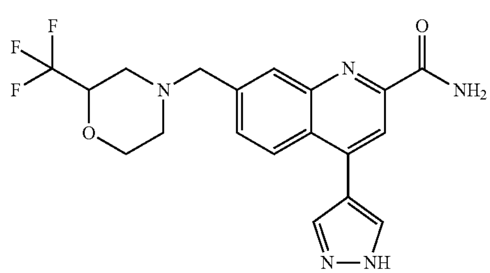 [SMILES: NC(=O)c1cc(-c2cn[nH]c2)c2ccc(CN3CCOC(C(F)(F)F)C3)cc2n1] | 4-(1H-pyrazol-4-yl)-7-{[2-(trifluoromethyl)morpholin-4-yl]methyl}quinoline-2-carboxamide | Calc'd 406.1, Found 406.2 |
| 4-68 | 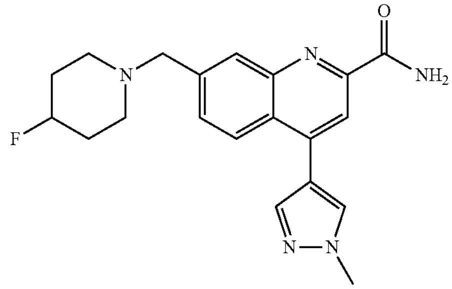 [SMILES: Cn1cc(-c2cc(C(N)=O)nc3cc(CN4CCC(F)CC4)ccc23)cn1] | 7-[(4-fluoropiperidin-1-yl)methyl]-4-(1-methyl-1H-pyrazol-4-yl)quinoline-2-carboxamide | Calc'd 368.2, Found 368.2 |

TABLE 4-continued

| Example | Structure | IUPAC Name | Exact Mass [M + H]+ |
|---|---|---|---|
| 4-69 | 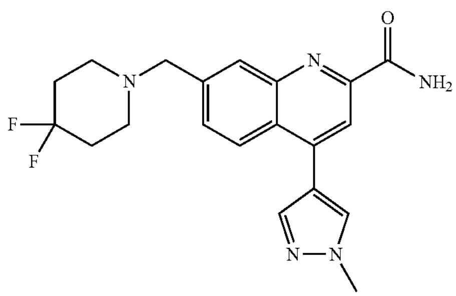 [SMILES: Cn1cc(-c2cc(C(N)=O)nc3cc(CN4CCC(F)(F)CC4)ccc23)cn1] | 7-[(4,4-difluoropiperidin-1-yl)methyl]-4-(1-methyl-1H-pyrazol-4-yl)quinoline-2-carboxamide | Calc'd 386.2, Found 386.2 |
| 4-70 | 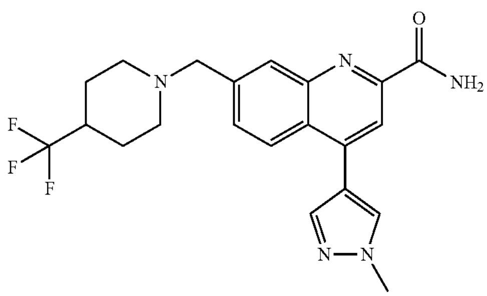 [SMILES: Cn1cc(-c2cc(C(N)=O)nc3cc(CN4CCC(C(F)(F)F)CC4)ccc23)cn1] | 4-(1-methyl-1H-pyrazol-4-yl)-7-{[4-(trifluoromethyl)piperidin-1-yl]methyl}quinoline-2-carboxamide | Calc'd 418.2, Found 418.2 |
| 4-71 | 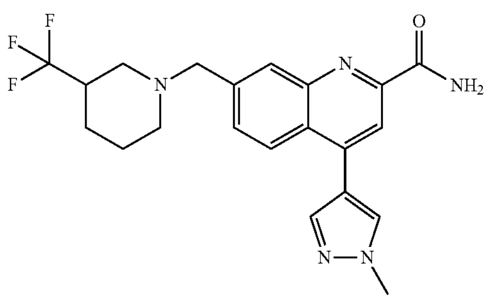 | 4-(1-methyl-1H-pyrazol-4-yl)-7-{[3-(trifluoromethyl)piperidin-1-yl]methyl}quinoline-2-carboxamide | Calc'd 418.2, Found 418.2 |
| 4-72 | 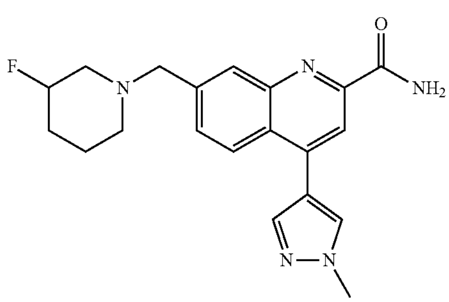 [SMILES: Cn1cc(-c2cc(C(N)=O)nc3cc(CN4CCCC(F)C4)ccc23)cn1] | 7-[(3-fluoropiperidin-1-yl)methyl]-4-(1-methyl-1H-pyrazol-4-yl)quinoline-2-carboxamide | Calc'd 368.2, Found 368.3 |
| 4-73 | 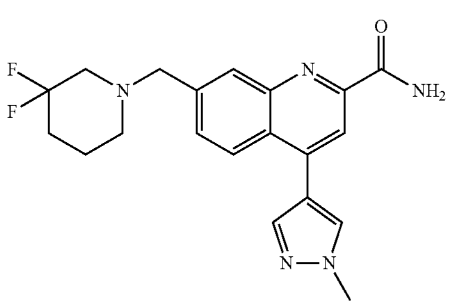 [SMILES: Cn1cc(-c2cc(C(N)=O)nc3cc(CN4CCCC(F)(F)C4)ccc23)cn1] | 7-[(3,3-difluoropiperidin-1-yl)methyl]-4-(1-methyl-1H-pyrazol-4-yl)quinoline-2-carboxamide | Calc'd 386.2, Found 386.3 |

TABLE 4-continued

| Example | Structure | IUPAC Name | Exact Mass [M + H]+ |
|---------|-----------|------------|---------------------|
| 4-74 | 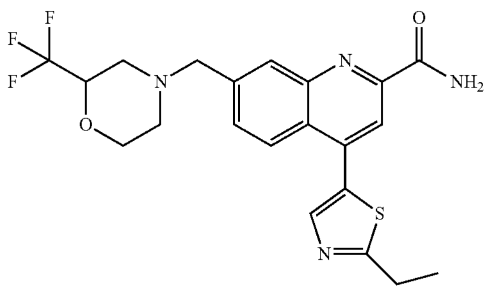 [SMILES: CCc1ncc(-c2cc(C(N)=O)nc3cc(CN4CCOC(C(F)(F)F)C4)ccc23)s1] | 4-(2-ethyl-1,3-thiazol-5-yl)-7-{[2-(trifluoromethyl)morpholin-4-yl]methyl}quinoline-2-carboxamide | Calc'd 451.1, Found 451.3 |
| 4-75 | 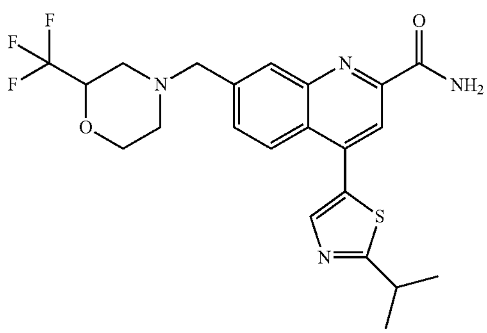 [SMILES: CC(C)c1ncc(-c2cc(C(N)=O)nc3cc(CN4CCOC(C(F)(F)F)C4)ccc23)s1] | 4-[2-(1-methylethyl)-1,3-thiazol-5-yl]-7-{[2-(trifluoromethyl)morpholin-4-yl]methyl}quinoline-2-carboxamide | Calc'd 465.2, Found 465.3 |
| 4-76 | 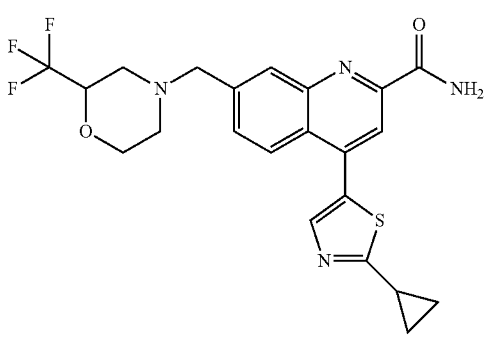 [SMILES: NC(=O)c1cc(-c2cnc(C3CC3)s2)c2ccc(CN3CCOC(C(F)(F)F)C3)cc2n1] | 4-(2-cyclopropyl-1,3-thiazol-5-yl)-7-{[2-(trifluoromethyl)morpholin-4-yl]methyl}quinoline-2-carboxamide | Calc'd 463.1, Found 463.3 |
| 4-77 | 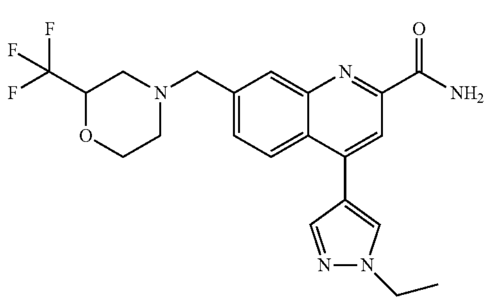 [SMILES: CCn1cc(-c2cc(C(N)=O)nc3cc(CN4CCOC(C(F)(F)F)C4)ccc23)cn1] | 4-(1-ethyl-1H-pyrazol-4-yl)-7-{[2-(trifluoromethyl)morpholin-4-yl]methyl}quinoline-2-carboxamide | Calc'd 434.2, Found 434.3 |

TABLE 4-continued

| Example | Structure | IUPAC Name | Exact Mass [M + H]+ |
|---|---|---|---|
| 4-78 | 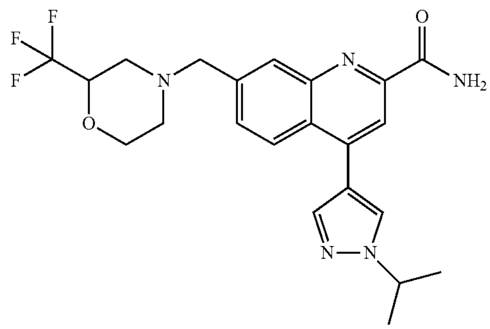 [SMILES: CC(C)n1cc(-c2cc(C(N)=O)nc3cc(CN4CCOC(C(F)(F)F)C4)ccc23)cn1] | 4-[1-(1-methylethyl)-1H-pyrazol-4-yl]-7-{[2-(trifluoromethyl)morpholin-4-yl]methyl}quinoline-2-carboxamide | Calc'd 448.2, Found 448.3 |
| 4-79 | 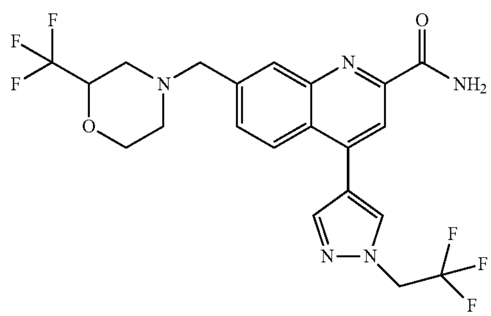 [SMILES: NC(=O)c1cc(-c2cnn(CC(F)(F)F)c2)c2ccc(CN3CCOC(C(F)(F)F)C3)cc2n1] | 4-[1-(2,2,2-trifluoroethyl)-1H-pyrazol-4-yl]-7-{[2-(trifluoromethyl)morpholin-4-yl]methyl}quinoline-2-carboxamide | Calc'd 488.2, Found 488.3 |
| 4-80 | 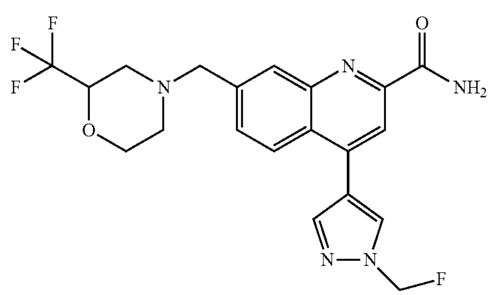 [SMILES: NC(=O)c1cc(-c2cnn(CF)c2)c2ccc(CN3CCOC(C(F)(F)F)C3)cc2n1] | 4-[1-(fluoromethyl)-1H-pyrazol-4-yl]-7-{[2-(trifluoromethyl)morpholin-4-yl]methyl}quinoline-2-carboxamide | Calc'd 438.2, Found 438.3 |
| 4-81 | 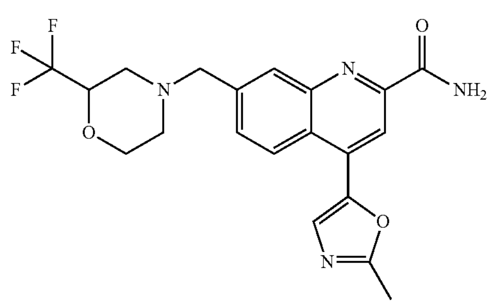 [SMILES: Cc1ncc(-c2cc(C(N)=O)nc3cc(CN4CCOC(C(F)(F)F)C4)ccc23)o1] | 4-(2-methyl-1,3-oxazol-5-yl)-7-{[2-(trifluoromethyl)morpholin-4-yl]methyl}quinoline-2-carboxamide | Calc'd 421.1, Found 421.3 |

TABLE 4-continued

| Example | Structure | IUPAC Name | Exact Mass [M + H]+ |
|---|---|---|---|
| 4-82 | 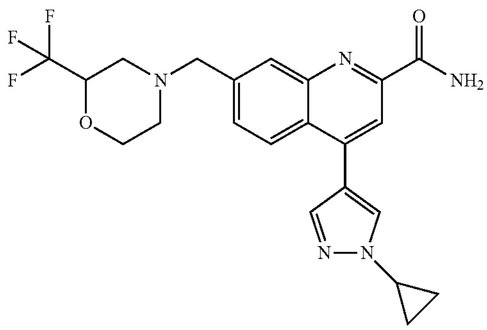 [SMILES: NC(=O)c1cc(-c2cnn(C3CC3)c2)c2ccc(CN3CCOC(C(F)(F)F)C3)cc2n1] | 4-(1-cyclopropyl-1H-pyrazol-4-yl)-7-{[2-(trifluoromethyl)morpholin-4-yl]methyl}quinoline-2-carboxamide | Calc'd 446.2, Found 446.3 |
| 4-83 | 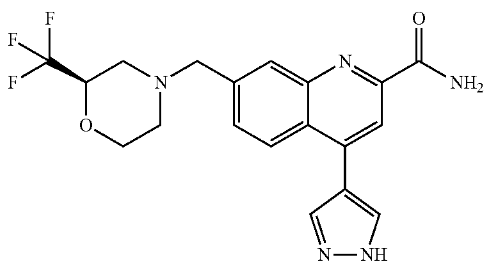 [SMILES: NC(=O)c1cc(-c2cn[nH]c2)c2ccc(CN3CCO[C@@H](C(F)(F)F)C3)cc2n1] | 4-(1H-pyrazol-4-yl)-7-{[(2R)-2-(trifluoromethyl)morpholin-4-yl]methyl}quinoline-2-carboxamide | Calc'd 406.1, Found 406.3 |
| 4-84 | 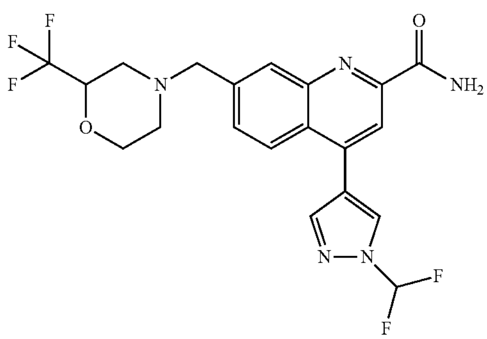 [SMILES: NC(=O)c1cc(-c2cnn(C(F)F)c2)c2ccc(CN3CCOC(C(F)(F)F)C3)cc2n1] | 4-[1-(difluoromethyl)-1H-pyrazol-4-yl]-7-{[2-(trifluoromethyl)morpholin-4-yl]methyl}quinoline-2-carboxamide | Calc'd 456.1, Found 456.3 |
| 4-85 | 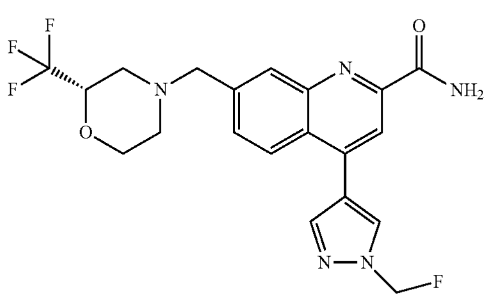 [SMILES: NC(=O)c1cc(-c2cnn(CF)c2)c2ccc(CN3CCO[C@H](C(F)(F)F)C3)cc2n1] | 4-[1-(fluoromethyl)-1H-pyrazol-4-yl]-7-{[(2)S-2-(trifluoromethyl)morpholin-4-yl]methyl}quinoline-2-carboxamide | Calc'd 438.2, Found 438.3 |
| 4-86 | 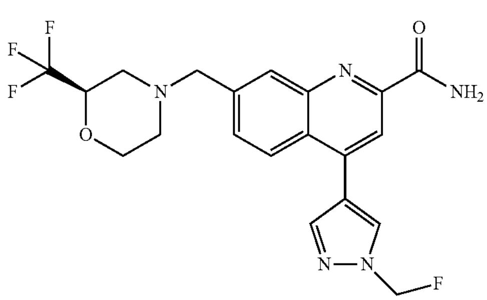 [SMILES: NC(=O)c1cc(-c2cnn(CF)c2)c2ccc(CN3CCO[C@@H](C(F)(F)F)C3)cc2n1] | 4-[1-(fluoromethyl)-1H-pyrazol-4-yl]-7-{[(2R)-2-(trifluoromethyl)morpholin-4-yl]methyl}quinoline-2-carboxamide | Calc'd 438.2, Found 438.3 |

TABLE 4-continued

| Example | Structure | IUPAC Name | Exact Mass [M + H]+ |
|---|---|---|---|
| 4-87 | 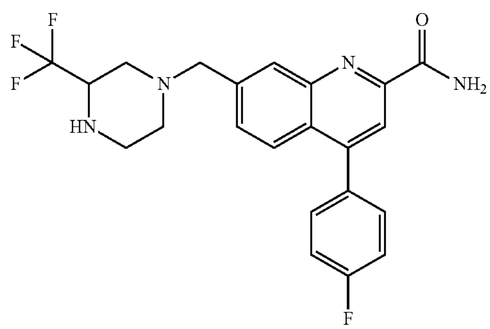 [SMILES: NC(=O)c1cc(-c2ccc(F)cc2)c2ccc(CN3CCNC(C(F)(F)F)C3)cc2n1] | 4-(4-fluorophenyl)-7-{[3-(trifluoromethyl)piperazin-1-yl]methyl}quinoline-2-carboxamide | Calc'd 433.2, Found 433.3 |
| 4-88 | 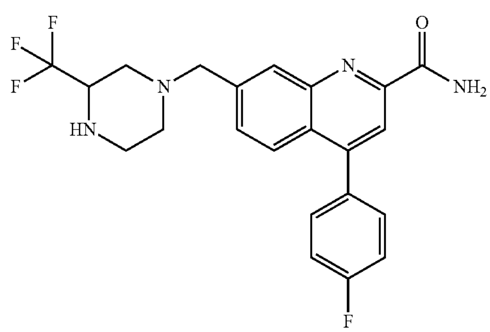 [SMILES: NC(=O)c1cc(-c2ccc(F)cc2)c2ccc(CN3CCNC(C(F)(F)F)C3)cc2n1] | 4-(4-fluorophenyl)-7-{[3-(trifluoromethyl)piperazin-1-yl]methyl}quinoline-2-carboxamide | Calc'd 433.2, Found 433.3 |
| 4-89 | 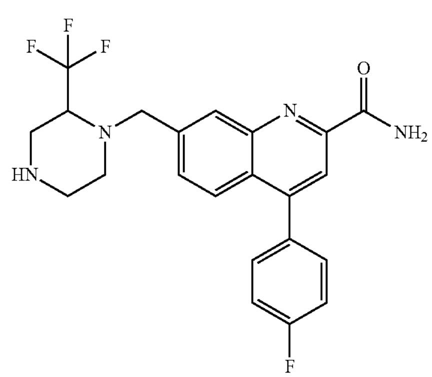 [SMILES: NC(=O)c1cc(-c2ccc(F)cc2)c2ccc(CN3CCNCC3C(F)(F)F)cc2n1] | 4-(4-fluorophenyl)-7-{[2-(trifluoromethyl)piperazin-1-yl]methyl}quinoline-2-carboxamide | Calc'd 433.2, Found 433.3 |
| 4-90 | 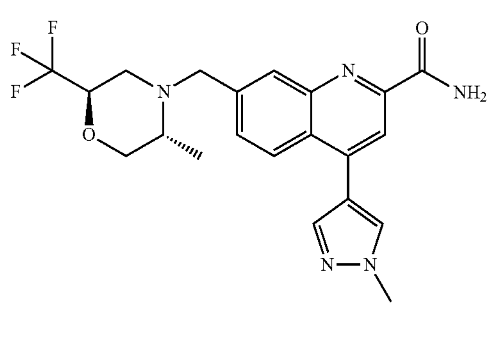 [SMILES: C[C@@H]1CO[C@@H](C(F)(F)F)CN1Cc1ccc2c(-c3cnn(C)c3)cc(C(N)=O)nc2c1] | 4-(1-methyl-1H-pyrazol-4-yl)-7-{[(2R,5R)-5-methyl-2-(trifluoromethyl)morpholin-4-yl]methyl}quinoline-2-carboxamide | Calc'd 434.2, Found 434.3 |

TABLE 4-continued

| Example | Structure | IUPAC Name | Exact Mass [M + H]+ |
|---|---|---|---|
| 4-91 | 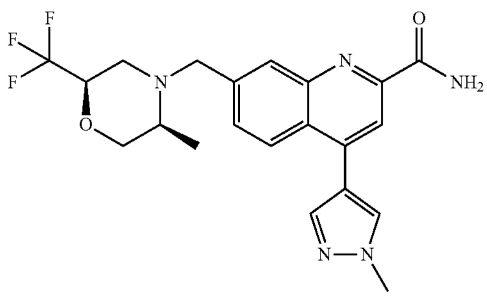 [SMILES: C[C@H]1CO[C@@H](C(F)(F)F)CN1Cc1ccc2c(-c3cnn(C)c3)cc(C(N)=O)nc2c1] | 4-(1-methyl-1H-pyrazol-4-yl)-7-{[(2R,5S)-5-methyl-2-(trifluoromethyl)morpholin-4-yl]methyl}quinoline-2-carboxamide | Calc'd 434.2, Found 434.2 |
| 4-92 | 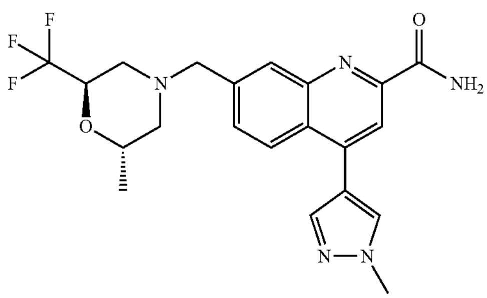 [SMILES: C[C@H]1CN(Cc2ccc3c(-c4cnn(C)c4)cc(C(N)=O)nc3c2)C[C@H](C(F)(F)F)O1] | 4-(1-methyl-1H-pyrazol-4-yl)-7-{[(2S,6R)-2-methyl-6-(trifluoromethyl)morpholin-4-yl]methyl}quinoline-2-carboxamide | Calc'd 434.2, Found 434.3 |
| 4-93 | 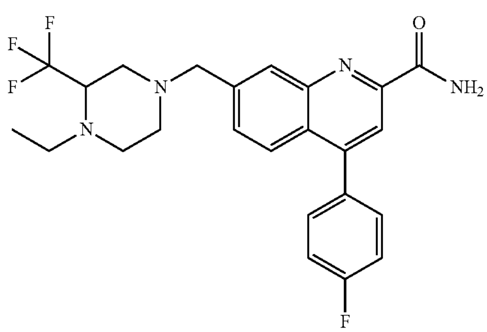 [SMILES: CCN1CCN(Cc2ccc3c(-c4ccc(F)cc4)cc(C(N)=O)nc3c2)CC1C(F)(F)F] | 7-{[4-ethyl-3-(trifluoromethyl)piperazin-1-yl]methyl}-4-(4-fluorophenyl)quinoline-2-carboxamide | Calc'd 461.2, Found 461.3 |
| 4-94 | 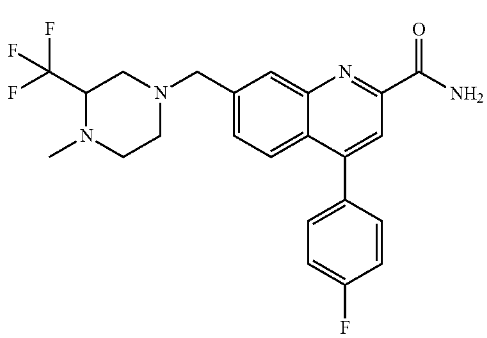 [SMILES: CN1CCN(Cc2ccc3c(-c4ccc(F)cc4)cc(C(N)=O)nc3c2)CC1C(F)(F)F] | 4-(4-fluorophenyl)-7-{[4-methyl-3-(trifluoromethyl)piperazin-1-yl]methyl}quinoline-2-carboxamide | Calc'd 447.2, Found 447.3 |

TABLE 4-continued

| Example | IUPAC Name | Exact Mass [M + H]+ |
|---|---|---|
| 4-95 | 7-{[(6R)-2,2-dimethyl-6-(trifluoromethyl)morpholin-4-yl]methyl}-4-(1-methyl-1H-pyrazol-4-yl)quinoline-2-carboxamide | Calc'd 448.2, Found 448.3 |
| 4-96 | 7-{[(2R)-5,5-dimethyl-2-(trifluoromethyl)morpholin-4-yl]methyl}-4-(1-methyl-1H-pyrazol-4-yl)quinoline-2-carboxamide | Calc'd 448.2, Found 448.3 |
| 4-97 | 7-{[(2R,6R)-2-methyl-6-(trifluoromethyl)morpholin-4-yl]methyl}-4-(1H-pyrazol-4-yl)quinoline-2-carboxamide | Calc'd 420.2, Found 420.2 |
| 4-98 | 4-(1-methyl-1H-pyrazol-4-yl)-7-{[2-(2,2,2-trifluoroethyl)morpholin-4-yl]methyl}quinoline-2-carboxamide | Calc'd 434.2, Found 434.3 |
| 4-99 | 7-[(2-ethylmorpholin-4-yl)methyl]-4-(1-methyl-1H-pyrazol-4-yl)quinoline-2-carboxamide | Calc'd 380.2, Found 380.3 |

TABLE 4-continued

| Example | Structure | IUPAC Name | Exact Mass [M + H]+ |
|---|---|---|---|
| 4-100 | 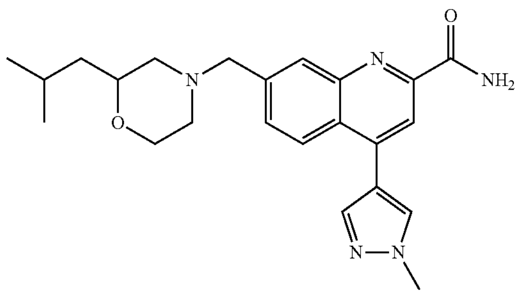 [SMILES: CC(C)CC1CN(Cc2ccc3c(-c4cnn(C)c4)cc(C(N)=O)nc3c2)CCO1] | 7-{[2-(2-methylpropyl)morpholin-4-yl]methyl}-4-(1-methyl-1H-pyrazol-4-yl)quinoline-2-carboxamide | Calc'd 408.2, Found 408.3 |
| 4-101 | 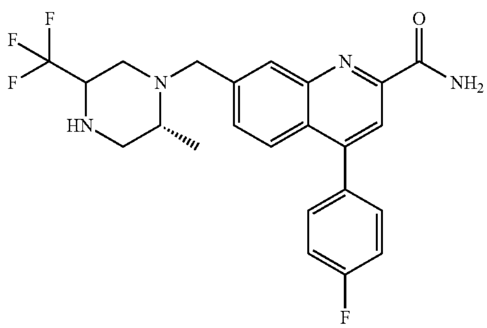 [SMILES: C[C@@H]1CNC(C(F)(F)F)CN1Cc1ccc2c(-c3ccc(F)cc3)cc(C(N)=O)nc2c1] | 4-(4-fluorophenyl)-7-{[(2R)-2-methyl-5-(trifluoromethyl)piperazin-1-yl]methyl}quinoline-2-carboxamide | Calc'd 447.2, Found 447.3 |
| 4-102 | 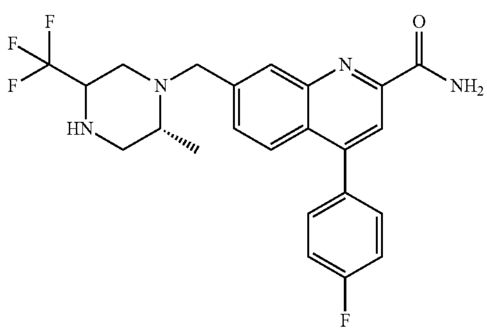 [SMILES: C[C@@H]1CNC(C(F)(F)F)CN1Cc1ccc2c(-c3ccc(F)cc3)cc(C(N)=O)nc2c1] | 4-(4-fluorophenyl)-7-{[(2R)-2-methyl-5-(trifluoromethyl)piperazin-1-yl]methyl}quinoline-2-carboxamide | Calc'd 447.2, Found 447.3 |
| 4-103 | 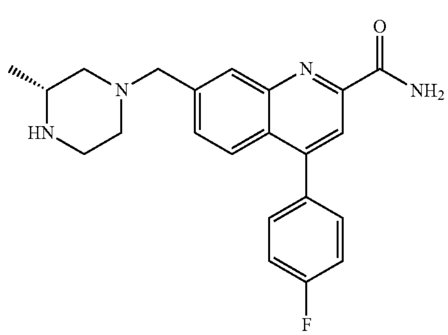 [SMILES: C[C@@H]1CN(Cc2ccc3c(-c4ccc(F)cc4)cc(C(N)=O)nc3c2)CCN1] | 4-(4-fluorophenyl)-7-{[(3R)-3-methylpiperazin-1-yl]methyl}quinoline-2-carboxamide | Calc'd 379.2, Found 379.3 |

TABLE 4-continued

| Example | Structure | IUPAC Name | Exact Mass [M + H]+ |
|---|---|---|---|
| 4-104 | 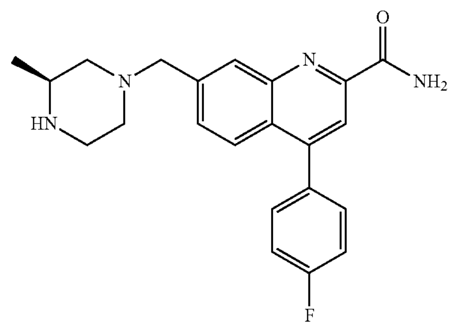 [SMILES: C[C@H]1CN(Cc2ccc3c(-c4ccc(F)cc4)cc(C(N)=O)nc3c2)CCN1] | 4-(4-fluorophenyl)-7-{[(3S)-3-methylpiperazin-1-yl]methyl}quinoline-2-carboxamide | Calc'd 379.2, Found 379.3 |
| 4-105 | 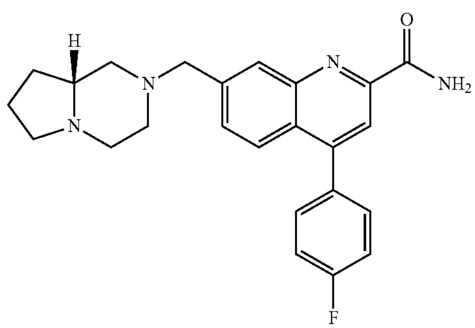 [SMILES: NC(=O)c1cc(-c2ccc(F)cc2)c2ccc(CN3CCN4CCC[C@@H]4C3)cc2n1] | 4-(4-fluorophenyl)-7-[(8aR)-hexahydropyrrolo[1,2-a]pyrazin-2(1H)-ylmethyl]quinoline-2-carboxamide | Calc'd 405.2, Found 405.3 |
| 4-106 | 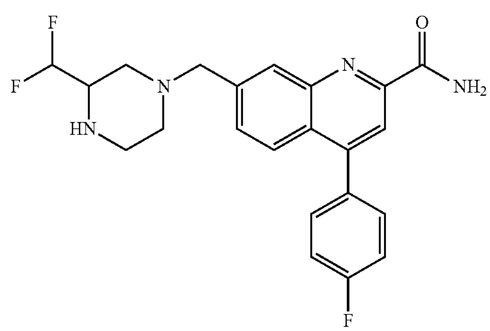 [SMILES: NC(=O)c1cc(-c2ccc(F)cc2)c2ccc(CN3CCNC(C(F)F)C3)cc2n1] | 7-{[3-(difluoromethyl)piperazin-1-yl]methyl}-4-(4-fluorophenyl)quinoline-2-carboxamide | Calc'd 415.2, Found 415.2 |
| 4-107 | 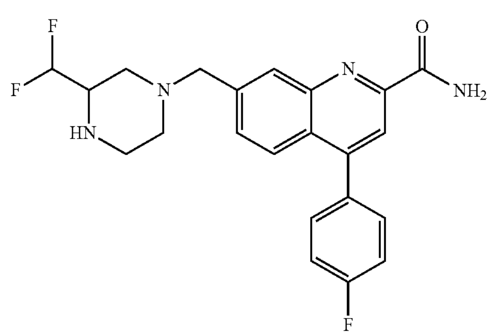 [SMILES: NC(=O)c1cc(-c2ccc(F)cc2)c2ccc(CN3CCNC(C(F)F)C3)cc2n1] | 7-{[3-(difluoromethyl)piperazin-1-yl]methyl}-4-(4-fluorophenyl)quinoline-2-carboxamide | Calc'd 415.2, Found 415.2 |

TABLE 4-continued

| Example | Structure | IUPAC Name | Exact Mass [M + H]+ |
|---|---|---|---|
| 4-108 | 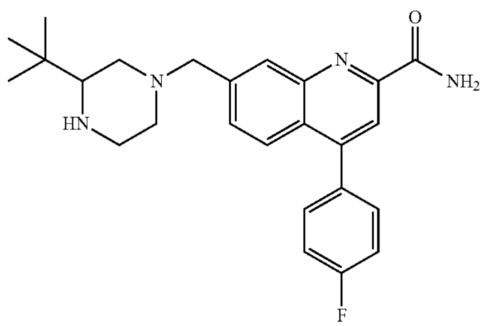 [SMILES: CC(C)(C)C1CN(Cc2ccc3c(-c4ccc(F)cc4)cc(C(N)=O)nc3c2)CCN1] | 7-[(3-tert-butylpiperazin-1-yl)methyl]-4-(4-fluorophenyl)quinoline-2-carboxamide | Calc'd 421.2, Found 421.3 |
| 4-109 | 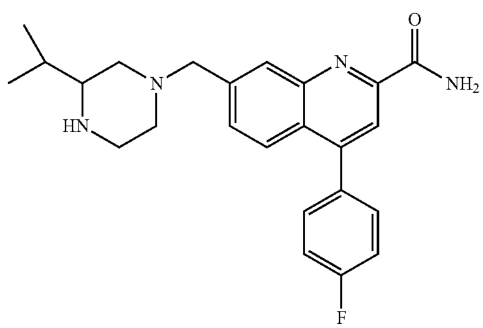 [SMILES: CC(C)C1CN(Cc2ccc3c(-c4ccc(F)cc4)cc(C(N)=O)nc3c2)CCN1] | 4-(4-fluorophenyl)-7-{[3-(1-methylethyl)piperazin-1-yl]methyl}quinoline-2-carboxamide | Calc'd 407.2, Found 407.3 |
| 4-110 | 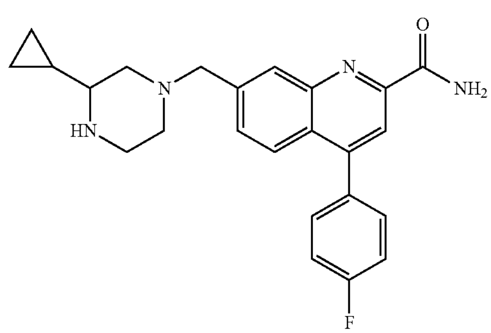 [SMILES: NC(=O)c1cc(-c2ccc(F)cc2)c2ccc(CN3CCNC(C4CC4)C3)cc2n1] | 7-[(3-cyclopropylpiperazin-1-yl)methyl]-4-(4-fluorophenyl)quinoline-2-carboxamide | Calc'd 405.2, Found 405.3 |
| 4-111 | 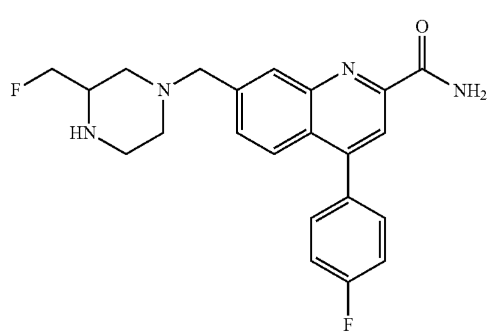 [SMILES: NC(=O)c1cc(-c2ccc(F)cc2)c2ccc(CN3CCNC(CF)C3)cc2n1] | 7-{[3-(fluoromethyl)piperazin-1-yl]methyl}-4-(4-fluorophenyl)quinoline-2-carboxamide | Calc'd 397.2, Found 397.3 |

TABLE 4-continued

| Example | Structure | IUPAC Name | Exact Mass [M + H]+ |
|---|---|---|---|
| 4-112 | 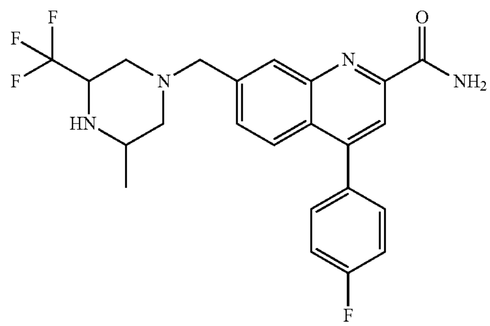 [SMILES: CC1CN(Cc2ccc3c(-c4ccc(F)cc4)cc(C(N)=O)nc3c2)CC(C(F)(F)F)N1] | 4-(4-fluorophenyl)-7-{[3-methyl-5-(trifluoromethyl)piperazin-1-yl]methyl}quinoline-2-carboxamide | Calc'd 447.2, Found 447.3 |
| 4-113 | 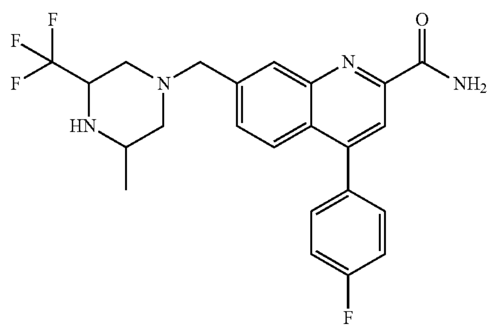 [SMILES: CC1CN(Cc2ccc3c(-c4ccc(F)cc4)cc(C(N)=O)nc3c2)CC(C(F)(F)F)N1] | 4-(4-fluorophenyl)-7-{[3-methyl-5-(trifluoromethyl)piperazin-1-yl]methyl}quinoline-2-carboxamide | Calc'd 447.2, Found 447.3 |
| 4-114 | 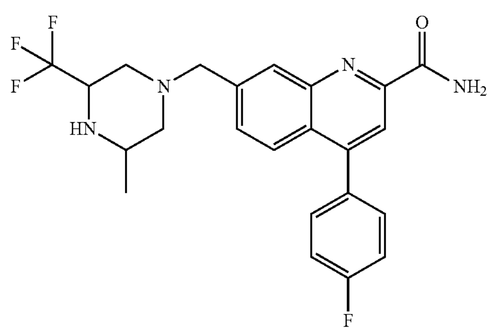 [SMILES: CC1CN(Cc2ccc3c(-c4ccc(F)cc4)cc(C(N)=O)nc3c2)CC(C(F)(F)F)N1] | 4-(4-fluorophenyl)-7-{[3-methyl-5-(trifluoromethyl)piperazin-1-yl]methyl}quinoline-2-carboxamide | Calc'd 447.2, Found 447.3 |
| 4-115 | 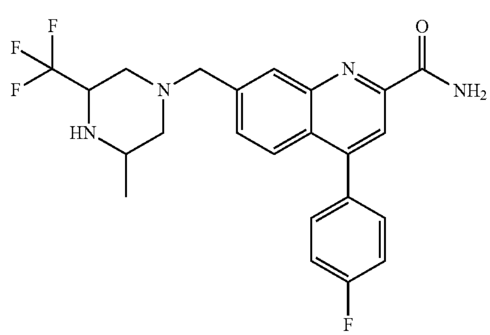 [SMILES: CC1CN(Cc2ccc3c(-c4ccc(F)cc4)cc(C(N)=O)nc3c2)CC(C(F)(F)F)N1] | 4-(4-fluorophenyl)-7-{[3-methyl-5-(trifluoromethyl)piperazin-1-yl]methyl}quinoline-2-carboxamide | Calc'd 447.2, Found 447.3 |

TABLE 4-continued

| Example | Structure | IUPAC Name | Exact Mass [M + H]+ |
|---------|-----------|------------|---------------------|
| 4-116 | 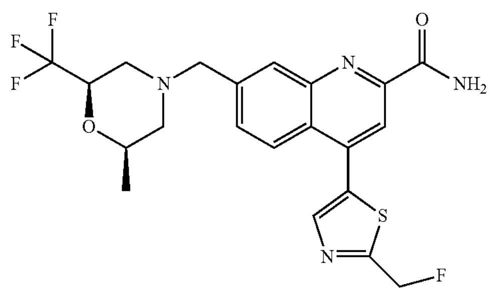 [SMILES: C[C@@H]1CN(Cc2ccc3c(-c4cnc(CF)s4)cc(C(N)=O)nc3c2)C[C@H](C(F)(F)F)O1] | 4-[2-(fluoromethyl)-1,3-thiazol-5-yl]-7-{[(2R,6R)-2-methyl-6-(trifluoromethyl)morpholin-4-yl]methyl}quinoline-2-carboxamide | Calc'd 469.1, Found 469.2 |
| 4-117 | 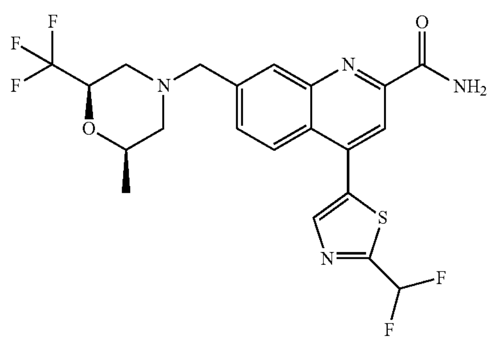 [SMILES: C[C@@H]1CN(Cc2ccc3c(-c4cnc(C(F)F)s4)cc(C(N)=O)nc3c2)C[C@H](C(F)(F)F)O1] | 4-[2-(difluoromethyl)-1,3-thiazol-5-yl]-7-{[(2R,6R)-2-methyl-6-(trifluoromethyl)morpholin-4-yl]methyl}quinoline-2-carboxamide | Calc'd 487.1, Found 487.2 |
| 4-118 | 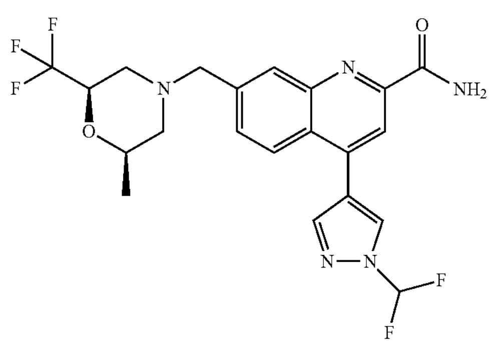 [SMILES: C[C@@H]1CN(Cc2ccc3c(-c4cnn(C(F)F)c4)cc(C(N)=O)nc3c2)C[C@H](C(F)(F)F)O1] | 4-[1-(difluoromethyl)-1H-pyrazol-4-yl]-7-{[(2R,6R)-2-methyl-6-(trifluoromethyl)morpholin-4-yl]methyl}quinoline-2-carboxamide | Calc'd 470.2, Found 470.2 |
| 4-119 | 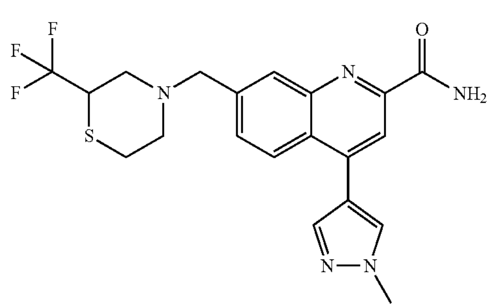 | 4-(1-methyl-1H-pyrazol-4-yl)-7-{[2-(trifluoromethyl)thiomorpholin-4-yl]methyl}quinoline-2-carboxamide | Calc'd 436.1, Found 436.2 |

TABLE 4-continued

| Example | Structure | IUPAC Name | Exact Mass [M + H]+ |
|---|---|---|---|
| 4-120 | 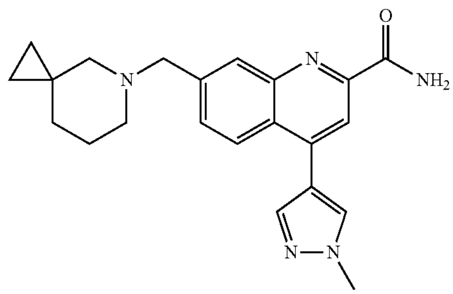 [SMILES: Cn1cc(-c2cc(C(N)=O)nc3cc(CN4CCCC5(CC5)C4)ccc23)cn1] | 7-(5-azaspiro[2.5]oct-5-ylmethyl)-4-(1-methyl-1H-pyrazol-4-yl)quinoline-2-carboxamide | Calc'd 376.2, Found 376.3 |
| 4-121 | 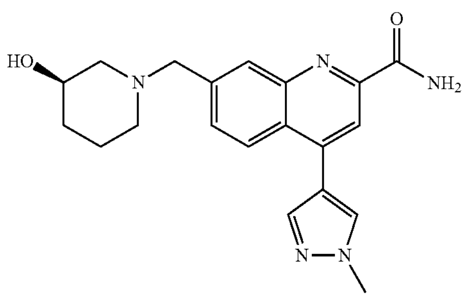 [SMILES: Cn1cc(-c2cc(C(N)=O)nc3cc(CN4CCC[C@@H](O)C4)ccc23)cn1] | 7-{[(3R)-3-hydroxypiperidin-1-yl]methyl}-4-(1-methyl-1H-pyrazol-4-yl)quinoline-2-carboxamide | Calc'd 366.2, Found 366.3 |
| 4-122 | 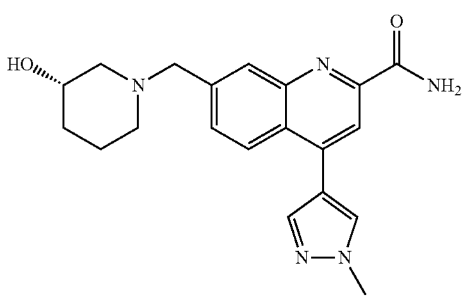 [SMILES: Cn1cc(-c2cc(C(N)=O)nc3cc(CN4CCC[C@H](O)C4)ccc23)cn1] | 7-{[(3S)-3-hydroxypiperidin-1-yl]methyl}-4-(1-methyl-1H-pyrazol-4-yl)quinoline-2-carboxamide | Calc'd 366.2, Found 366.3 |
| 4-123 | Isomer A | 4-(4-fluorophenyl)-7-{[3-(trifluoromethyl)piperidin-1-yl]methyl}quinoline-2-carboxamide | Calc'd 432.2, Found 432.3 |

TABLE 4-continued

| Example | Structure | IUPAC Name | Exact Mass [M + H]+ |
|---|---|---|---|
| 4-124 | Isomer B | 4-(4-fluorophenyl)-7-{[3-(trifluoromethyl)piperidin-1-yl]methyl}quinoline-2-carboxamide | Calc'd 432.2, Found 432.3 |
| 4-125 | 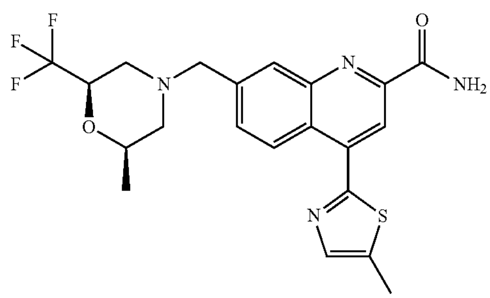 [SMILES: Cc1cnc(-c2cc(C(N)=O)nc3cc(CN4C[C@@H](C)O[C@@H](C(F)(F)F)C4)ccc23)s1] | 4-(5-methyl-1,3-thiazol-2-yl)-7-{[(2R,6R)-2-methyl-6-(trifluoromethyl)morpholin-4-yl]methyl}quinoline-2-carboxamide | Calc'd 451.1, Found 451.2 |
| 4-126 | 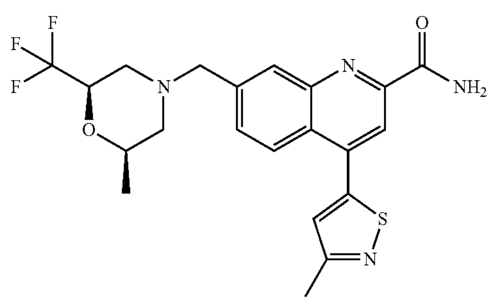 [SMILES: Cc1cc(-c2cc(C(N)=O)nc3cc(CN4C[C@@H](C)O[C@@H](C(F)(F)F)C4)ccc23)sn1] | 4-(3-methylisothiazol-5-yl)-7-{[(2R,6R)-2-methyl-6-(trifluoromethyl)morpholin-4-yl]methyl}quinoline-2-carboxamide | Calc'd 451.1, Found 451.2 |
| 4-127 | 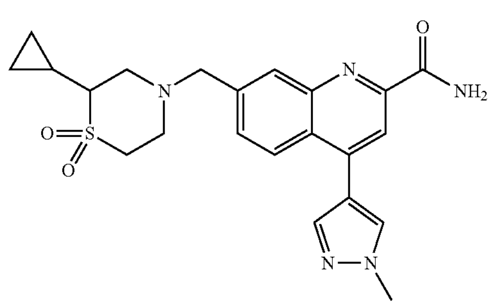 [SMILES: Cn1cc(-c2cc(C(N)=O)nc3cc(CN4CCS(=O)(=O)C(C5CC5)C4)ccc23)cn1] | 7-[(2-cyclopropyl-1,1-dioxidothiomorpholin-4-yl)methyl]-4-(1-methyl-1H-pyrazol-4-yl)quinoline-2-carboxamide | Calc'd 440.2, Found 440.3 |

TABLE 4-continued

| Example | Structure | IUPAC Name | Exact Mass [M + H]+ |
|---|---|---|---|
| 4-128 | 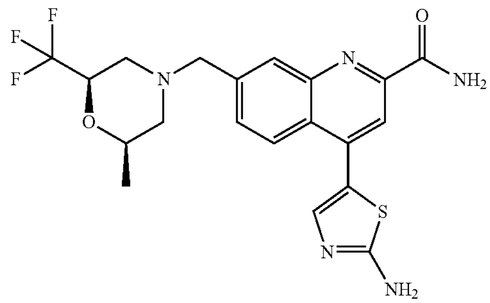 [SMILES: C[C@@H]1CN(Cc2ccc3c(-c4cnc(N)s4)cc(C(N)=O)nc3c2)C[C@H](C(F)(F)F)O1] | 4-(2-amino-1,3-thiazol-5-yl)-7-{[(2R,6R)-2-methyl-6-(trifluoromethyl)morpholin-4-yl]methyl}quinoline-2-carboxamide | Calc'd 452.1, Found 452.2 |
| 4-129 | 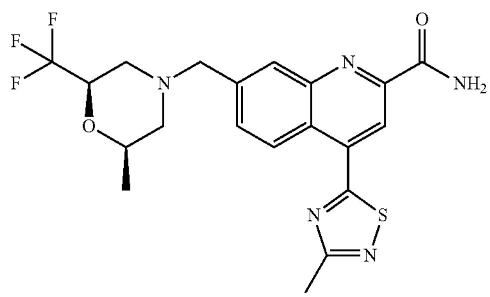 [SMILES: Cc1nsc(-c2cc(C(N)=O)nc3cc(CN4C[C@@H](C)O[C@@H](C(F)(F)F)C4)ccc23)n1] | 4-(3-methyl-1,2,4-thiadiazol-5-yl)-7-{[(2R,6R)-2-methyl-6-(trifluoromethyl)morpholin-4-yl]methyl}quinoline-2-carboxamide | Calc'd 452.1, Found 452.2 |
| 4-130 | 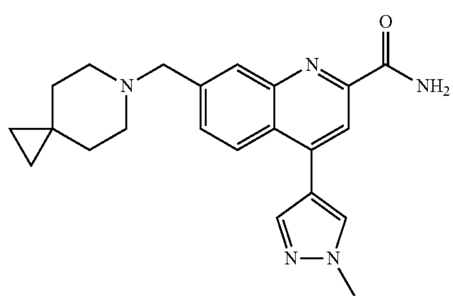 [SMILES: Cn1cc(-c2cc(C(N)=O)nc3cc(CN4CCC5(CC4)CC5)ccc23)cn1] | 7-(6-azaspiro[2.5]oct-6-ylmethyl)-4-(1-methyl-1H-pyrazol-4-yl)quinoline-2-carboxamide | Calc'd 376.2, Found 376.3 |
| 4-131 | 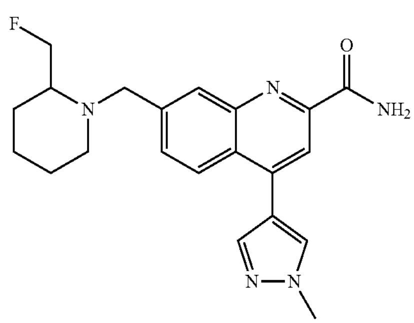 [SMILES: Cn1cc(-c2cc(C(N)=O)nc3cc(CN4CCCCC4CF)ccc23)cn1] | 7-{[2-(fluoromethyl)piperidin-1-yl]methyl}-4-(1-methyl-1H-pyrazol-4-yl)quinoline-2-carboxamide | Calc'd 382.2, Found 382.3 |
| 4-132 | 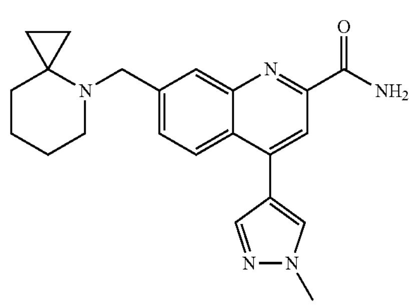 [SMILES: Cn1cc(-c2cc(C(N)=O)nc3cc(CN4CCCCC45CC5)ccc23)cn1] | 7-(4-azaspiro[2.5]oct-4-ylmethyl)-4-(1-methyl-1H-pyrazol-4-yl)quinoline-2-carboxamide | Calc'd 376.2, Found 376.3 |

TABLE 4-continued

| Example | Structure | IUPAC Name | Exact Mass [M + H]+ |
|---|---|---|---|
| 4-133 | 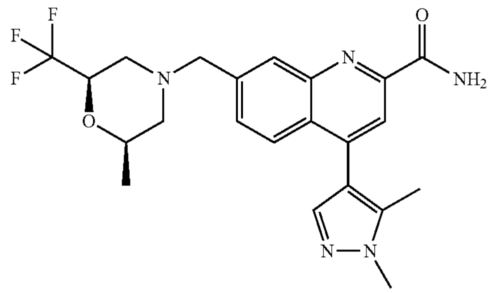 [SMILES: Cc1c(-c2cc(C(N)=O)nc3cc(CN4C[C@@H](C)O[C@@H](C(F)(F)F)C4)ccc23)cnn1C] | 4-(1,5-dimethyl-1H-pyrazol-4-yl)-7-{[(2R,6R)-2-methyl-6-(trifluoromethyl)morpholin-4-yl]methyl}quinoline-2-carboxamide | Calc'd 448.5, Found 448.4 |
| 4-134 | 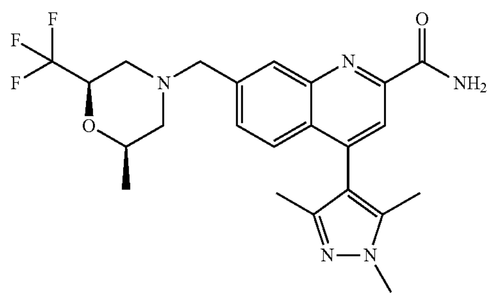 [SMILES: Cc1nn(C)c(C)c1-c1cc(C(N)=O)nc2cc(CN3C[C@@H](C)O[C@@H](C(F)(F)F)C3)ccc12] | 7-{[(2R,6R)-2-methyl-6-(trifluoromethyl)morpholin-4-yl]methyl}-4-(1,3,5-trimethyl-1H-pyrazol-4-yl)quinoline-2-carboxamide | Calc'd 462.5, Found 462.4 |
| 4-135 | 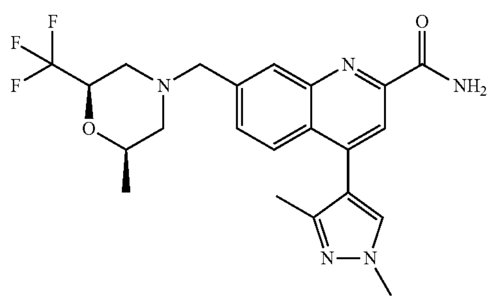 [SMILES: Cc1nn(C)cc1-c1cc(C(N)=O)nc2cc(CN3C[C@@H](C)O[C@@H](C(F)(F)F)C3)ccc12] | 4-(1,3-dimethyl-1H-pyrazol-4-yl)-7-{[(2R,6R)-2-methyl-6-(trifluoromethyl)morpholin-4-yl]methyl}quinoline-2-carboxamide | Calc'd 448.5, Found 448.4 |

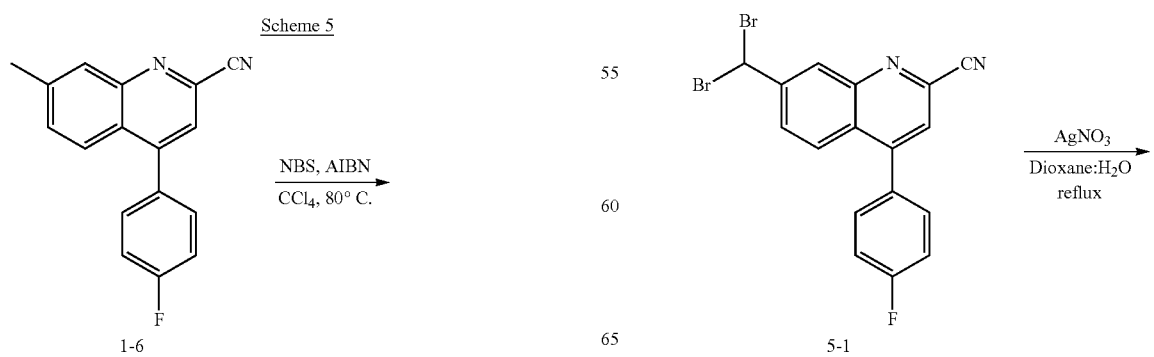

Scheme 5

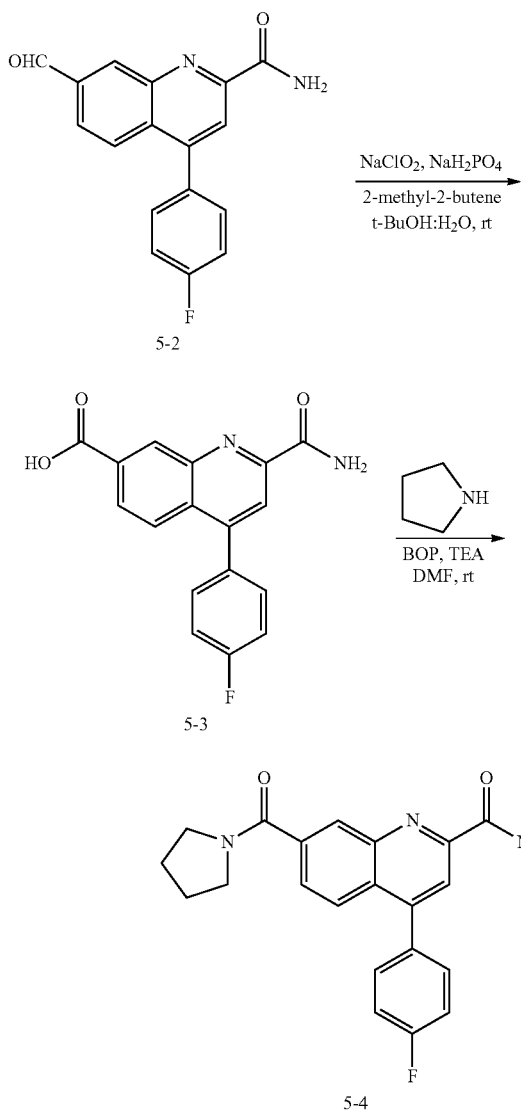

afford 7-(dibromomethyl)-4-(4-fluorophenyl)quinoline-2-carbonitrile (5-1, 1.27 g, 10.1%). LRMS m/z (M+H)+ 421.1 found, 421.1 required.

4-(4-Fluorophenyl)-7-formylquinoline-2-carboxamide (5-2)

To a solution of 7-(dibromomethyl)-4-(4-fluorophenyl)quinoline-2-carbonitrile (5-1, 1.27 g, 3.02 mmol, 1.0 equiv.) in 1, 4-dioxane (40.0 mL, 0.075 M) was added a slurry of silver nitrate (2.05 g, 12.1 mmol, 4.0 equiv.) in water (20.0 mL). The resulting mixture was heated to reflux for 24 hours, then cooled, and filtered through a pad of celite. The filtrate was washed with ethyl acetate, the layers were separated and the organic layer was washed with brine, dried over MgSO$_4$, filtered and concentrated to give 4-(4-fluorophenyl)-7-formylquinoline-2-carboxamide (5-2, 850.0 mg, 96.0%) as a white solid. LRMS m/z (M+H)+ 295.1 found, 295.1 required.

2-(Aminocarbonyl)-4-(4-fluorophenyl)quinoline-7-carboxylic acid (5-3)

To a solution of 4-(4-fluorophenyl)-7-formylquinoline-2-carboxamide (5-2, 200.0 mg, 0.680 mmol, 1.0 equiv.) and 2-methyl-2-butene (3.96 mL, 37.4 mmol, 55 equiv.) in t-BuOH (14.0 mL, 0.05 M) was added a solution of sodium chlorite (553.0 mg, 6.12 mmol, 9 equiv.) and sodium dihydrogen phosphate monohydrate (559.0 mg, 4.08 mmol, 6 equiv.) in water (6.5 mL). The resulting mixture was stirred at room temperature for 1 hour. A white solid precipitated. Water (100.0 ml) was added and the mixture stirred for 30 minutes. The solid was collected via suction filtration, washed with water, dried in vacuo to give 2-(aminocarbonyl)-4-(4-fluorophenyl)quinoline-7-carboxylic acid (5-3, 150.0 mg, 71.1%) as a white solid. LRMS m/z (M+H)+ 311.1 found, 311.1 required.

4-(4-Fluorophenyl)-7-(pyrrolidin-1-ylcarbonyl)quinoline-2-carboxamide (5-4)

2-(Aminocarbonyl)-4-(4-fluorophenyl)quinoline-7-carboxylic acid (5-3, 50.0 mg, 0.161 mmol, 1.0 equiv), pyrrolidine (11.5 mg, 0.161 mmol, 1.0 equiv.), BOP (93.0 mg, 0.209 mmol, 1.3 equiv.), and TEA (0.0670 mL, 0.483 mmol, 3 equiv) were dissolved into DMF (1.0 mL) and stirred at room temperature for 1 hour. The mixture was diluted with methylene chloride, washed with water, brine, dried over MgSO$_4$, filtered and concentrated. The crude residue was purified by reverse phase HPLC (H$_2$O/CH$_3$CN gradient w/ 0.1% TFA modifier) to afford 4-(4-Fluorophenyl)-7-(pyrrolidin-1-ylcarbonyl)quinoline-2-carboxamide (5-4, 50.0 mg, 85.0%) as a colorless solid. $^1$H NMR (500 MHz, CDCl$_3$): δ 8.324 (d, J=1.47 Hz, 1H); 8.273 (s, 1H); 8.251 (br s, 1H); 8.026 (d, J 8.78 Hz, 1H); 7.762 (dd, J$_1$=8.54 Hz, J$_2$=1.71 Hz, 1H); 7.501-7.529 (m, 2H); 7.246-7.286 (m, 2H); 6.750 (br s, 1H); 3.765 (tr, J=6.95 Hz, 2H); 3.567 (tr, J=6.68 Hz, 2H); 2.055 (quint, J=6.78 Hz, 2H); 1.962 (quint, J=6.65 Hz, 2H). LRMS m/z (M+H)+ 364.1 found, 364.1 required.

The following compounds have been prepared according to procedures similar to those found in Scheme 5 selecting the appropriate quinoline derivative and boronic acid derivatives and provide examples of compounds in the invention.

Example 5

Synthesis of 4-(4-fluorophenyl)-7-(pyrrolidin-1-ylcarbonyl)quinoline-2-carboxamide (5-4)

7-(Dibromomethyl)-4-(4-fluorophenyl)quinoline-2-carbonitrile (5-1)

4-(4-Fluorophenyl)-7-methylquinoline-2-carbonitrile (1-6, 7.86 g, 30.0 mmol, 1.0 equiv.) was dissolved in carbon tetrachloride (150.0 mL, 0.2 M). NBS (5.44 g, 30.6 mmol, 1.02 equiv) and AIBN (148.0 mg, 0.899 mmol, 0.03 equiv.) were added and the mixture was heated to reflux for 5 hours. The mixture was cooled to room temperature and the white precipitate was filtered off. The filtrate was concentrated and the residue was purified by column chromatography on a silica gel column, eluting with EtOAc/Isohexane (0-50%) to TABLE 5
| Example | Structure | IUPAC Name | Exact Mass [M + H]+ |
|---|---|---|---|
| 5-5 | 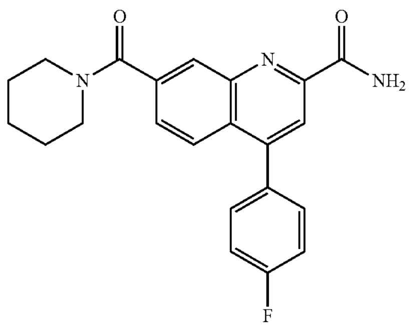 [SMILES: NC(=O)c1cc(-c2ccc(F)cc2)c2ccc(C(=O)N3CCCCC3)cc2n1] | 4-(4-fluorophenyl)-7-(piperidin-1-ylcarbonyl)quinoline-2-carboxamide | Calc'd 378.2, Found 378.2 |
| 5-6 | 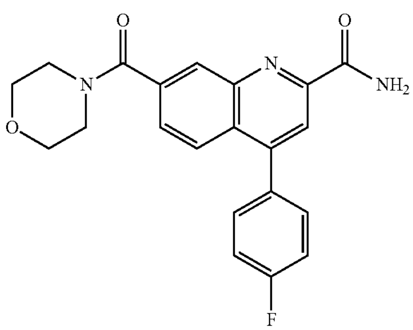 [SMILES: NC(=O)c1cc(-c2ccc(F)cc2)c2ccc(C(=O)N3CCOCC3)cc2n1] | 4-(4-fluorophenyl)-7-(morpholin-4-ylcarbonyl)quinoline-2-carboxamide | Calc'd 380.1, Found 380.3 |
Scheme 6.1
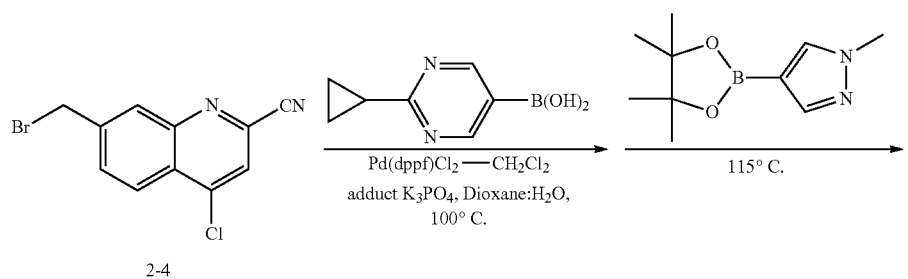
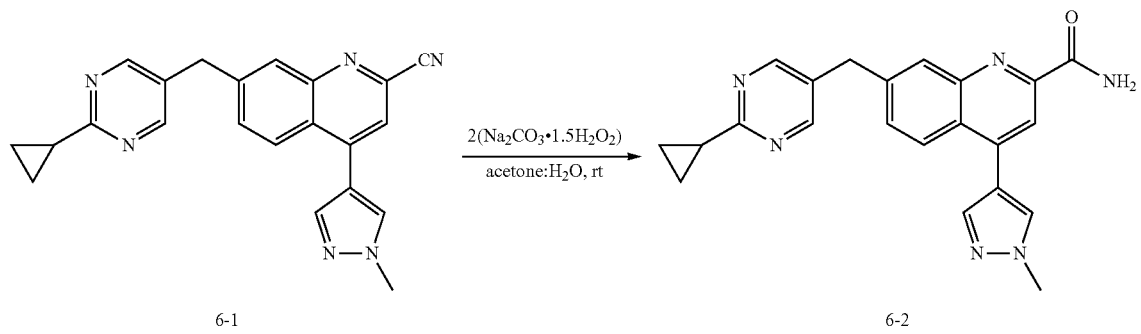

Example 6.1

Synthesis of 7-((2-cyclopropylpyrimidin-5-yl)methyl)-4-(1-methyl-1H-pyrazol-4-yl)quinoline-2-carboxamide (6-2)

7-((2-Cyclopropylpyrimidin-5-yl)methyl)-4-(1-methyl-1H-pyrazol-4-yl)quinoline-2-carbonitrile (6-1)

After degassing with $N_2$, a mixture of 7-(bromomethyl)-4-chloroquinoline-2-carbonitrile (2-4, 650 mg, 2.31 mmol), 2-cyclopropyl-5-(4,4,5,5-tetramethyl-1,3,2-dioxaborolan-2-yl)pyrimidine (580 mg, 2.36 mmol), Pd(dppf)Cl$_2$—CH$_2$Cl$_2$ adduct (94 mg, 0.11 mmol), and K$_3$PO$_4$ (1960 mg, 9.24 mmol) in 1,4-dioxane (13.7 mL) and H$_2$O (1.7 mL) was heated at 100° C. for 30 min under microwave condition. The mixture was cooled to room temperature, and 1-methyl-4-(4,4,5,5-tetramethyl-1,3,2-dioxaborolan-2-yl)-1H-pyrazole (528 mg, 2.54 mmol) was added. After degassing with $N_2$, the mixture was then heated at 115° C. for 30 min under microwave condition. The reaction mixture was cooled, diluted with H$_2$O (10 mL) and the mixture was extracted with ethyl acetate (2×50 mL). The combined organic fractions were washed with brine, dried (Na$_2$SO$_4$), filtered and the solvent was evaporated under reduced pressure. The crude product was purified by column chromatography on silica gel, eluting with EtOAc/Hexane (0-100%) to afford 7-((2-cyclopropylpyrimidin-5-yl)methyl)-4-(1-methyl-1H-pyrazol-4-yl)quinoline-2-carbonitrile (6-1, 649 mg, 77%). LRMS (M+H)$^+$ 367.3 found, 367.2 required.

7-((2-Cyclopropylpyrimidin-5-yl)methyl)-4-(1-methyl-1H-pyrazol-4-yl)quinoline-2-carboxamide (6-2)

7-(2-Cyclopropylpyrimidin-5-yl)methyl)-4-(1-methyl-1H-pyrazol-4-yl)quinoline-2-carbonitrile (5-1, 71.3 mg, 0.19 mmol.) was dissolved in acetone (6.5 mL) and sodium percarbonate (85 mg, 0.58 mmol.) in H$_2$O (3.24 mL) was added slowly. The resulting mixture was stirred at room temperature for one hour. Saturated NH$_4$Cl (1.5 mL) was added, followed by H$_2$O (30 mL) to give a white precipitation. The solid was collected by filtration, washed with H$_2$O and then Hexane, and dried under vacuum to provide 7-((2-cyclopropylpyrimidin-5-yl)methyl)-4-(1-methyl-1H-pyrazol-4-yl)quinoline-2-carboxamide (6-2, 72.1 mg, 96.0%) as a white solid. LRMS m/z (M+H)$^+$ 385.3 found, 385.2 required.

Scheme 6.2

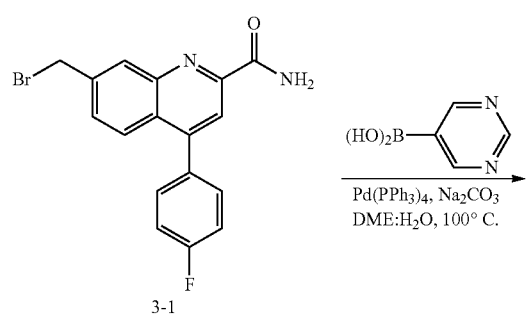

3-1

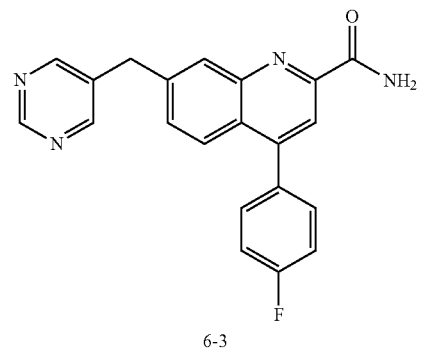

6-3

Example 6.2

Synthesis of 4-(4-fluorophenyl)-7-(pyrimidin-5-ylmethyl)quinoline-2-carboxamide (6-3)

4-(4-Fluorophenyl)-7-(pyrimidin-5-ylmethyl)quinoline-2-carboxamide (6-3)

Degassed DME (1237 μl)/Water (619 up was added to 7-(bromomethyl)-4-(4-fluorophenyl)quinoline-2-carboxamide (3-1, 100 mg, 0.278 mmol), pyrimidin-5-ylboronic acid (41.4 mg, 0.334 mmol), Pd(PPh$_3$)$_4$ (16.09 mg, 0.014 mmol), and Na$_2$CO$_3$ (62.0 mg, 0.585 mmol). The reaction was heated at 100° C. in the microwave for 10 minutes. The reaction was quenched with water and the mixture was extracted with ethyl acetate (×3). The combined organic fractions were dried (MgSO$_4$), filtered and the solvent was evaporated under reduced pressure. The crude material was purified by flash column chromatography (12 g SiO$_2$, 0-100% EtOAc/hexanes) to afford impure product. The material was purified further by reverse phase HPLC (20× 150 mm, Waters Sunfire, Solvent A=0.1% TFA/H$_2$O, Solvent B=0.1% TFA/MeCN, 20 ml/min) to afford, after basic workup, 4-(4-fluorophenyl)-7-(pyrimidin-5-ylmethyl)quinoline-2-carboxamide (6-3, 8.16 mg, 8.18% yield) as a white solid. $^1$H NMR (500 MHz, CDCl$_3$): δ 9.14 (s, 1H); 8.68 (s, 2H); 8.23 (s, 1H); 8.05 (s, 1H); 7.97 (s, 1H); 7.93 (d, J=8.7 Hz, 1H); 7.50 (dd, J=8.5, 5.4 Hz, 2H); 7.42 (dd, J=8.7, 1.8 Hz, 1H); 7.24 (t, J=8.5 Hz, 2H); 5.64 (s, 1H); 4.22 (s, 2H). LRMS m/z (M+H)$^+$ 359.2 found, 359.4 required.

The following compounds have been prepared according to procedures similar to those found in Scheme 6.1 and 6.2 selecting the appropriate quinoline derivative and boronic acid derivatives and provide examples of compounds in the invention.

TABLE 6

| Example | Structure | IUPAC Name | Exact Mass [M + H]+ |
|---|---|---|---|
| 6-4 | 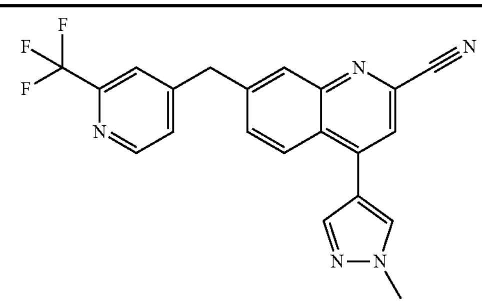 | 4-(1-methyl-1H-pyrazol-4-yl)-7-{[2-(trifluoromethyl)pyridin-4-yl]methyl}quinoline-2-carbonitrile | Calc'd 394.1, Found 394.1 |
| 6-5 | 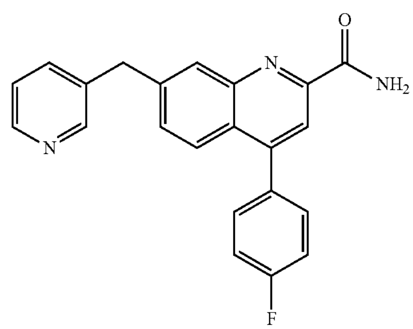 [SMILES: NC(=O)c1cc(-c2ccc(F)cc2)c2ccc(Cc3cccnc3)cc2n1] | 4-(4-fluorophenyl)-7-(pyridin-3-ylmethyl)quinoline-2-carboxamide | Calc'd 358.1, Found 358.2 |
| 6-6 | 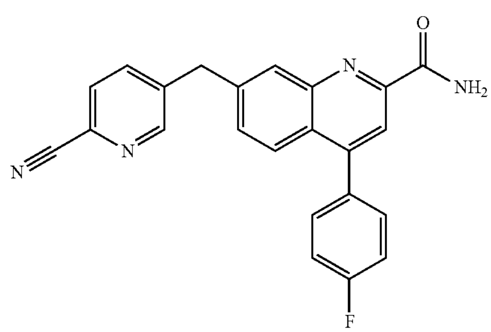 [SMILES: N#Cc1ccc(Cc2ccc3c(-c4ccc(F)cc4)cc(C(N)=O)nc3c2)cn1] | 7-[(6-cyanopyridin-3-yl)methyl]-4-(4-fluorophenyl)quinoline-2-carboxamide | Calc'd 383.1, Found 383.1 |
| 6-7 | 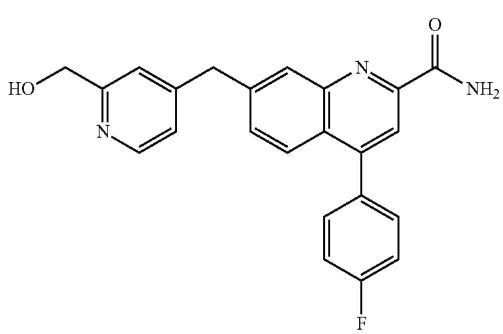 [SMILES: NC(=O)c1cc(-c2ccc(F)cc2)c2ccc(Cc3ccnc(CO)c3)cc2n1] | 4-(4-fluorophenyl)-7-{[2-(hydroxymethyl)pyridin-4-yl]methyl}quinoline-2-carboxamide | Calc'd 388.1, Found 388.1 |
| 6-8 | 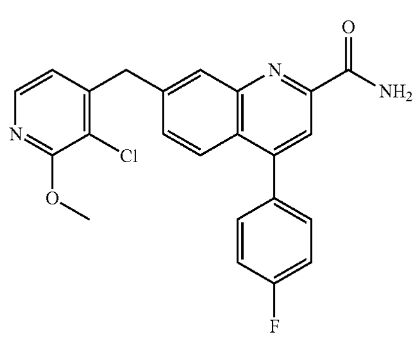 [SMILES: COc1nccc(Cc2ccc3c(-c4ccc(F)cc4)cc(C(N)=O)nc3c2)c1Cl] | 7-[(3-chloro-2-methoxypyridin-4-yl)methyl]-4-(4-fluorophenyl)quinoline-2-carboxamide | Calc'd 422.1, Found 422.1 |

TABLE 6-continued

| Example | Structure | IUPAC Name | Exact Mass [M + H]+ |
|---|---|---|---|
| 6-9 | 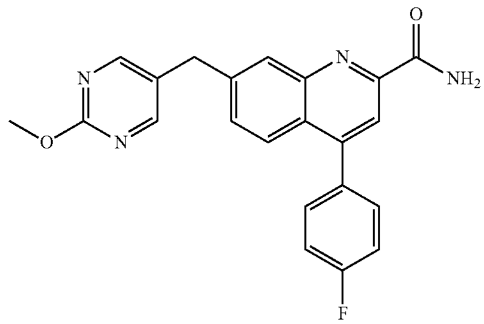 [SMILES: COc1ncc(Cc2ccc3c(-c4ccc(F)cc4)cc(C(N)=O)nc3c2)cn1] | 4-(4-fluorophenyl)-7-[(2-methoxy-pyrimidin-5-yl)methyl]quinoline-2-carboxamide | Calc'd 389.1, Found 389.1 |
| 6-10 | 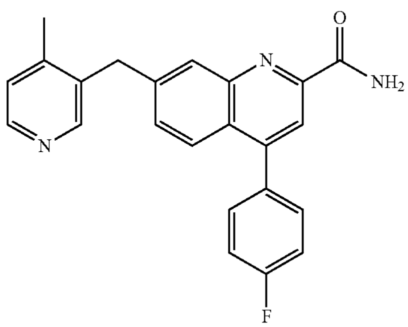 [SMILES: Cc1ccncc1Cc1ccc2c(-c3ccc(F)cc3)cc(C(N)=O)nc2c1] | 4-(4-fluorophenyl)-7-[(4-methylpyridin-3-yl)methyl]quinoline-2-carboxamide | Calc'd 372.2, Found 372.1 |
| 6-11 | 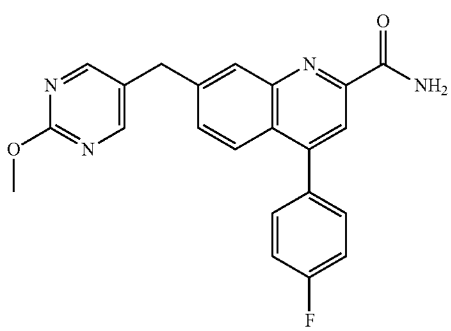 [SMILES: COc1ncc(Cc2ccc3c(-c4ccc(F)cc4)cc(C(N)=O)nc3c2)cn1] | 4-(4-fluorophenyl)-7-[(2-methoxy-pyrimidin-5-yl)methyl]quinoline-2-carboxamide | Calc'd 389.1, Found 389.1 |
| 6-12 | 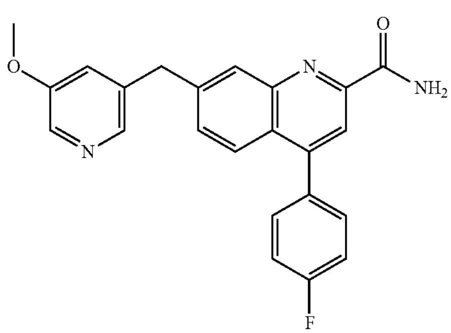 [SMILES: COc1cncc(Cc2ccc3c(-c4ccc(F)cc4)cc(C(N)=O)nc3c2)c1] | 4-(4-fluorophenyl)-7-[(5-methoxy-pyridin-3-yl)methyl]quinoline-2-carboxamide | Calc'd 388.1, Found 388.1 |

TABLE 6-continued

| Example | Structure | IUPAC Name | Exact Mass [M + H]+ |
|---|---|---|---|
| 6-13 | 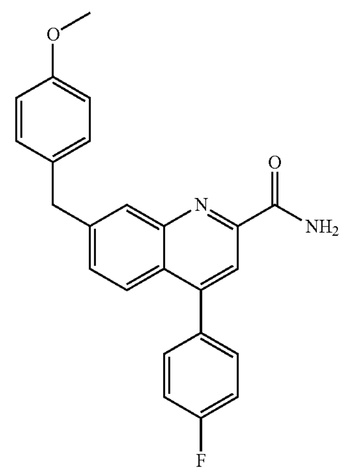 [SMILES: COc1ccc(Cc2ccc3c(-c4ccc(F)cc4)cc(C(N)=O)nc3c2)cc1] | 4-(4-fluorophenyl)-7-(4-methoxybenzyl)quinoline-2-carboxamide | Calc'd 387.2, Found 387.1 |
| 6-14 | 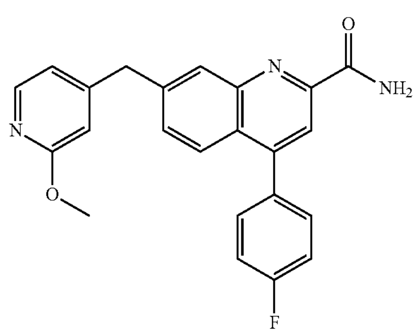 [SMILES: COc1cc(Cc2ccc3c(-c4ccc(F)cc4)cc(C(N)=O)nc3c2)ccn1] | 4-(4-fluorophenyl)-7-[(2-methoxypyridin-4-yl)methyl]quinoline-2-carboxamide | Calc'd 388.1, Found 388.1 |
| 6-15 | 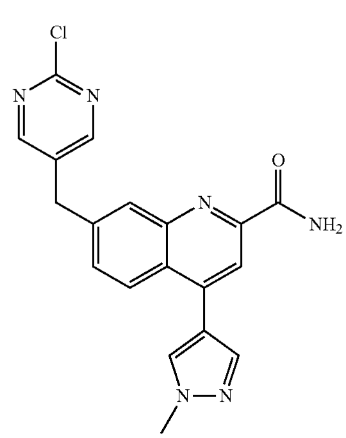 | 7-[(2-chloropyrimidin-5-yl)methyl]-4-(1-methyl-1H-pyrazol-4-yl)quinoline-2-carboxamide | Calc'd 379.1, Found 379.1 |

TABLE 6-continued

| Example | Structure | IUPAC Name | Exact Mass [M + H]+ |
|---|---|---|---|
| 6-16 | 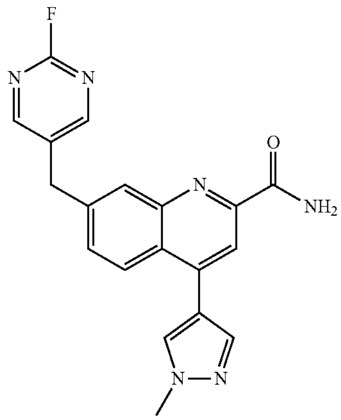 [SMILES: Cn1cc(-c2cc(C(N)=O)nc3cc(Cc4cnc(F)nc4)ccc23)cn1] | 7-[(2-fluoropyrimidin-5-yl)methyl]-4-(1-methyl-1H-pyrazol-4-yl)quinoline-2-carboxamide | Calc'd 363.1, Found 363.1 |
| 6-17 | 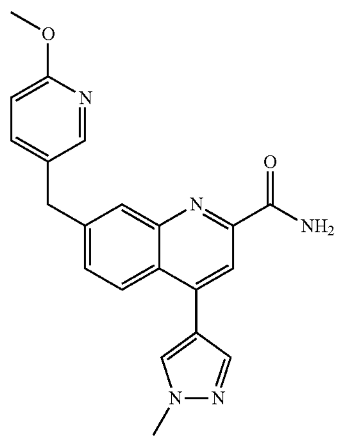 [SMILES: COc1ccc(Cc2ccc3c(-c4cnn(C)c4)cc(C(N)=O)nc3c2)cn1] | 7-[(6-methoxypyridin-3-yl)methyl]-4-(1-methyl-1H-pyrazol-4-yl)quinoline-2-carboxamide | Calc'd 374.2, Found 374.2 |
| 6-18 | 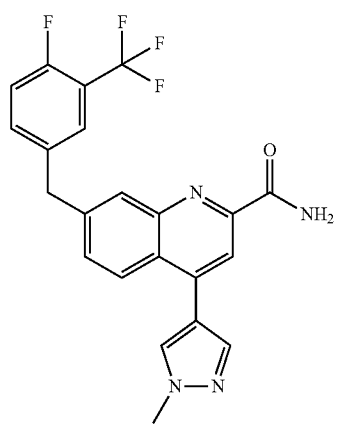 [SMILES: Cn1cc(-c2cc(C(N)=O)nc3cc(Cc4ccc(F)c(C(F)(F)F)c4)ccc23)cn1] | 7-[4-fluoro-3-(trifluoromethyl)benzyl]-4-(1-methyl-1H-pyrazol-4-yl)quinoline-2-carboxamide | Calc'd 429.1, Found 429.1 |
| 6-19 | 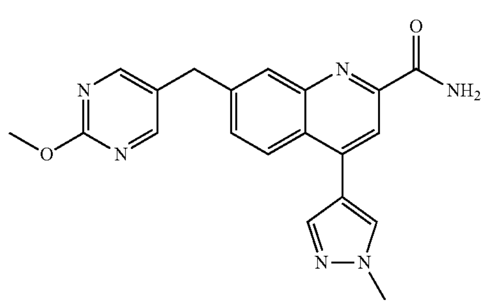 [SMILES: COc1ncc(Cc2ccc3c(-c4cnn(C)c4)cc(C(N)=O)nc3c2)cn1] | 7-[(2-methoxypyrimidin-5-yl)methyl]-4-(1-methyl-1H-pyrazol-4-yl)quinoline-2-carboxamide | Calc'd 375.2, Found 375.1 |

TABLE 6-continued

| Example | Structure | IUPAC Name | Exact Mass [M + H]+ |
|---------|-----------|------------|---------------------|
| 6-20 | 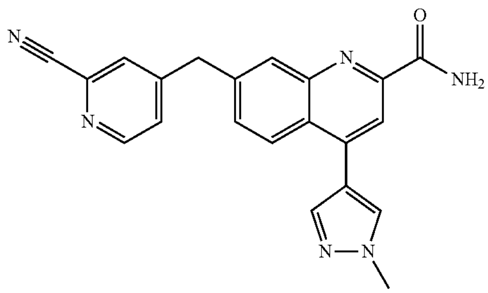 [SMILES: Cn1cc(-c2cc(C(N)=O)nc3cc(Cc4ccnc(C#N)c4)ccc23)cn1] | 7-[(2-cyanopyridin-4-yl)methyl]-4-(1-methyl-1H-pyrazol-4-yl)quinoline-2-carboxamide | Calc'd 369.1, Found 369.1 |
| 6-21 | 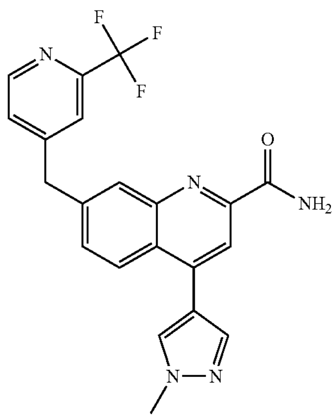 [SMILES: Cn1cc(-c2cc(C(N)=O)nc3cc(Cc4ccnc(C(F)(F)F)c4)ccc23)cn1] | 4-(1-methyl-1H-pyrazol-4-yl)-7-{[2-(trifluoromethyl)pyridin-4-yl]methyl}quinoline-2-carboxamide | Calc'd 412.1, Found 412.3 |
| 6-22 | 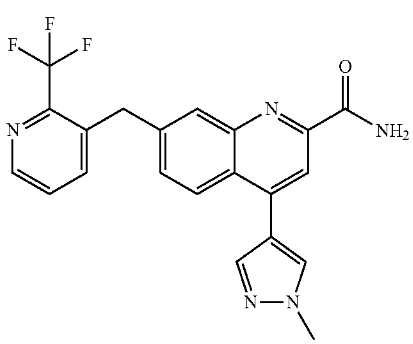 [SMILES: Cn1cc(-c2cc(C(N)=O)nc3cc(Cc4cccnc4C(F)(F)F)ccc23)cn1] | 4-(1-methyl-1H-pyrazol-4-yl)-7-{[2-(trifluoromethyl)pyridin-3-yl]methyl}quinoline-2-carboxamide | Calc'd 412.1, Found 412.1 |
| 6-23 | 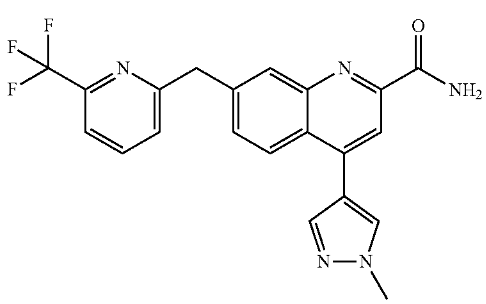 [SMILES: Cn1cc(-c2cc(C(N)=O)nc3cc(Cc4cccc(C(F)(F)F)n4)ccc23)cn1] | 4-(1-methyl-1H-pyrazol-4-yl)-7-{[6-(trifluoromethyl)pyridin-2-yl]methyl}quinoline-2-carboxamide | Calc'd 412.1, Found 412.1 |

TABLE 6-continued
| Example | Structure | IUPAC Name | Exact Mass [M + H]+ |
|---|---|---|---|
| 6-24 | 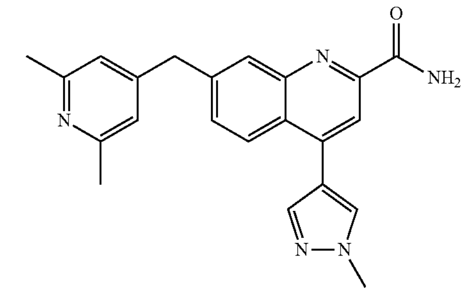 [SMILES: Cc1cc(Cc2ccc3c(-c4cnn(C)c4)cc(C(N)=O)nc3c2)cc(C)n1] | 7-[(2,6-dimethylpyridin-4-yl)methyl]-4-(1-methyl-1H-pyrazol-4-yl)quinoline-2-carboxamide | Calc'd 372.2, Found 372.3 |
| 6-25 | 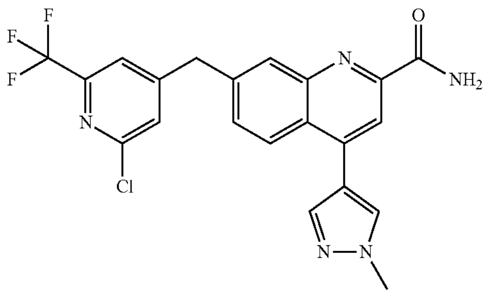 [SMILES: Cn1cc(-c2cc(C(N)=O)nc3cc(Cc4cc(Cl)nc(C(F)(F)F)c4)ccc23)cn1] | 7-{[2-chloro-6-(trifluoromethyl)pyridin-4-yl]methyl}-4-(1-methyl-1H-pyrazol-4-yl)quinoline-2-carboxamide | Calc'd 446.1, Found 446.2 |
| 6-26 | 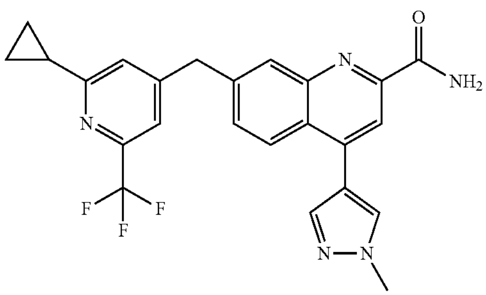 [SMILES: Cn1cc(-c2cc(C(N)=O)nc3cc(Cc4cc(C5CC5)nc(C(F)(F)F)c4)ccc23)cn1] | 7-{[2-cyclopropyl-6-(trifluoromethyl)pyridin-4-yl]methyl}-4-(1-methyl-1H-pyrazol-4-yl)quinoline-2-carboxamide | Calc'd 452.2, Found 452.3 |
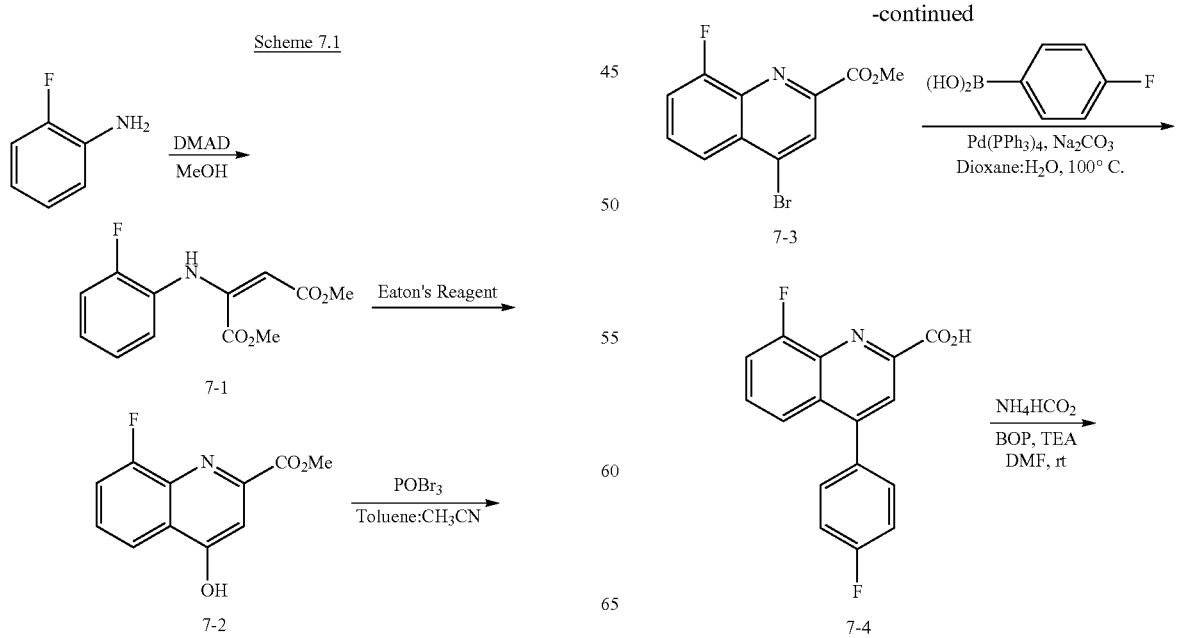
Scheme 7.1

193

-continued

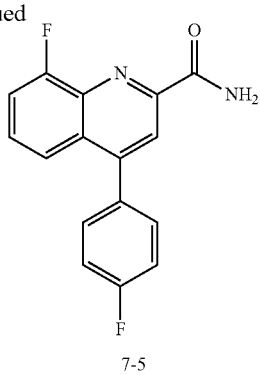

7-5

Example 7.1

Synthesis of 8-fluoro-4-(4-fluorophenyl)quinoline-2-carboxamide (7-5)

Dimethyl (2E)-2-[(2-fluorophenyl)amino]but-2-enedioate (7-1)

To a solution 2-fluoroaniline (1.00 g, 9.00 mmol) in MeOH (11.1 mL) at 0° C. was added dimethyl acetylenedicarboxylate (DMAD, 1.34 mL, 10.8 mmol). The reaction was stirred at room temperature for 2 h. The mixture was concentrated and the residue was purified by silica gel flash chromatography (gradient 0-25% EtOAc in Hexanes) to give dimethyl (2E)-2-[(2-fluorophenyl)amino]but-2-enedioate (7-1, 1.9 g, 83%). LRMS m/z (M+H)$^+$ 254.4 found, 254.4 required.

8-Fluoro-4-hydroxyquinoline-2-carboxylate (7-2)

Dimethyl (2E)-2-[(2-fluorophenyl)amino]but-2-enedioate (7-1, 1.90 g, 7.50 mmol) was dissolved in Eaton's reagent (8.00 mL, 50.4 mmol) and heated at 55° C. for 1 h. The LC-MS showed clean conversion. The reaction mixture was cooled to room temperature and slowly poured into a cold saturated solution of NaHCO$_3$. The light-yellow precipitate formed was collected by filtration, washed with H$_2$O and dried in vacuum to provide methyl 8-fluoro-4-hydroxyquinoline-2-carboxylate (7-2). LRMS m/z (M+H)$^+$ 222.4 found, 222.4 required.

Methyl 4-bromo-8-fluoroquinoline-2-carboxylate (7-3)

To a solution of 8-fluoro-4-hydroxyquinoline-2-carboxylate (7-2, 0.860 g, 3.89 mmol) in a mixture of acetonitrile (0.884 mL) and toluene (8.84 ml) was added phosphorus oxybromide (1.23 g, 4.28 mmol). The reaction mixture was heated at 75° C. for 0.5 h. A second portion of phosphorus oxybromide (0.50 g) was added and heated at 75° C. for another 30 min. The LC-MS showed completed reaction. The reaction was cooled and carefully quenched with ice-water. The mixture was extracted with CH$_2$Cl$_2$ and EtOAc consecutively. The combined organic layers were dried and concentrated. The residue was purified by silica gel flash chromatography (gradient 0-25% EtOAc in hexanes) to give methyl 4-bromo-8-fluoroquinoline-2-carboxylate (7-3). LRMS m/z (M+H)$^+$ 284.3 found, 284.3 required.

194

8-Fluoro-4-(4-fluorophenyl)quinoline-2-carboxylic acid (7-4)

Methyl 4-bromo-8-fluoroquinoline-2-carboxylate (7-3, 100.0 mg, 0.352 mmol), 4-Fluorophenylboronic acid (59.1 g, 0.422 mmol), Tetrakis (20.3 mg, 0.0180 mmol), and Na$_2$CO$_3$ (0.704 ml, 0.704 mmol) were added into 1,4-Dioxane (1.0 mL) in a microwave reaction vessel. The mixture was irradiated with microwave at 100° C. for 30 min. Cooled to room temperature, aqueous Sodium Hydrogen Carbonate (saturate, 2.0 mL) was added and extracted with Ethyl Acetate (2×10.0 mL). The combined organic fractions were washed with brine, dried over MgSO$_4$, filtered and the solvent was evaporated under reduced pressure to give 8-Fluoro-4-(4-fluorophenyl)quinoline-2-carboxylic acid (7-4, 100.0 mg, 100.0% crude). LRMS m/z (M+H)$^+$ 286.2 found, 2862 required.

8-Fluoro-4-(4-fluorophenyl)quinoline-2-carboxamide (7-5)

8-Fluoro-4-(4-fluorophenyl)quinoline-2-carboxylic acid (7-4, 100.0 mg, 0.351 mmol), ammonium formate (88.0 mg, 1.40 mmol), BOP (202.0 mg, 0.456 mmol), and triethylamine (0.147 ml, 1.052 mmol) were dissolved into DMF (1.0 mL), and the resulting mixture was stirred at 60° C. for 5 hours. The mixture was cooled and diluted with Methylene Chloride, washed with water, brine, dried over MgSO$_4$, filtered and concentrated. The crude residue was purified by reverse phase HPLC (H$_2$O/CH$_3$CN gradient w/ 0.1% TFA modifier) to afford 8-Fluoro-4-(4-fluorophenyl)quinoline-2-carboxamide (7-5, 9.00 mg, 9.0%) as a colorless solid. $^1$H NMR (400 MHz, CDCl$_3$): δ 8.209 (s, 1H); 8.138 (br s, 1H); 8.658 (d, J=8.62 Hz, 1H); 7.379-7.493 (m, 4H); 7.145-7.214 (m, 2H); 6.004 (br s, 1H). LRMS m/z (M+H) 285.1 found, 285.1 required.

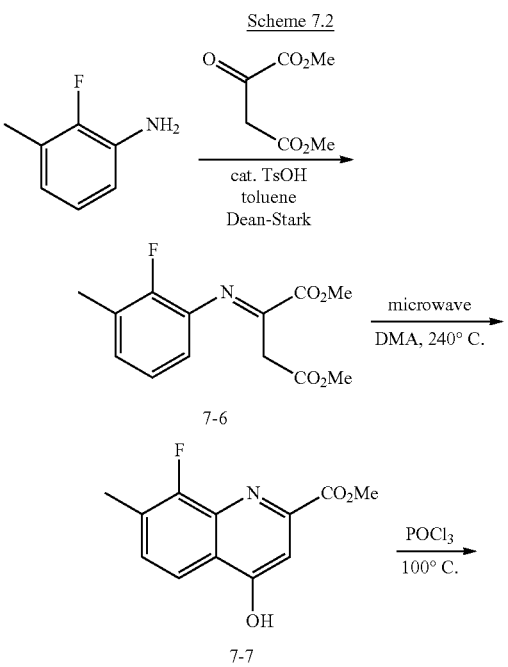

Scheme 7.2

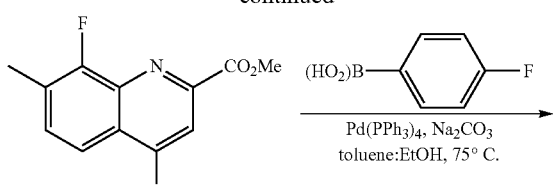

7-8

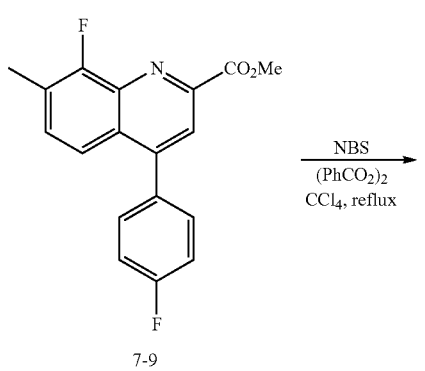

7-9

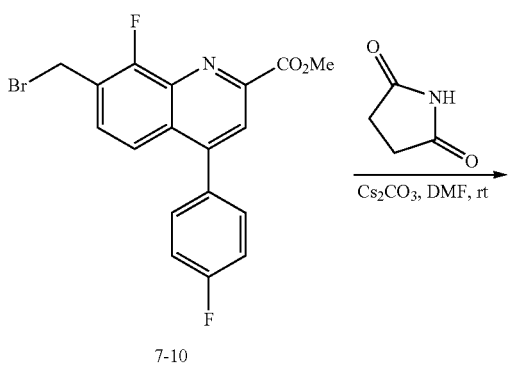

7-10

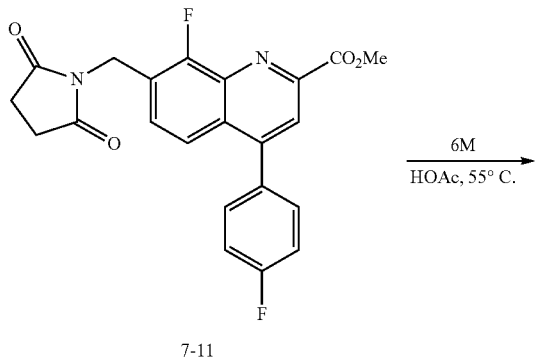

7-11

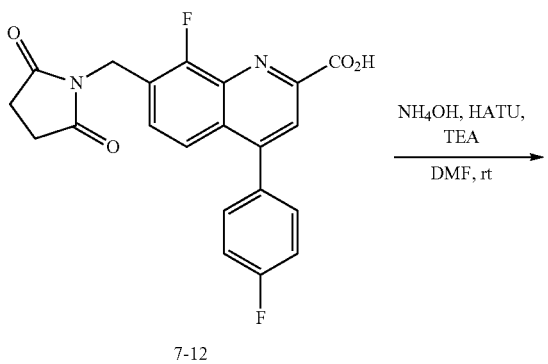

7-12

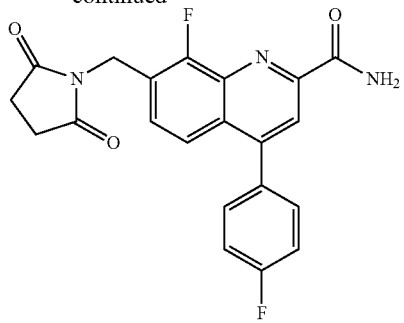

7-13

Example 7.2

Synthesis of 7-[(2,5-dioxopyrrolidin-1-yl)methyl]-8-fluoro-4-(4-fluorophenyl)quinoline-2-carboxamide (7-13)

Dimethyl (2E)-2-[(2-fluoro-3-methylphenyl)imino]butanedioate (7-6)

3-Amino-2-fluorotoluene (4.89 g, 39.1 mmol), dimethyl 2-oxobutanedioate (6.26 g, 39.1 mmol), and TosicAcid (0.223 g, 1.172 mmol) were heated at reflux under Dean-Stark conditions for 1 hour. The solvent was removed in vacuo and the residue purified by column chromatography on a silica gel column, eluting with EtOAc/hexane (0-15%) to afford Dimethyl (2E)-2-[(2-fluoro-3-methylphenyl)imino]butanedioate (7-6, 5.48 g, 53% yield) as a clear oil, LCMS shows the compound is 100% pure, LRMS m/z (M+H)$^+$ 268.2 found, 268.1 required.

Methyl 8-fluoro-7-methyl-4-oxo-1,4-dihydroquinoline-2-carboxylate (7-7)

Dimethyl (2E)-2-[(2-fluoro-3-methylphenyl)imino]butanedioate (7-6, 3.27 g, 12.24 mmol) in DMA (24.47 ml) was heated at 240° C. in the microwave for 5 min. The solvent was evaporated under reduced pressure and the residue triturated with ether to afford a tan solid. The desired product was filtered off and washed with ether till the ether ran colorless affording Methyl 8-fluoro-7-methyl-4-oxo-1,4-dihydroquinoline-2-carboxylate (7-7, 1.23 g, 43% yield) as a tan solid, LCMS shows 93% pure, LRMS m/z (M+H)$^+$ 236.1 found, 236.1 required.

Methyl 4-chloro-8-fluoro-7-methylquinoline-2-carboxylate (7-8)

Methyl 8-fluoro-7-methyl-4-oxo-1,4-dihydroquinoline-2-carboxylate (7-7, 1.23 g, 5.23 mmol) in POCl$_3$ (11 ml) was heated at 100° C. for 1 hour. The excess POCl$_3$ was removed in vacuo. The resulting residue was triturated with ether, then filtered and washed with ether till no brown color remained in the ether. The remaining solid was Methyl 4-chloro-8-fluoro-7-methylquinoline-2-carboxylate (7-8, 993 mg, 75% yield) 100% pure by LCMS, LRMS m/z (M+H)$^+$ 254.0 found, 254.1 required.

Methyl 8-fluoro-4-(4-fluorophenyl)-7-methylquinoline-2-carboxylate (7-9)

Methyl 4-chloro-8-fluoro-7-methylquinoline-2-carboxylate (7-8, 993 mg, 3.91 mmol), (4-Fluorophenyl)boronic acid (575 mg, 4.11 mmol), and Pd(Ph$_3$P)$_4$ (226 mg, 0.196 mmol) were dissolved in degassed toluene (25 mL). Degasses EtOH (2.7 mL) was added followed by degassed 2M aq. Sodium Carbonate (4.31 mL, 8.61 mmol). The reaction was heated at 75° C. overnight then quenched with water and the mixture was extracted with ethyl acetate (×3). The combined organic fractions were dried (MgSO$_4$), filtered and the solvent was evaporated under reduced pressure. The residue was triturated with ether to afford Methyl 8-fluoro-4-(4-fluorophenyl)-7-methylquinoline-2-carboxylate (7-9, 991 mg, 81% yield) as a tan solid, LCMS shows the compound is 89% pure, LRMS m/z (M+H)$^+$ 314.1 found, 314.0 required.

Methyl 7-(bromomethyl)-8-fluoro-4-(4-fluorophenyl)quinoline-2-carboxylate (7-10)

Methyl 8-fluoro-4-(4-fluorophenyl)-7-methylquinoline-2-carboxylate 7-9 (991 mg, 3.16 mmol), Benzoyl peroxide (102 mg, 0.316 mmol), and NBS (591 mg, 3.32 mmol) were heated at reflux in CCl$_4$ for 5 hours. The solvent was removed in vacuo and the residue purified by column chromatography on a silica gel column, eluting with EtOAc/hexane (0-50%) to afford Methyl 7-(bromomethyl)-8-fluoro-4-(4-fluorophenyl)quinoline-2-carboxylate 7-10 (1.05 g, 85% yield) as a white solid, LCMS shows the compound is 67% pure, LRMS m/z (M+H)$^+$ 392.0 found, 392.1 required.

Methyl 7-[(2,5-dioxopyrrolidin-1-yl)methyl]-8-fluoro-4-(4-fluorophenyl)quinoline-2-carboxylate (7-11)

Cs$_2$CO$_3$ (1.745 g, 5.35 mmol) was added to a solution of Succinimide (0.292 g, 2.94 mmol) and methyl 7-(bromomethyl)-8-fluoro-4-(4-fluorophenyl)quinoline-2-carboxylate 7-10 (1.05 g, 2.68 mmol) in DMF (13.39 ml) and the reactant stirred at it for 30 min. The reaction was quenched with KH$_2$PO$_4$ (saturated) and the mixture was extracted with ethyl acetate (×3). The combined organic fractions were dried (MgSO$_4$), filtered and the solvent was evaporated under reduced pressure. The solvent was removed in vacuo and the residue purified by column chromatography on a silica gel column, eluting with EtOAc/hexane (0-100%) to afford Methyl 7-[(2,5-dioxopyrrolidin-1-yl)methyl]-8-fluoro-4-(4-fluorophenyl)quinoline-2-carboxylate 7-11 as a white solid, LCMS shows the compound is 90% pure, LRMS m/z (M+H)$^+$ 411.2 found, 411.1 required.

7-[(2,5-Dioxopyrrolidin-1-yl)methyl]-8-fluoro-4-(4-fluorophenyl)quinoline-2-carboxylic acid (7-12)

6M HCl (2964 µl) was added to a solution of methyl 7-[(2,5-dioxopyrrolidin-1-yl)methyl]-8-fluoro-4-(4-fluorophenyl)quinoline-2-carboxylate 7-11 (629 mg, 1.482 mmol) in Acetic Acid (2964 µl) and the reaction heated at 120° C. for 10 min in the microwave. The reaction was quenched with KH$_2$PO$_4$ (saturated) and the mixture was extracted with ethyl acetate (×3). The combined organic fractions were dried (MgSO$_4$), filtered and the solvent was evaporated under reduced pressure to afford 7-[(2,5-dioxopyrrolidin-1-yl)methyl]-8-fluoro-4-(4-fluorophenyl)quinoline-2-carboxylic acid 7-12 (499 mg, 85% yield) as a white solid, 100% pure by LCMS, LRMS m/z (M+H)$^+$ 397.2 found, 397.1 required.

7-[(2,5-dioxopyrrolidin-1-yl)methyl]-8-fluoro-4-(4-fluorophenyl)quinoline-2-carboxamide (7-13)

TEA (105 µl, 0.757 mmol) was added to a solution of 7-[(2,5-dioxopyrrolidin-1-yl)methyl]-8-fluoro-4-(4-fluorophenyl)quinoline-2-carboxylic acid 7-12 (100 mg, 0.252 mmol) and HATU (96 mg, 0.252 mmol) in DMF (1262 µl). Ammonium Hydroxide (50.5 µl, 0.757 mmol) was added and the reaction stirred for 15 min at rt. The reaction was quenched with aqueous sodium hydrogen carbonate (saturated) and the mixture was extracted with ethyl acetate (×3). The combined organic fractions were dried (MgSO$_4$), filtered and the solvent was evaporated under reduced pressure. The residue was purified by column chromatography on a silica gel column, eluting with EtOAc/hexane (0-100%) to afford 7-[(2,5-dioxopyrrolidin-1-yl)methyl]-8-fluoro-4-(4-fluorophenyl)quinoline-2-carboxamide 7-13 (63 mg, 63% yield) as a white solid, LCMS shows the compound is 100% pure $^1$H NMR (500 MHz, CDCl$_3$): δ 8.28 (1H, s), 8.14 (1H, s), 7.68 (1H, d, J=8.85 Hz), 7.54 (1H, dd, J=8.86, 6.65 Hz), 7.50-7.46 (2H, m), 7.25-7.20 (2H, m), 5.69 (1H, s), 4.99 (2H, s), 2.78 (4H, s). LRMS m/z (M+H)$^+$ 396.2 found, 396.1 required.

Scheme 7.3

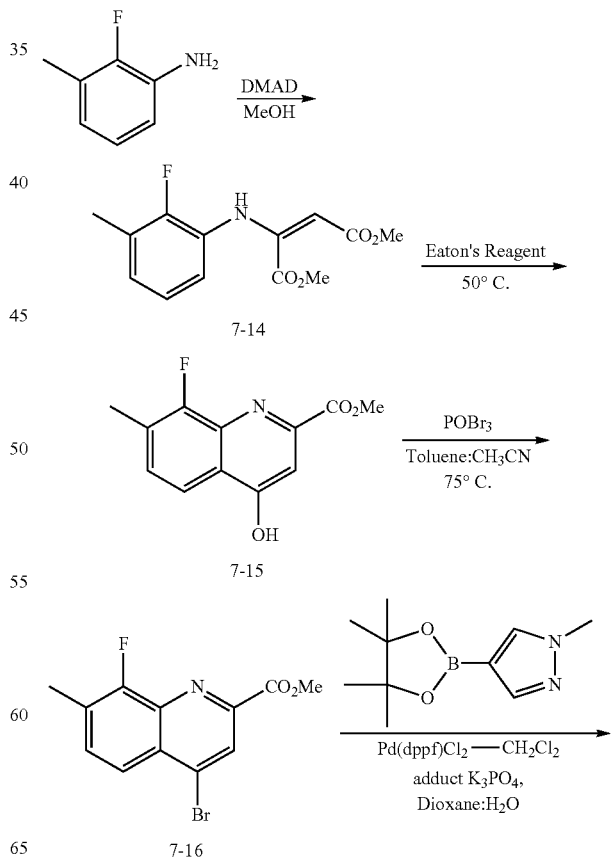

-continued

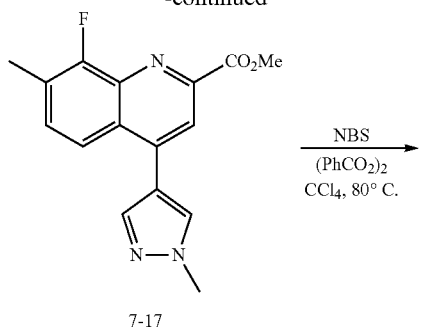

7-17

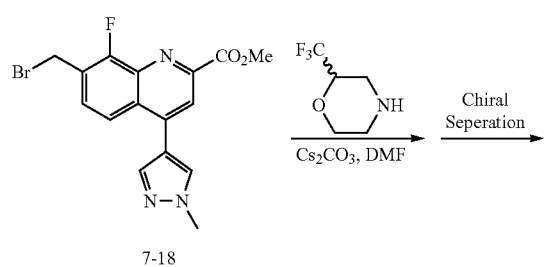

7-18

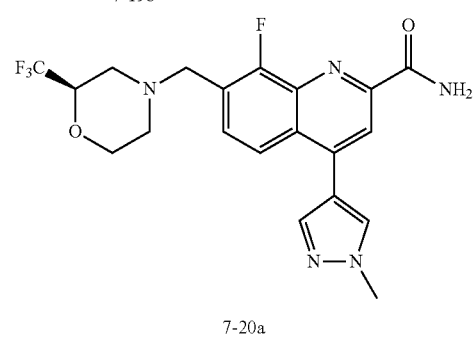

7-19a

+

7-19b 7-20a

-continued

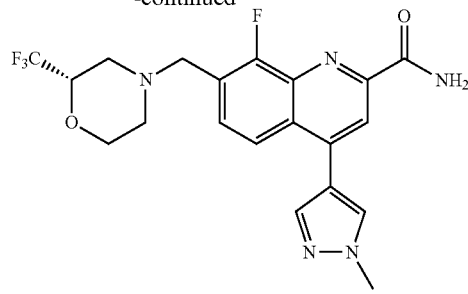

7-20b

Example 7.3

Synthesis of (R)- and (S)-(S)-8-fluoro-4-(1-methyl-1H-pyrazol-4-yl)-7-((2-(trifluoromethyl)morpholino)methyl)quinoline-2-carboxamide (7-20a and 7-20b)

(E)-dimethyl 2-(2-fluoro-3-methylphenylimino)succinate (7-14)

At 0° C., dimethyl acetylenedicarboxylate (8.70 mL, 70.4 mmol) was added dropwise to a solution 2-fluoro-3-methylaniline (7.34 g, 58.7 mmol) in MeOH (58.7 mL). After stirring at room temperature overnight, the reaction mixture was concentrated to dryness. The residue was purified by silica gel flash chromatography (gradient 0-60% EtOAc/Hexanes) to give (E)-dimethyl 2-(2-fluoro-3-methylphenylimino)succinate (7-14, 14.59 g, 93%). LRMS m/z (M+H)$^+$ 268.3 found, 268.1 required.

Methyl 8-fluoro-4-hydroxy-7-methylquinoline-2-carboxylate (7-15)

A mixture of (E)-dimethyl 2-(2-fluoro-3-methylphenylimino)succinate (7-14, 14.59 g, 54.6 mmol) and Eaton's reagent (52.0 mL, 328 mmol) was heated at 50° C. for 1 h. After cooling to room temperature, the mixture was added slowly to a cold sat. NaHCO$_3$ solution (gas released!), followed by EtOAc extraction (twice). The combined organic fractions were washed with brine, dried (Na$_2$SO$_4$), filtered and the solvent was evaporated under reduced pressure to afford methyl 8-fluoro-4-hydroxy-7-methylquinoline-2-carboxylate (7-15, 11.9 g). LRMS m/z (M+H)$^+$ 236.2 found, 236.1 required.

Methyl 4-bromo-8-fluoro-7-methylquinoline-2-carboxylate (7-16)

A mixture of (methyl 8-fluoro-4-hydroxy-7-methylquinoline-2-carboxylate (7-15, 842.1 mg, 3.58 mmol) and POBr$_3$ (1129 mg, 3.94 mmol) in Toluene (8.14 mL) and CH$_3$CN (0.81 mL) was heated at 75° C. for 1 h. After cooling to room temperature, the mixture was poured to a mixture of ice-H$_2$O, followed by CH$_2$Cl$_2$ extraction (twice). The combined organic fractions were dried (Na$_2$SO$_4$), filtered and the solvent was evaporated under reduced pressure. The residue was purified by silica gel flash chromatography (gradient 0-50% EtOAc/Hexanes) to afford methyl 4-bromo-8-fluoro-7-methylquinoline-2-carboxylate (7-16, 710 mg). LRMS (M+H)$^+$298.1 found, 298.0 required.

Methyl 8-fluoro-7-methyl-4-(1-methyl-1H-pyrazol-4-yl)quinoline-2-carboxylate (7-17)

After degassing with $N_2$, a mixture of methyl 4-bromo-8-fluoro-7-methylquinoline-2-carboxylate (7-16, 650 mg, 2.18 mmol.), 1-methyl-4-(4,4,5,5-tetramethyl-1,3,2-dioxaborolan-2-yl)-1H-pyrazole (544 mg, 2.62 mmol) Pd(dppf)Cl$_2$—CH$_2$Cl$_2$ adduct (89 mg, 0.11 mmol), and K$_3$PO$_4$ (1388 mg, 6.54 mmol) in 1,4-dioxane (12.9 mL) and H$_2$O (1.6 mL) was heated at 100° C. for 20 min under microwave condition. After cooling to room temperature, the reaction mixture was filtered and concentrated. The residue was purified by column chromatography on silica gel, eluting with EtOAc/Hexane (0-100%) to afford methyl 8-fluoro-7-methyl-4-(1-methyl-1H-pyrazol-4-yl)quinoline-2-carboxylate (7-17, 481 mg, 74%). LRMS m/z (M+H)$^+$ 300.3 found, 300.1 require.

Methyl 7-(bromomethyl)-8-fluoro-4-(1-methyl-1H-pyrazol-4-yl)quinoline-2-carboxylate (7-18)

After degassing with $N_2$, a mixture of methyl 8-fluoro-7-methyl-4-(1-methyl-1H-pyrazol-4-yl)quinoline-2-carboxylate (7-17, 169.2 mg, 0.57 mmol), NBS (106 mg, 0.59 mmol) and benzoyl peroxide (13.7 mg, 0.057 mmol) in CCl$_4$ (2.8 ml) was stirred at 80° C. After 5 h, the solvent was removed and the residue was partitioned between EtOAC and sat. NaHCO$_3$. The organic layer was washed with water, dried over Na$_2$SO$_4$ and filtered. Concentration afforded the crude methyl 7-(bromomethyl)-8-fluoro-4-(1-methyl-1H-pyrazol-4-yl)quinoline-2-carboxylate, which was used without further purification (7-18). LRMS m/z (M+H)$^+$ 378.2 found, 378.0 required.

(R)-Methyl 8-fluoro-4-(1-methyl-1H-pyrazol-4-yl)-7-((2-(trifluoromethyl)morpholino)methyl)quinoline-2-carboxylate (7-19a) and (S)-Methyl 8-fluoro-4-(1-methyl-1H-pyrazol-4-yl)-7-((2-(trifluoromethyl)morpholino)methyl)quinoline-2-carboxylate (7-19b)

Cs$_2$CO$_3$ (345 mg, 1.06 mmol) was added to a mixture of methyl 7-(bromomethyl)-8-fluoro-4-(1-methyl-1H-pyrazol-4-yl)quinoline-2-carboxylate (7-18, 160 mg, 0.42 mmol) and 2-(trifluoromethyl)morpholine (79 mg, 0.51 mmol) in DMF (4.2 mL). After stirring at room temperature for 2 h, the mixture was diluted with EtOAc, washed with H$_2$O, then brine. The organic layer was dried over Na$_2$SO$_4$, filtered and concentrated. The residue was purified by column chromatography on silica gel, eluting with EtOAc/Hexane (0-100%) to afford methyl 8-fluoro-7-methyl-4-(1-methyl-1H-pyrazol-4-yl)quinoline-2-carboxylate as racemic mixture (31.4 mg, 16%). LRMS m/z (M+H)$^+$ 453.3 found, 453.1 required. Chiral separation using SFC chromatography provided (R)-methyl 8-fluoro-4-(1-methyl-1H-pyrazol-4-yl)-7-((2-(trifluoromethyl)morpholino)methyl)quinoline-2-carboxylate (7-19a, 15 mg) and (S)-methyl 8-fluoro-4-(1-methyl-1H-pyrazol-4-yl)-7-((2-(trifluoromethyl)morpholino)methyl)quinoline-2-carboxylate (7-19b, 14.3 mg).

(R)-8-Fluoro-4-(1-methyl-1H-pyrazol-4-yl)-7-((2-(trifluoromethyl)morpholino)methyl)quinoline-2-carboxamide (7-20a)

A mixture of (R)-8-fluoro-4-(1-methyl-1H-pyrazol-4-yl)-7-((2-(trifluoromethyl)morpholino)methyl)quinoline-2-carboxamide (7-19a, 15.3 mg) in 7 N NH$_3$ in MeOH (372 uL) was stirred at room temperature for 2 h. Concentration and washing with the solid with hexane provided (R)-8-fluoro-4-(1-methyl-1H-pyrazol-4-yl)-7-((2-(trifluoromethyl)morpholino)methyl)quinoline-2-carboxamide (7-20a, 12.8 mg) as white solid. LRMS m/z (M+H)$^+$ 438.3 found, 438.3 required.

(S)-8-Fluoro-4-(1-methyl-1H-pyrazol-4-yl)-7-((2-(trifluoromethyl)morpholino)methyl)quinoline-2-carboxamide (7-20b)

By applying the same synthetic procedure for 7-20a, from (S)-8-fluoro-4-(1-methyl-1H-pyrazol-4-yl)-7-((2-(trifluoromethyl)morpholino)methyl)quinoline-2-carboxamide (7-19b, 14 mg), (S)-8-fluoro-4-(1-methyl-1H-pyrazol-4-yl)-7-((2-(trifluoromethyl)morpholino)methyl)quinoline-2-carboxamide (7-20b, 13 mg) was prepared as white solid. LRMS m/z (M+H)$^+$ 438.3 found, 438.3 required.

The following compounds have been prepared according to procedures similar to those found in Scheme 7.1, 7.2, and 7.3 selecting the appropriate aniline derivative, boronic acid derivatives, and nucleophile and provide examples of compounds in the invention.

TABLE 7

| Example | Structure | IUPAC Name | Exact Mass [M + H]$^+$ |
|---|---|---|---|
| 7-21 | 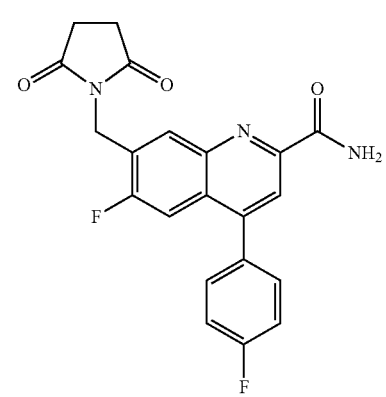 [SMILES: NC(=O)c1cc(-c2ccc(F)cc2)c2cc(F)c(CN3C(=O)CCC3=O)cc2n1] | 7-[(2,5-dioxopyrrolidin-1-yl)methyl]-6-fluoro-4-(4-fluorophenyl)quinoline-2-carboxamide | Calc'd 396.1, Found 396.1 |

TABLE 7-continued

| Example | Structure | IUPAC Name | Exact Mass [M + H]+ |
|---|---|---|---|
| 7-22 | 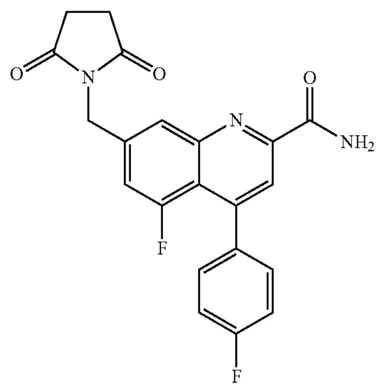 [SMILES: NC(=O)c1cc(-c2ccc(F)cc2)c2c(F)cc(CN3C(=O)CCC3=O)cc2n1] | 7-[(2,5-dioxopyrrolidin-1-yl)methyl]-5-fluoro-4-(4-fluorophenyl)quinoline-2-carboxamide | Calc'd 396.1, Found 396.1 |
| 7-23 | 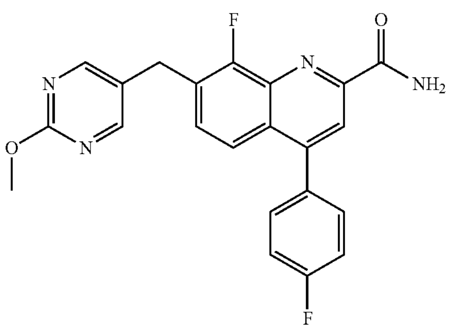 [SMILES: COc1ncc(Cc2ccc3c(-c4ccc(F)cc4)cc(C(N)=O)nc3c2F)cn1] | 8-fluoro-4-(4-fluorophenyl)-7-[(2-methoxypyrimidin-5-yl)methyl]quinoline-2-carboxamide | Calc'd 407.1, Found 407.1 |
| 7-24 | 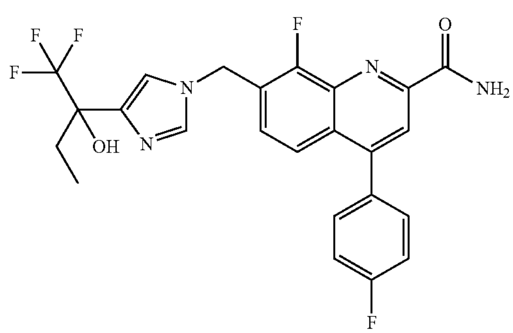 [SMILES: CCC(O)(c1cn(Cc2ccc3c(-c4ccc(F)cc4)cc(C(N)=O)nc3c2F)cn1)C(F)(F)F] | 8-fluoro-4-(4-fluorophenyl)-7-({4-[1-hydroxy-1-(trifluoromethyl)propyl]-1H-imidazol-1-yl}methyl)quinoline-2-carboxamide | Calc'd 491.2, Found 491.2 |
| 7-25 | 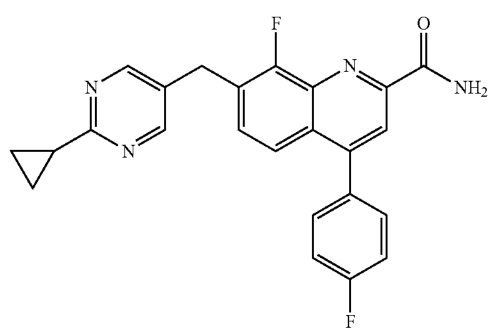 [SMILES: NC(=O)c1cc(-c2ccc(F)cc2)c2ccc(Cc3cnc(C4CC4)nc3)c(F)c2n1] | 7-[(2-cyclopropylpyrimidin-5-yl)methyl]-8-fluoro-4-(4-fluorophenyl)quinoline-2-carboxamide | Calc'd 417.2, Found 417.1 |

TABLE 7-continued

| Example | IUPAC Name | Exact Mass [M + H]⁺ |
|---|---|---|
| 7-26 | 8-fluoro-4-(4-fluorophenyl)-7-{[6-(hydroxymethyl)pyridin-3-yl]methyl}quinoline-2-carboxamide | Calc'd 406.1, Found 406.1 |
| 7-27 | 8-fluoro-7-[(4-fluoropiperidin-1-yl)methyl]-4-(1-methyl-1H-pyrazol-4-yl)quinoline-2-carboxamide | Calc'd 386.2, Found 386.3 |
| 7-28 | 8-fluoro-4-(3-fluoro-4-methoxyphenyl)-7-({4-[1-hydroxy-1-(trifluoromethyl)propyl]-1H-imidazol-1-yl}methyl)quinoline-2-carboxamide | Calc'd 521.2, Found 521.2 |
| 7-29 | 8-fluoro-4-(2-fluoro-4-methoxyphenyl)-7-({4-[1-hydroxy-1-(trifluoromethyl)propyl]-1H-imidazol-1-yl}methyl)quinoline-2-carboxamide | Calc'd 521.2, Found 521.2 |

TABLE 7-continued

| Example | Structure | IUPAC Name | Exact Mass [M + H]+ |
|---|---|---|---|
| 7-30 | 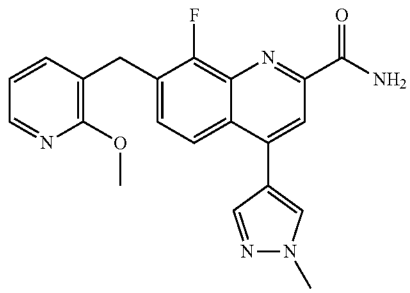 [SMILES: COc1ncccc1Cc1ccc2c(-c3cnn(C)c3)cc(C(N)=O)nc2c1F] | 8-fluoro-7-[(2-methoxypyridin-3-yl)methyl]-4-(1-methyl-1H-pyrazol-4-yl)quinoline-2-carboxamide | Calc'd 392.2, Found 392.1 |
| 7-31 | 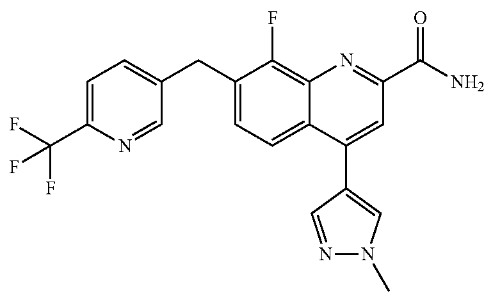 [SMILES: Cn1cc(-c2cc(C(N)=O)nc3c(F)c(Cc4ccc(C(F)(F)F)nc4)ccc23)cn1] | 8-fluoro-4-(1-methyl-1H-pyrazol-4-yl)-7-{[6-(trifluoromethyl)pyridin-3-yl]methyl}quinoline-2-carboxamide | Calc'd 430.1, Found 430.1 |
| 7-32 | 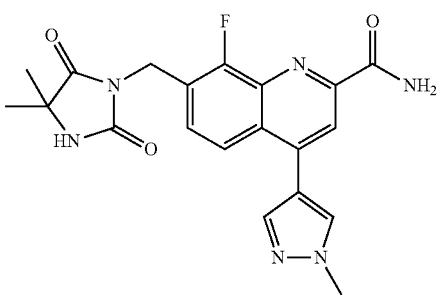 [SMILES: Cn1cc(-c2cc(C(N)=O)nc3c(F)c(CN4C(=O)NC(C)(C)C4=O)ccc23)cn1] | 7-[(4,4-dimethyl-2,5-dioxoimidazolidin-1-yl)methyl]-8-fluoro-4-(1-methyl-1H-pyrazol-4-yl)quinoline-2-carboxamide | Calc'd 411.2, Found 411.1 |
| 7-33 | 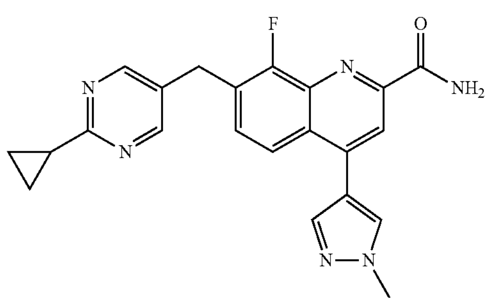 [SMILES: Cn1cc(-c2cc(C(N)=O)nc3c(F)c(Cc4cnc(C5CC5)nc4)ccc23)cn1] | 7-[(2-cyclopropylpyrimidin-5-yl)methyl]-8-fluoro-4-(1-methyl-1H-pyrazol-4-yl)quinoline-2-carboxamide | Calc'd 403.2, Found 403.2 |
| 7-34 | 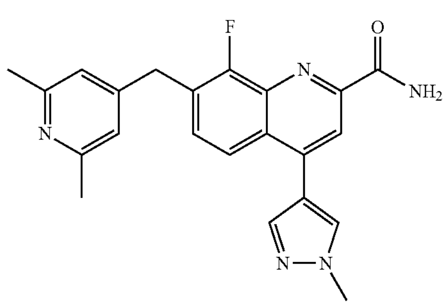 [SMILES: Cc1cc(Cc2ccc3c(-c4cnn(C)c4)cc(C(N)=O)nc3c2F)cc(C)n1] | 7-[(2,6-dimethylpyridin-4-yl)methyl]-8-fluoro-4-(1-methyl-1H-pyrazol-4-yl)quinoline-2-carboxamide | Calc'd 390.2, Found 390.2 |

TABLE 7-continued

| Example | Structure | IUPAC Name | Exact Mass [M + H]+ |
|---|---|---|---|
| 7-35 | 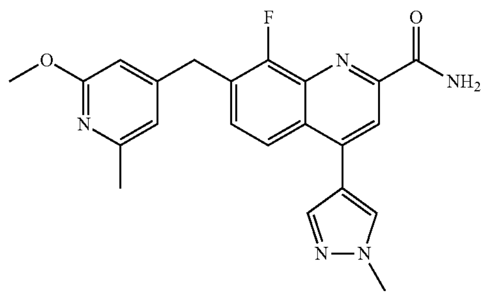 [SMILES: COc1cc(Cc2ccc3c(-c4cnn(C)c4)cc(C(N)=O)nc3c2F)cc(C)n1] | 8-fluoro-7-[(2-methoxy-6-methylpyridin-4-yl)methyl]-4-(1-methyl-1H-pyrazol-4-yl)quinoline-2-carboxamide | Calc'd 406.2, Found 406.2 |
| 7-36 | 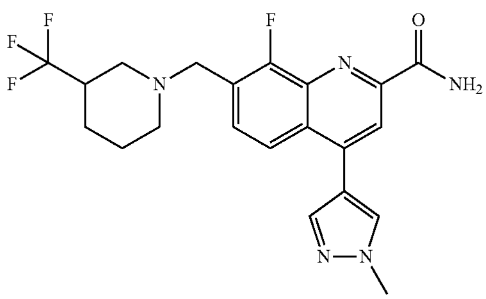 [SMILES: Cn1cc(-c2cc(C(N)=O)nc3c(F)c(CN4CCCC(C(F)(F)F)C4)ccc23)cn1] | 8-fluoro-4-(1-methyl-1H-pyrazol-4-yl)-7-{[3-(trifluoromethyl)piperidin-1-yl]methyl}quinoline-2-carboxamide | Calc'd 436.2, Found 436.2 |
| 7-37 | 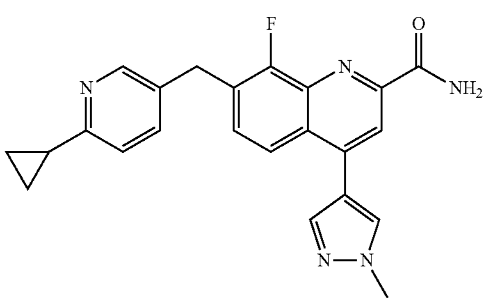 [SMILES: Cn1cc(-c2cc(C(N)=O)nc3c(F)c(Cc4ccc(C5CC5)nc4)ccc23)cn1] | 7-[(6-cyclopropylpyridin-3-yl)methyl]-8-fluoro-4-(1-methyl-1H-pyrazol-4-yl)quinoline-2-carboxamide | Calc'd 402.2, Found 402.2 |
| 7-38 | 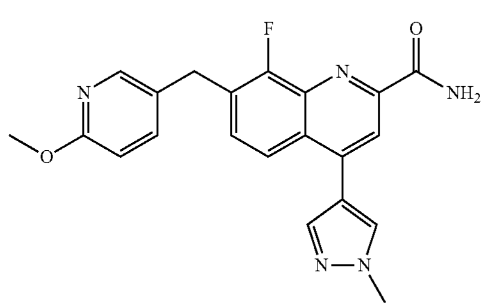 [SMILES: COc1ccc(Cc2ccc3c(-c4cnn(C)c4)cc(C(N)=O)nc3c2F)cn1] | 8-fluoro-7-[(6-methoxypyridin-3-yl)methyl]-4-(1-methyl-1H-pyrazol-4-yl)quinoline-2-carboxamide | Calc'd 392.2, Found 392.1 |

Scheme 8.1

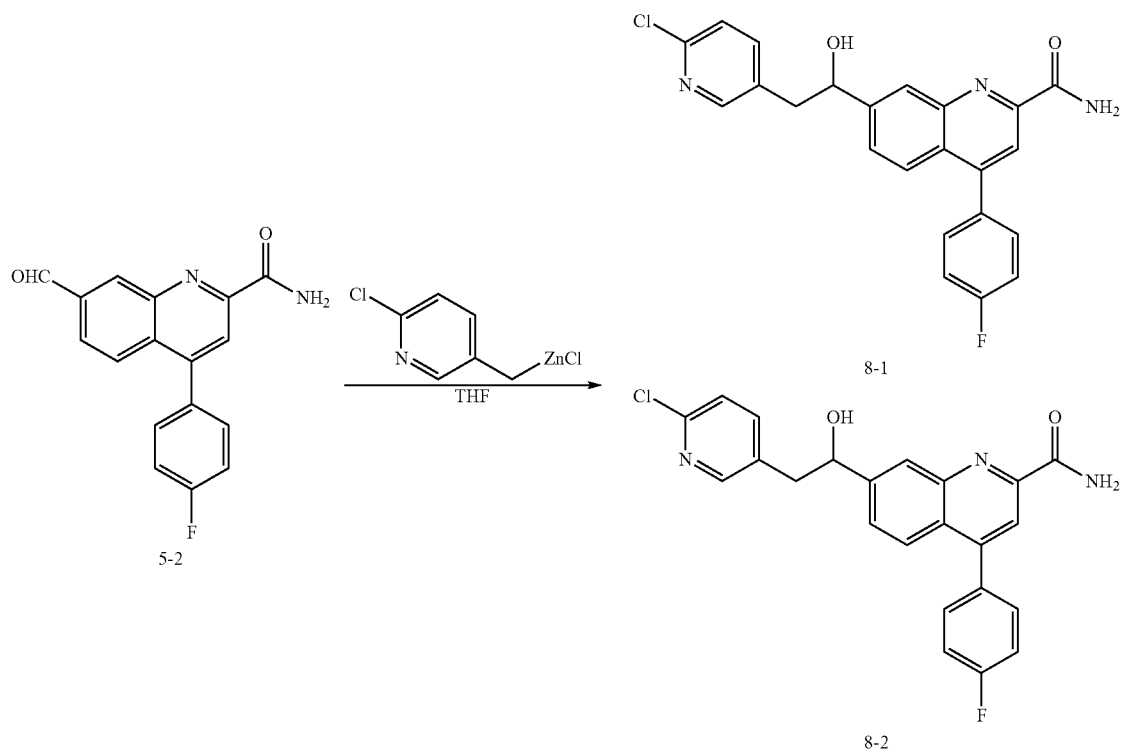

Example 8.1

Synthesis of 7-[2-(6-chloropyridin-3-yl)-1(R or S)-hydroxyethyl]-4-(4-fluorophenyl)quinoline-2-carboxamide (8-1 (Isomer A), 8-2 (Isomer B))

7-[2-(6-Chloropyridin-3-yl)-1(R or S)-hydroxyethyl]-4-(4-fluorophenyl)quinoline-2-carboxamide (8-1, 8-2)

To a stirred solution of 4-(4-fluorophenyl)-7-formylquinoline-2-carboxamide (275 mg, 0.934 mmol) and THF (2336 µl) was added (2-chloro-5-pyridyl)methylzinc chloride (0.5M THF, 9345 µl, 4.67 mmol) dropwise over 1 minute. The solution was heated to 50° C. for 20 minutes. Allowed to cool to ambient temperature and then was quenched with saturated $NH_4Cl$. The mixture was extracted with EtOAc. The organic portion was washed with brine, dried ($MgSO_4$) and concentrated. The residue was purified by column chromatography on silica gel, eluting with $CHCl_3$ to 70:25:5 $CHCl_3$/EtOAc/MeOH to give the racemic amide as a colorless solid. The racemic amide was purified by preparative HPLC Chiralpak AD, eluting with 60% EtOH/hexanes+0.1% $Et_2NH$, 50 ml/min to give 8-1 (isomer A, 38 mg, 0.090 mmol, 9.64% yield) as a colorless solid and 8-2 (isomer B, 43 mg, 0.102 mmol, 10.91% yield) as a colorless solid.

8-1 (LCMS, LRMS m/z (M+H)+ 422.2 found, 422.8 required.

8-2 LCMS, LRMS m/z (M+H)+ 422.2 found, 422.8 required.

Scheme 8.2

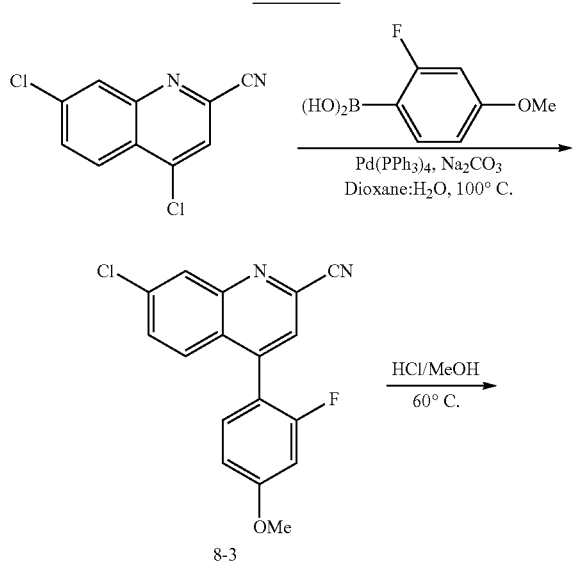

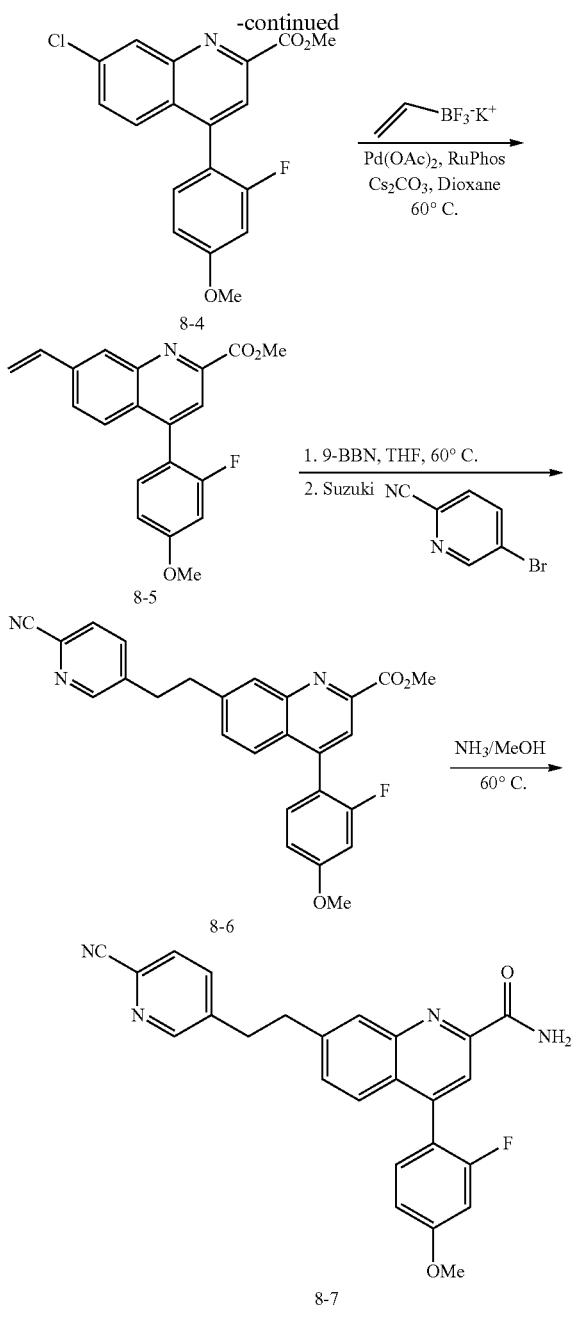

Example 8.2

Synthesis of 7-[2-(6-cyanopyridin-3-yl)ethyl]-4-(2-fluoro-4-methoxyphenyl)quinoline-2-carboxamide (8-7)

7-Chloro-4-(2-fluoro-4-methoxyphenyl)quinoline-2-carbonitrile (8-3)

To a stirred solution of 4,7-dichloroquinoline-2-carbonitrile (6 g, 26.9 mmol), (2-fluoro-4-methoxyphenyl)boronic acid (5.03 g, 29.6 mmol), 2M sodium carbonate (29.6 ml, 59.2 mmol) in 10:1 toluene (48.9 ml) ethanol (4.89 ml) was added tetrakis(triphenylphosphine)palladium(O) (0.777 g, 0.672 mmol). The mixture was stirred at 75° C. under $N_2$ for 18 hours. The reaction was allowed to cool to ambient temperature. The cooled reaction mixture was diluted with EtOAc and then washed with $H_2O$, brine, dried ($MgSO_4$) and concentrated. The residue was mostly dissolved in warm EtOAc (100 ml), added 100 ml of $Et_2O$, allowed to stand at ambient temperature for 1 hour. The solid was collected and washed with cold $Et_2O$ (50 ml) to give 7-chloro-4-(2-fluoro-4-methoxyphenyl)quinoline-2-carbonitrile (4.4 g, 14.07 mmol, 52.3% yield) as a yellow solid.

(LCMS, LRMS m/z (M+H)$^+$ 313.1 found, 313.7 required.

Methyl 7-chloro-4-(2-fluoro-4-methoxyphenyl)quinoline-2-carboxylate (8-4)

7-Chloro-4-(2-fluoro-4-methoxyphenyl)quinoline-2-carbonitrile (4.4 g, 14.07 mmol) was suspended in MeOH (70.3 ml), added 200 ml sat HCl/MeOH and then heated to 60° C. for 4 hours. The reaction was allowed to cool to ambient temperature and then was concentrated. The residue was dissolved in EtOAc and then washed with 1:1 1N NaOH/sat $NaHCO_3$, brine, dried ($MgSO_4$) and concentrated to afford methyl 7-chloro-4-(2-fluoro-4-methoxyphenyl)quinoline-2-carboxylate (4.4 g, 12.73 mmol, 90% yield) as a yellow solid.

(LCMS, LRMS m/z (M+H)$^+$ 346.2 found, 346.8 required.

Methyl 7-ethenyl-4-(2-fluoro-4-methoxyphenyl)quinoline-2-carboxylate (8-5)

Methyl 7-chloro-4-(2-fluoro-4-methoxyphenyl)quinoline-2-carboxylate (1.8 g, 5.21 mmol) was dissolved in dioxane (23.43 ml), degassed 10 minutes with $N_2$. Added potassium vinyltrifluoroborate (1.395 g, 10.41 mmol), palladium(II) acetate (0.088 g, 0.390 mmol), 2-bicyclohexylphosphino-2',6'-dimethoxybiphenyl (0.321 g, 0.781 mmol) and cesium carbonate (5.09 g, 15.62 mmol) followed by degassed water (2.60 ml). Degassed with N2 for another 10 minutes and then the mixture was stirred at 85° C. for 1 hour. Reaction was complete. The reaction mixture was cooled to ambient temperature and then diluted with EtOAc. Partitioned EtOAc with water, washed EtOAc extract with brine, dried using anhy. $MgSO_4$ and then concentrated. The residue was purified by column chromatography on silica gel, eluting with hexanes to EtOAc to afford methyl 7-ethenyl-4-(2-fluoro-4-methoxyphenyl)quinoline-2-carboxylate (1.25 g, 3.71 mmol, 71.2% yield) as a yellow solid.

(LCMS, LRMS m/z (M+H)$^+$ 338.3 found, 338.3 required.

Methyl 7-[2-(6-cyanopyridin-3-yl)ethyl]-4-(2-fluoro-4-methoxyphenyl)quinoline-2-carboxylate (8-6)

Methyl 7-ethenyl-4-(2-fluoro-4-methoxyphenyl)quinoline-2-carboxylate (250 mg, 0.741 mmol) was dissolved in THF (1.3 ml), heated to 60° C. and then added 9-BBN (0.5M THF, 1.85 ml, 0.93 mmol) dropwise over 5 minutes. After 1 hour, allowed to cool to ambient. Added 5-bromopyridine-2-carbonitrile (203 mg, 1.112 mmol), $Pd_2(dba)_3$ (33.9 mg, 0.037 mmol), butyldi-1-adamantylphosphine (26.6 mg, 0.074 mmol), potassium carbonate (410 mg, 2.96 mmol) and water (135 µl), degassed 5 minutes with $N_2$ and then heated to 90° C. in a sealed tube for 30 minutes. Reaction proceeded, allowed to cool to ambient. Added brine and then EtOAc. The organic portion was collected, dried ($MgSO_4$) and concentrated. The residue was purified by column chromatography on silica gel, eluting with hexanes to EtOAc to afford methyl 7-[2-(6-cyanopyridin-3-yl)ethyl]-4-

(2-fluoro-4-methoxyphenyl)quinoline-2-carboxylate (160 mg, 0.362 mmol, 48.9% yield) as an orange oil.

(LCMS, LRMS m/z (M+H)+ 442.3 found, 442.4 required.

7-[2-(6-Cyanopyridin-3-yl)ethyl]-4-(2-fluoro-4-methoxyphenyl)quinoline-2-carboxamide (8-7)

A stirred solution of methyl 7-[2-(6-cyanopyridin-3-yl)ethyl]-4-(2-fluoro-4-methoxyphenyl)quinoline-2-carboxylate (160 mg, 0.362 mmol) and MeOH (1450 µl) was treated with 5 ml 7N NH$_3$/MeOH and then heated to 60° C. in a sealed tube for 30 minutes. The reaction was allowed to cool to ambient temperature and then was concentrated. The solid was triturated with EtOH, collected, washed with 5 ml Et$_2$O and then dried in vacuo to afford 7-[2-(6-cyanopyridin-3-yl)ethyl]-4-(2-fluoro-4-methoxyphenyl)quinoline-2-carboxamide (105 mg, 0.246 mmol, 67.9% yield) as a colorless solid.

(LCMS, LRMS m/z (M+H)+ 427.3 found, 427.4 required.
$^1$H NMR (500 MHz, DMSO): 8.68 (1H, s), 8.27 (1H, s), 8.01 (1H, s), 7.97 (3H, s), 7.83 (1H, s), 7.64 (2H, d, J=4.55 Hz), 7.49 (1H, t, J=8.59 Hz), 7.09 (1H, d, J=12.11 Hz), 7.02 (1H, d, J=8.60 Hz), 3.89 (3H, s), 3.19 (4H, dd, J=18.34, 7.14 Hz).

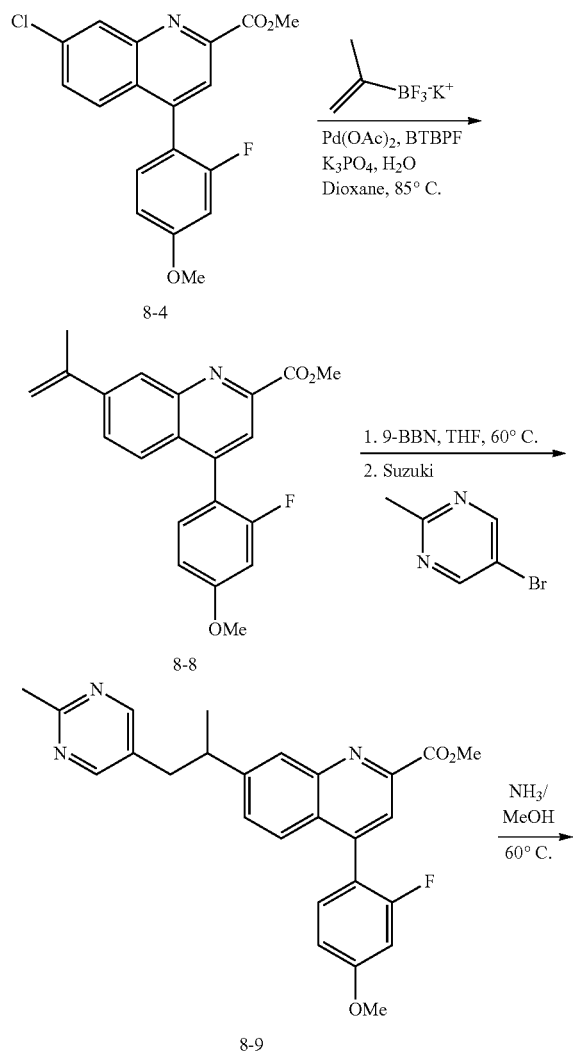

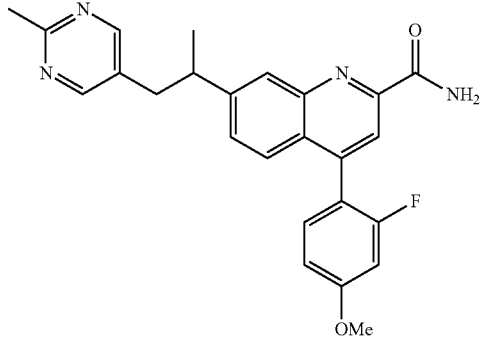

8-10

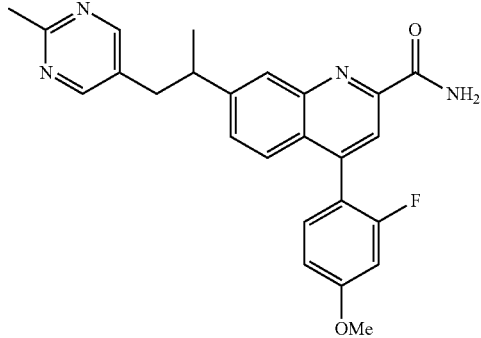

8-11

Example 8.3

Synthesis of 4-(2-fluoro-4-methoxyphenyl)-7-[1-(2-methylpyrimidin-5-yl)propan-2(R or S)-yl]quinoline-2-carboxamide (8-10, 8-11)

Methyl 4-(2-fluoro-4-methoxyphenyl)-7-(prop-1-en-2-yl)quinoline-2-carboxylate (8-8)

Isopropenylboronic acid pinacol ester (2.67 g, 15.91 mmol), methyl 7-chloro-4-(2-fluoro-4-methoxyphenyl)quinoline-2-carboxylate (5 g, 14.46 mmol), potassium phosphate tribasic (9.21 g, 43.4 mmol) and dioxane (43.8 ml)/water (4.38 ml) were combined and then degassed with nitrogen for 5 minutes. Added palladium(II) acetate (0.243 g, 1.085 mmol) and 1,1'-bis(di-tert-butylphosphino)ferrocene (0.515 g, 1.085 mmol) and then heated to 85° C. for 4 hours. Reaction was complete and was allowed to cool to ambient temperature. The mixture was diluted with EtOAc and then washed with H$_2$O, brine, dried (MgSO$_4$) and concentrated. The residue was purified by column chromatography on silica gel, eluting with hexanes to EtOAc to afford methyl 4-(2-fluoro-4-methoxyphenyl)-7-(prop-1-en-2-yl)quinoline-2-carboxylate (3.3 g, 9.39 mmol, 64.9% yield) as a yellow solid.

(LCMS, LRMS m/z (M+H)+ 352.3 found, 352.4 required.

Methyl 4-(2-fluoro-4-methoxyphenyl)-7-[1-(2-methylpyrimidin-5-yl)propan-2-yl]quinoline-2-carboxylate (8-9)

Methyl 4-(2-fluoro-4-methoxyphenyl)-7-(prop-1-en-2-yl)quinoline-2-carboxylate (1.5 g, 4.27 mmol) was dissolved in THF (7.8 ml), heated to 60° C. and then added 9-BBN (0.5M THF, 10.7 ml, 5.35 mmol) dropwise over 5 minutes. After 1 hour, allowed to cool to ambient. Added 5-bromo-2-methylpyrimidine (0.886 g, 5.12 mmol), Pd$_2$(dba)$_3$ (0.195 g, 0.213 mmol), butyldi-1-adamantylphosphine (0.153 g, 0.427 mmol), potassium carbonate (2.360 g, 17.08 mmol) and water (0.776 ml), degassed 5 minutes with nitrogen and then heated to 90° C. in a sealed tube for 30 minutes. The reaction was allowed to cool to ambient temperature. To the mixture was added brine and then EtOAc. The organic portion was collected, dried (MgSO$_4$) and then concentrated. The residue was purified by column chromatography on silica gel, eluting with CHCl$_3$ to 70:25:5 CHCl$_3$/EtOAc/MeOH to afford methyl 4-(2-fluoro-4-methoxyphenyl)-7-[1-(2-methylpyrimidin-5-yl)propan-2-yl]quinoline-2-carboxylate (335 mg, 0.752 mmol, 17.62% yield) as an orange oil.
(LCMS, LRMS m/z (M+H)$^+$ 446.4 found, 446.5 required.

4-(2-Fluoro-4-methoxyphenyl)-7-[1-(2-methylpyrimidin-5-yl)propan-2(R or S)-yl]quinoline-2-carboxamide (8-10, 8-11)

A stirred solution of methyl 4-(2-fluoro-4-methoxyphenyl)-7-[1-(2-methylpyrimidin-5-yl)propan-2-yl]quinoline-2-carboxylate (335 mg, 0.752 mmol) and MeOH (3008 μl) was treated with 5 ml 7N NH$_3$/MeOH and then heated to 60° C. in a sealed tube for 30 minutes. The reaction was allowed to cool to ambient temperature and then was concentrated. The solid was azeotroped with 5 ml Et$_2$O and then dried in vacuo to give racemic product as a colorless foam.

The residue was purified by preparative HPLC Chiralpak AD, 5 cm, 40 ml/min, eluting with 100% EtOH, to afford 8-10 (isomer A, 95 mg, 0.221 mmol, 58.7% yield) as a colorless foam and 8-11 (isomer B, 85 mg, 0.197 mmol, 52.5% yield) as a colorless foam.

8-10, Isomer A (LCMS, LRMS m/z (M+H)$^+$ 431.3 found, 431.5 required.

$^1$H NMR (500 MHz, CDCl$_3$): 8.32 (2H, s), 8.21 (1H, s), 8.05 (1H, s), 7.89 (1H, s), 7.73 (1H, d, J=8.58 Hz), 7.41 (1H, d, J=8.42 Hz), 7.34 (1H, t, J=8.40 Hz), 6.89-6.85 (1H, m), 6.80 (1H, dd, J=11.53, 2.48 Hz), 5.61 (1H, s), 3.90 (3H, s), 3.26-3.21 (1H, m), 3.00-2.92 (2H, m), 2.65 (3H, s).

8-11, Isomer B (LCMS, LRMS m/z (M+H)$^+$ 431.4 found, 431.5 required.

$^1$H NMR (500 MHz, CDCl$_3$): 8.32 (2H, s), 8.21 (1H, s), 8.05 (1H, s), 7.89 (1H, s), 7.73 (1H, dd, J=8.63, 2.83 Hz), 7.41 (1H, d, J=8.49 Hz), 7.34 (1H, t, J=8.43 Hz), 6.87 (1H, dd, J=8.51, 2.54 Hz), 6.80 (1H, dd, J=11.56, 2.53 Hz), 5.61 (1H, s), 3.90 (3H, s), 3.26-3.21 (1H, m), 3.01-2.90 (2H, m), 2.65 (3H, s).

The following compounds have been prepared according to procedures similar to those found in Scheme 8.1, 8.2, and 8.3 selecting the appropriate quinoline derivative, boronic acid derivatives, and aryl or heteroaryl halide and provide examples of compounds in the invention.

TABLE 8

| Example | Structure | IUPAC Name | Exact Mass [M + H]$^+$ |
|---------|-----------|------------|------------------------|
| 8-12 | 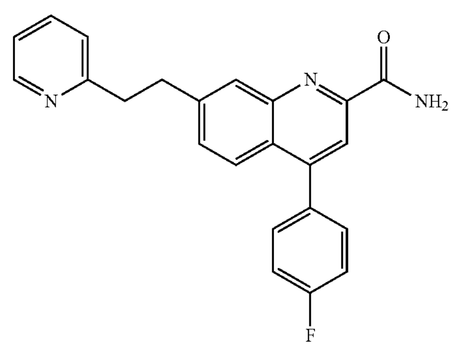 [SMILES: NC(=O)c1cc(-c2ccc(F)cc2)c2ccc(CCc3ccccn3)cc2n1] | 4-(4-fluorophenyl)-7-(2-pyridin-2-ylethyl)quinoline-2-carboxamide | Calc'd 372.2, Found 372.2 |
| 8-13 | 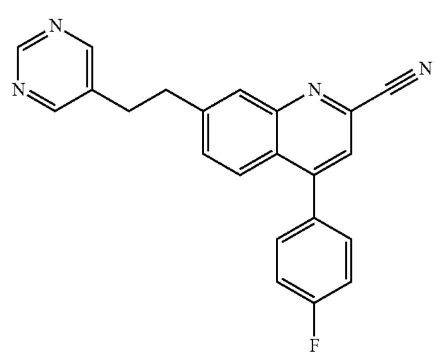 [SMILES: N#Cc1cc(-c2ccc(F)cc2)c2ccc(CCc3cncnc3)cc2n1] | 4-(4-fluorophenyl)-7-(2-pyrimidin-5-ylethyl)quinoline-2-carbonitrile | Calc'd 355.1, Found 355.1 |

TABLE 8-continued

| Example | Structure | IUPAC Name | Exact Mass [M + H]+ |
|---|---|---|---|
| 8-14 | 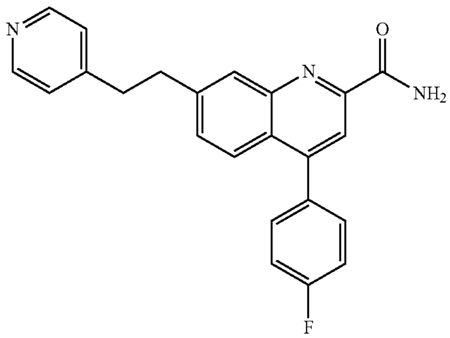 [SMILES: NC(=O)c1cc(-c2ccc(F)cc2)c2ccc(CCc3ccncc3)cc2n1] | 4-(4-fluorophenyl)-7-(2-pyridin-4-ylethyl)quinoline-2-carboxamide | Calc'd 372.2, Found 372.2 |
| 8-15 | 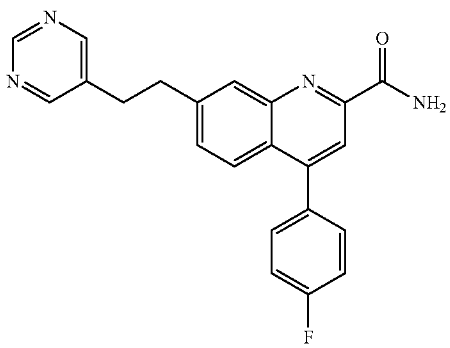 [SMILES: NC(=O)c1cc(-c2ccc(F)cc2)c2ccc(CCc3cncnc3)cc2n1] | 4-(4-fluorophenyl)-7-(2-pyrimidin-5-ylethyl)quinoline-2-carboxamide | Calc'd 373.1, Found 373.1 |
| 8-16 | 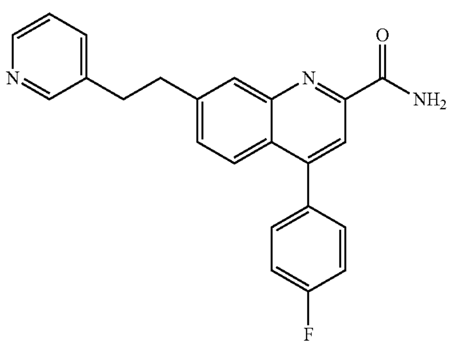 [SMILES: NC(=O)c1cc(-c2ccc(F)cc2)c2ccc(CCc3cccnc3)cc2n1] | 4-(4-fluorophenyl)-7-(2-pyridin-3-ylethyl)quinoline-2-carboxamide | Calc'd 372.2, Found 372.2 |
| 8-17 | 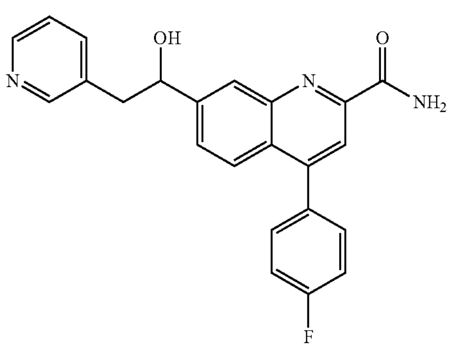 | 4-(4-fluorophenyl)-7-(1-hydroxy-2-pyridin-3-ylethyl)quinoline-2-carboxamide | Calc'd 388.1, Found 388.1 |

TABLE 8-continued

| Example | Structure | IUPAC Name | Exact Mass [M + H]+ |
|---|---|---|---|
| 8-18 | 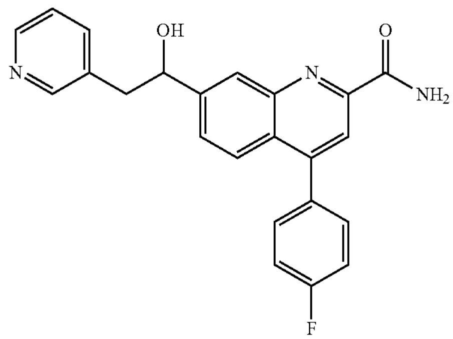 [SMILES: NC(=O)c1cc(-c2ccc(F)cc2)c2ccc(C(O)Cc3cccnc3)cc2n1] | 4-(4-fluorophenyl)-7-(1-hydroxy-2-pyridin-3-ylethyl)quinoline-2-carboxamide | Calc'd 388.1, Found 388.1 |
| 8-19 | 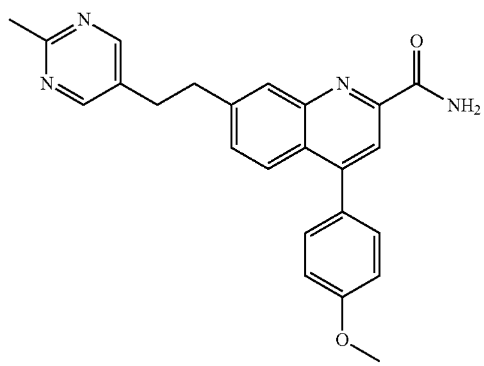 [SMILES: COc1ccc(-c2cc(C(N)=O)nc3cc(CCc4cnc(C)nc4)ccc23)cc1] | 4-(4-methoxyphenyl)-7-[2-(2-methylpyrimidin-5-yl)ethyl]quinoline-2-carboxamide | Calc'd 399.2, Found 399.1 |
| 8-20 | 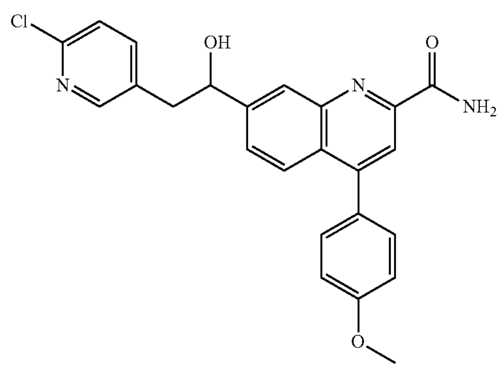 [SMILES: COc1ccc(-c2cc(C(N)=O)nc3cc(C(O)Cc4ccc(Cl)nc4)ccc23)cc1] | 7-[2-(6-chloropyridin-3-yl)-1-hydroxyethyl]-4-(4-methoxyphenyl)quinoline-2-carboxamide | Calc'd 434.1, Found 434.0 |
| 8-21 | 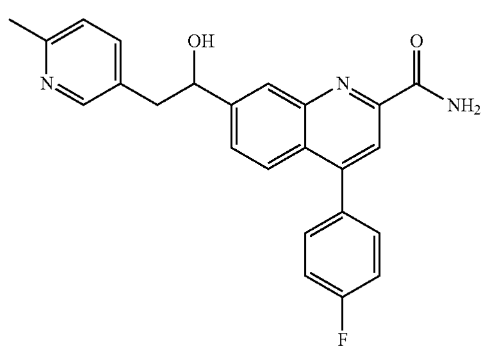 [SMILES: Cc1ccc(CC(O)c2ccc3c(-c4ccc(F)cc4)cc(C(N)=O)nc3c2)cn1] | 4-(4-fluorophenyl)-7-[1-hydroxy-2-(6-methylpyridin-3-yl)ethyl]quinoline-2-carboxamide | Calc'd 402.2, Found 402.2 |

TABLE 8-continued

| Example | Structure | IUPAC Name | Exact Mass [M + H]+ |
|---|---|---|---|
| 8-22 | 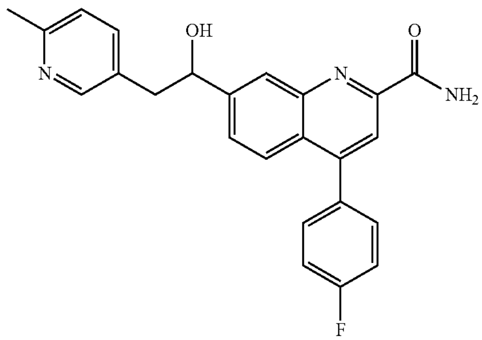 [SMILES: Cc1ccc(CC(O)c2ccc3c(-c4ccc(F)cc4)cc(C(N)=O)nc3c2)cn1] | 4-(4-fluorophenyl)-7-[1-hydroxy-2-(6-methylpyridin-3-yl)ethyl]quinoline-2-carboxamide | Calc'd 402.2, Found 402.2 |
| 8-23 | 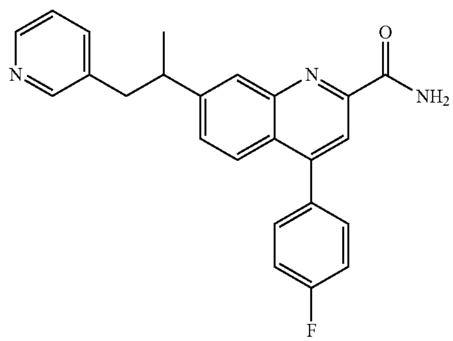 [SMILES: CC(Cc1cccnc1)c1ccc2c(-c3ccc(F)cc3)cc(C(N)=O)nc2c1] | 4-(4-fluorophenyl)-7-(1-methyl-2-pyridin-3-ylethyl)quinoline-2-carboxamide | Calc'd 386.2, Found 386.2 |
| 8-24 | 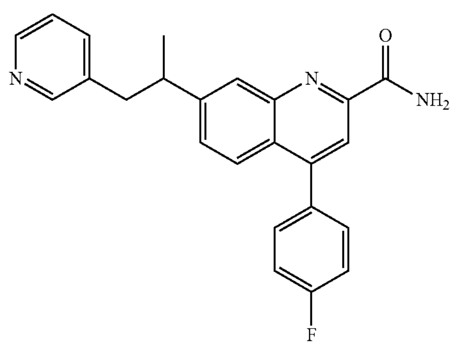 [SMILES: CC(Cc1cccnc1)c1ccc2c(-c3ccc(F)cc3)cc(C(N)=O)nc2c1] | 4-(4-fluorophenyl)-7-(1-methyl-2-pyridin-3-ylethyl)quinoline-2-carboxamide | Calc'd 386.2, Found 386.2 |
| 8-25 | 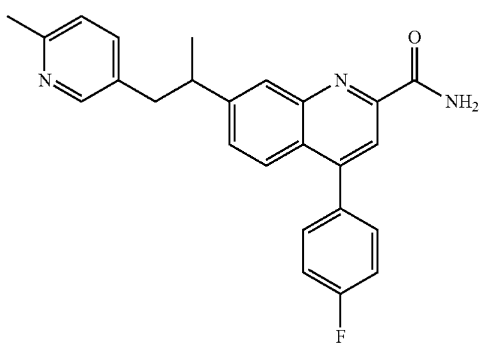 [SMILES: Cc1ccc(CC(C)c2ccc3c(-c4ccc(F)cc4)cc(C(N)=O)nc3c2)cn1] | 4-(4-fluorophenyl)-7-[1-methyl-2-(6-methylpyridin-3-yl)ethyl]quinoline-2-carboxamide | Calc'd 400.2, Found 400.2 |

TABLE 8-continued

| Example | Structure | IUPAC Name | Exact Mass [M + H]+ |
|---|---|---|---|
| 8-26 | 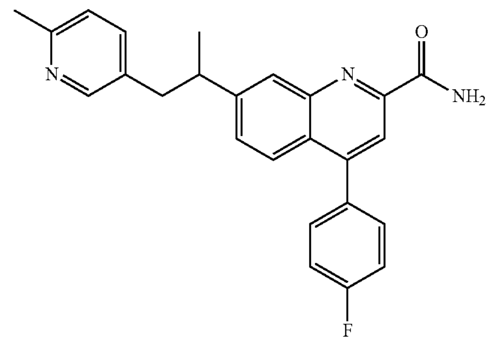 | 4-(4-fluorophenyl)-7-[1-methyl-2-(6-methylpyridin-3-yl)ethyl]quinoline-2-carboxamide | Calc'd 400.2, Found 400.2 |
| 8-27 | 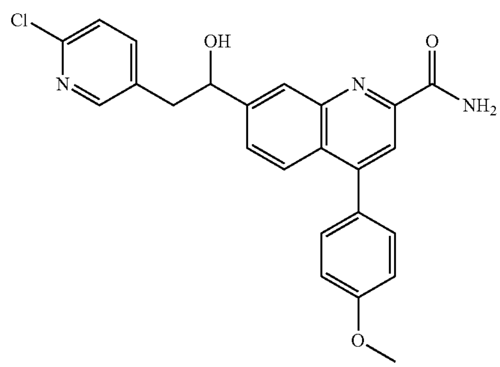 [SMILES: COc1ccc(-c2cc(C(N)=O)nc3cc(C(O)Cc4ccc(Cl)nc4)ccc23)cc1] | 7-[2-(6-chloropyridin-3-yl)-1-hydroxyethyl]-4-(4-methoxyphenyl)quinoline-2-carboxamide | Calc'd 434.1, Found 434.5 |
| 8-28 | 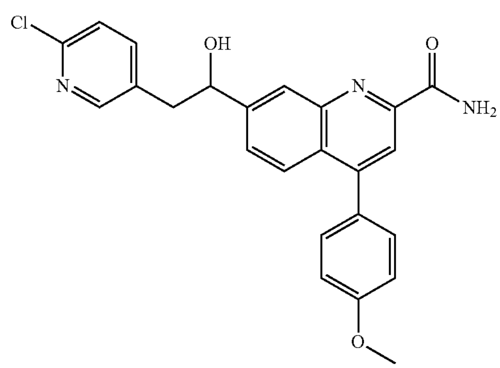 [SMILES: COc1ccc(-c2cc(C(N)=O)nc3cc(C(O)Cc4ccc(Cl)nc4)ccc23)cc1] | 7-[2-(6-chloropyridin-3-yl)-1-hydroxyethyl]-4-(4-methoxyphenyl)quinoline-2-carboxamide | Calc'd 434.1, Found 434.5 |
| 8-29 | 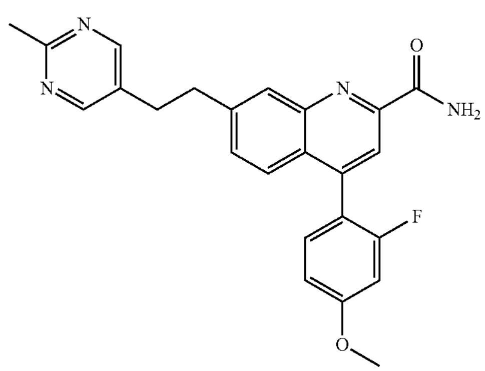 [SMILES: COc1ccc(-c2cc(C(N)=O)nc3cc(CCc4cnc(C)nc4)ccc23)c(F)c1] | 4-(2-fluoro-4-methoxyphenyl)-7-[2-(2-methylpyrimidin-5-yl)ethyl]quinoline-2-carboxamide | Calc'd 417.2, Found 417.2 |

TABLE 8-continued

| Example | Structure | IUPAC Name | Exact Mass [M + H]+ |
|---|---|---|---|
| 8-30 | 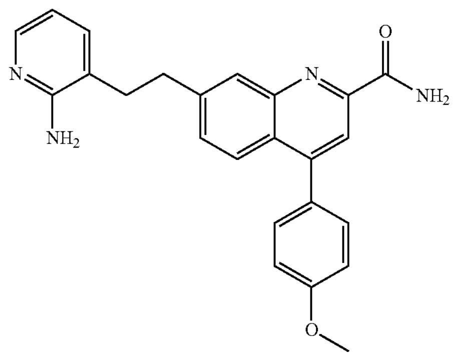 [SMILES: COc1ccc(-c2cc(C(N)=O)nc3cc(CCc4cccnc4N)ccc23)cc1] | 7-[2-(2-aminopyridin-3-yl)ethyl]-4-(4-methoxyphenyl)quinoline-2-carboxamide | Calc'd 399.2, Found 399.4 |
| 8-31 | 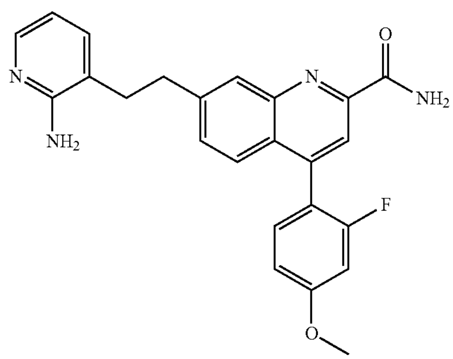 [SMILES: COc1ccc(-c2cc(C(N)=O)nc3cc(CCc4cccnc4N)ccc23)c(F)c1] | 7-[2-(2-aminopyridin-3-yl)ethyl]-4-(2-fluoro-4-methoxyphenyl)quinoline-2-carboxamide | Calc'd 417.2, Found 417.4 |
| 8-32 | 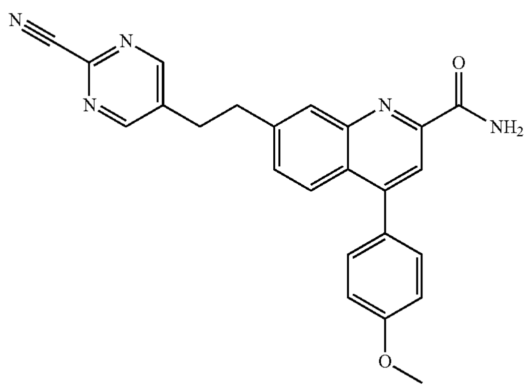 [SMILES: COc1ccc(-c2cc(C(N)=O)nc3cc(CCc4cnc(C#N)nc4)ccc23)cc1] | 7-[2-(2-cyanopyrimidin-5-yl)ethyl]-4-(4-methoxyphenyl)quinoline-2-carboxamide | Calc'd 410.2, Found 410.5 |
| 8-33 | 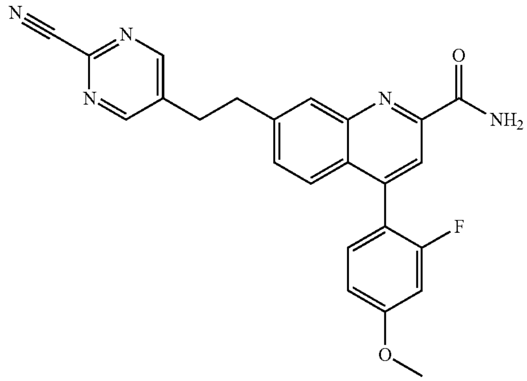 [SMILES: COc1ccc(-c2cc(C(N)=O)nc3cc(CCc4cnc(C#N)nc4)ccc23)c(F)c1] | 7-[2-(2-cyanopyrimidin-5-yl)ethyl]-4-(2-fluoro-4-methoxyphenyl)quinoline-2-carboxamide | Calc'd 428.2, Found 428.4 |

TABLE 8-continued

| Example | Structure | IUPAC Name | Exact Mass [M + H]+ |
|---|---|---|---|
| 8-34 | 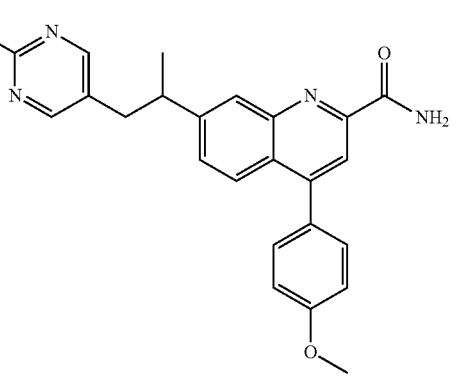 | 7-[2-(2-cyanopyrimidin-5-yl)-1-methylethyl]-4-(4-methoxyphenyl)quinoline-2-carboxamide | Calc'd 424.2, Found 424.5 |
| 8-35 | 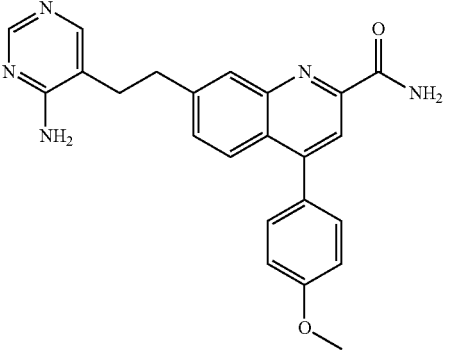 [SMILES: COc1ccc(-c2cc(C(N)=O)nc3cc(CCc4cncnc4N)ccc23)cc1] | 7-[2-(4-aminopyrimidin-5-yl)ethyl]-4-(4-methoxyphenyl)quinoline-2-carboxamide | Calc'd 400.2, Found 400.5 |
| 8-36 | 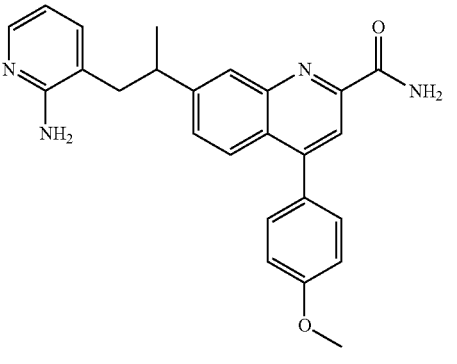 [SMILES: COc1ccc(-c2cc(C(N)=O)nc3cc(C(C)Cc4cccnc4N)ccc23)cc1] | 7-[2-(2-aminopyridin-3-yl)-1-methylethyl]-4-(4-methoxyphenyl)quinoline-2-carboxamide | Calc'd 413.2, Found 413.5 |
| 8-37 | 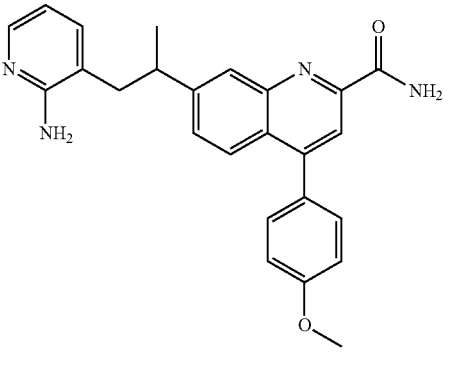 [SMILES: COc1ccc(-c2cc(C(N)=O)nc3cc(C(C)Cc4cccnc4N)ccc23)cc1] | 7-[2-(2-aminopyridin-3-yl)-1-methylethyl]-4-(4-methoxyphenyl)quinoline-2-carboxamide | Calc'd 413.2, Found 413.5 |

TABLE 8-continued

| Example | Structure | IUPAC Name | Exact Mass [M + H]+ |
|---------|-----------|------------|---------------------|
| 8-38 | 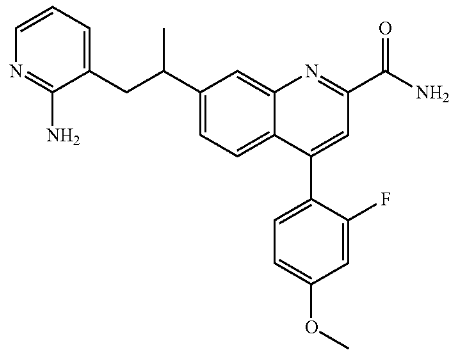 [SMILES: COc1ccc(-c2cc(C(N)=O)nc3cc(C(C)Cc4cccnc4N)ccc23)c(F)c1] | 7-[2-(2-aminopyridin-3-yl)-1-methylethyl]-4-(2-fluoro-4-methoxyphenyl)quinoline-2-carboxamide | Calc'd 431.2, Found 431.5 |
| 8-39 | 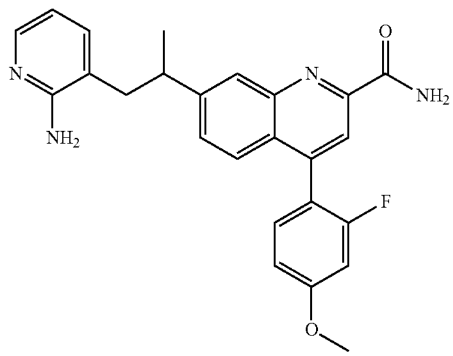 [SMILES: COc1ccc(-c2cc(C(N)=O)nc3cc(C(C)Cc4cccnc4N)ccc23)c(F)c1] | 7-[2-(2-aminopyridin-3-yl)-1-methylethyl]-4-(2-fluoro-4-methoxyphenyl)quinoline-2-carboxamide | Calc'd 431.2, Found 431.5 |
| 8-40 | 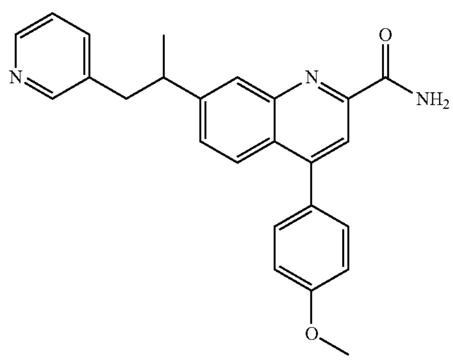 [SMILES: COc1ccc(-c2cc(C(N)=O)nc3cc(C(C)Cc4cccnc4)ccc23)cc1] | 4-(4-methoxyphenyl)-7-(1-methyl-2-pyridin-3-ylethyl)quinoline-2-carboxamide | Calc'd 398.2, Found 398.4 |
| 8-41 | 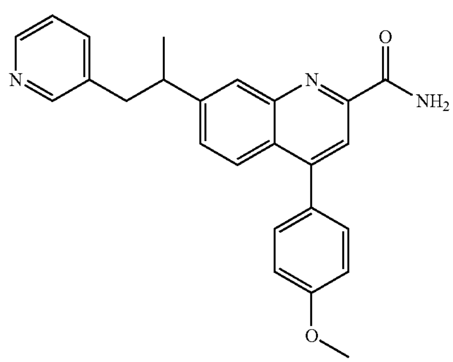 [SMILES: COc1ccc(-c2cc(C(N)=O)nc3cc(C(C)Cc4cccnc4)ccc23)cc1] | 4-(4-methoxyphenyl)-7-(1-methyl-2-pyridin-3-ylethyl)quinoline-2-carboxamide | Calc'd 398.2, Found 398.4 |

TABLE 8-continued

| Example | Structure | IUPAC Name | Exact Mass [M + H]+ |
|---|---|---|---|
| 8-42 | 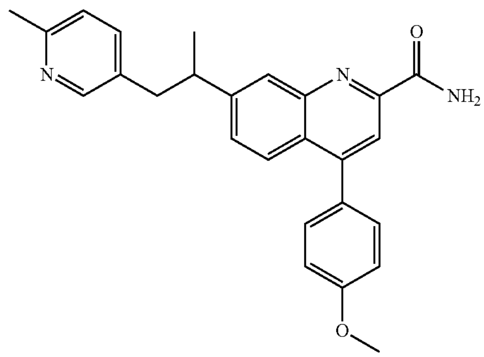 [SMILES: COc1ccc(-c2cc(C(N)=O)nc3cc(C(C)Cc4ccc(C)nc4)ccc23)cc1] | 4-(4-methoxyphenyl)-7-[1-methyl-2-(6-methylpyridin-3-yl)ethyl]quinoline-2-carboxamide | Calc'd 412.2, Found 412.4 |
| 8-43 | 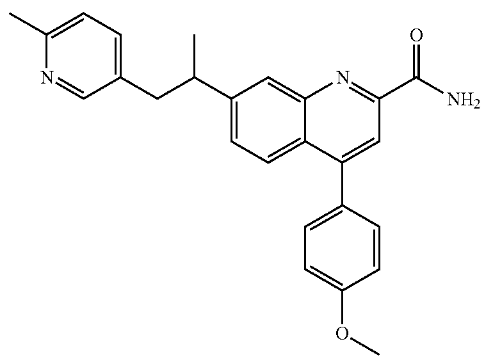 [SMILES: COc1ccc(-c2cc(C(N)=O)nc3cc(C(C)Cc4ccc(C)nc4)ccc23)cc1] | 4-(4-methoxyphenyl)-7-[1-methyl-2-(6-methylpyridin-3-yl)ethyl]quinoline-2-carboxamide | Calc'd 412.2, Found 412.4 |
| 8-44 | 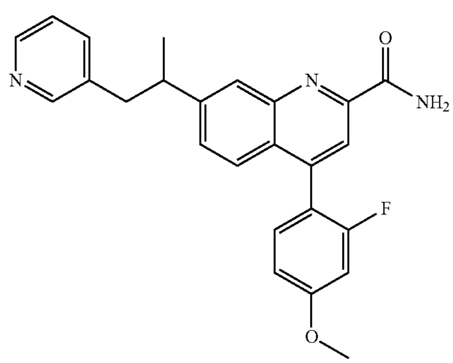 [SMILES: COc1ccc(-c2cc(C(N)=O)nc3cc(C(C)Cc4cccnc4)ccc23)c(F)c1] | 4-(2-fluoro-4-methoxyphenyl)-7-(1-methyl-2-pyridin-3-ylethyl)quinoline-2-carboxamide | Calc'd 416.2, Found 416.4 |
| 8-45 | 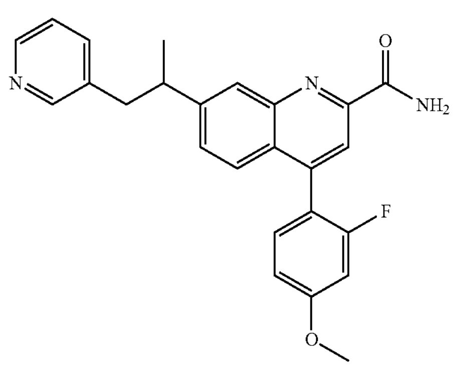 [SMILES: COc1ccc(-c2cc(C(N)=O)nc3cc(C(C)Cc4cccnc4)ccc23)c(F)c1] | 4-(2-fluoro-4-methoxyphenyl)-7-(1-methyl-2-pyridin-3-ylethyl)quinoline-2-carboxamide | Calc'd 416.2, Found 416.4 |

TABLE 8-continued

| Example | Structure | IUPAC Name | Exact Mass [M + H]+ |
|---|---|---|---|
| 8-46 | 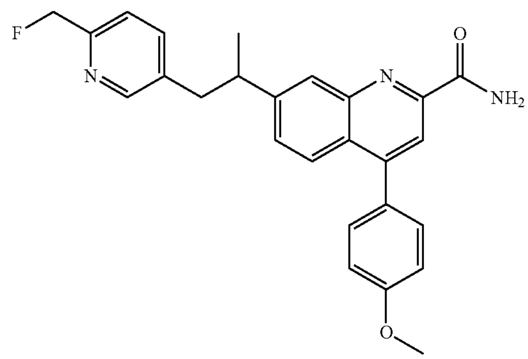 [SMILES: COc1ccc(-c2cc(C(N)=O)nc3cc(C(C)Cc4ccc(CF)nc4)ccc23)cc1] | 7-{2-[6-(fluoromethyl)pyridin-3-yl]-1-methylethyl}-4-(4-methoxyphenyl)quinoline-2-carboxamide | Calc'd 430.2, Found 430.4 |
| 8-47 | 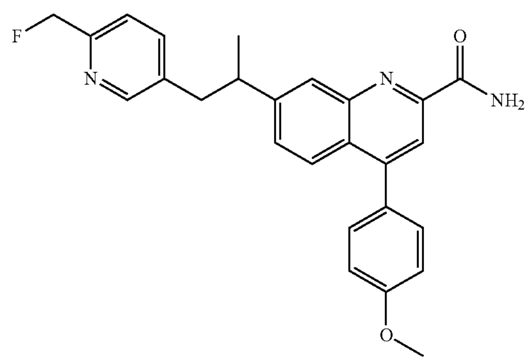 [SMILES: COc1ccc(-c2cc(C(N)=O)nc3cc(C(C)Cc4ccc(CF)nc4)ccc23)cc1] | 7-{2-[6-(fluoromethyl)pyridin-3-yl]-1-methylethyl}-4-(4-methoxyphenyl)quinoline-2-carboxamide | Calc'd 430.2, Found 430.4 |
| 8-48 | 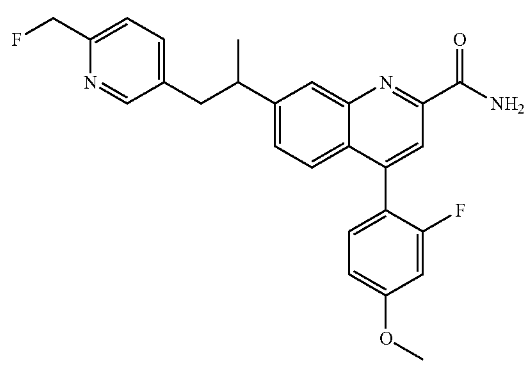 [SMILES: COc1ccc(-c2cc(C(N)=O)nc3cc(C(C)Cc4ccc(CF)nc4)ccc23)c(F)c1] | 4-(2-fluoro-4-methoxyphenyl)-7-{2-[6-(fluoromethyl)pyridin-3-yl]-1-methylethyl}quinoline-2-carboxamide | Calc'd 448.2, Found 448.4 |
| 8-49 | 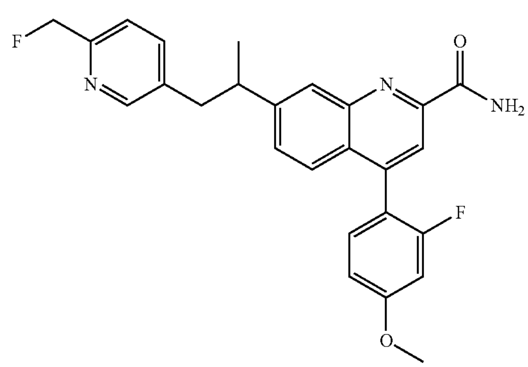 [SMILES: COc1ccc(-c2cc(C(N)=O)nc3cc(C(C)Cc4ccc(CF)nc4)ccc23)c(F)c1] | 4-(2-fluoro-4-methoxyphenyl)-7-{2-[6-(fluoromethyl)pyridin-3-yl]-1-methylethyl}quinoline-2-carboxamide | Calc'd 448.2, Found 448.4 |

TABLE 8-continued

| Example | Structure | IUPAC Name | Exact Mass [M + H]+ |
|---|---|---|---|
| 8-50 | 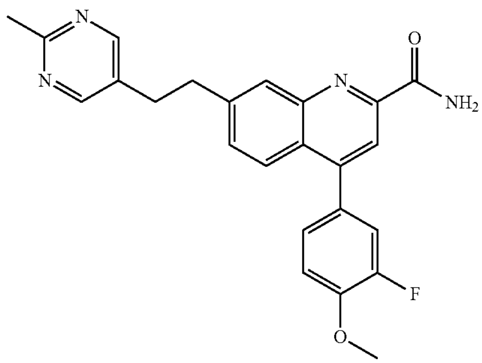 [SMILES: COc1ccc(-c2cc(C(N)=O)nc3cc(CCc4cnc(C)nc4)ccc23)cc1F] | 4-(3-fluoro-4-methoxyphenyl)-7-[2-(2-methylpyrimidin-5-yl)ethyl]quinoline-2-carboxamide | Calc'd 417.2, Found 417.3 |
| 8-51 | 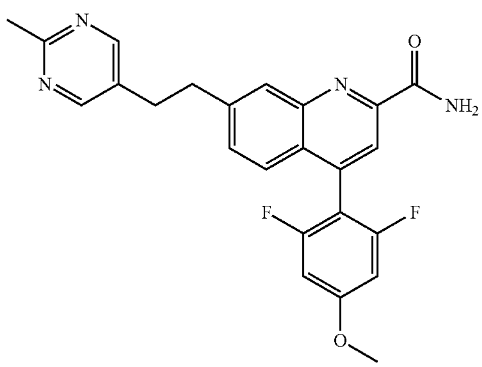 [SMILES: COc1cc(F)c(-c2cc(C(N)=O)nc3cc(CCc4cnc(C)nc4)ccc23)c(F)c1] | 4-(2,6-difluoro-4-methoxyphenyl)-7-[2-(2-methylpyrimidin-5-yl)ethyl]quinoline-2-carboxamide | Calc'd 435.2, Found 435.3 |
| 8-52 | 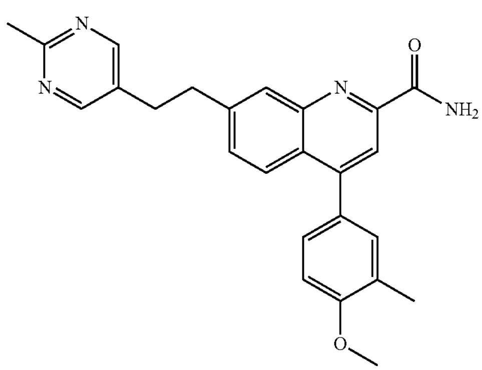 [SMILES: COc1ccc(-c2cc(C(N)=O)nc3cc(CCc4cnc(C)nc4)ccc23)cc1C] | 4-(4-methoxy-3-methylphenyl)-7-[2-(2-methylpyrimidin-5-yl)ethyl]quinoline-2-carboxamide | Calc'd 413.2, Found 413.3 |
| 8-53 | 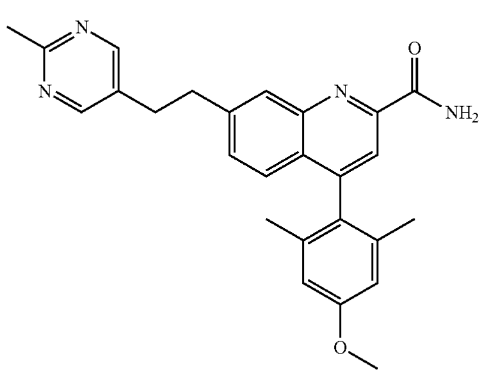 [SMILES: COc1cc(C)c(-c2cc(C(N)=O)nc3cc(CCc4cnc(C)nc4)ccc23)c(C)c1] | 4-(4-methoxy-2,6-dimethylphenyl)-7-[2-(2-methylpyrimidin-5-yl)ethyl]quinoline-2-carboxamide | Calc'd 427.2, Found 427.3 |

TABLE 8-continued

| Example | Structure | IUPAC Name | Exact Mass [M + H]+ |
|---|---|---|---|
| 8-54 | 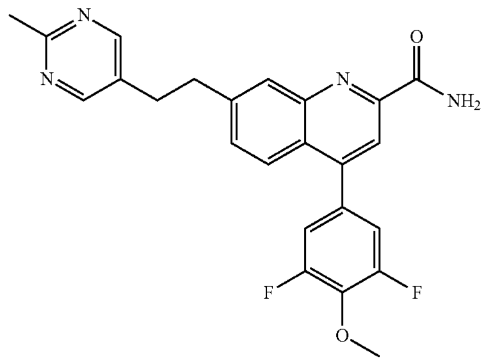 [SMILES: COc1c(F)cc(-c2cc(C(N)=O)nc3cc(CCc4cnc(C)nc4)ccc23)cc1F] | 4-(3,5-difluoro-4-methoxyphenyl)-7-[2-(2-methylpyrimidin-5-yl)ethyl]quinoline-2-carboxamide | Calc'd 435.2, Found 435.3 |
| 8-55 | 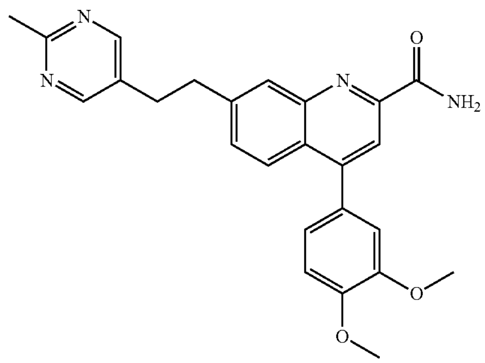 | 4-(3,4-dimethoxyphenyl)-7-[2-(2-methylpyrimidin-5-yl)ethyl]quinoline-2-carboxamide | Calc'd 429.2, Found 429.4 |

Biological Assays

The utility of the compounds in accordance with the present invention as antagonists of metabotropic glutamate receptor activity, in particular mGluR2 activity, may be demonstrated by methodology known in the art. Antagonist constants are determined as follows. The compounds of the present invention were tested in a fluorescence laser imaging plate reader based assay. This assay is a common functional assay to monitor Ca2+ mobilization in whole cells expressing recombinant receptor coupled with a promiscuous G-protein. CHO dhfr-cells stably expressing recombinant human mGluR2 and Gα16 loaded with Fluo-4 AM (Invitrogen, Carlsbad Calif.) are treated with various concentrations of antagonists of compounds and the Ca2+ response is monitored on a FLIPR384 (Molecular Devices, Sunnydale Calif.) for agonist activity. Then 2,500 nM glutamate is added and the antagonist response is monitored. The maximum calcium response at each concentration of compound for agonist or antagonist were plotted as dose responses and the curves were fitted with a four parameter logistic equation giving $IC_{50}$ and Hill coefficient using the iterative non linear curve fitting software ADA (Merck & Co). In particular, the compounds of the examples shown in the tables above had activity in antagonizing the mGluR2 receptor in the aforementioned assays, with an $IC_{50}$ of less than about 700 nM, indicating their activity as antagonists of mGluR2 function. Specific IC 50 values for representative example compounds of the invention are provided in the table below:

| Example | IC$_{50}$ Value (nM) |
|---|---|
| 1-7 | 159 |
| 1-9 | 171 |
| 1-10 | 660 |
| 1-11 | 822 |
| 1-12 | 678 |
| 1-13 | 641 |
| 1-14 | 667 |
| 1-15 | 169 |
| 1-16 | 681 |
| 1-17 | 368 |
| 1-18 | 58 |
| 1-19 | 100 |
| 1-20 | 139 |
| 1-21 | 124 |
| 1-22 | 505 |
| 1-23 | 135 |
| 1-24 | 169 |
| 1-25 | 407 |
| 1-26 | 217 |
| 1-27 | 377 |
| 1-28 | 393 |
| 1-29 | 190 |
| 2-3 | 21 |
| 2-7 | 9 |
| 2-8 | 38 |
| 2-9 | 416 |
| 2-10 | 21 |
| 2-11 | 25 |
| 2-12 | 475 |
| 2-13 | 71 |
| 2-14 | 30 |
| 2-15 | 64 |
| 2-16 | 59 |
| 2-17 | 398 |
| 2-18 | 28 |

| Example | IC$_{50}$ Value (nM) |
|---|---|
| 2-19 | 588 |
| 2-20 | 27 |
| 2-21 | 23 |
| 2-22 | 47 |
| 2-23 | 456 |
| 2-24 | 12 |
| 2-25 | 16 |
| 2-26 | 29 |
| 2-27 | 7 |
| 2-28 | 17 |
| 2-29 | 5 |
| 2-30 | 123 |
| 2-31 | 109 |
| 2-32 | 129 |
| 2-33 | 42 |
| 2-34 | 105 |
| 2-35 | 228 |
| 2-36 | 3059 |
| 2-37 | 59 |
| 2-38 | 27 |
| 2-39 | 8 |
| 3-2 | 46 |
| 3-6 | 21 |
| 3-7 | 24 |
| 3-10 | 63 |
| 3-11 | 31 |
| 3-15 | 85 |
| 3-16 | 21 |
| 3-17 | 74 |
| 3-18 | 36 |
| 3-19 | 112 |
| 3-20 | 21 |
| 3-21 | 40 |
| 3-22 | 47 |
| 3-23 | 192 |
| 3-24 | 31 |
| 3-25 | 43 |
| 3-26 | 25 |
| 3-27 | 23 |
| 3-28 | 84 |
| 3-29 | 64 |
| 3-30 | 31 |
| 3-31 | 54 |
| 3-32 | 23 |
| 3-33 | 69 |
| 3-34 | 55 |
| 3-35 | 27 |
| 3-36 | 189 |
| 3-37 | 42 |
| 3-38 | 24 |
| 3-39 | 73 |
| 3-40 | 81 |
| 3-41 | 89 |
| 3-42 | 46 |
| 3-43 | 66 |
| 3-44 | 15 |
| 3-45 | 19 |
| 3-46 | 206 |
| 3-47 | 67 |
| 3-48 | 16 |
| 3-49 | 16 |
| 3-50 | 15 |
| 3-51 | 10 |
| 4-1 | 163 |
| 4-9 | 11 |
| 4-16 | 13 |
| 4-22-A | 9 |
| 4-22-B | 11 |
| 4-23 | 137 |
| 4-24 | 78 |
| 4-25 | 61 |
| 4-26 | 118 |
| 4-27 | 183 |
| 4-28 | 82 |
| 4-29 | 82 |
| 4-30 | 241 |
| 4-31 | 84 |
| 4-32 | 478 |
| 4-33 | 138 |
| 4-34 | 330 |
| 4-35 | 187 |
| 4-36 | 274 |
| 4-37 | 55 |
| 4-38 | 57 |
| 4-39 | 42 |
| 4-40 | 392 |
| 4-41 | 118 |
| 4-42 | 56 |
| 4-43 | 252 |
| 4-44 | 59 |
| 4-45 | 136 |
| 4-46 | 24 |
| 4-47 | 170 |
| 4-48 | 53 |
| 4-49 | 38 |
| 4-50 | 381 |
| 4-51 | 9 |
| 4-52 | 93 |
| 4-53 | 25 |
| 4-54 | 12 |
| 4-55 | 33 |
| 4-56 | 88 |
| 4-57 | 237 |
| 4-58 | 163 |
| 4-59 | 394 |
| 4-60 | 196 |
| 4-61 | 166 |
| 4-62 | 252 |
| 4-63 | 46 |
| 4-64 | 73 |
| 4-65 | 17 |
| 4-66 | 16 |
| 4-67 | 1153 |
| 4-68 | 149 |
| 4-69 | 46 |
| 4-70 | 114 |
| 4-71 | 25 |
| 4-72 | 243 |
| 4-73 | 30 |
| 4-74 | 91 |
| 4-75 | 1090 |
| 4-76 | 261 |
| 4-77 | 15 |
| 4-78 | 81 |
| 4-79 | 159 |
| 4-80 | 15 |
| 4-81 | 1629 |
| 4-82 | 188 |
| 4-83 | 513 |
| 4-84 | 11 |
| 4-85 | 15 |
| 4-86 | 9 |
| 4-87 | 14 |
| 4-88 | 14 |
| 4-89 | 235 |
| 4-90 | 8 |
| 4-91 | 8 |
| 4-92 | 17 |
| 4-93 | 66 |
| 4-94 | 63 |
| 4-95 | 11 |
| 4-96 | 8 |
| 4-97 | 260 |
| 4-98 | 52 |
| 4-99 | 55 |
| 4-100 | 24 |
| 4-101 | 10 |
| 4-102 | 10 |
| 4-103 | 114 |
| 4-104 | 120 |
| 4-105 | 172 |
| 4-106 | 50 |
| 4-107 | 25 |
| 4-108 | 161 |

| Example | IC$_{50}$ Value (nM) |
|---|---|
| 4-109 | 116 |
| 4-110 | 90 |
| 4-111 | 80 |
| 4-112 | 23 |
| 4-113 | 24 |
| 4-114 | 15 |
| 4-115 | 34 |
| 4-116 | 14 |
| 4-117 | 53 |
| 4-118 | 13 |
| 4-119 | 18 |
| 4-120 | 238 |
| 4-121 | >1000 |
| 4-122 | 931 |
| 4-123 | 49 |
| 4-124 | 48 |
| 4-125 | 76 |
| 4-126 | 13 |
| 4-127 | 97 |
| 4-128 | 142 |
| 4-129 | >1000 |
| 4-130 | 245 |
| 4-131 | 112 |
| 4-132 | 149 |
| 4-133 | 272 |
| 4-134 | 86 |
| 4-135 | 8 |
| 5-4 | 299 |
| 5-5 | 125 |
| 5-6 | 987 |
| 6-2 | 21 |
| 6-3 | 55 |
| 6-4 | 145 |
| 6-5 | 47 |
| 6-6 | 13 |
| 6-7 | 8 |
| 6-8 | 56 |
| 6-9 | 10 |
| 6-10 | 31 |
| 6-11 | 14 |
| 6-12 | 31 |
| 6-13 | 76 |
| 6-14 | 18 |
| 6-15 | 34 |
| 6-16 | 76 |
| 6-17 | 48 |
| 6-18 | 35 |
| 6-19 | 41 |
| 6-20 | 15 |
| 6-21 | 6 |
| 6-22 | 42 |
| 6-23 | 28 |
| 6-24 | 25 |
| 6-25 | 7 |
| 6-26 | 12 |
| 7-5 | 338 |
| 7-13 | 13 |
| 7-20-A | 14 |
| 7-20-B | 21 |
| 7-21 | 21 |
| 7-22 | 74 |
| 7-23 | 10 |
| 7-24 | 17 |
| 7-25 | 20 |
| 7-26 | 15 |
| 7-27 | 169 |
| 7-28 | 10 |
| 7-29 | 8 |
| 7-30 | 21 |
| 7-31 | 28 |
| 7-32 | 214 |
| 7-33 | 36 |
| 7-34 | 39 |
| 7-35 | 14 |
| 7-36 | 13 |
| 7-37 | 30 |
| 7-38 | 39 |
| 8-1 | 10 |
| 8-2 | 15 |
| 8-7 | 13 |
| 8-10 | 7 |
| 8-11 | 6 |
| 8-12 | 86 |
| 8-13 | 170 |
| 8-14 | 44 |
| 8-15 | 7 |
| 8-16 | 10 |
| 8-17 | 5 |
| 8-18 | 5 |
| 8-19 | 22 |
| 8-20 | 12 |
| 8-21 | 19 |
| 8-22 | 14 |
| 8-23 | 21 |
| 8-24 | 20 |
| 8-25 | 21 |
| 8-26 | 19 |
| 8-27 | 11 |
| 8-28 | 6 |
| 8-29 | 6 |
| 8-30 | 9 |
| 8-31 | 9 |
| 8-32 | 7 |
| 8-33 | 6 |
| 8-34 | 8 |
| 8-35 | 7 |
| 8-36 | 15 |
| 8-37 | 16 |
| 8-38 | 33 |
| 8-39 | 14 |
| 8-40 | 10 |
| 8-41 | 5 |
| 8-42 | 12 |
| 8-43 | 10 |
| 8-44 | 8 |
| 8-45 | 10 |
| 8-46 | 10 |
| 8-47 | 8 |
| 8-48 | 10 |
| 8-49 | 9 |
| 8-50 | 4 |
| 8-51 | 5 |
| 8-52 | 27 |
| 8-53 | 52 |
| 8-54 | 11 |
| 8-55 | 96 |

The following abbreviations may be used throughout the text:

Me=methyl; Et=ethyl; t-Bu: =tert-butyl; Ar: =aryl; Ph=phenyl; Bn=benzyl; DCE=dichloroethylene; HMDS=hexamethyldisilazane; DMF:=dimethylformamide; DMFDMA=N,N-dimethylformamide dimethylacetal; THF=tetrahydrofuran; BOP:=benzotriazolyloxytris (dimethylamino) phosphonium hexafluorophosphate; Boc=tert-butyloxycarbonyl; TEA=triethylamine; TPAP=tetra-n-propyl ammonium perruthenate; NMO=N-methyl morpholine N-oxide; ClZn=Chlorozinc; dppf=diphenylphosphorousferrocenyl; PMB=p-methoxybenzyl; Ms=mesyl; Ac=acetyl; DMSO=dimethylsulfoxide; DCM=dichloromethane; m-CPBA=meta-chloroperoxybenzoic acid; DMEM=Dulbecco's Modified Eagle Medium (High Glucose); FBS=fetal bovine serum; rt=room temperature; aq=aqueous; HPLC=high performance liquid chromatography; MS=mass spectrometry While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A method of treating a disease or disorder mediated by the mGluR$_2$ receptor, said method comprising administering to an individual in need thereof an effective amount of a compound of Formula (V):

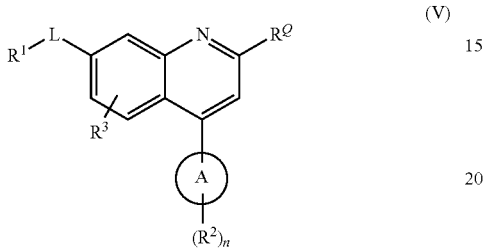

or a stereoisomer thereof, or a pharmaceutically acceptable salt of said compound or said stereoisomer, wherein:

ring A is a moiety selected from the group consisting of: phenyl, —(C$_5$-C$_6$) cycloalkyl, —(C$_5$-C$_6$) cycloalkyenl, -pyridinyl, pyrimidinyl, -pyrazolyl, -thienyl, -thiazolyl, -thiadiazolyl, and -oxazolyl;

R$^Q$ is selected from the group consisting of —CN and —C(O)NH$_2$;

-L- is a bond or a divalent moiety selected from the group consisting of:

—(C(R$^{1L}$)$_2$)$_p$—,

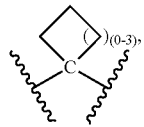

—C(O)—, —S(O)—, and —S(O)$_2$—;

p is 1, 2, or 3;

each R$^{1L}$ is independently selected from the group consisting of H, —CH$_3$, —CF$_3$, —OH, halogen, -cyclopropyl, —O—CH$_3$, and —O—CF$_3$;

R$^1$ is selected from the group consisting of:

(1) heterocycloalkyl, heterocycloalkenyl, wherein said heterocycloalkyl and said heterocycloalkenyl are monocyclic or multicyclic ring systems comprising from 3 to 10 ring atoms in which 1, 2, or 3 of the atoms of each said ring system is a ring heteroatom independently selected from the group consisting of N, S, S(O), S(O)$_2$, and O, and wherein each said heterocycloalkyl group and each said heterocycloalkenyl group is unsubstituted or substituted with 1 to 5 groups independently selected from the group consisting of oxo, CN, —OH, halogen, —(C$_1$-C$_6$) alkyl, hydroxy-substituted —(C$_1$-C$_6$) alkyl, —(C$_1$-C$_6$) alkynyl, —(C$_1$-C$_6$) haloalkyl, hydroxy-substituted —(C$_1$-C$_6$) haloalkyl, —O—(C$_1$-C$_6$) alkyl, —(C$_3$-C$_8$) cycloalkyl, -alkyl-cycloalkyl, —CH(OH)cycloalkyl, phenyl, -alkyl-phenyl, monocyclic heteroaryl, -alkyl-monocyclic heteroaryl, —(C$_3$-C$_8$) spirocycloalkyl, —(C$_3$-C$_8$) spiroheterocycloalkyl, —C(O)H, —C(O)OH, —C(O)—(C$_1$-C$_6$) alkyl, —C(O)O(C$_1$-C$_6$) alkyl, —N(R$^{1A}$)C(O)—(C$_1$-C$_6$) alkyl, —N(R$^{1A}$)$_2$, —C(O)N(R$^{1A}$)$_2$, —S(O)$_2$H, —S(O)-phenyl, —S(O)—(C$_1$-C$_6$) alkyl-phenyl, —S(O)$_2$-phenyl, —S(O)$_2$—(C$_1$-C$_6$) alkyl-phenyl, —S(O)$_2$OH, and —S(O)$_2$—(C$_1$-C$_6$) alkyl, wherein each R$^{1A}$ group is independently selected from the group consisting of H and —(C$_1$-C$_6$ alkyl);

(2) heteroaryl, wherein said heteroaryl is a monocyclic or multicyclic ring system comprising from 5 to 10 ring atoms in which from 1 to 4 of the atoms of said ring system is a ring nitrogen atom, and wherein said heteroaryl is unsubstituted or substituted with 1 to 5 groups independently selected from the group consisting of oxo, CN, —OH, halogen, —(C$_1$-C$_6$) alkyl, hydroxy-substituted —(C$_1$-C$_6$) alkyl, —(C$_1$-C$_6$) alkynyl, —(C$_1$-C$_6$) haloalkyl, hydroxy-substituted —(C$_1$-C$_6$) haloalkyl, —O—(C$_1$-C$_6$) alkyl, —(C$_3$-C$_8$) cycloalkyl, -alkyl-cycloalkyl, —CH(OH)cycloalkyl, phenyl, -alkyl-phenyl, monocyclic heteroaryl, -alkyl-monocyclic heteroaryl, —(C$_3$-C$_8$) spirocycloalkyl, —C(O)H, —C(O)OH, —C(O)—(C$_1$-C$_6$) alkyl, —C(O)O(C$_1$-C$_6$) alkyl, —N(R$^{1B}$)C(O)—(C$_1$-C$_6$) alkyl, —N(R$^{1B}$)$_2$, —C(O)N(R$^{1B}$)$_2$, —S(O)$_2$H, —S(O)-phenyl, —S(O)—(C$_1$-C$_6$) alkyl-phenyl, —S(O)$_2$-phenyl, —S(O)$_2$—(C$_1$-C$_6$) alkyl-phenyl, —S(O)$_2$OH, and —S(O)$_2$—(C$_1$-C$_6$) alkyl, wherein each R$^{1B}$ group is independently selected from the group consisting of H and —(C$_1$-C$_6$alkyl), with the proviso that R$^1$ is not unsubstituted or substituted triazolyl, and with the further proviso that when R$^1$ is substituted oxadiazolyl, substituted thiazolyl, or substituted thiadiazolyl, then -L- is selected from the group consisting of —(C(R$^{1L}$)$_2$)$_p$—, and

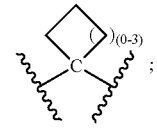

(3) phenyl, wherein said phenyl is unsubstituted or substituted with from 1 to 5 groups independently selected from the group consisting of oxo, CN, —OH, halogen, —(C$_1$-C$_6$) alkyl, —(C$_1$-C$_6$) alkynyl, —(C$_1$-C$_6$) haloalkyl, —O—(C$_1$-C$_6$) alkyl, —(C$_3$-C$_8$) cycloalkyl, -alkyl-cycloalkyl, —CH(OH)cycloalkyl, monocyclic heteroaryl, -alkyl-monocyclic heteroaryl, —(C$_3$-C$_8$) spirocycloalkyl, —C(O)H, —C(O)OH, —C(O)(C$_1$-C$_6$) alkyl, —C(O)O(C$_1$-C$_6$) alkyl, —N(R$^{1C}$)C(O)—(C$_1$-C$_6$) alkyl, —N(R$^{1C}$)$_2$, —C(O)N(R$^{1C}$)$_2$, —S(O)$_2$H, —S(O)-phenyl, —S(O)—(C$_1$-C$_6$) alkyl-phenyl, —S(O)$_2$-phenyl, —S(O)$_2$—(C$_1$-C$_6$) alkyl-phenyl, —S(O)$_2$OH, and —S(O)$_2$—(C$_1$-C$_6$) alkyl, wherein each R$^{1C}$ group is independently selected from the group consisting of H and —(C$_1$-C$_6$ alkyl);

(4) —CH$_2$N(R$^{1D}$)R$^{1E}$, wherein:

R$^{1D}$ is selected from the group consisting of H, —(C$_1$-C$_6$) alkyl, and —C(O)OR$^{1H}$; and R$^{1E}$ is selected from the group consisting of —O—(C$_1$-C$_6$) alkyl, heteroalkyl, -alkyl-C(O)N(R$^{1H}$), and —C(O)OR$^{1H}$, wherein each $R^{1H}$ is independently selected from the group consisting of H and —$(C_1$-$C_6)$ alkyl; and
(5) —$CH_2N(R^{1F})OR^{1G}$, wherein:
$R^{1F}$ is selected from the group consisting of H, —$(C_1$-$C_6)$ alkyl, and —$C(O)OR^{1H}$,
wherein each $R^{1H}$ is independently selected from the group consisting of H and —$(C_1$-$C_6)$ alkyl; and
$R^{1G}$ is selected from the group consisting of H and —$(C_1$-$C_6)$ alkyl;
n is 0, 1, 2, or 3;
each $R^2$ (when present) is independently selected from the group consisting of halogen, —CN, —OH, —$(C_1$-$C_6)$ alkyl, —O—$(C_1$-$C_6)$ alkyl, —$(C_1$-$C_6)$ haloalkyl, —O—$(C_1$-$C_6)$ haloalkyl, cyclopropyl, cyclobutyl, cyclopentyl, cyclohexyl, —$NH_2$, —$NH(C_1$-$C_6)$alkyl, —$N(C_1$-$C_6$alkyl$)_2$, —$C(O)O(C_1$-$C_6)$ alkyl, and phenyl; and
$R^3$ is selected from the group consisting of hydrogen and fluorine.

2. The method of claim 1, wherein said disease or disorder is selected from the group consisting of Alzheimer's disease, cognitive impairment, schizophrenia, mood disorder, pain, and sleep disorder.

3. The method of claim 1, wherein $R^1$ is selected from the group consisting of heterocycloalkyl and heterocycloalkenyl,
wherein each of said heterocycloalkyl and said heterocycloalkenyl contains 1, 2, or 3 ring heteroatoms independently selected from the group consisting of N, S, S(O), S(O)2, and O,
and wherein each said heterocycloalkyl group and each said heterocycloalkenyl group is unsubstituted or substituted with 1 to 5 groups independently selected from the group consisting of oxo, —CN, —OH, —$(C_1$-$C_6)$ alkyl, —O—$(C_1$-$C_6)$ alkyl, —N(H)C(O)—$(C_1$-$C_6)$ alkyl, —$C(O)NH_2$, —C(O)N(H)($C_1$-$C_6$ alkyl), —C(O)N($C_1$-$C_6$ alkyl$)_2$, —$(C_3$-$C_8)$ spirocycloalkyl, —$(C_3$-$C_8)$ cycloalkyl, —$(C_1$-$C_6)$ haloalkyl, and phenyl.

4. The method of claim 1, wherein $R^1$ is heteroaryl,
wherein said heteroaryl is mono or bicyclic and comprises from 1 to 3 ring nitrogen atoms,
and wherein said heteroaryl is unsubstituted or substituted with 1 to 5 groups independently selected from the group consisting of oxo, —CN, —OH, —$(C_1$-$C_6)$ alkyl, —O—$(C_1$-$C_6)$ alkyl, —N(H)C(O)—$(C_1$-$C_6)$ alkyl, —$C(O)NH_2$, —C(O)N(H)($C_1$-$C_6$ alkyl), —C(O)N($C_1$-$C_6$ alkyl$)_2$, —$(C_3$-$C_8)$ spirocycloalkyl, —$(C_3$-$C_8)$ cycloalkyl, —$(C_1$-$C_6)$ haloalkyl, and phenyl, with the proviso that $R^1$ is not unsubstituted or substituted triazolyl, substituted oxadiazolyl, substituted thiazolyl, or substituted thiadiazolyl.

5. The method of claim 1, wherein $R^1$ is phenyl,
wherein said phenyl is unsubstituted or substituted with from 1 to 5 groups independently selected from the group consisting of halogen, —O—$(C_1$-$C_6)$ alkyl, CN, —S(O)-phenyl, —S(O)$_2$-phenyl, —S(O)—$(C_1$-$C_6)$ alkyl-phenyl, and —S(O)$_2$—$(C_1$-$C_6)$ alkyl-phenyl.

6. The method of claim 1, wherein $R^1$ is —$CH_2N(R^{1D})R^{1E}$, wherein:
$R^{1D}$ is selected from the group consisting of H, —$(C_1$-$C_6)$ alkyl, and —$C(O)OR^{1H}$; and
$R^{1E}$ is selected from the group consisting of —O—$(C_1$-$C_6)$ alkyl, heteroalkyl, —$(C_1$-$C_6)$ alkyl-C(O)NH($R^{1H}$), and —$C(O)OR^{1H}$,
wherein each $R^{1H}$ is independently selected from the group consisting of H and —$(C_1$-$C_6)$ alkyl.

7. The method of claim 1, wherein $R^1$ is —$CH_2N(R^{1F})OR^{1G}$, wherein:
$R^{1F}$ is selected from the group consisting of H, —$(C_1$-$C_6)$ alkyl, and —$C(O)OR^{1H}$,
wherein each $R^{1H}$ is independently selected from the group consisting of H and —$(C_1$-$C_6)$ alkyl; and
$R^{1G}$ is selected from the group consisting of H and —$(C_1$-$C_6)$ alkyl;
n is 0, 1, 2, or 3.

8. The method of claim 1, wherein $R^Q$ is CN.

9. The method of claim 1, wherein $R^Q$ is —$C(O)NH_2$.

10. The method of claim 1, wherein -L- is selected from the group consisting of:

—$CH_2$—, —$CH_2CH_2$—, —$CH_2CH_2CH_2$—, —CH($CF_3$)—, —CH($CH_3$)—, —CH($CH_3$)$CH_2$—, —$CH_2CH(CH_3)$—, —C($CH_3$)$_2$—, —CH(OH)—, —$CH_2$CH(OH)—, —CH(OH)$CH_2$—, —CH(F)—, —$CF_2$—, —C($CH_3$)(OH)—, —CH($OCH_3$)—,

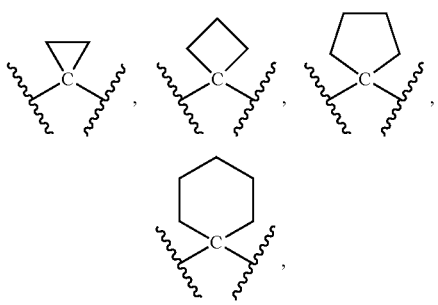

—C(O)—, —S(O)—, and —S(O)$_2$—.

11. The method of claim 1, wherein n is 0, 1, 2, or 3; and each $R^2$ is independently selected from the group consisting of F, Cl, Br, methyl, ethyl, propyl, i-propyl, n-propyl, i-butyl, n-butyl, tert-butyl, —$OCH_3$, —$OCH_2CH_3$, —$CFH_2$, —$CF_2H$, —$CF_3$, —$CH_2CFH_2$, —$CH_2CF_2H$, —$CH_2CF_3$, —$NH_2$, —NH($C_1$-$C_6$alkyl), —N($C_1$-$C_6$alkyl)$_2$, and phenyl.

12. A method of treating Alzheimer's disease, cognitive impairment, schizophrenia, mood disorder, pain, or sleep disorder, said method comprising administering to an individual in need thereof an effective amount of a compound, or a stereoisomer thereof, or a pharmaceutically acceptable salt thereof, said compound selected from:

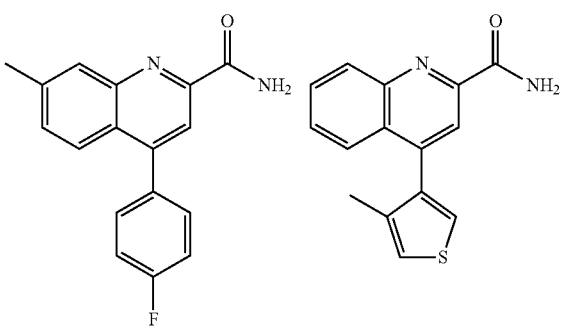

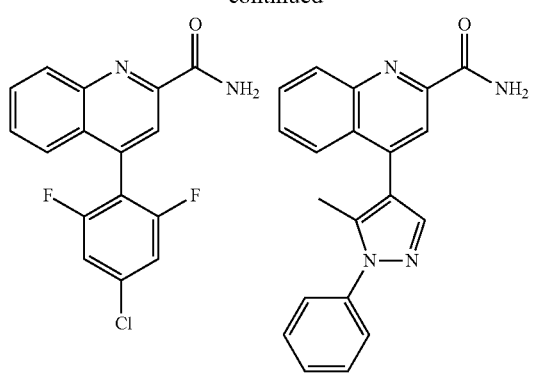
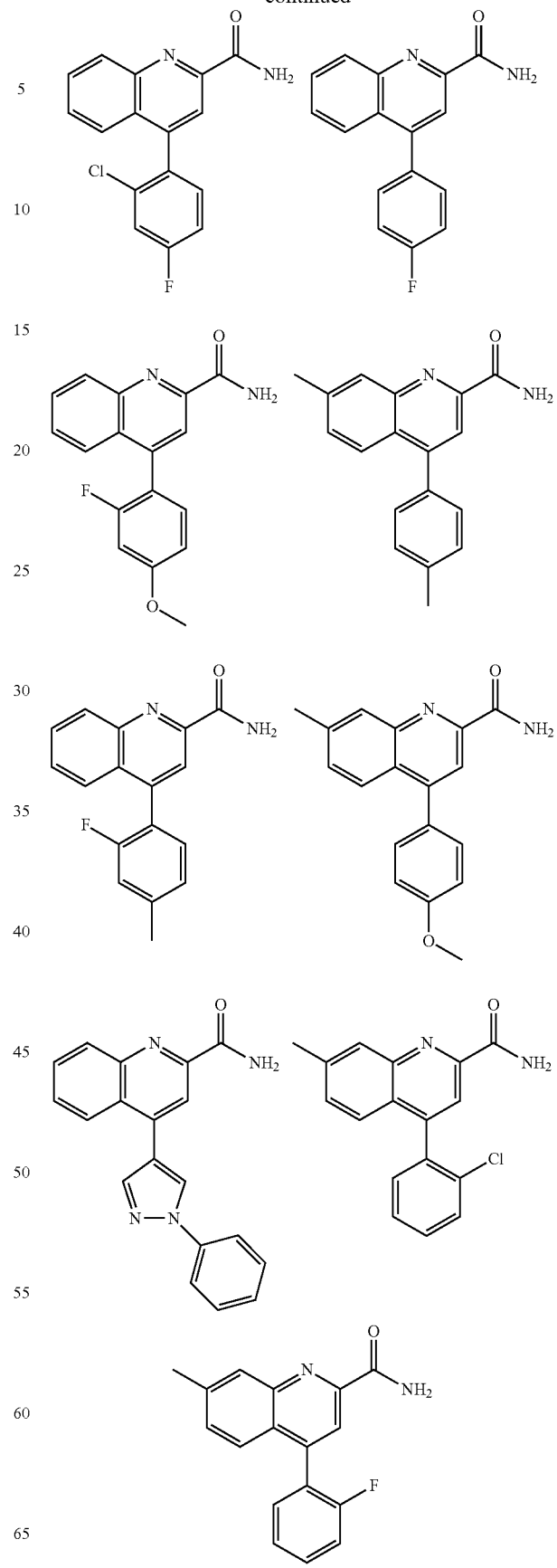

251
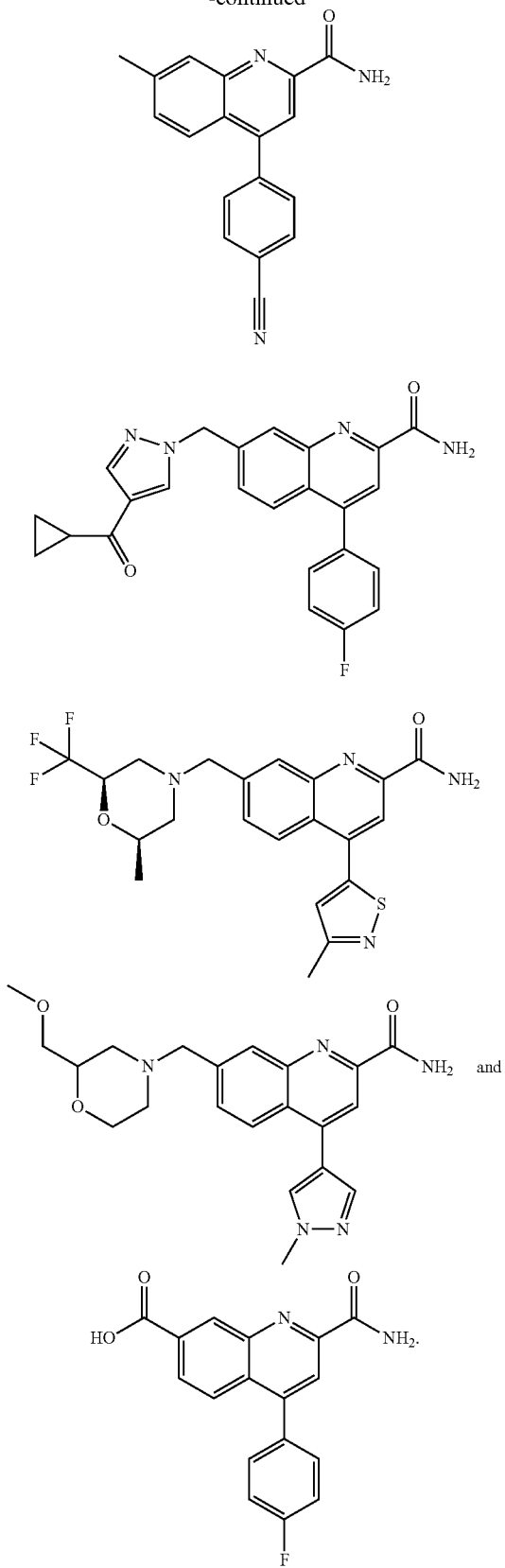
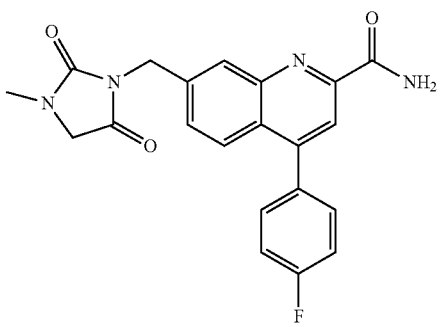
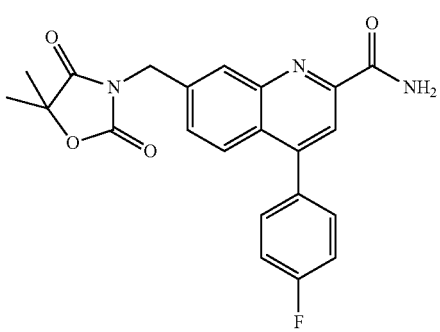
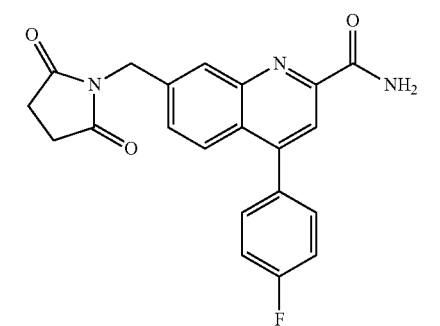
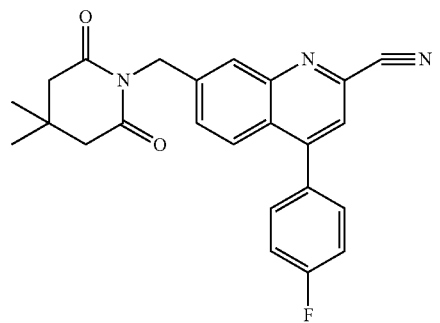
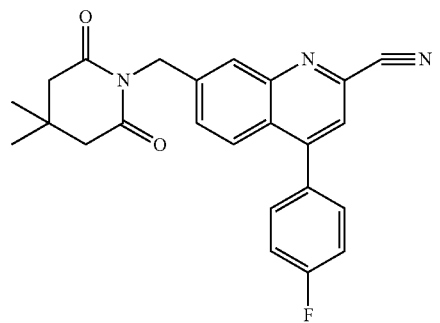
252
13. The method of claim 1, wherein said compound is selected from the group consisting of:

253
-continued
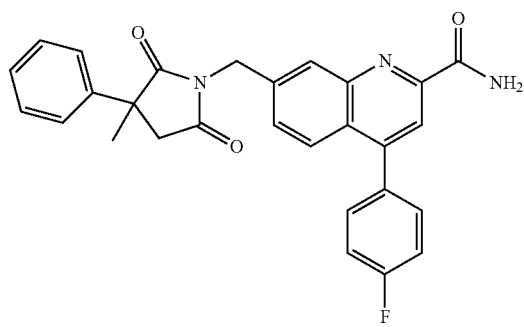
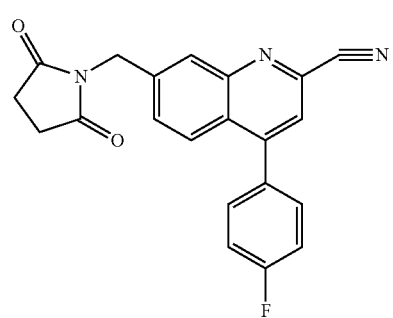
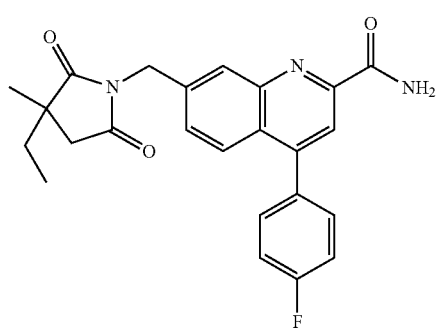
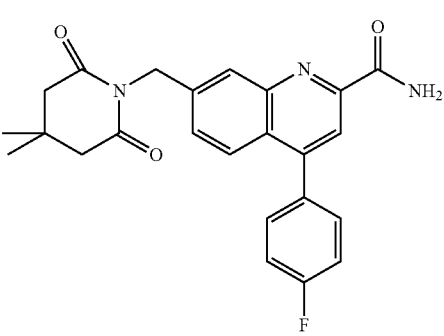
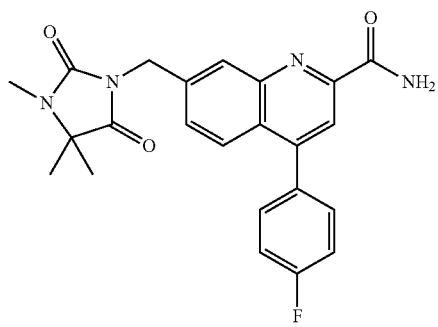
254
-continued
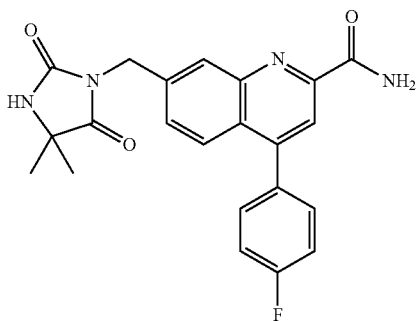
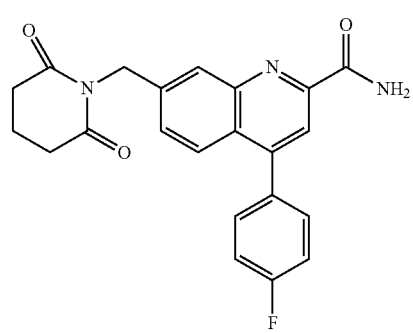
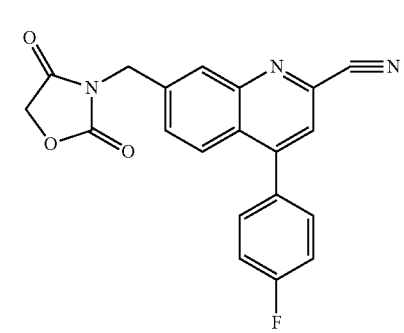
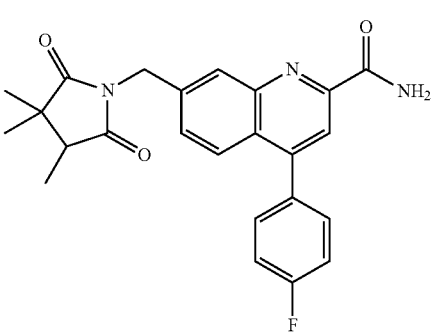
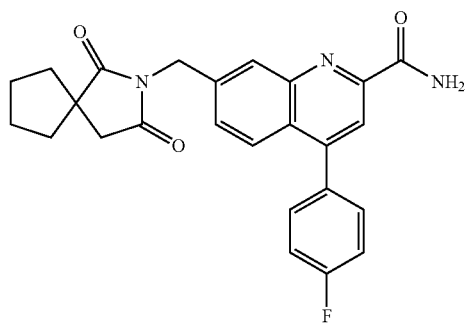

255
-continued
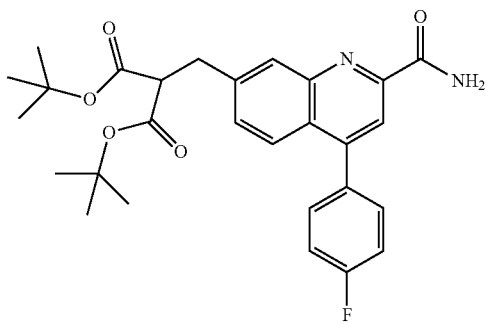
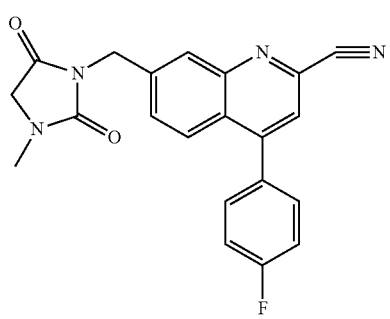
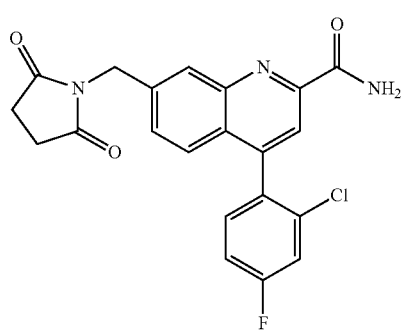
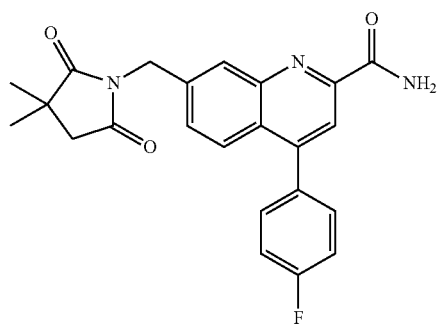
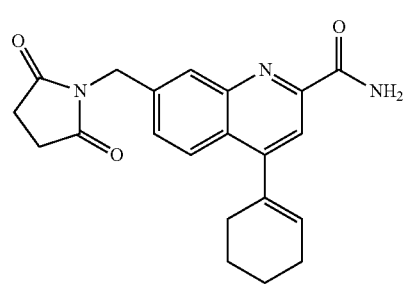
256
-continued
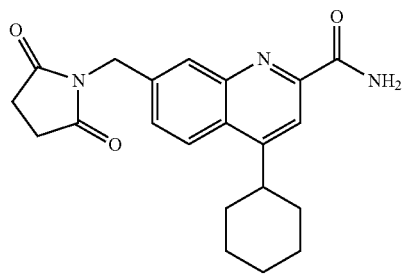
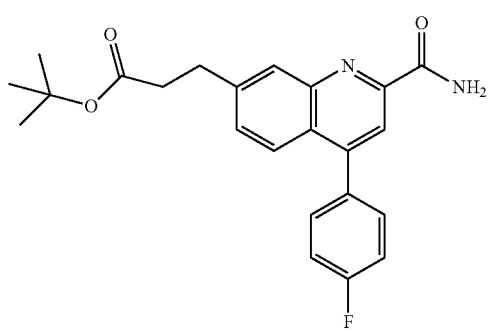
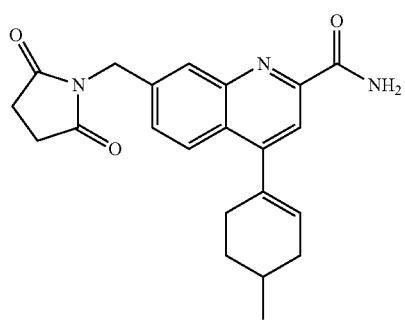
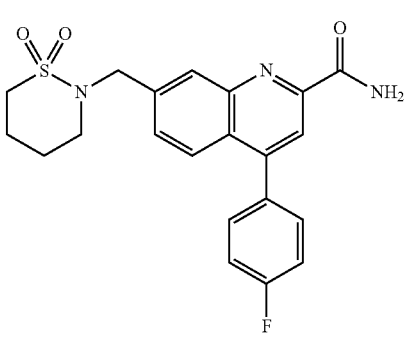
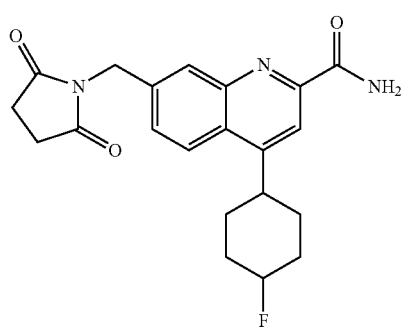

257
-continued
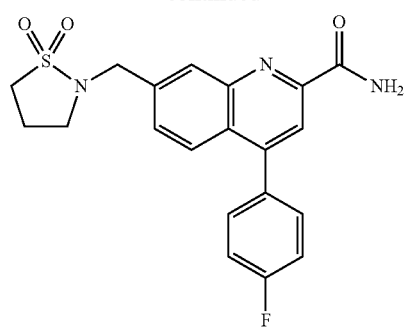
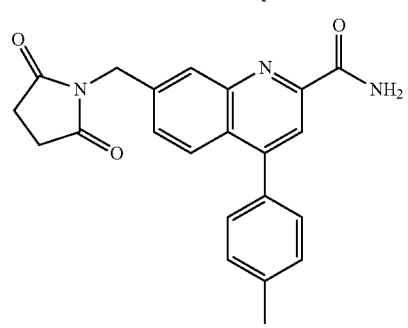
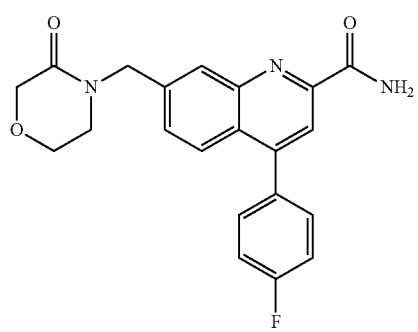
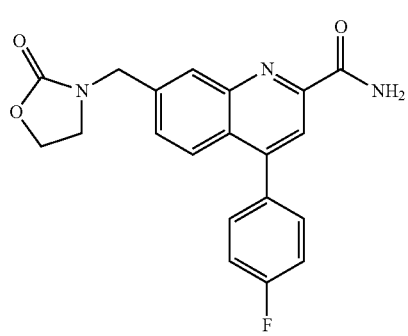
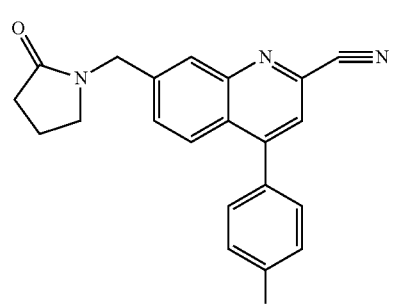
258
-continued
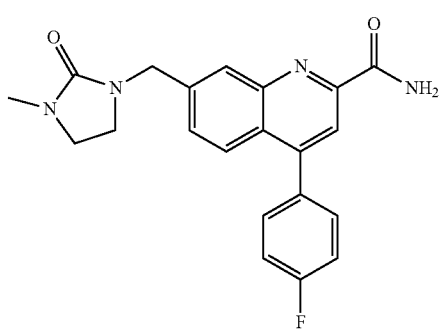
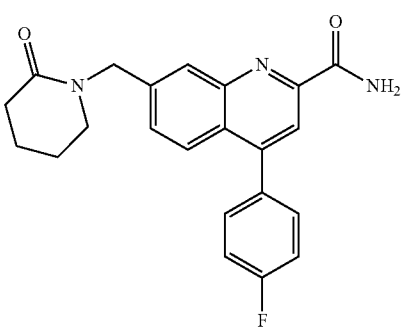
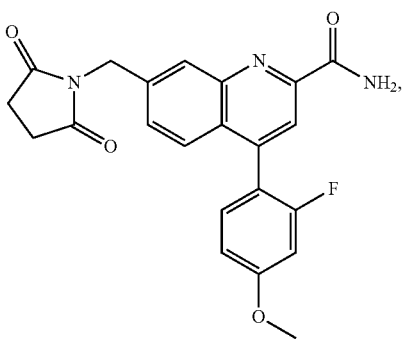
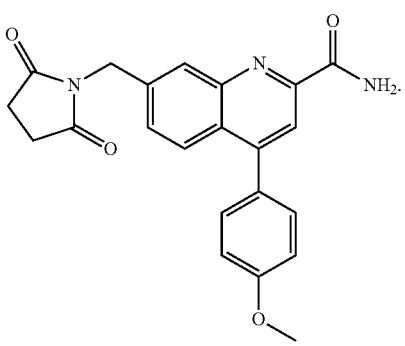
14. The method of claim 1, wherein said compound is selected from the group consisting of:

259
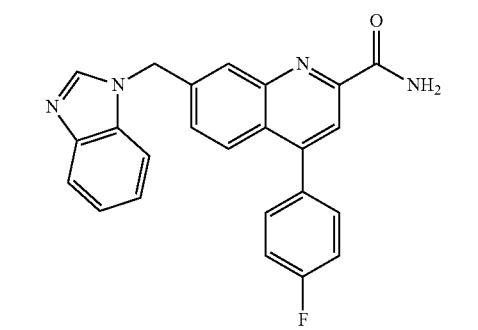
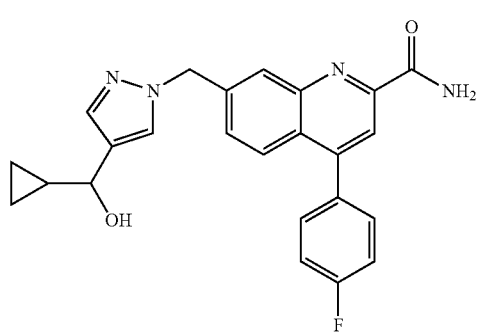
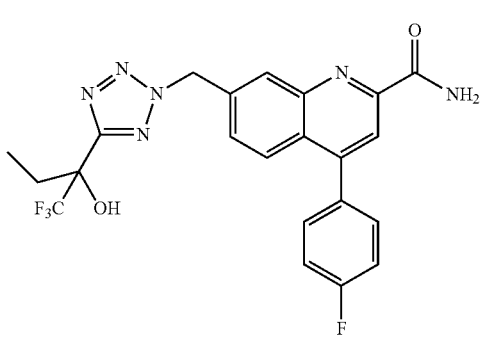
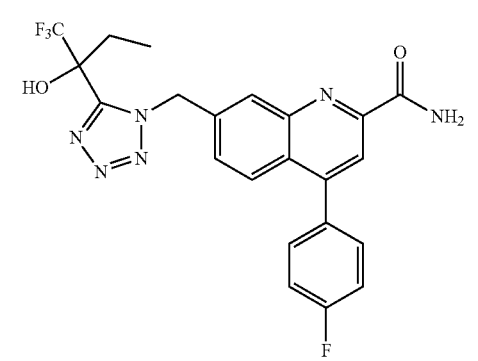
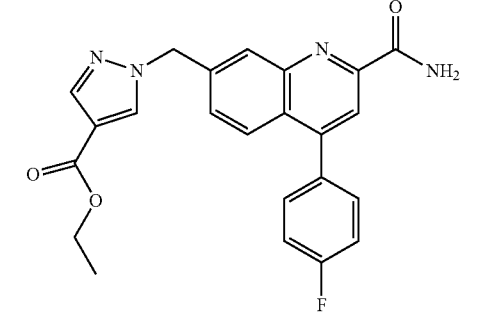
260
-continued
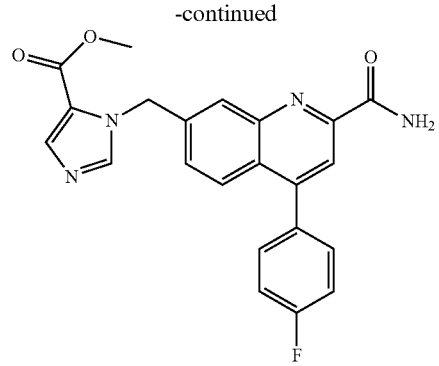
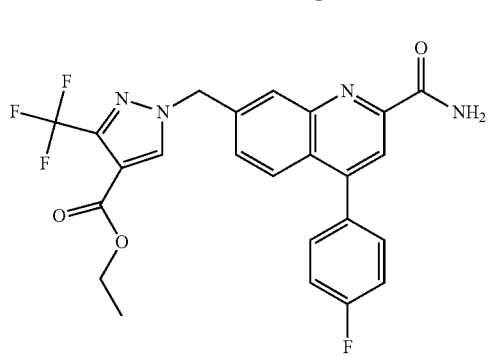
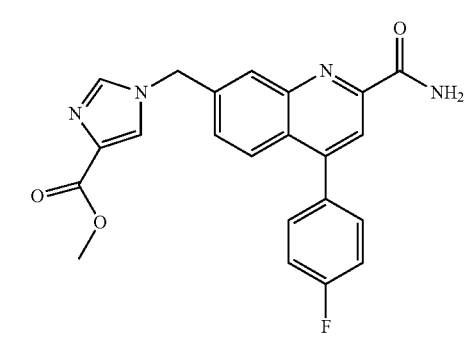
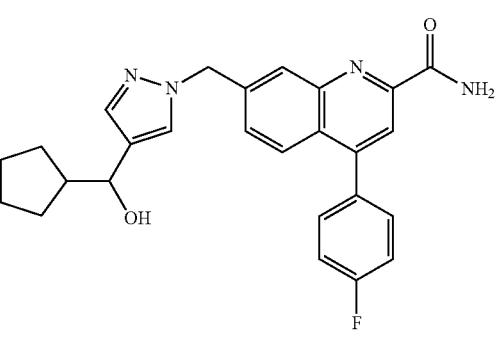
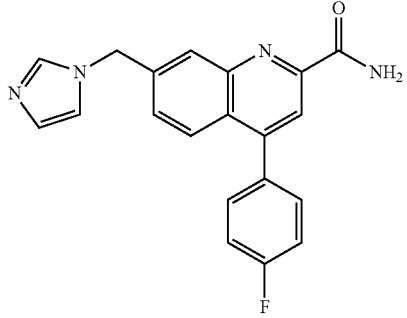

261
-continued
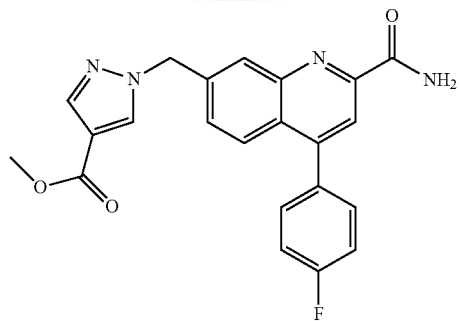
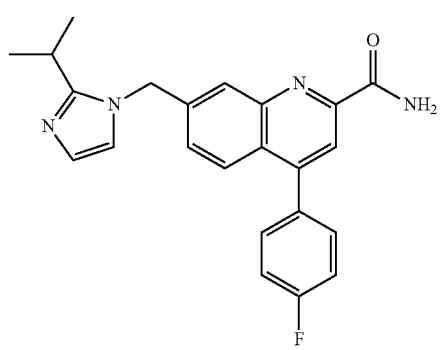
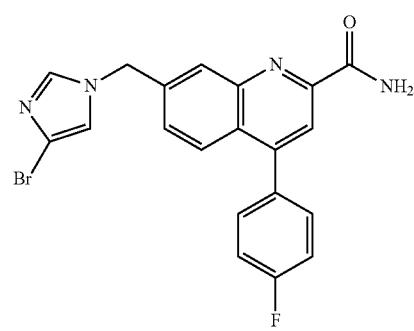
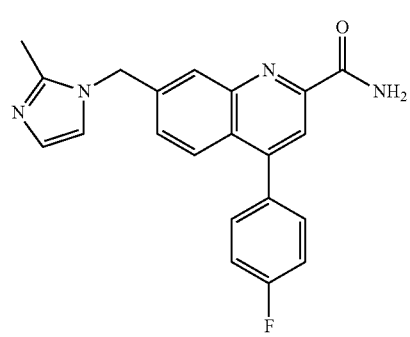
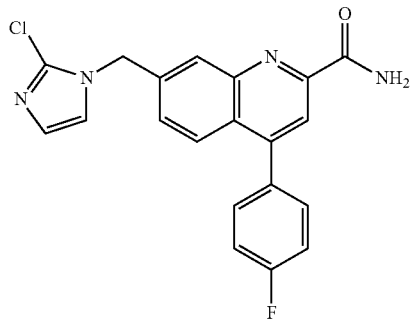
262
-continued
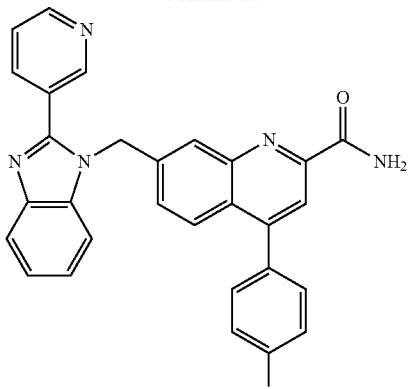
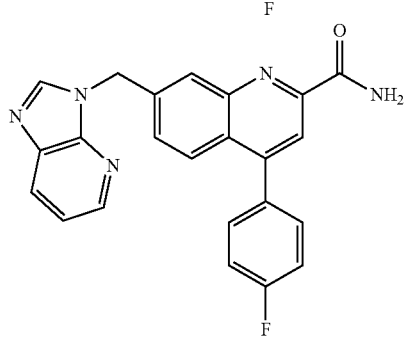
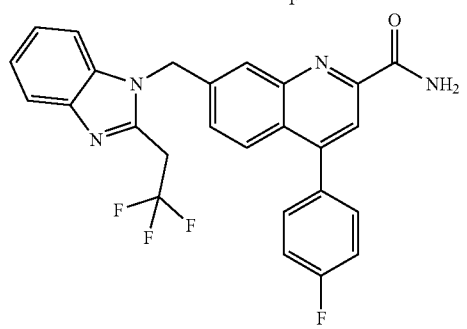
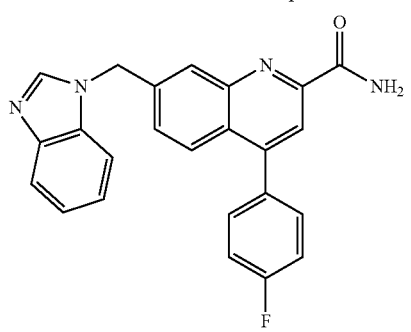
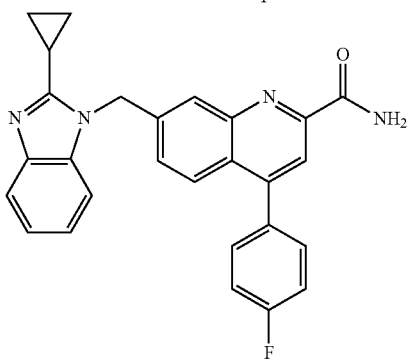

263
-continued
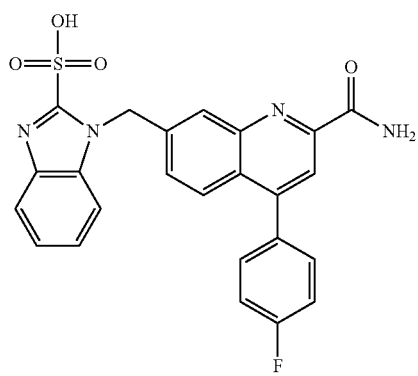
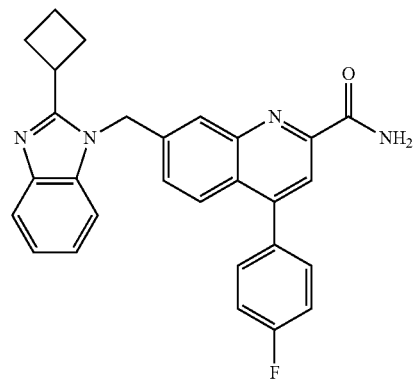
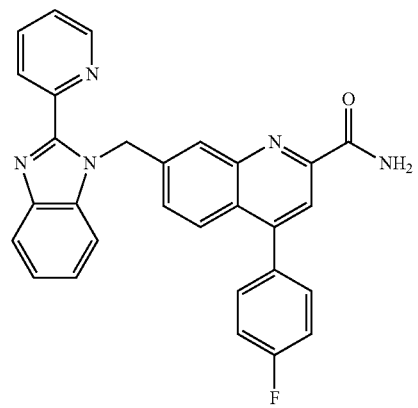
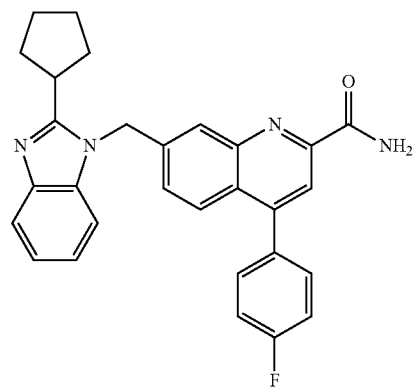
264
-continued
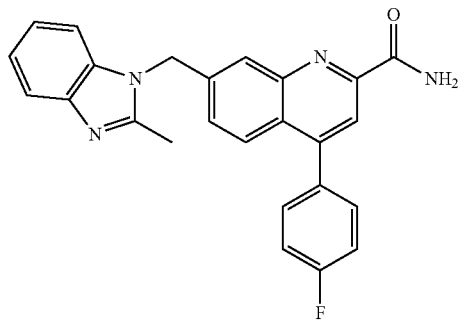
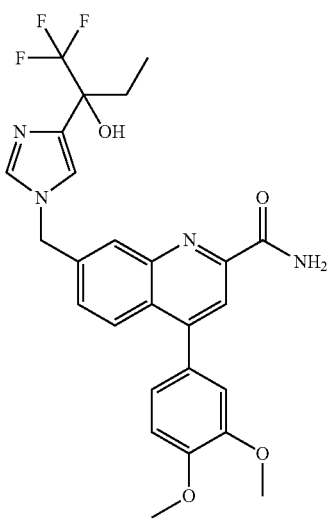
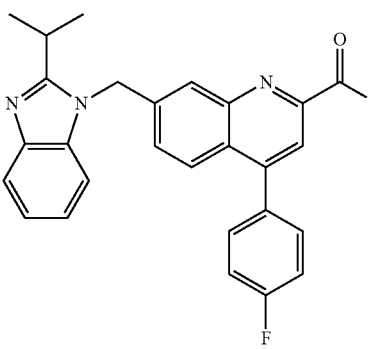

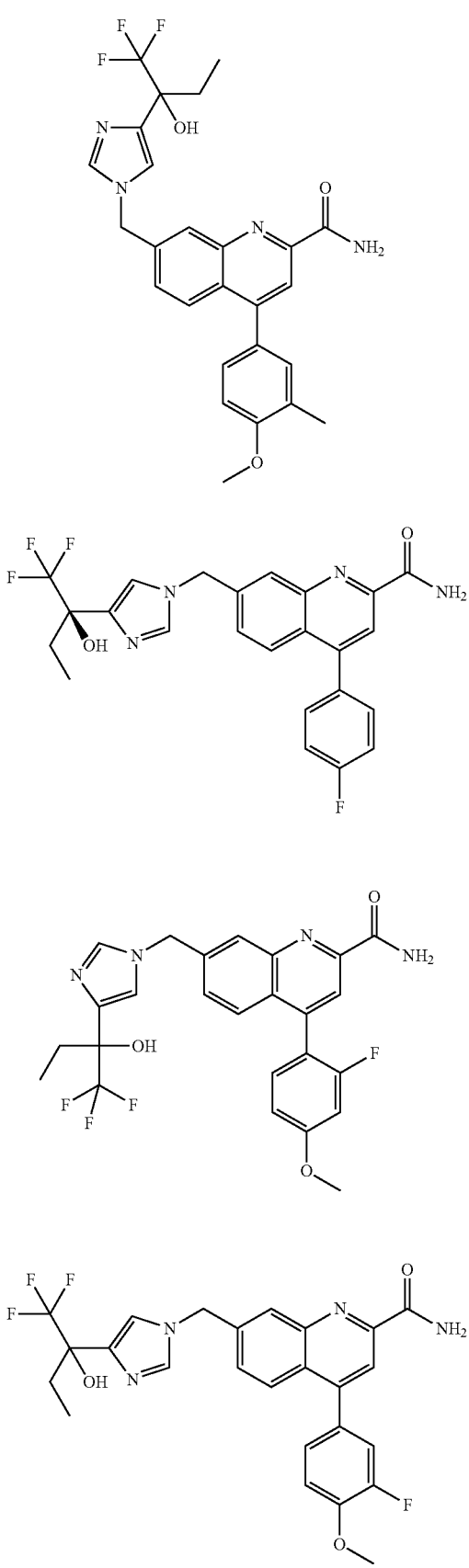
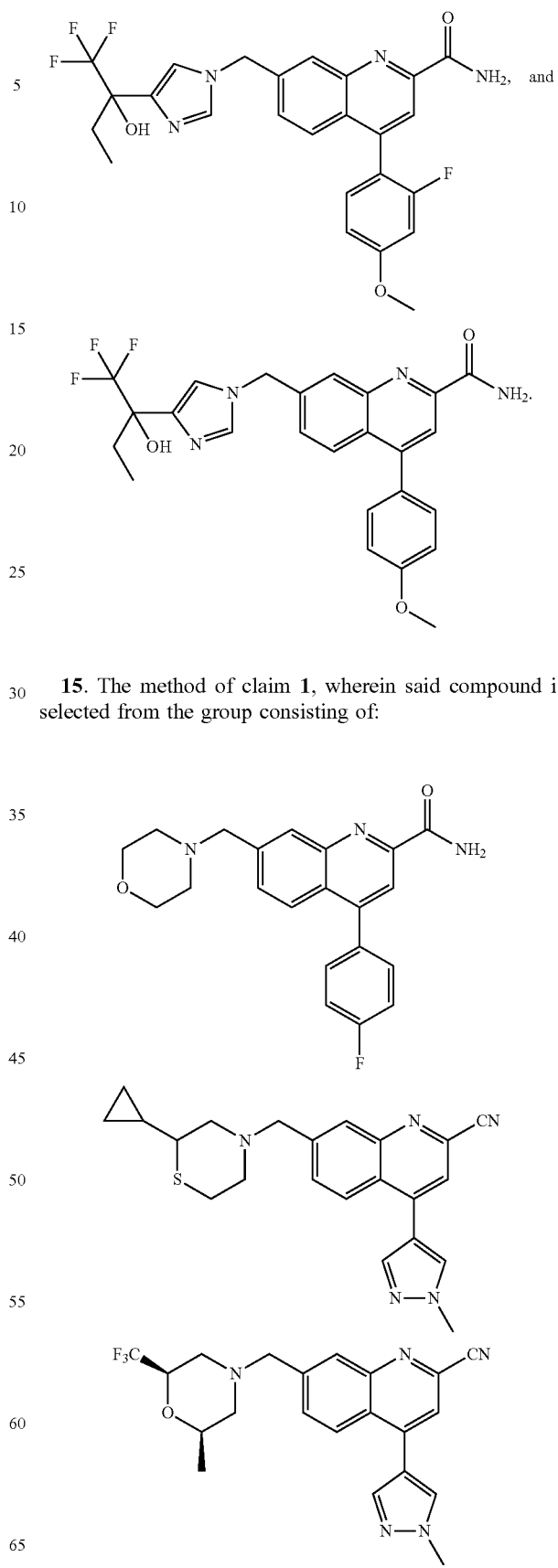
15. The method of claim 1, wherein said compound is selected from the group consisting of:

267
-continued
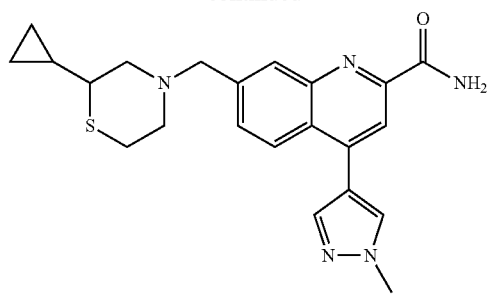
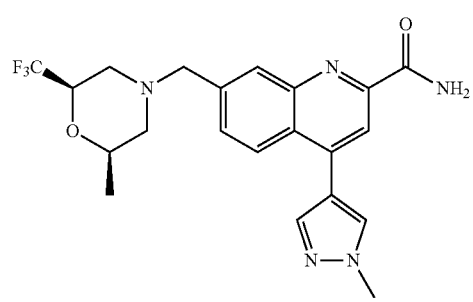
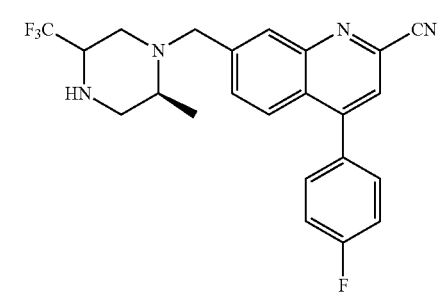
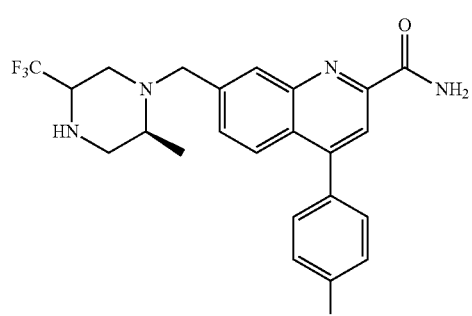
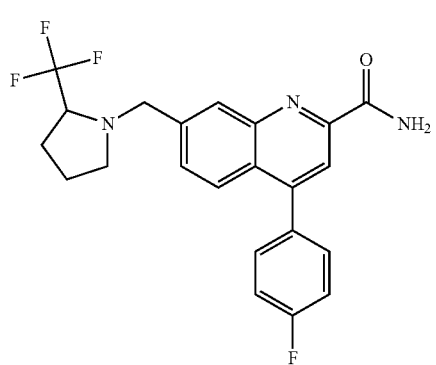
268
-continued
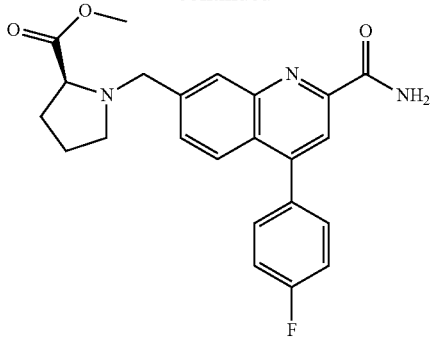
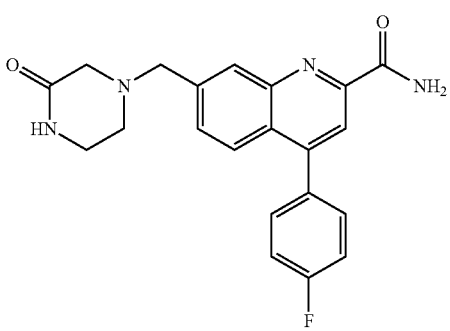
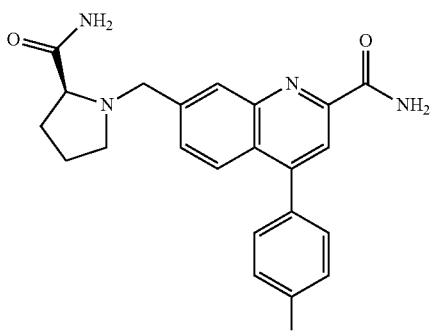
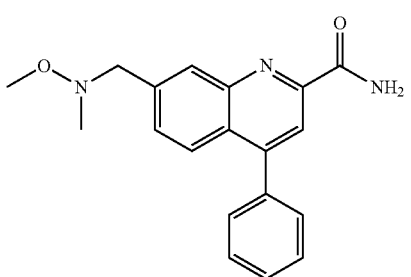
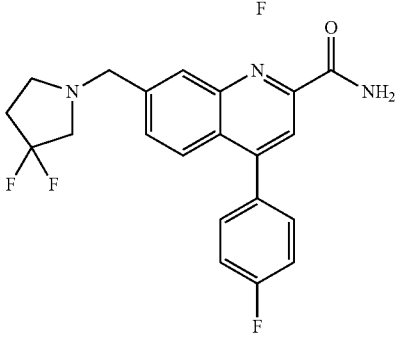

269
-continued
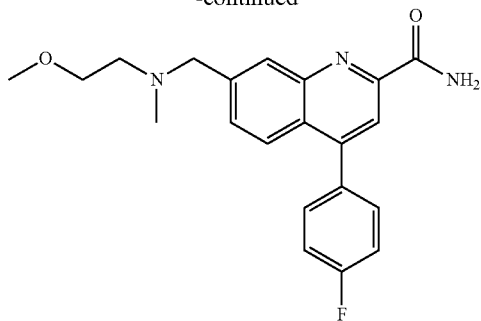
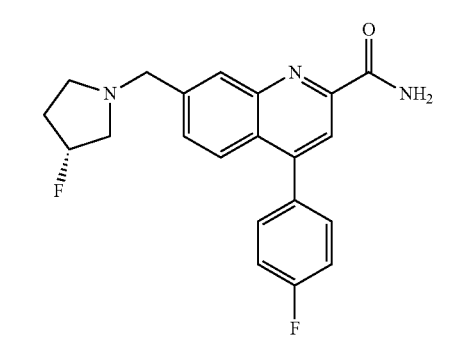
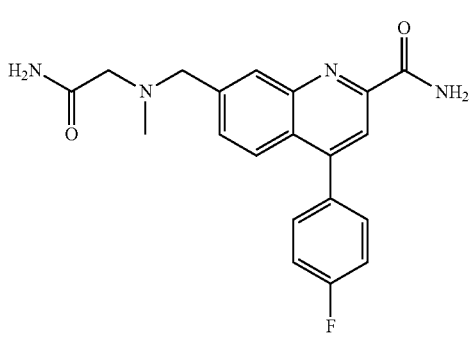
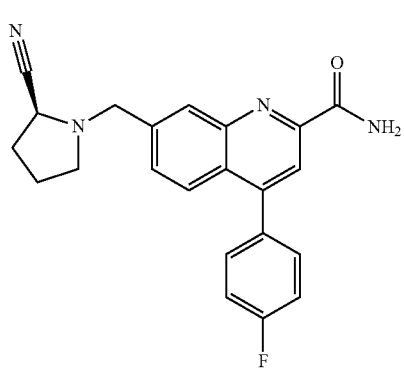
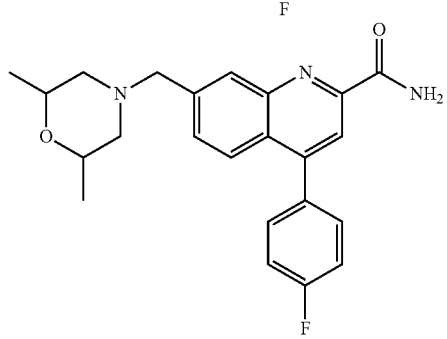
270
-continued
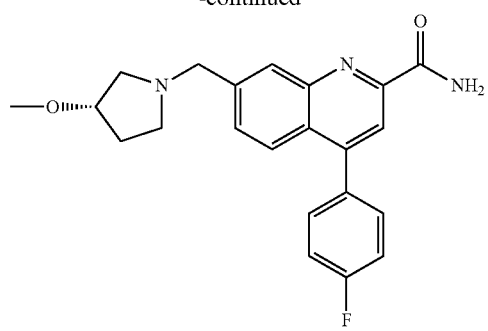
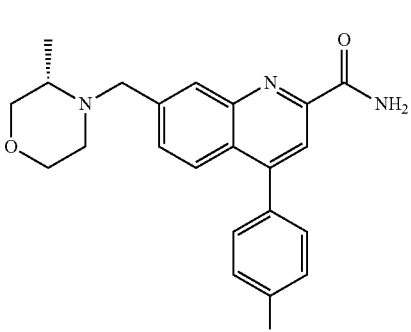
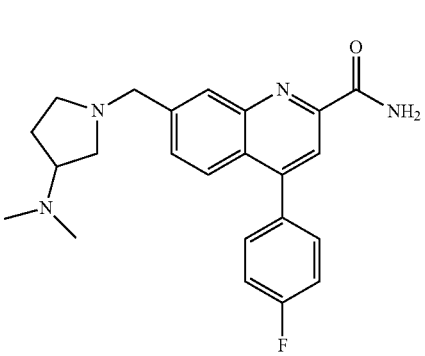
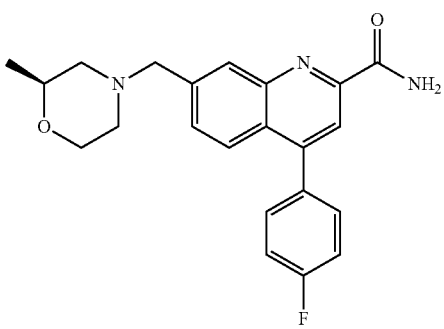
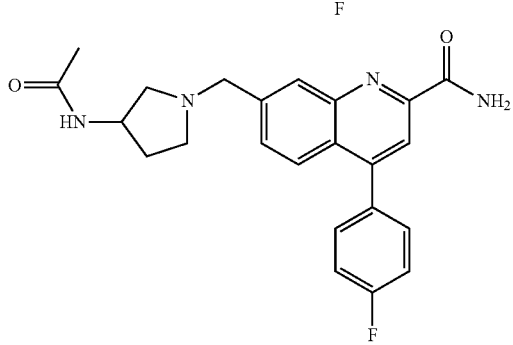

271
-continued
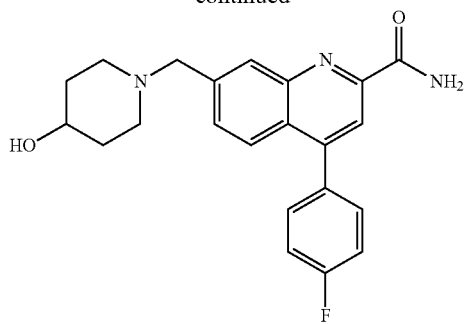
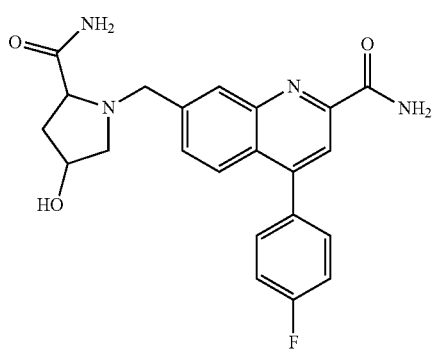
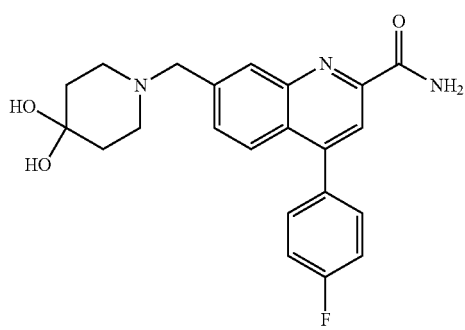
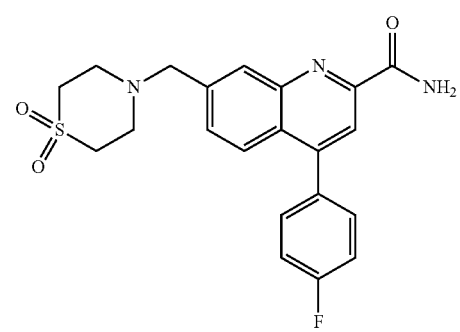
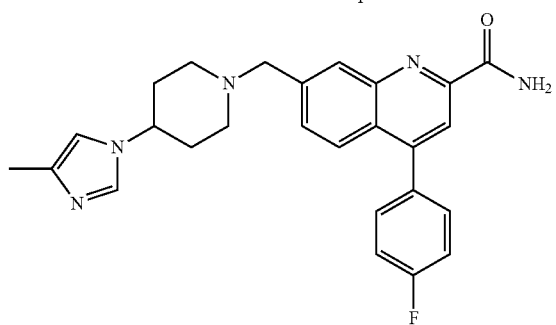
272
-continued
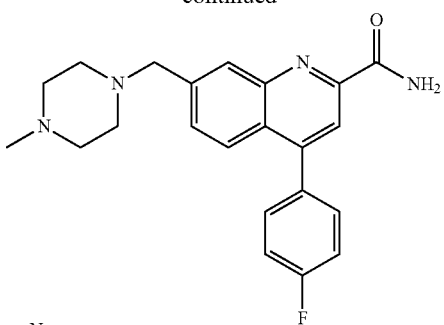
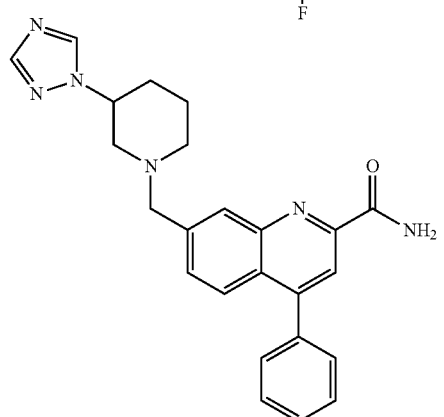
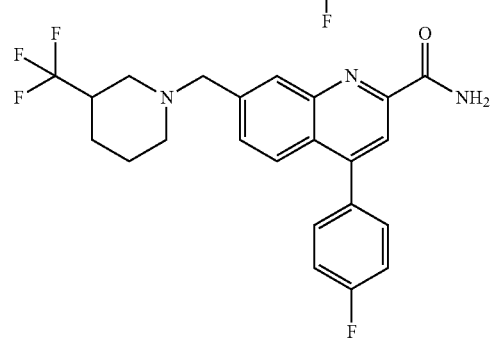
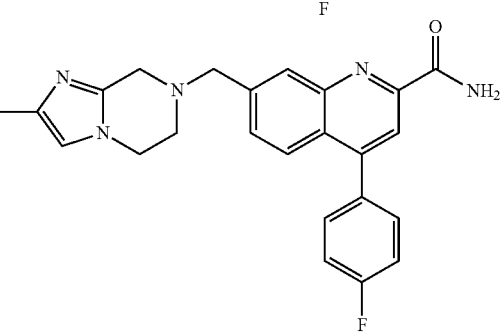
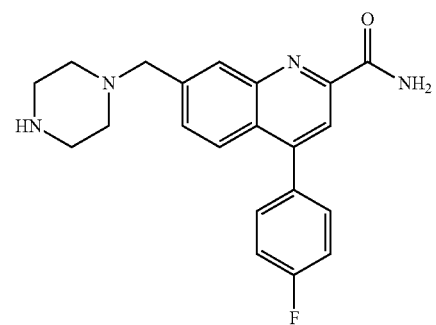

-continued
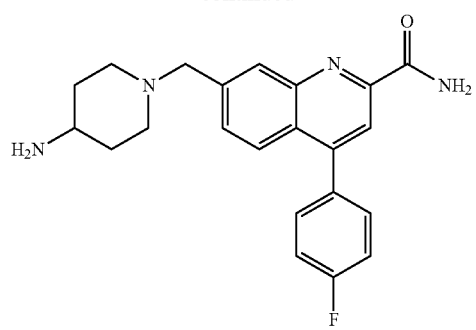
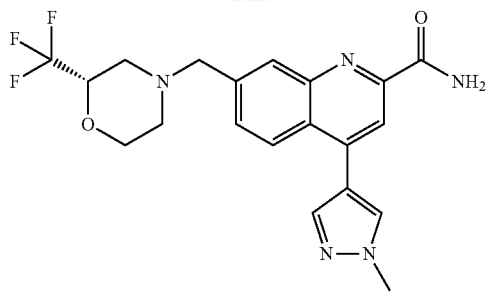
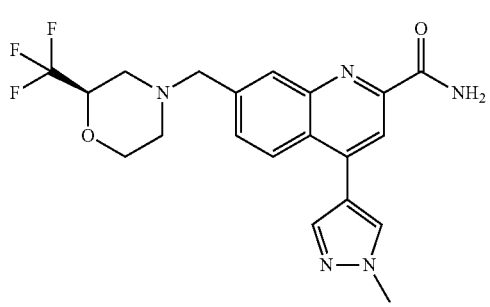
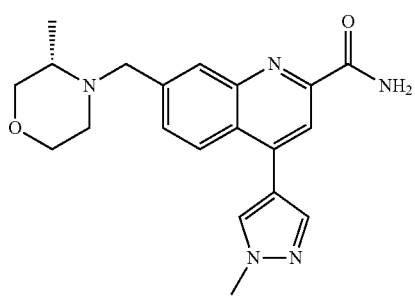
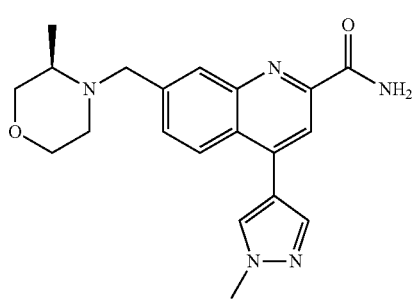
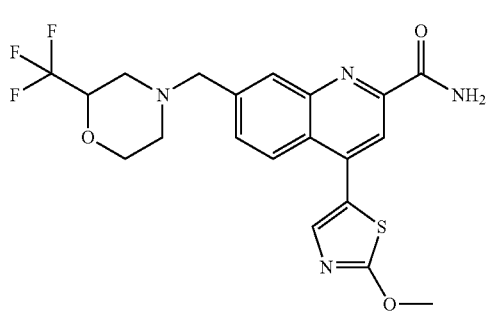

275
-continued
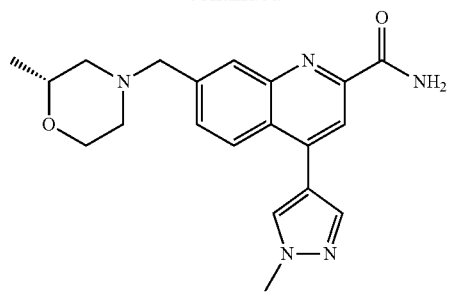
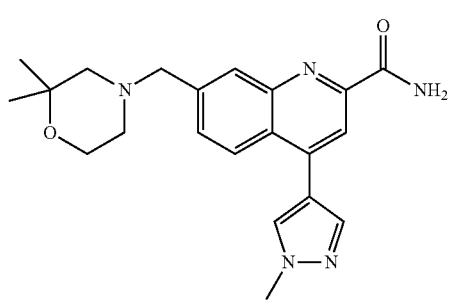
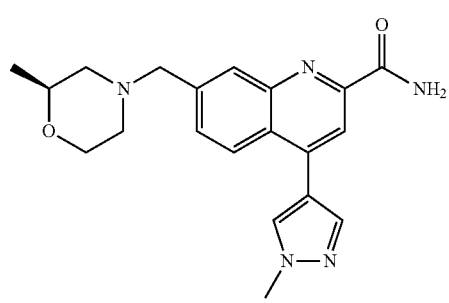
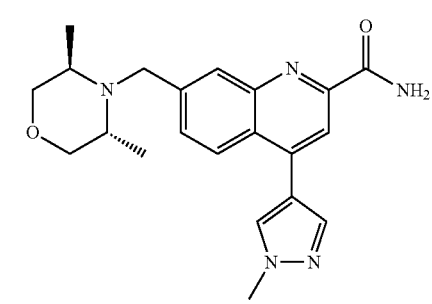
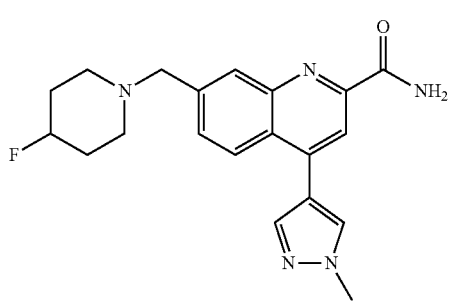
276
-continued
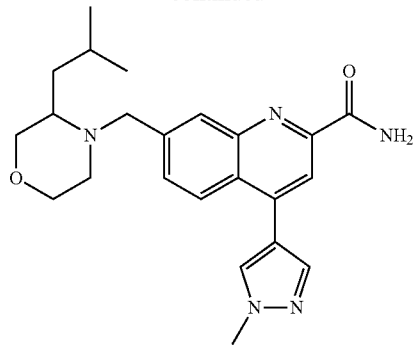
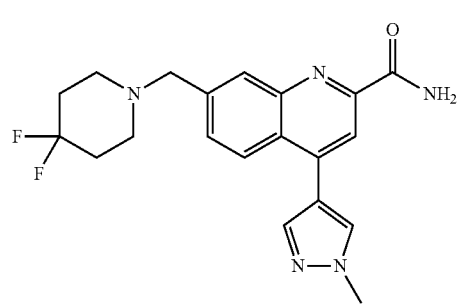
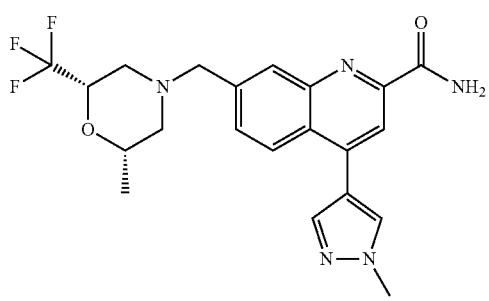
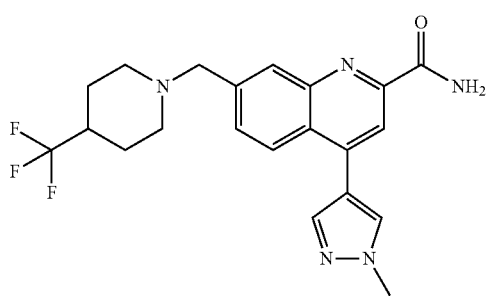
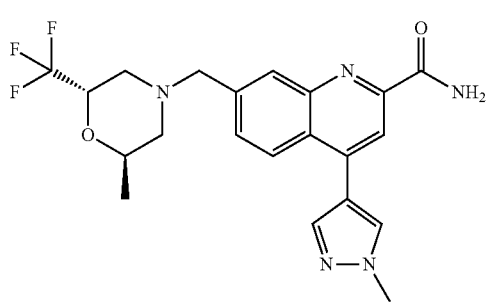

277
-continued
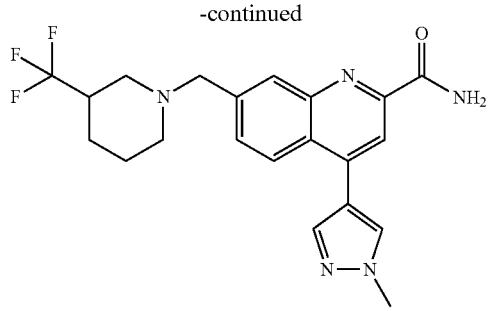
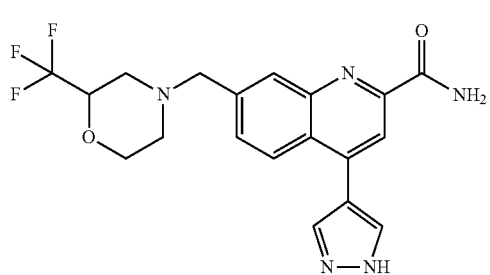
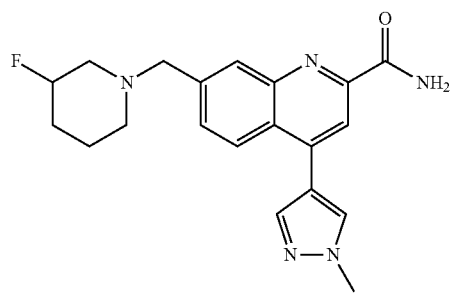
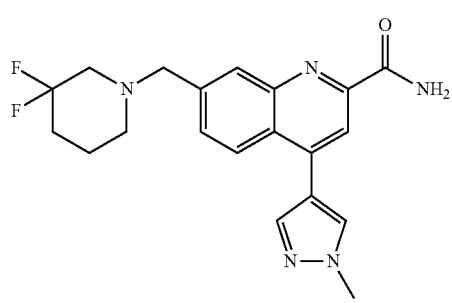
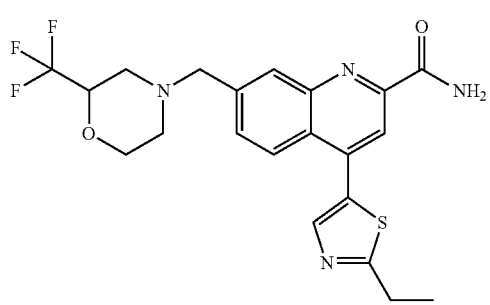
278
-continued
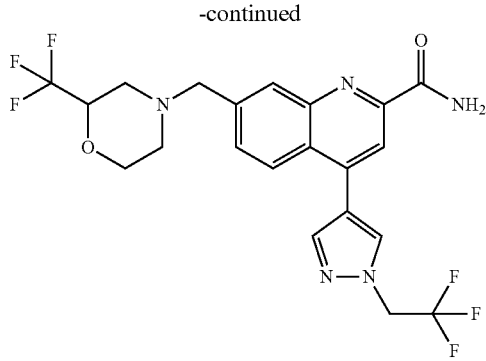
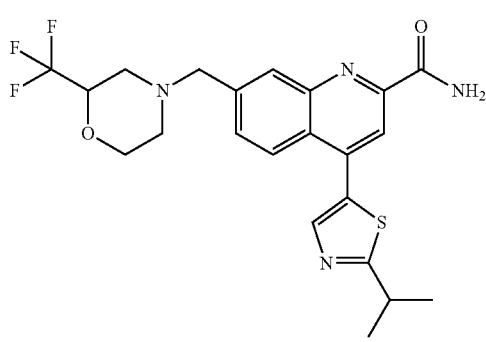
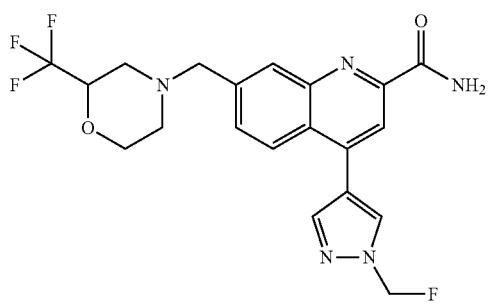
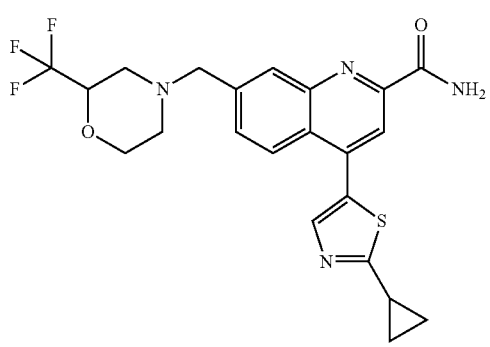
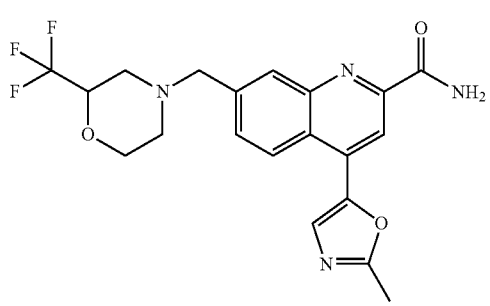

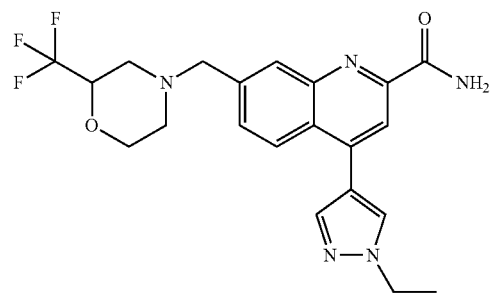
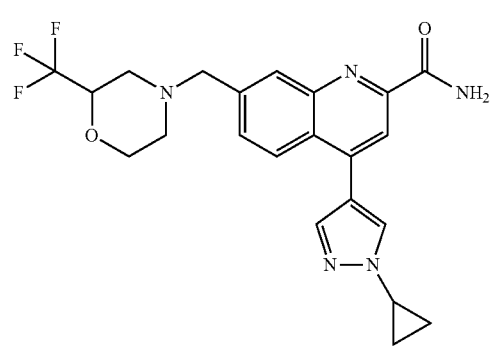
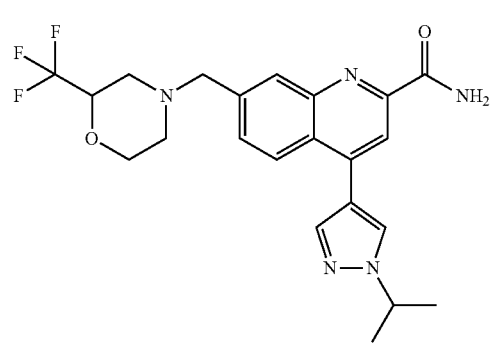
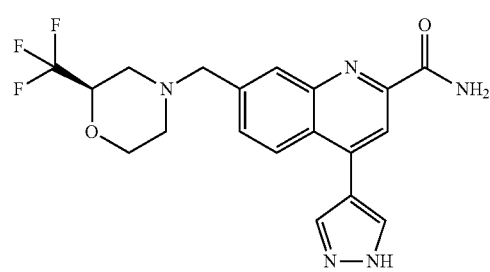
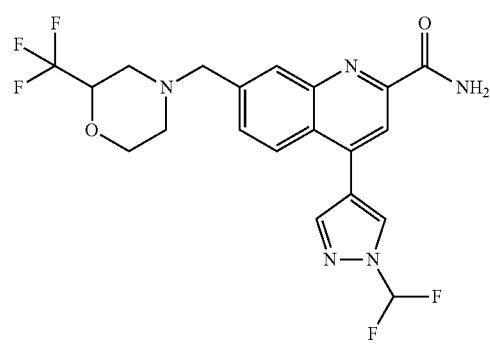
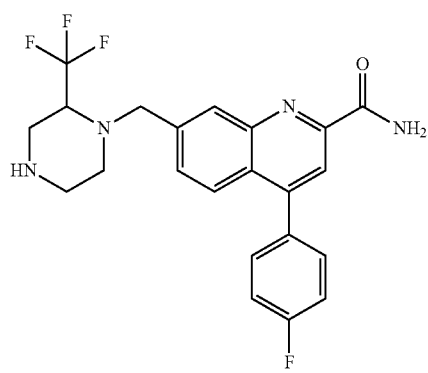
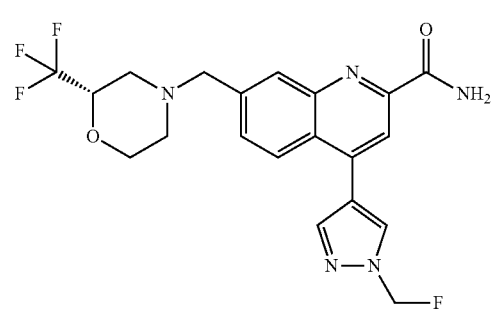
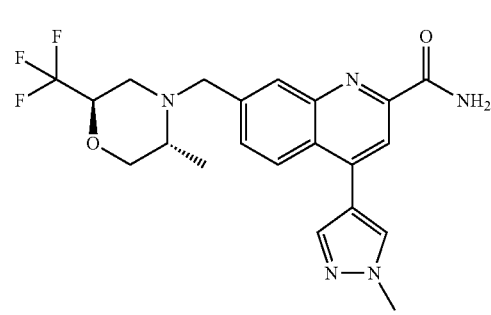
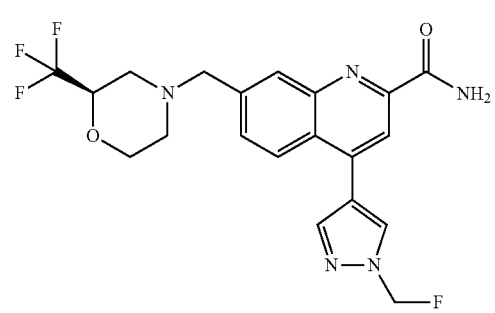
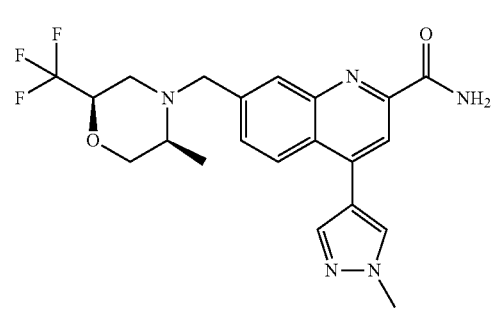

281
-continued
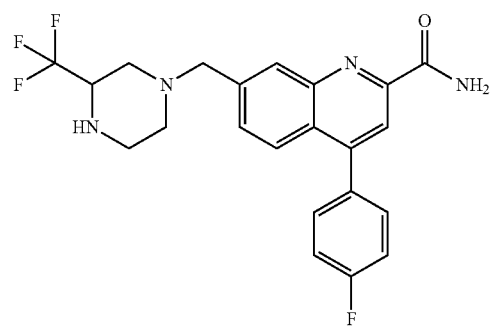
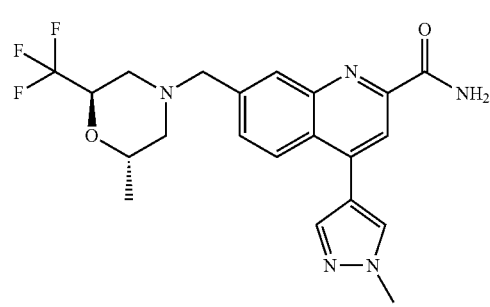
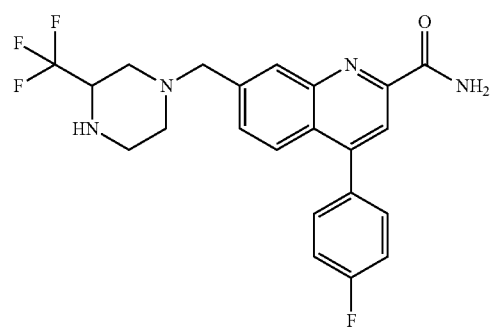
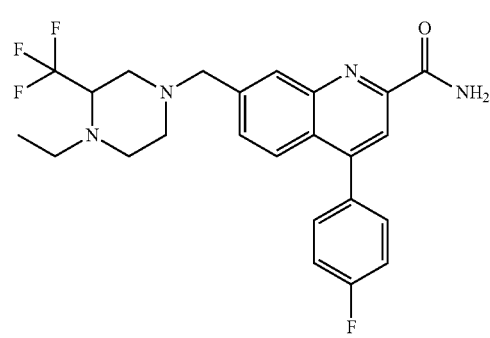
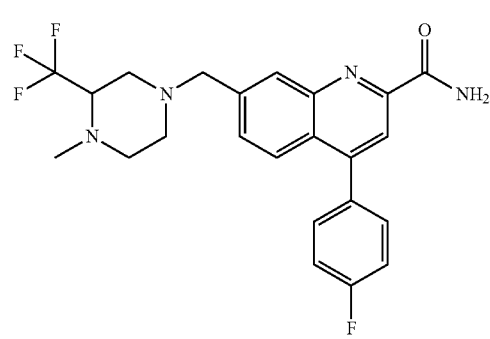
282
-continued
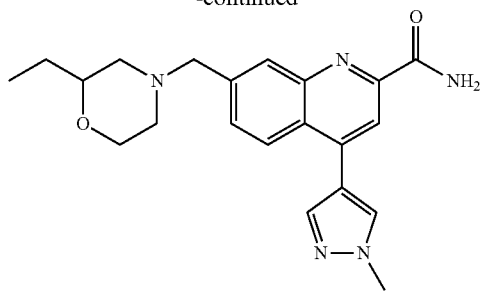
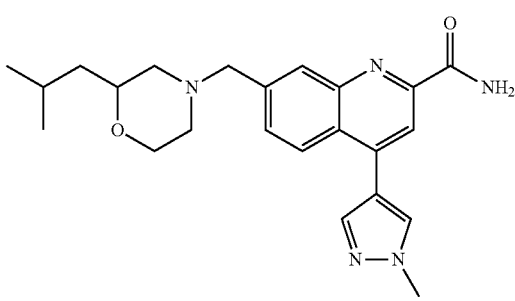
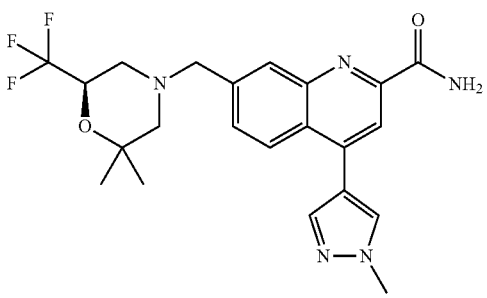
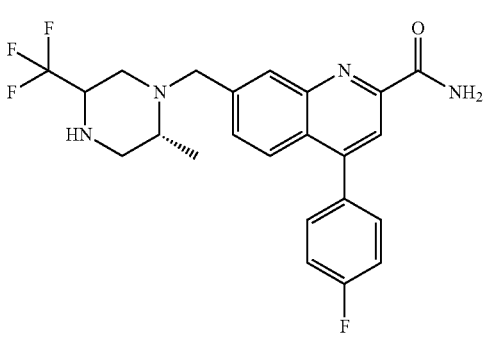
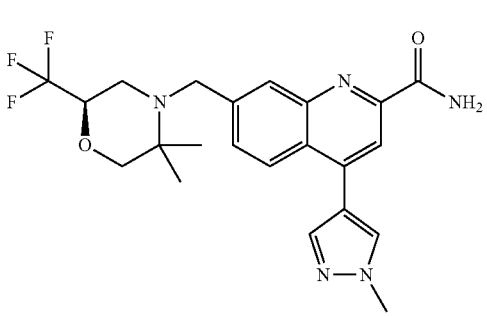

283
-continued
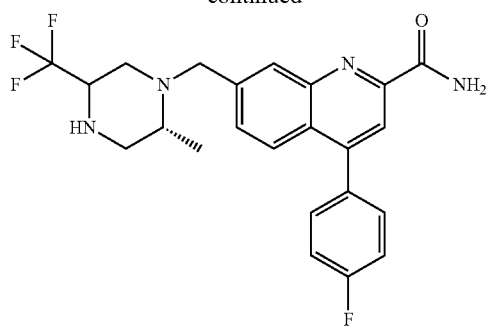
284
-continued
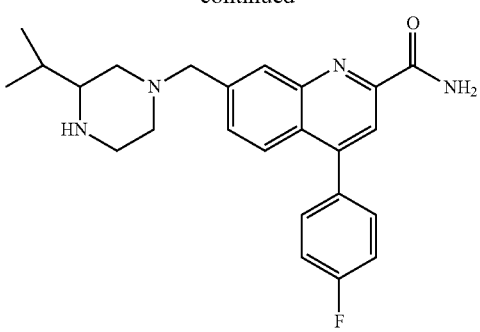
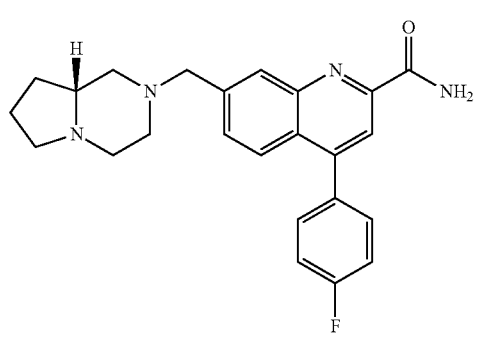
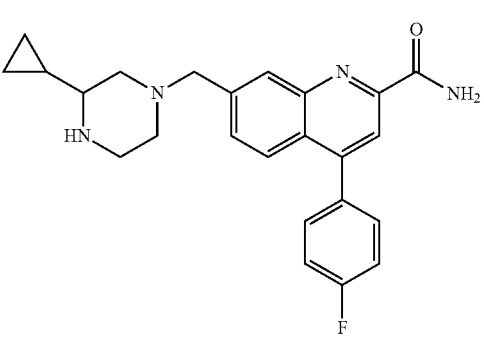
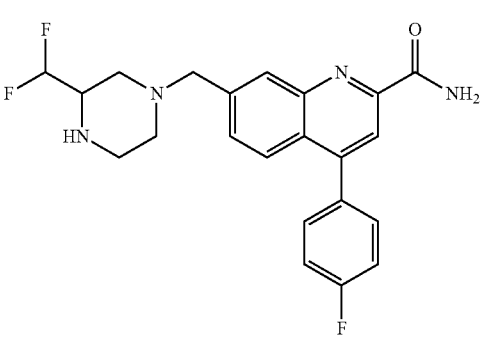
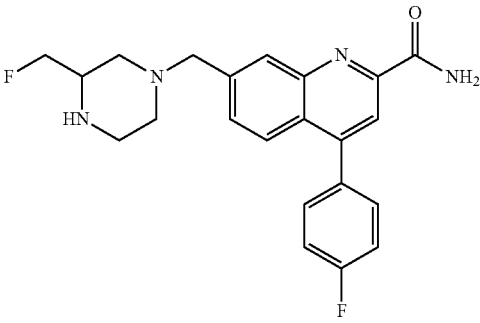

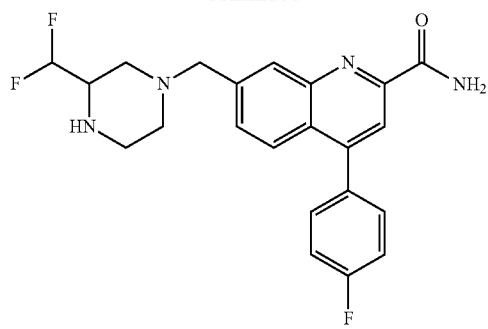
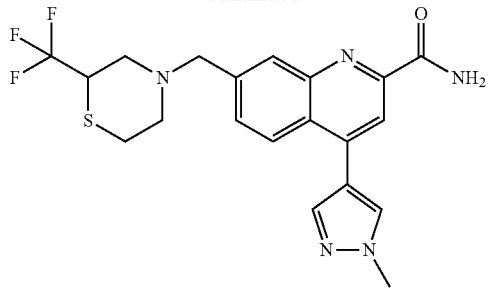
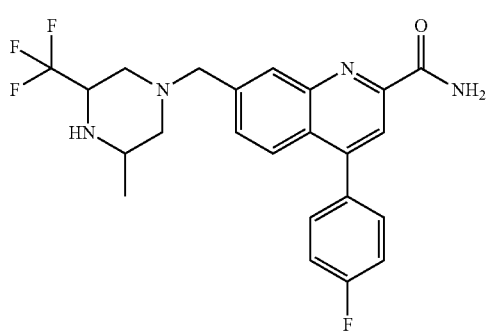
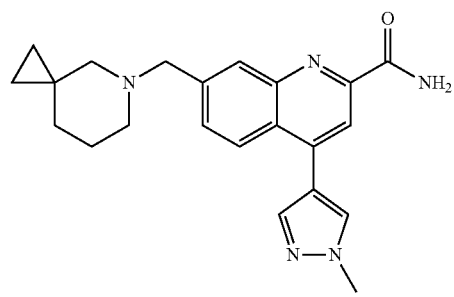
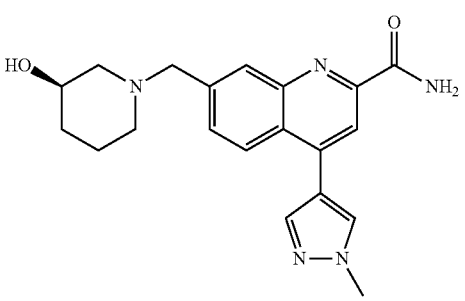
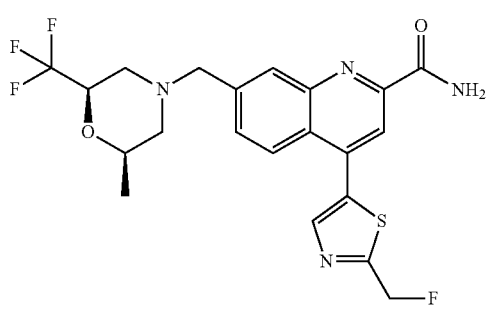

287
-continued
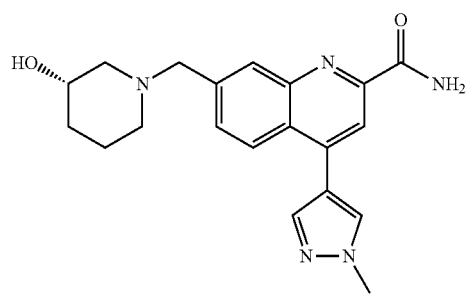
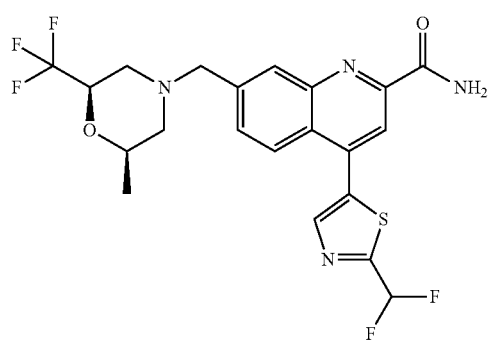
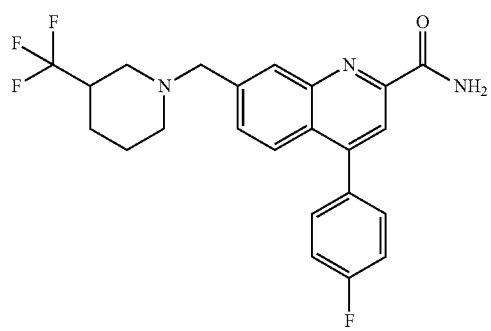
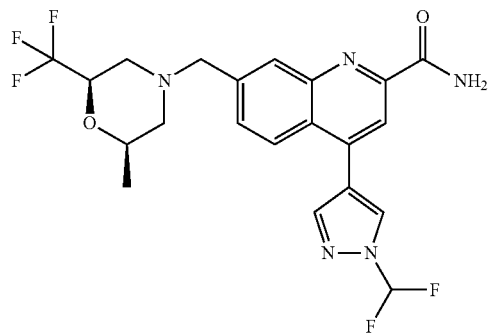
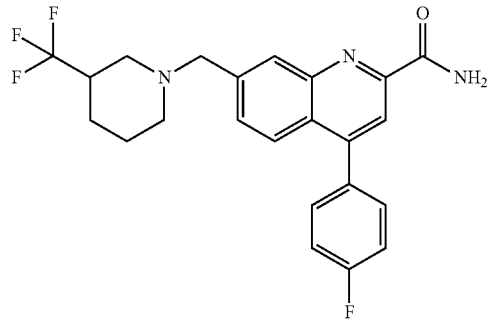
288
-continued
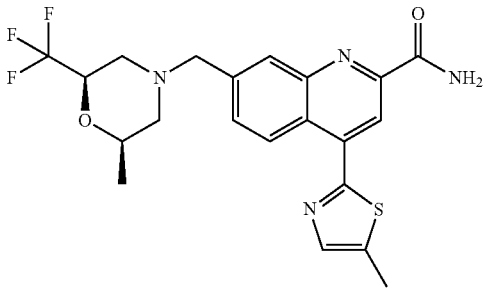
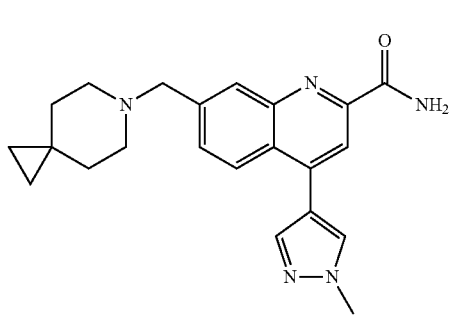
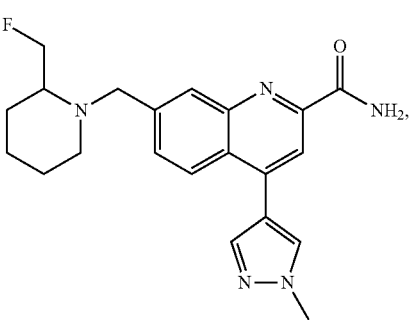
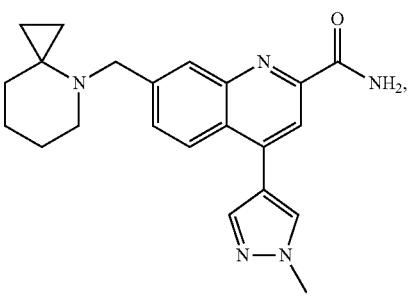
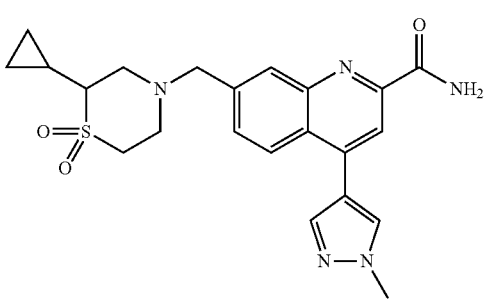

16. The method of claim 1, wherein said compound is selected from the group consisting of:
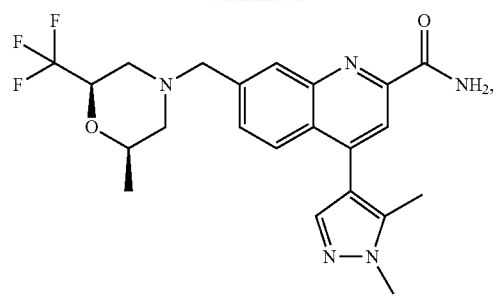
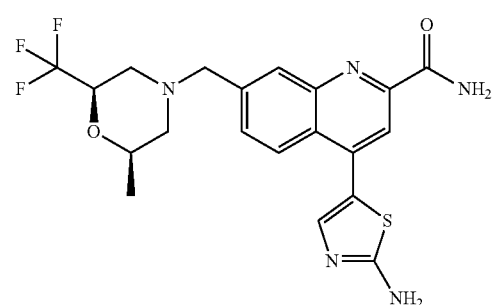
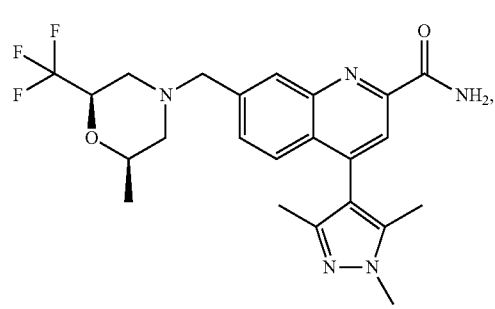
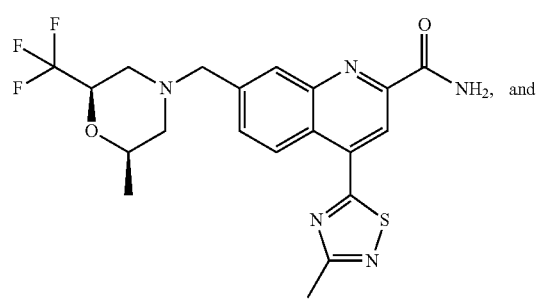
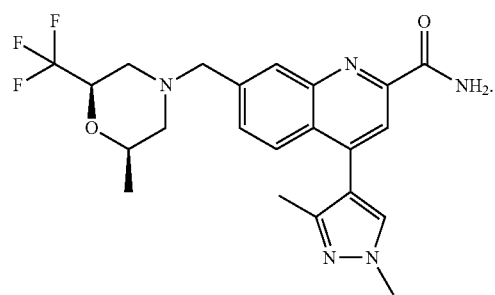
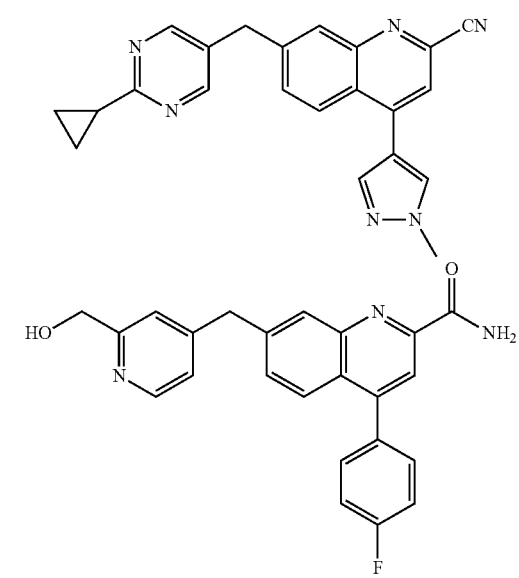
or a stereoisomer thereof, or a pharmaceutically acceptable salt of said compound or said stereoisomer.
17. The method of claim 1, wherein said compound is selected from the group consisting of:

291
-continued
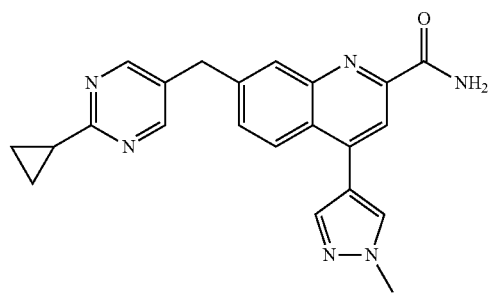
292
-continued
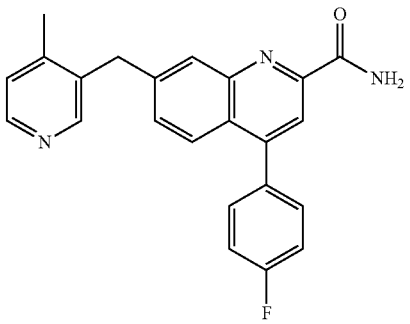
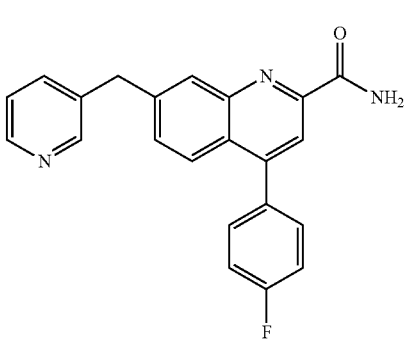
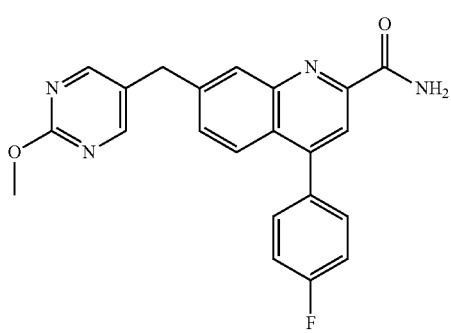
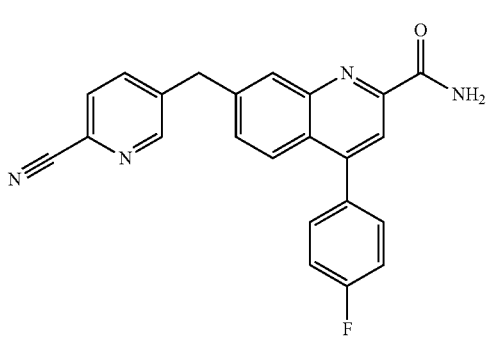
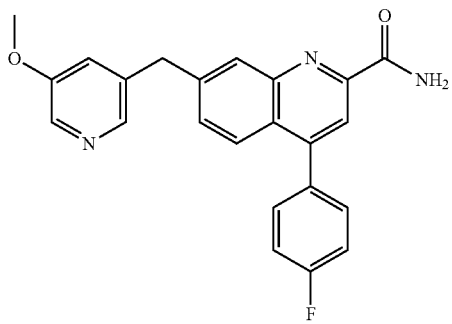

293
-continued
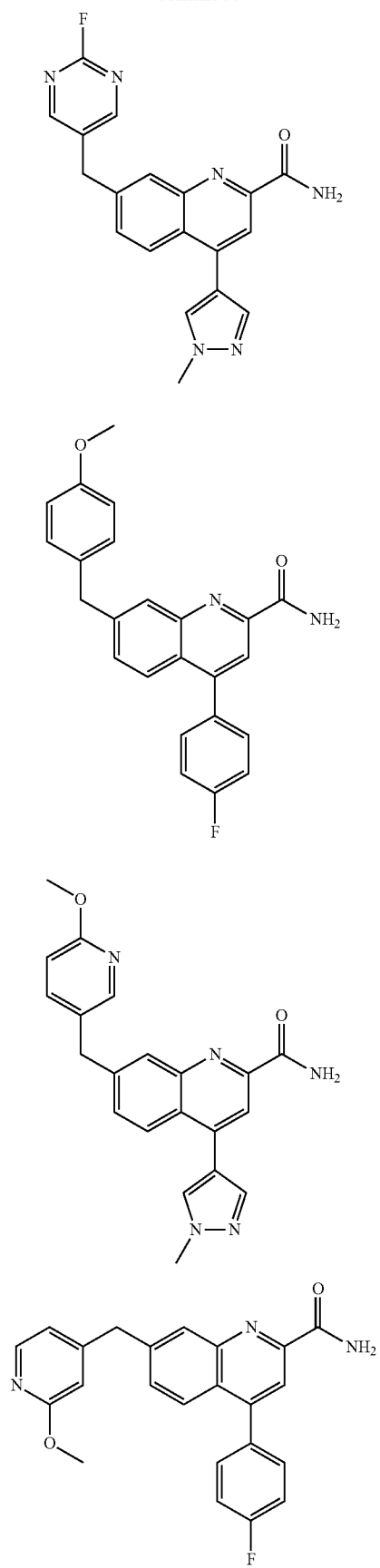
294
-continued
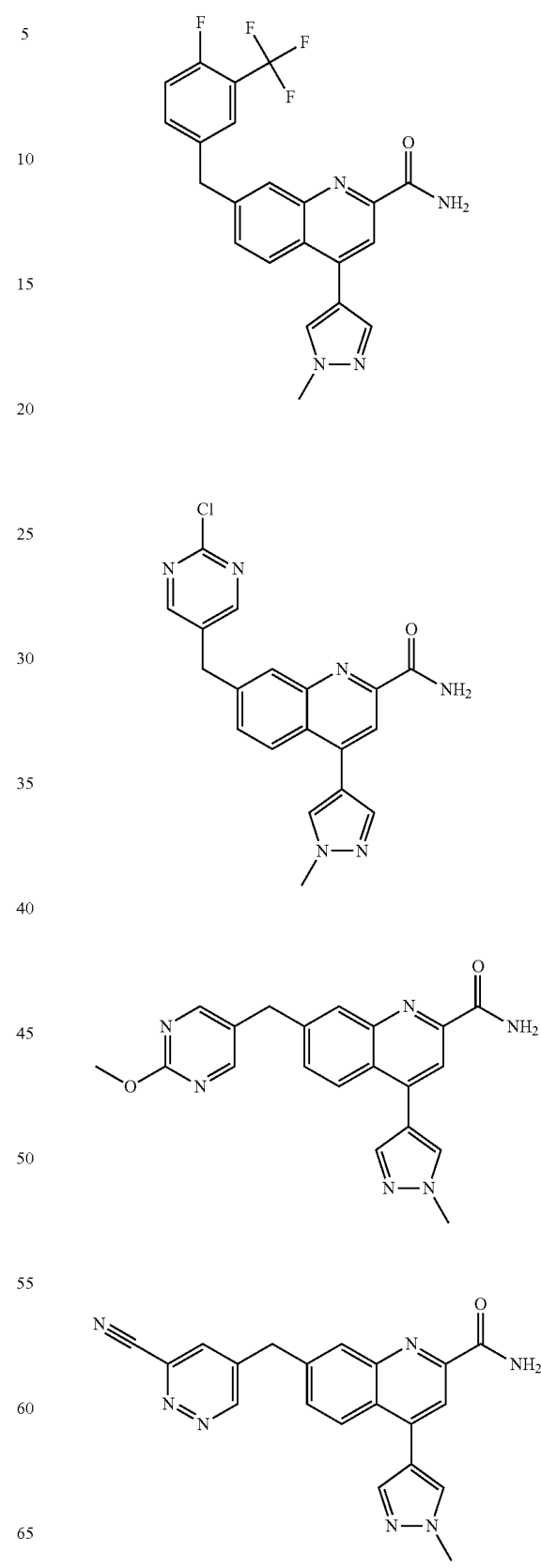

295
-continued
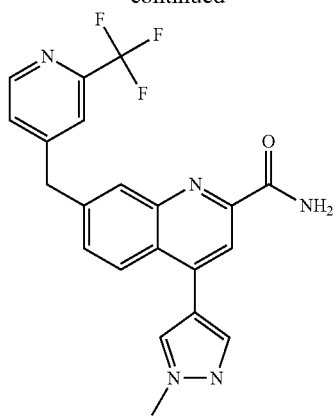
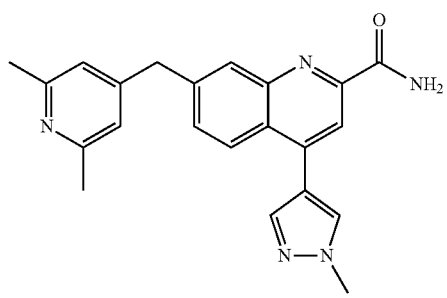
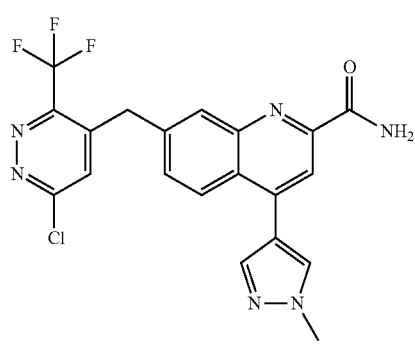
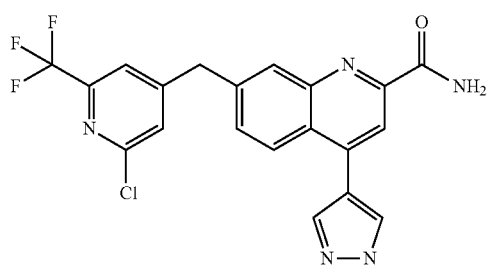
296
-continued
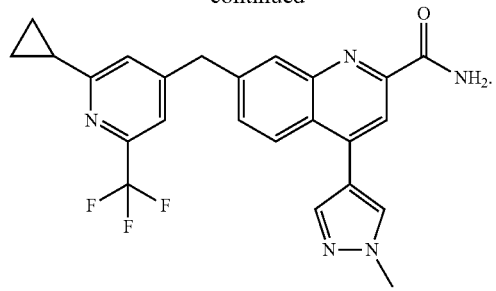
18. The method of claim 1, wherein said compound is selected from the group consisting of:
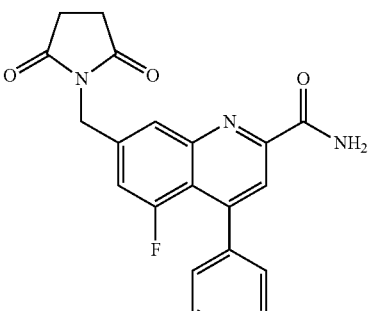
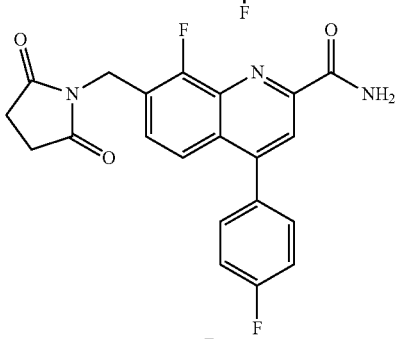
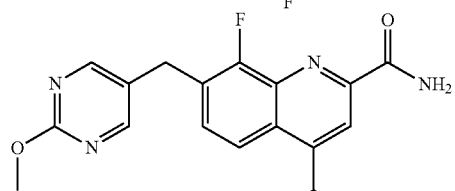
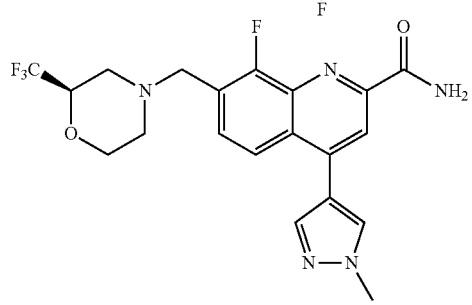
, and

297
-continued
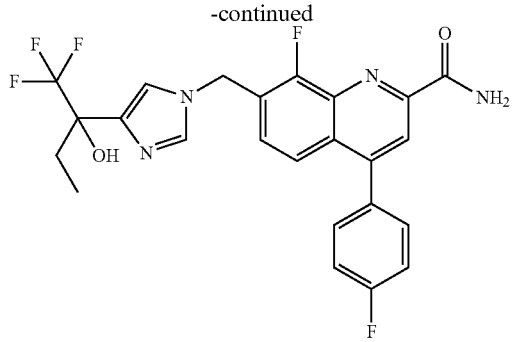
298
-continued
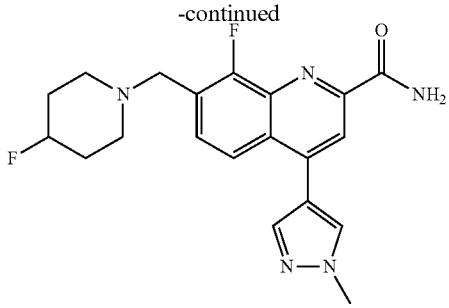
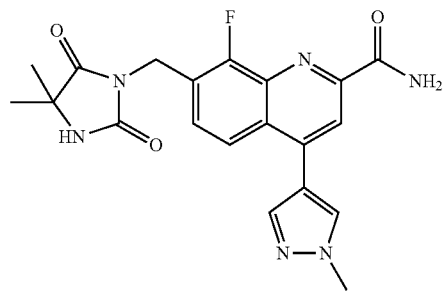
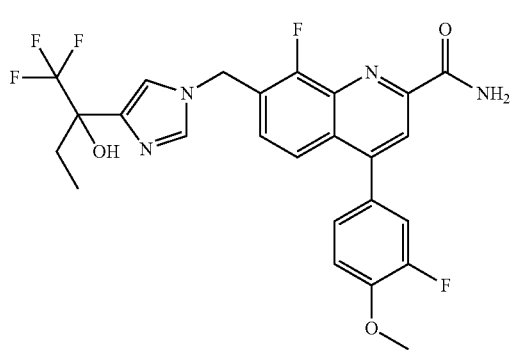
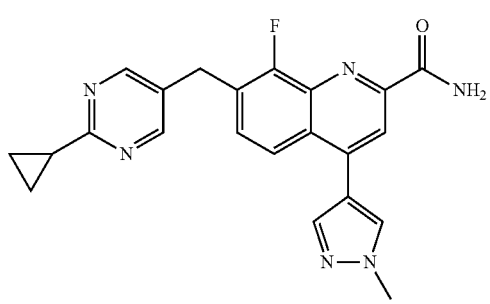
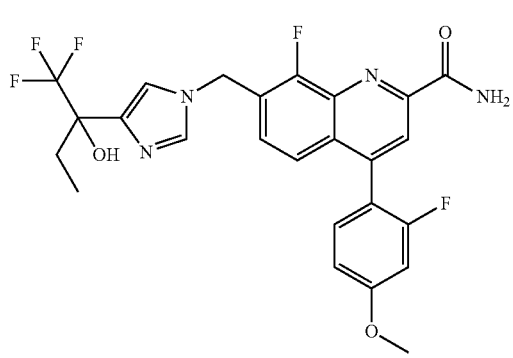

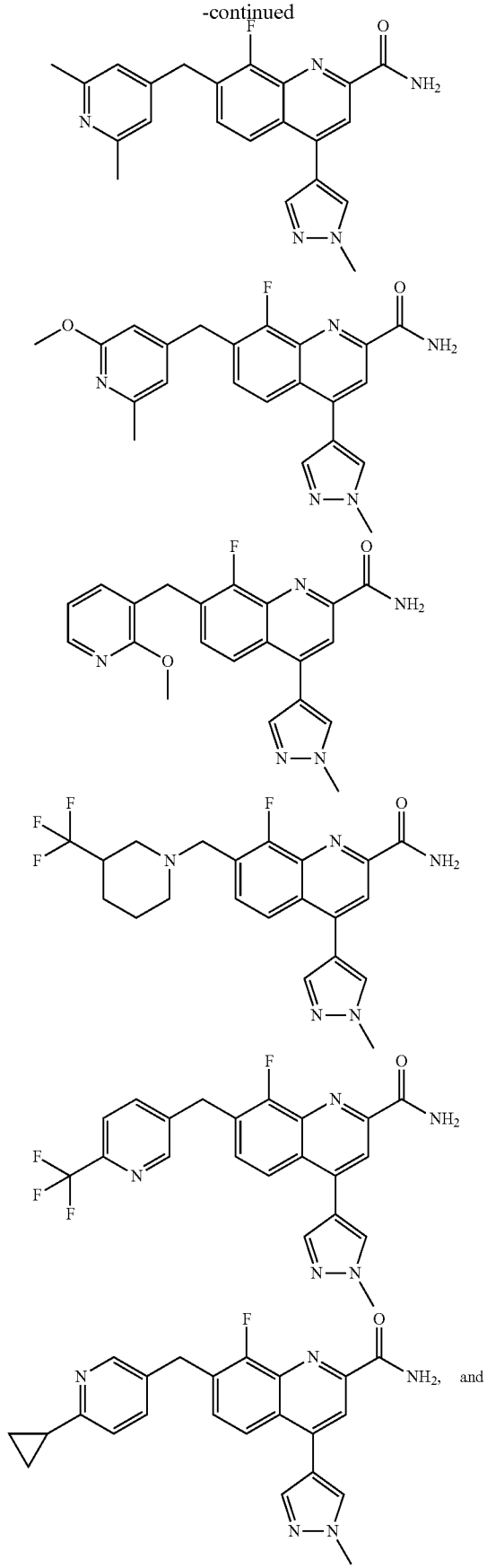
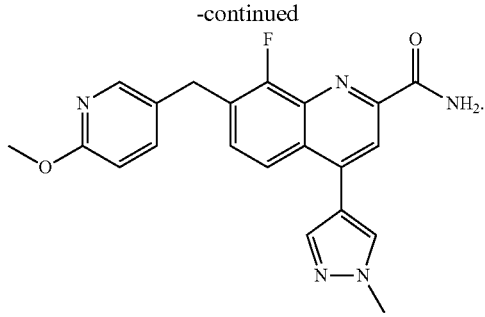
19. The method of claim 1, wherein said compound is selected from the group consisting of:
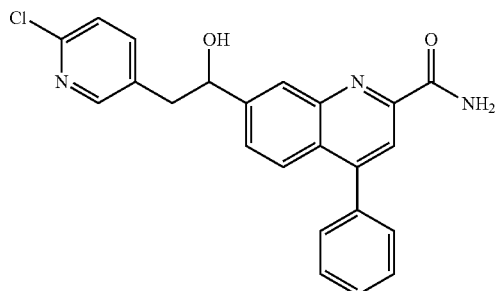
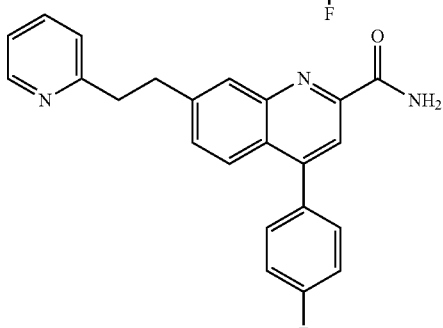
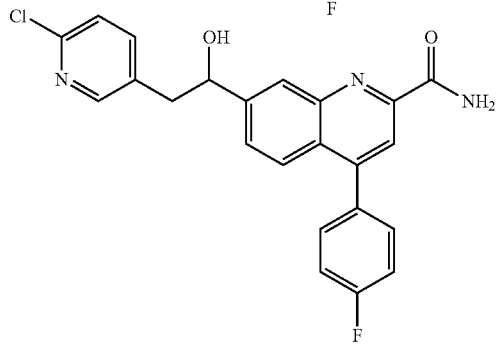
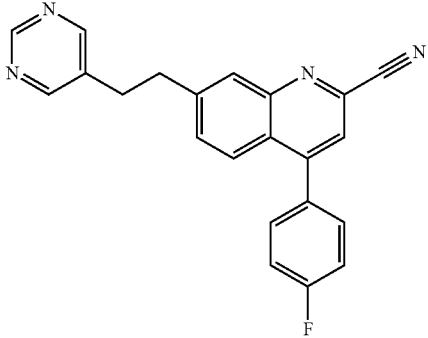

301
-continued
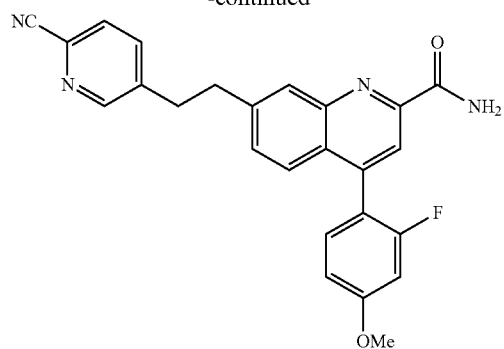
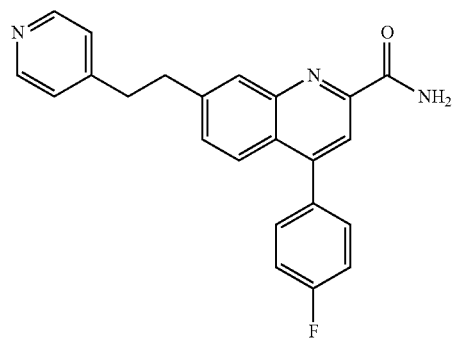
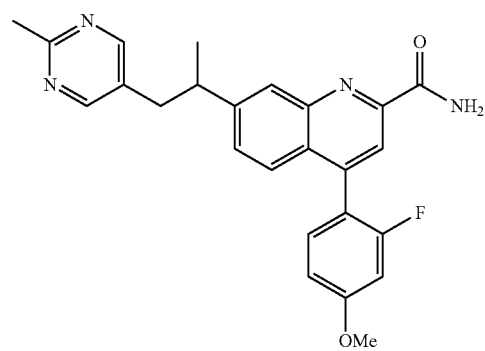
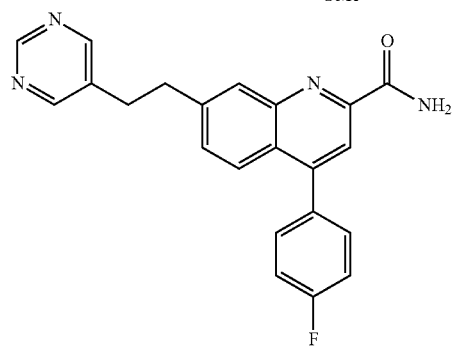
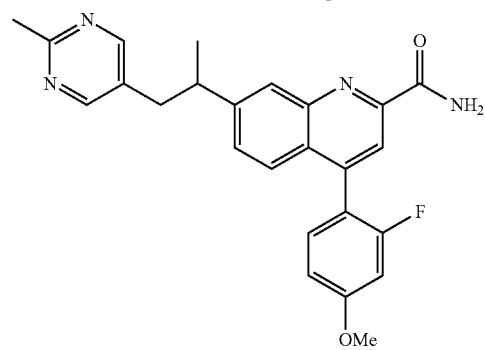
302
-continued
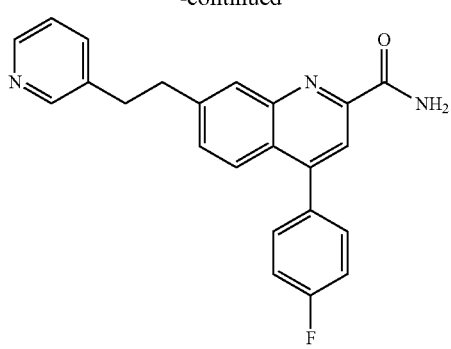
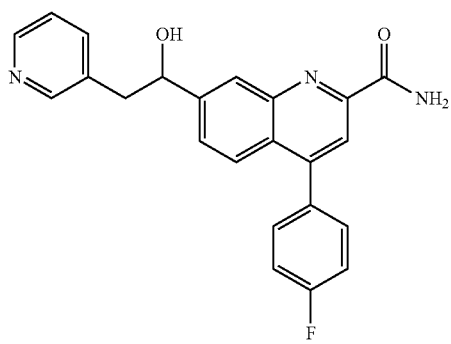
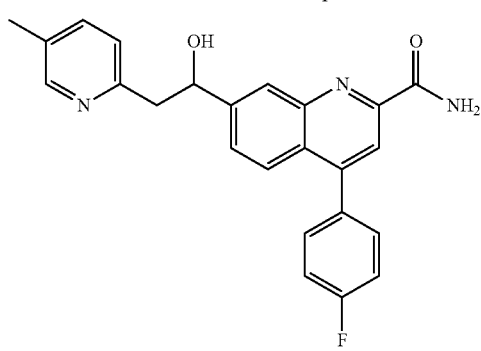
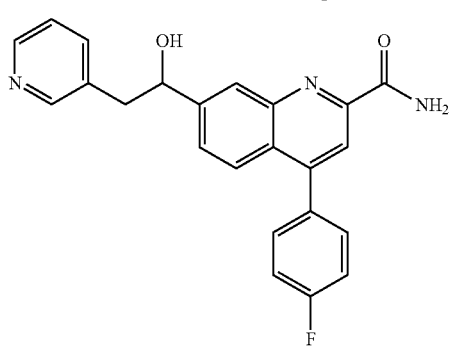
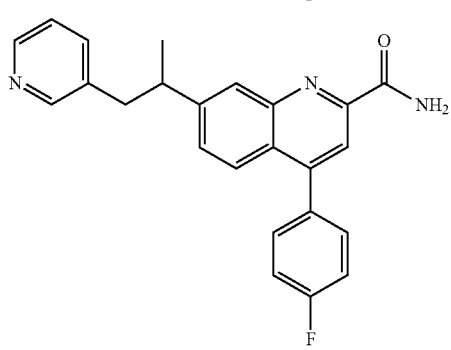

-continued
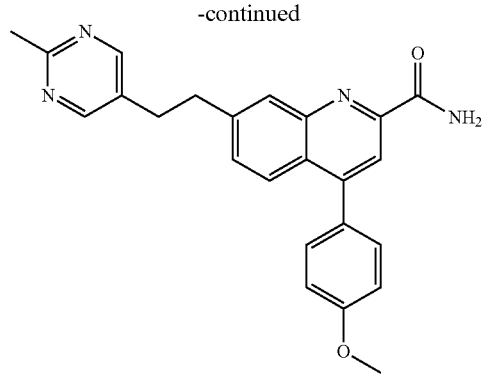
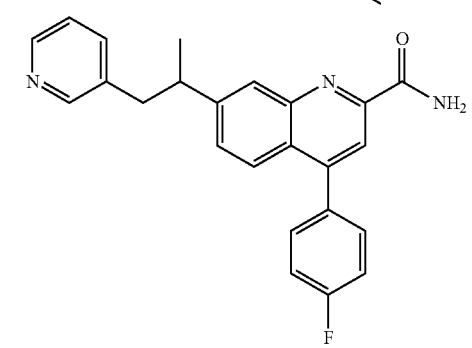
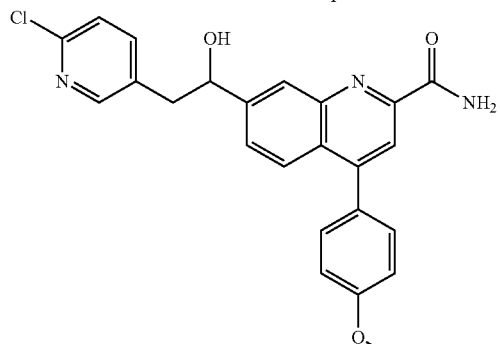
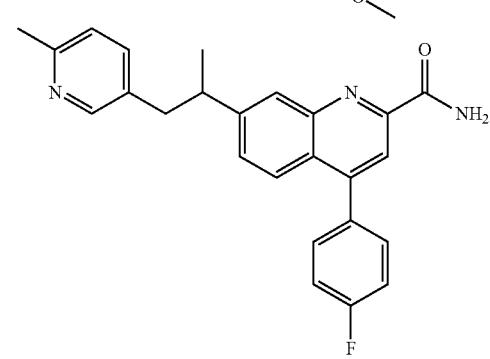
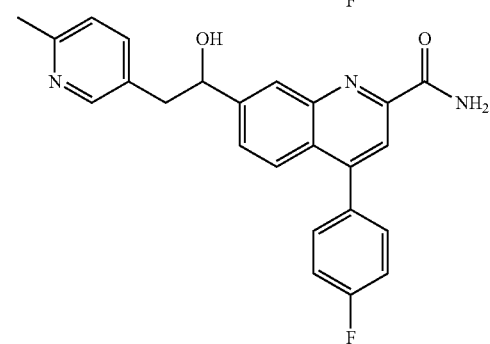
-continued
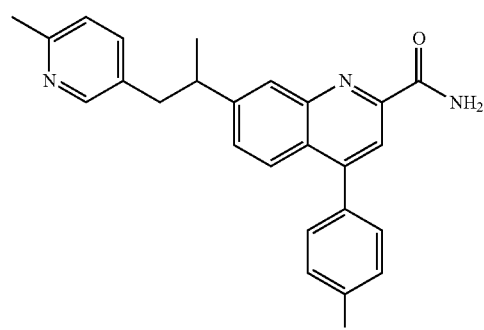
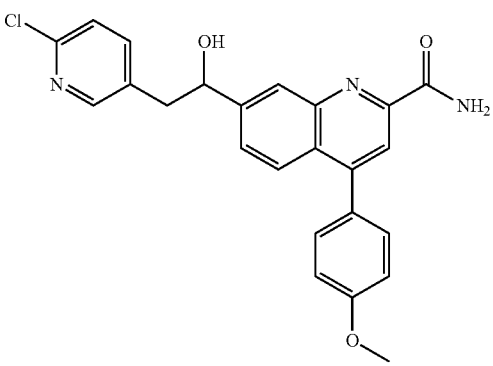
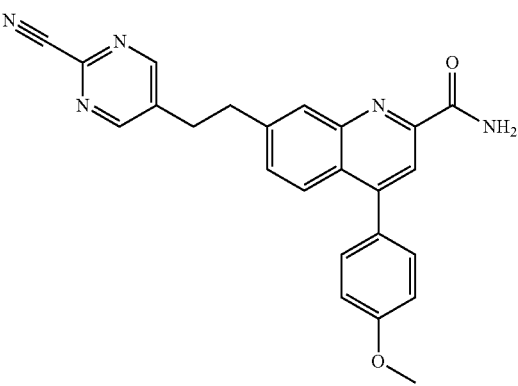
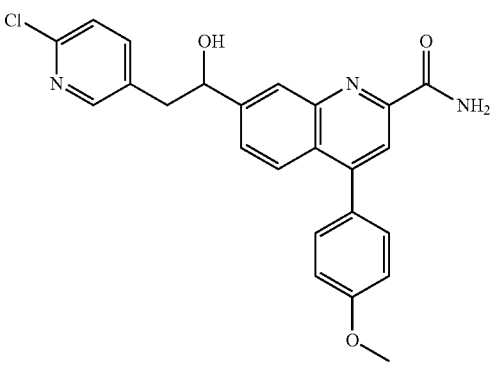

305
-continued
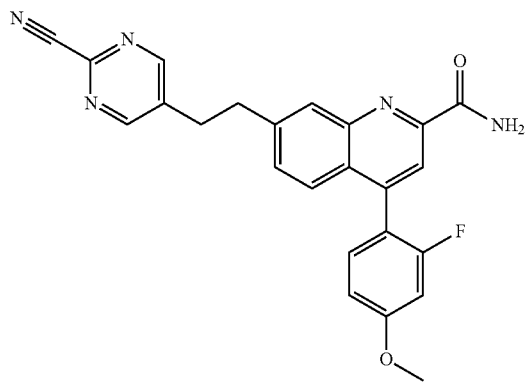
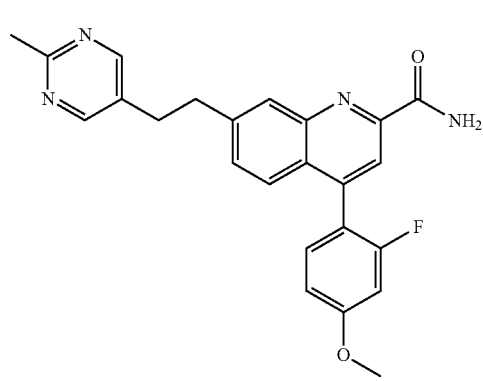
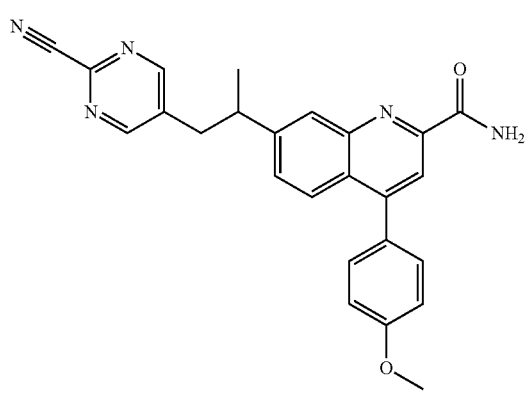
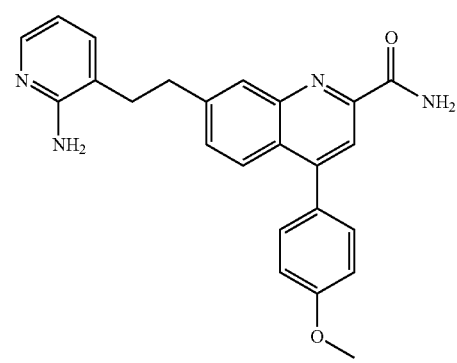
306
-continued
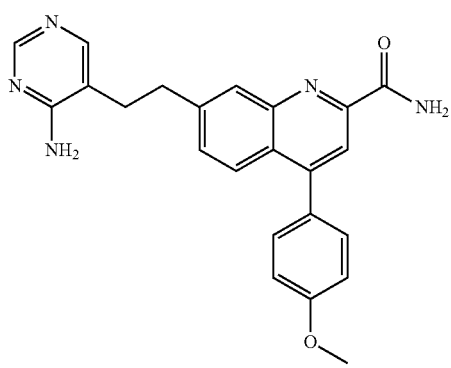
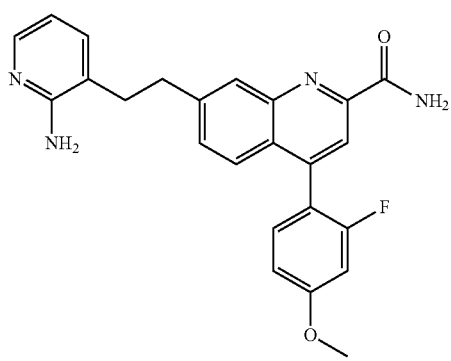
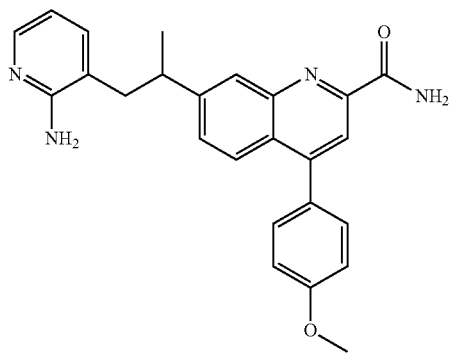
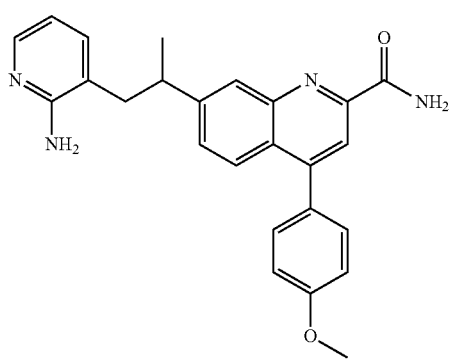

307
-continued
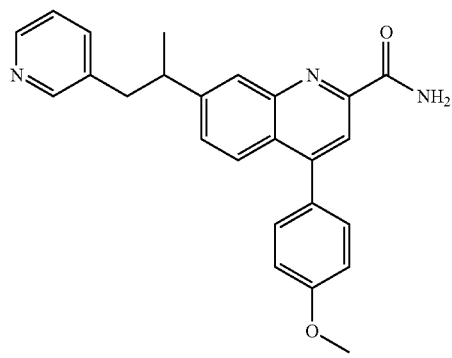
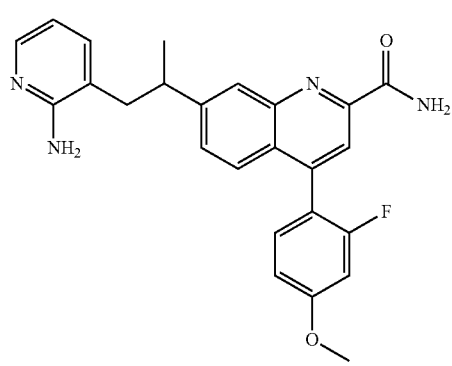
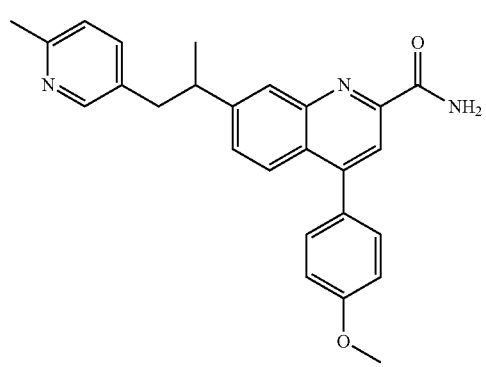
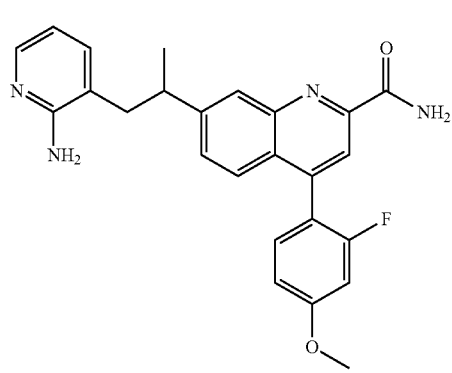
308
-continued
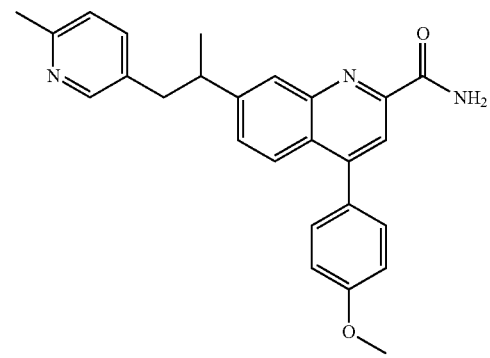
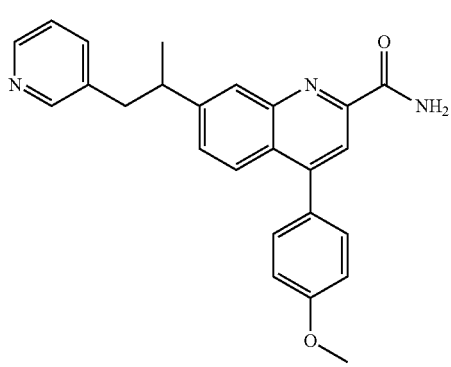
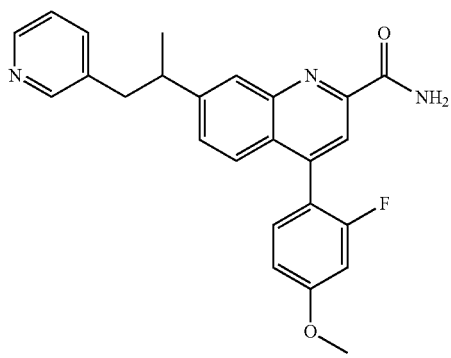
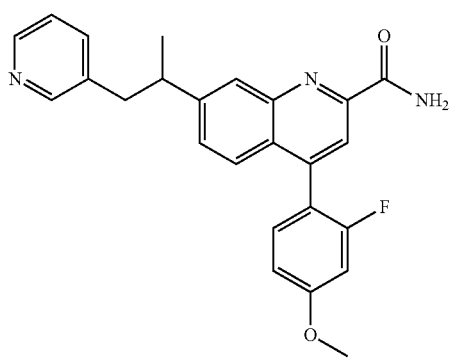

309
-continued
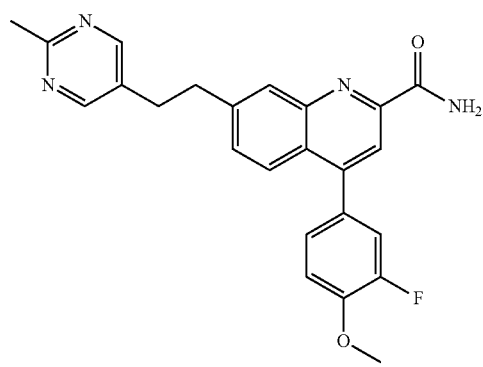
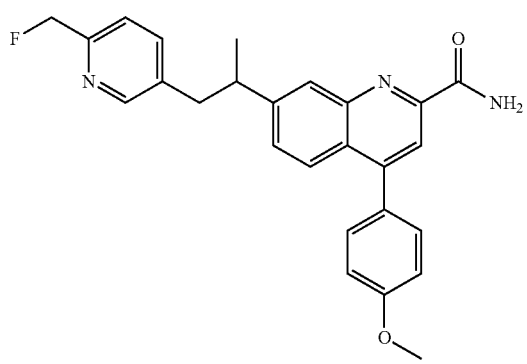
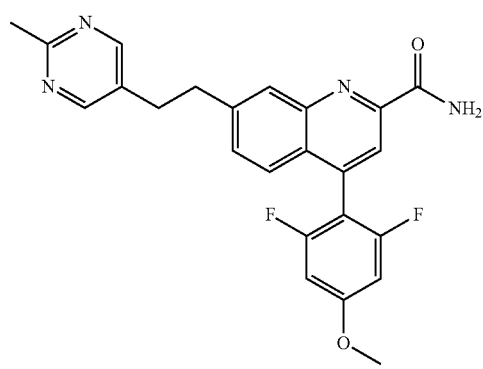
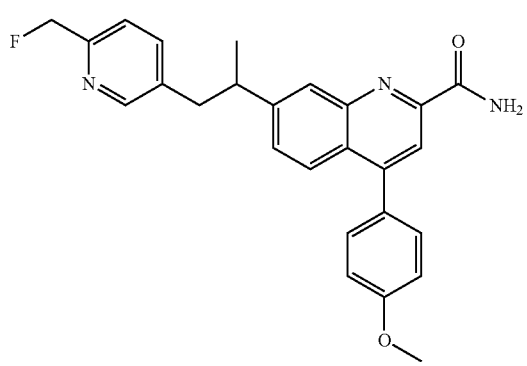
310
-continued
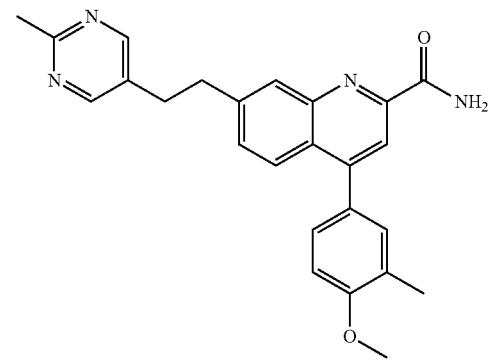
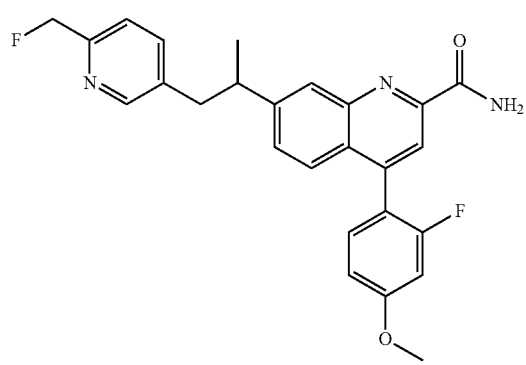
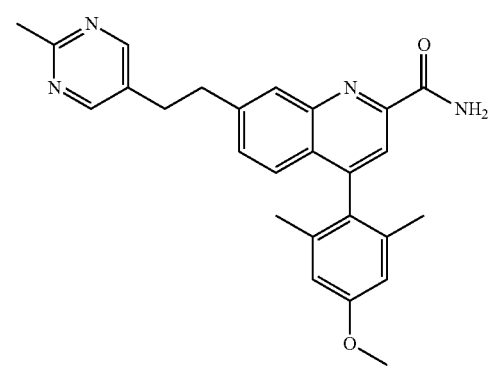
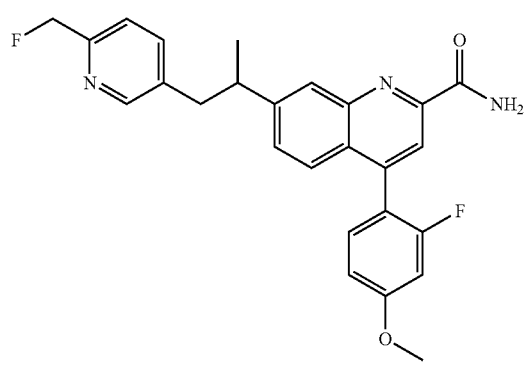

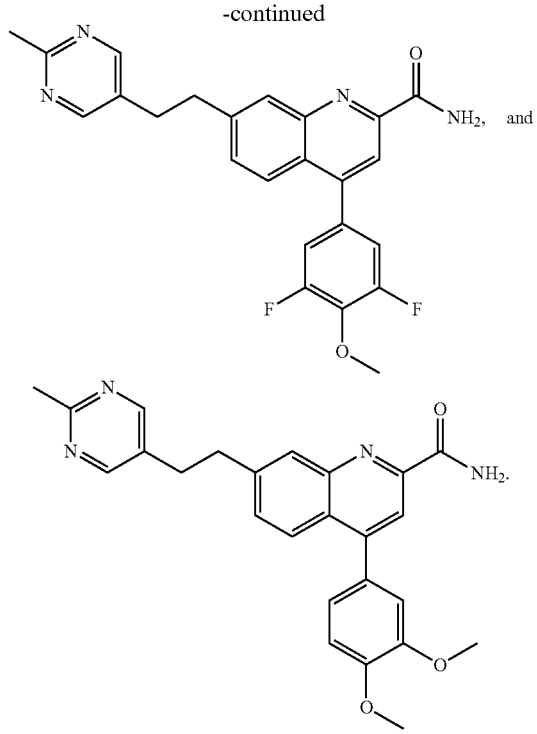

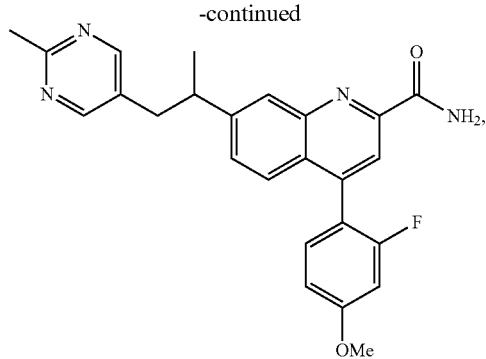

or a stereoisomer thereof, or a pharmaceutically acceptable salt of said compound or said stereoisomer.

21. The method of claim 1, wherein said compound is:

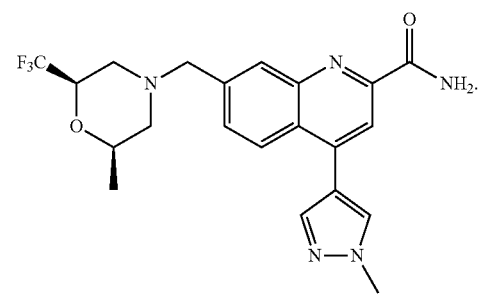 [SMILES: C[C@@H]1CN(Cc2ccc3c(-c4cnn(C)c4)cc(C(N)=O)nc3c2)C[C@H](C(F)(F)F)O1]

20. The method of claim 1, wherein said compound is selected from the group consisting of:

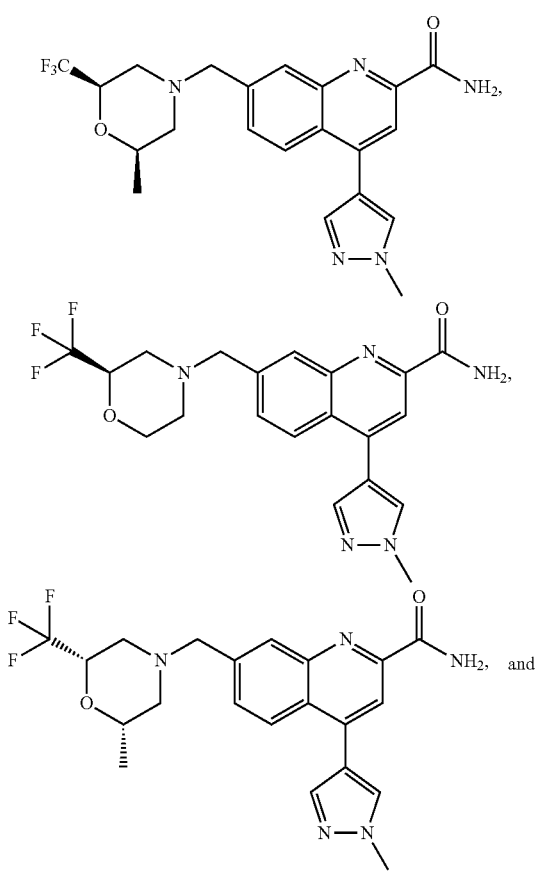

22. The method of claim 21, wherein said compound is in the form of a pharmaceutically acceptable salt.

23. The method of claim 1, wherein said compound is:

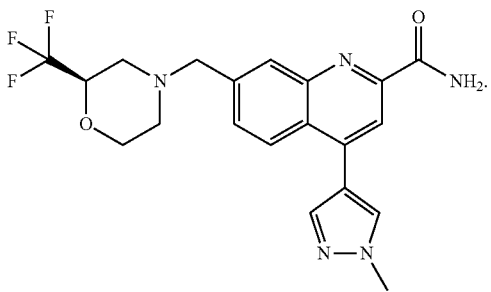 [SMILES: Cn1cc(-c2cc(C(N)=O)nc3cc(CN4CCO[C@@H](C(F)(F)F)C4)ccc23)cn1]

24. The method of claim 23, wherein said compound is in the form of a pharmaceutically acceptable salt.

25. The method of claim 1, wherein said compound is:

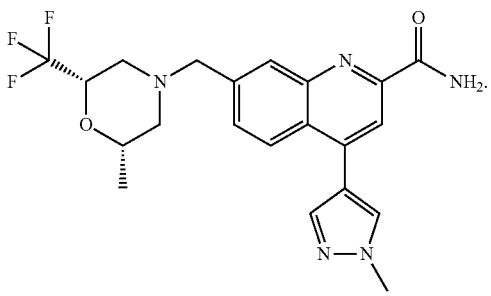 [SMILES: C[C@H]1CN(Cc2ccc3c(-c4cnn(C)c4)cc(C(N)=O)nc3c2)C[C@@H](C(F)(F)F)O1]

26. The method of claim 25, wherein said compound is in the form of a pharmaceutically acceptable salt.

27. The method of claim 1, wherein said compound is:

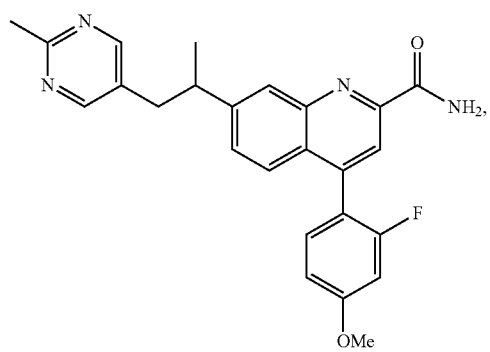 [SMILES: COc1ccc(-c2cc(C(N)=O)nc3cc(C(C)Cc4cnc(C)nc4)ccc23)c(F)c1]

or a stereoisomer thereof.

28. The method of claim 27, wherein said compound, or the stereoisomer thereof, is in the form of a pharmaceutically acceptable salt.

29. The method of claim 1, wherein said compound is:

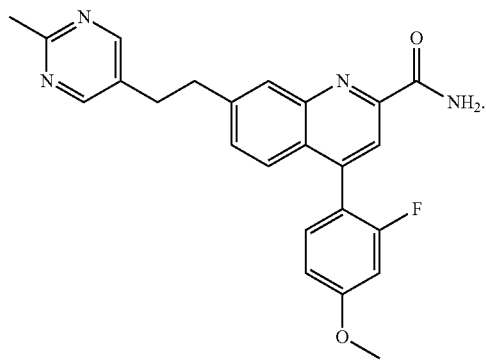 [SMILES: COc1ccc(-c2cc(C(N)=O)nc3cc(CCc4cnc(C)nc4)ccc23)c(F)c1]

30. The method of claim 29, wherein said compound is in the form of a pharmaceutically acceptable salt.

* * * * *